United States Patent
Heymach et al.

(10) Patent No.: US 11,365,189 B2
(45) Date of Patent: Jun. 21, 2022

(54) HETEROCYCLIC INHIBITORS OF TYROSINE KINASE

(71) Applicant: Board of Regents, The University of Texas System, Austin, TX (US)

(72) Inventors: John Heymach, Houston, TX (US); Jacqulyne Robichaux, Manvel, TX (US); Monique Nilsson, Sugar Land, TX (US); Philip Jones, Houston, TX (US); Jason Cross, Pearland, TX (US); Jay Theroff, Manvel, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/858,116

(22) Filed: Apr. 24, 2020

(65) Prior Publication Data
US 2020/0354343 A1 Nov. 12, 2020

Related U.S. Application Data

(60) Provisional application No. 62/838,696, filed on Apr. 25, 2019.

(51) Int. Cl.
| | | |
|---|---|---|
| *C07D 401/12* | (2006.01) | |
| *C07D 401/14* | (2006.01) | |
| *A61P 35/04* | (2006.01) | |
| *C07D 403/12* | (2006.01) | |
| *C07D 487/04* | (2006.01) | |
| *C07D 413/14* | (2006.01) | |

(52) U.S. Cl.
CPC .......... *C07D 403/12* (2013.01); *A61P 35/04* (2018.01); *C07D 401/12* (2013.01); *C07D 401/14* (2013.01); *C07D 413/14* (2013.01); *C07D 487/04* (2013.01)

(58) Field of Classification Search
CPC .. C07D 401/12; C07D 401/14; C07D 403/12; A61P 35/04
See application file for complete search history.

(56) References Cited

U.S. PATENT DOCUMENTS

| | | | | |
|---|---|---|---|---|
| 9,725,439 | B2 * | 8/2017 | Xiao | ................. C07D 403/12 |
| 2010/0179120 | A1 * | 7/2010 | Lee | ................. C07D 403/12 |
| | | | | 514/210.18 |
| 2013/0071452 | A1 | 3/2013 | Kim | |

FOREIGN PATENT DOCUMENTS

| | | | |
|---|---|---|---|
| EP | 2167492 | 3/2010 | |
| KR | 1020160058946 | 5/2016 | |
| WO | 2003082290 | 10/2003 | |
| WO | 2015154725 | 10/2015 | |
| WO | WO-2019165003 A1 * | 8/2019 | .......... C07D 215/54 |
| WO | 2020219904 | 10/2020 | |

OTHER PUBLICATIONS

Arcila, M. et al., "EGFR Exon 20 Insertion Mutations in Lung Adenocarcinomas: Prevalence, Molecular Heterogeneity, and Clinicopathologic Characteristics", Mol Cancer Ther., 12(2):220-9, (2013).
Connell, C. et al., "Activating HER2 Mutations as Emerging Targets in Multiple Solid Cancers", ESMO Open, 2(5):e000279, (2017).
Kosaka, T. et al., "Response Heterogeneity of EGFR and HER2 Exon 20 Insertions to Covalent EGFR and HER2 Inhibitors", Cancer Res., 77(10):2712-21, (2017).
Kourie, H. et al., "Pharmacodynamics, Pharmacokinetics and Clinical Efficacy of Neratinib in HER2-Positive Breast Cancer and Breast Cancer with HER2 Mutations", Expert Opin Drug Metab Toxicol., 12(8):947-57, (2016).
Kris, M. et al., "Targeting HER2 Aberrations as Actionable Drivers in Lung Cancers: Phase II Trial of the Pan-HER Tyrosine Kinase Inhibitor Dacomitinib in Patients with HER2-Mutant or Amplified Tumors", Ann Oncol., 26(7):1421-7, (2015).
Lee, J. et al., "Somatic Mutations of ERBB2 Kinase Domain in Gastric, Colorectal, and Breast Carcinomas", Clin Cancer Res., 12(1):57-61, (2006).
Nagano, M. et al., "High-Throughput Functional Evaluation of Variants of Unknown Significance in ERBB2", Clin Cancer Res., 24(20):5112-22, (2018).
Shan, L. et al., "Prevalence and Clinicopathological Characteristics of HER2 and BRAF Mutation in Chinese Patients with Lung Adenocarcinoma", PLoS One, 10(6):e0130447, (2015).
International Application No. PCT/US2020/029849; International Search Report and Written Opinion of the International Searching Authority, dated Aug. 7, 2020; 11 pages.
Kim, E. et al., "Metabolite Identification of A New Tyrosine Kinase Inhibitor, HM781-36B, and a Pharmacokinetic Study by Liquid Chromatography/Tandem Mass Spectrometry", Rapid Commun Mass Spectrom, 27(11):1183-95, (2013).

\* cited by examiner

*Primary Examiner* — Samira J Jean-Louis
(74) *Attorney, Agent, or Firm* — Dennis A. Bennett; Lauren L. Stevens; Cynthia Hathaway

(57) ABSTRACT

The present disclosure relates to heterocyclic compounds and methods which may be useful as inhibitors of HER2 or EGFR for the treatment or prevention of disease, including cancer.

30 Claims, 23 Drawing Sheets

FIG. 1
(a)
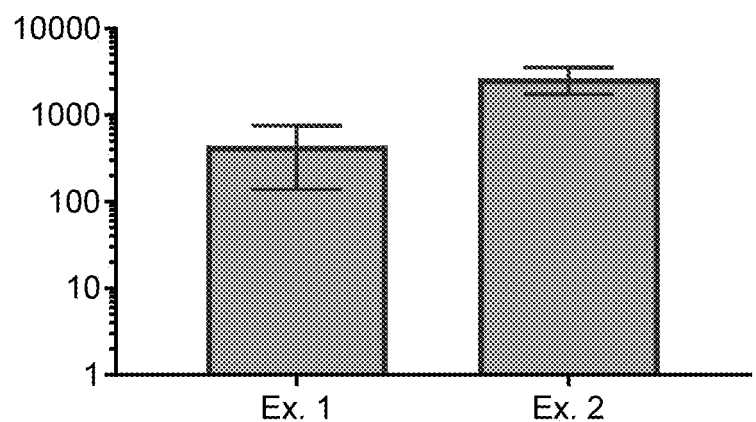
(b)
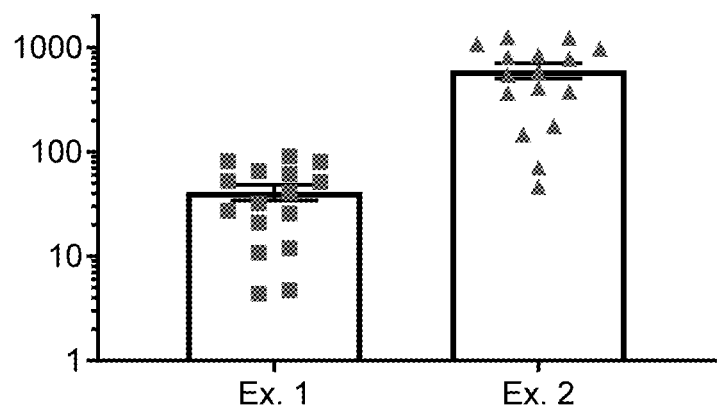
(c)
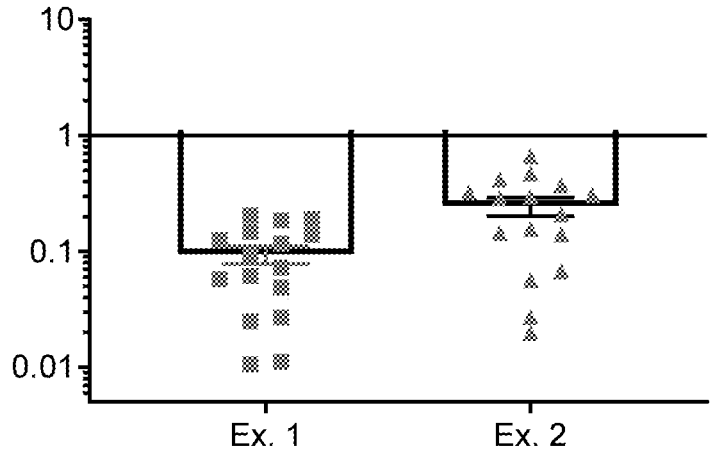

FIG. 4
(a)
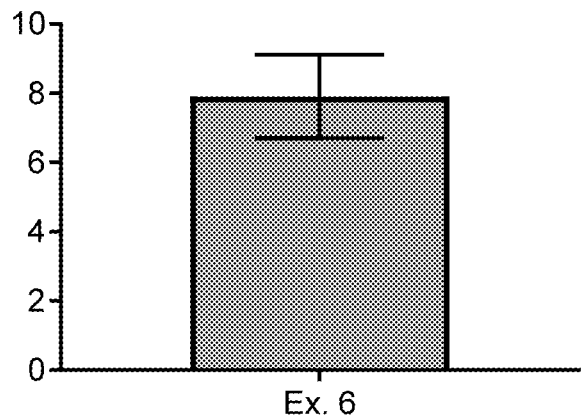
(b)
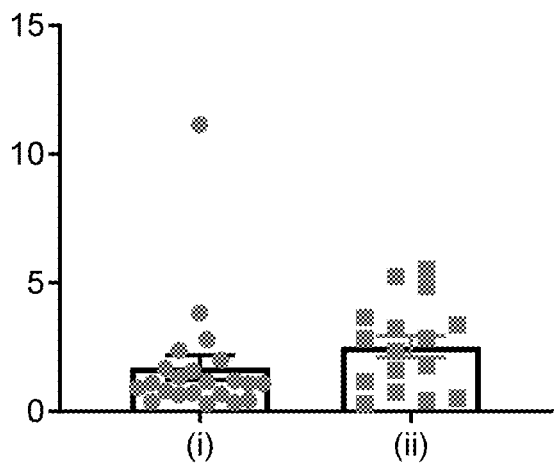
(c)
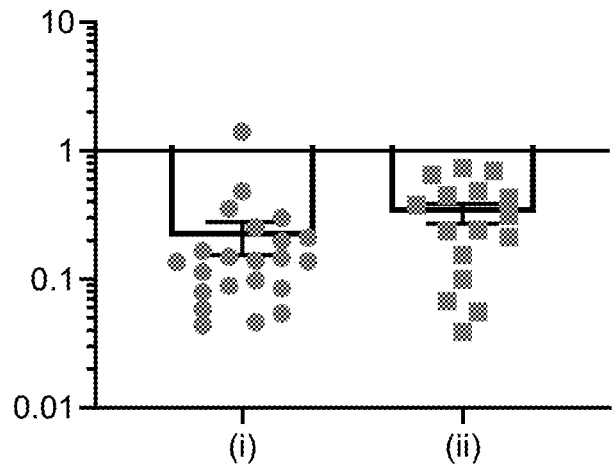

FIG. 5
(a)
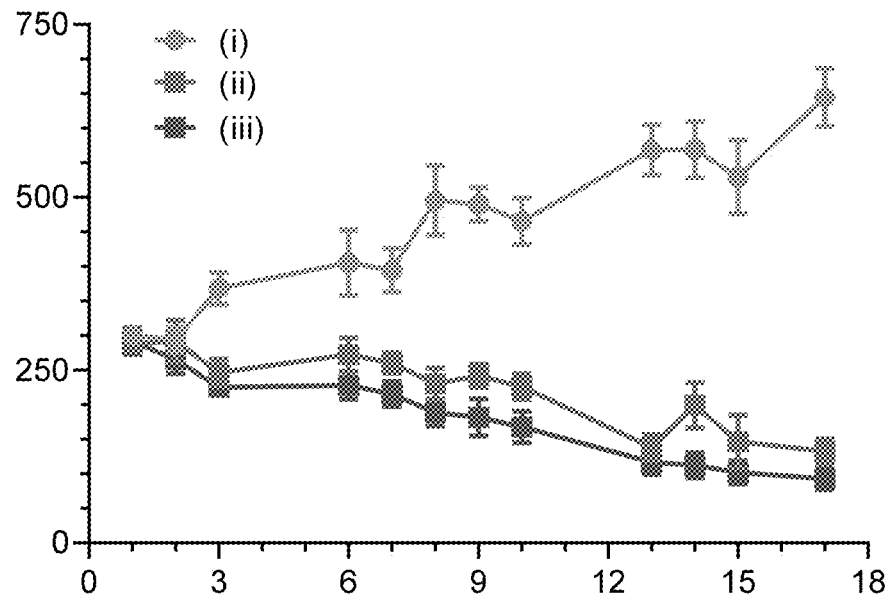
(b)
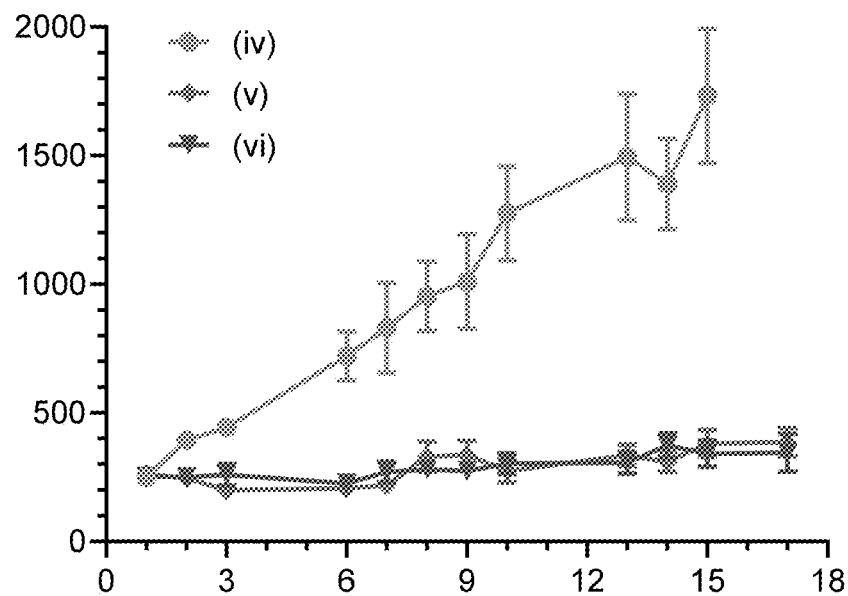

FIG. 7
(a)
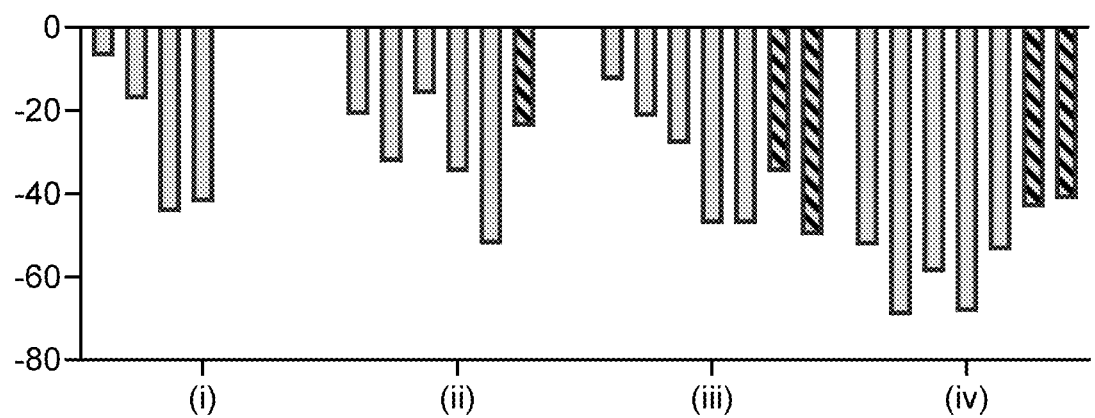
(b)
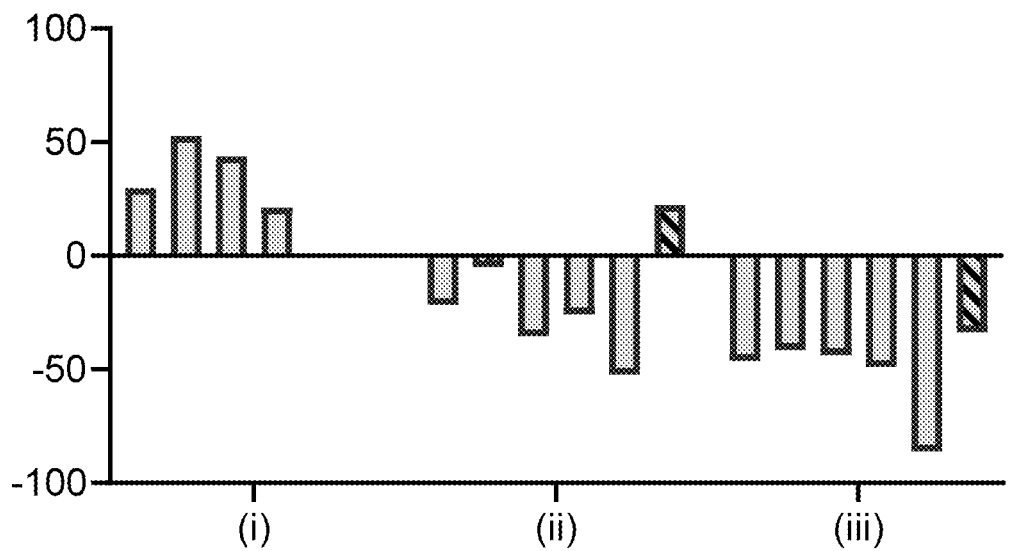

FIG. 8
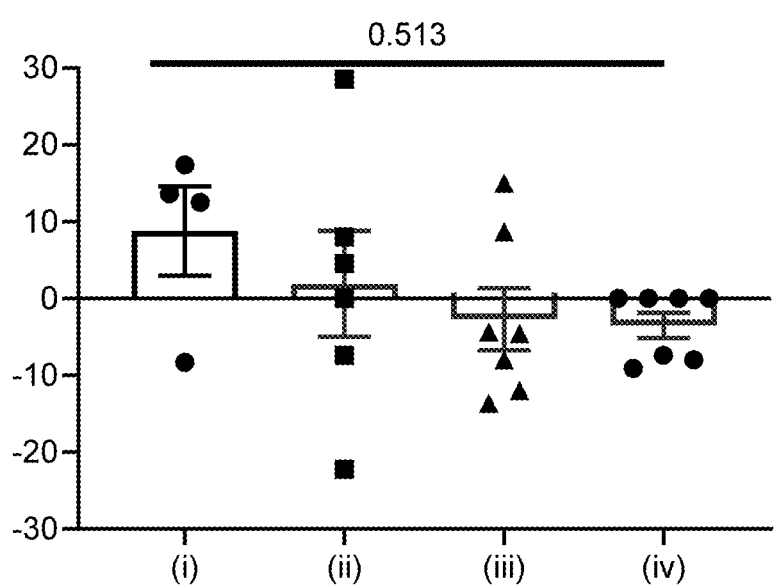
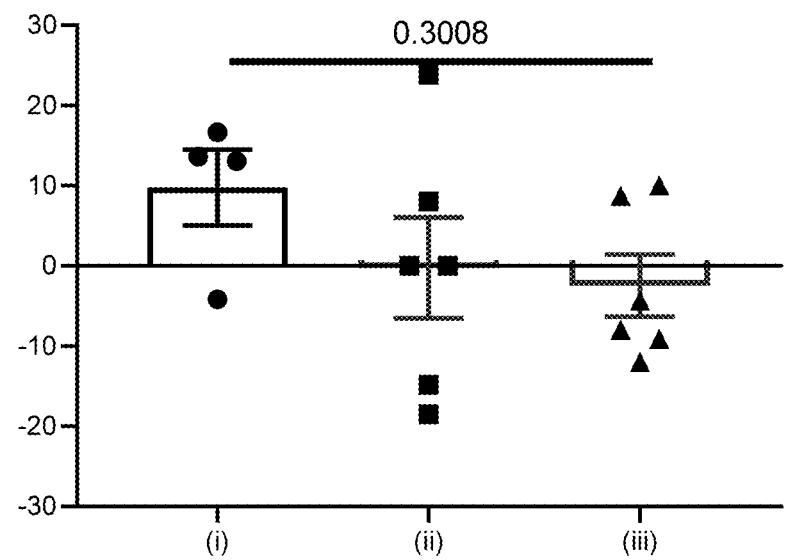

FIG. 10
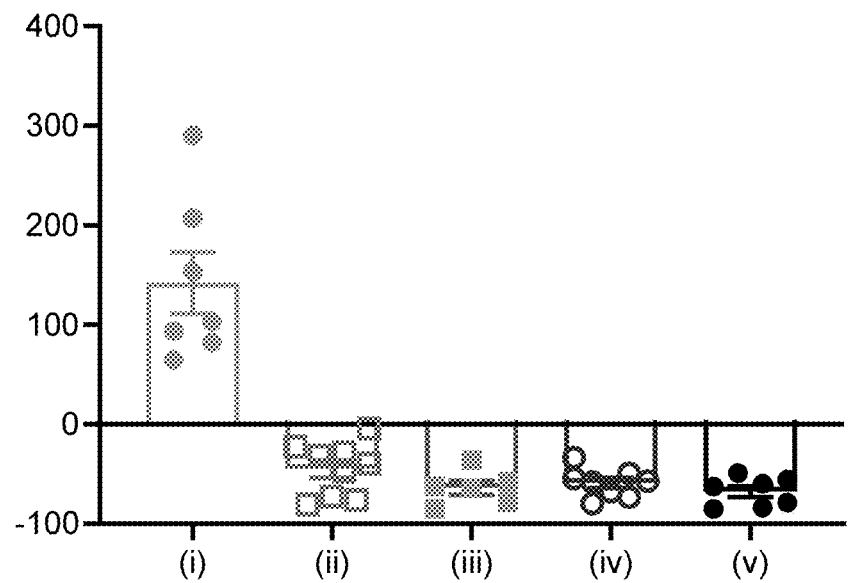
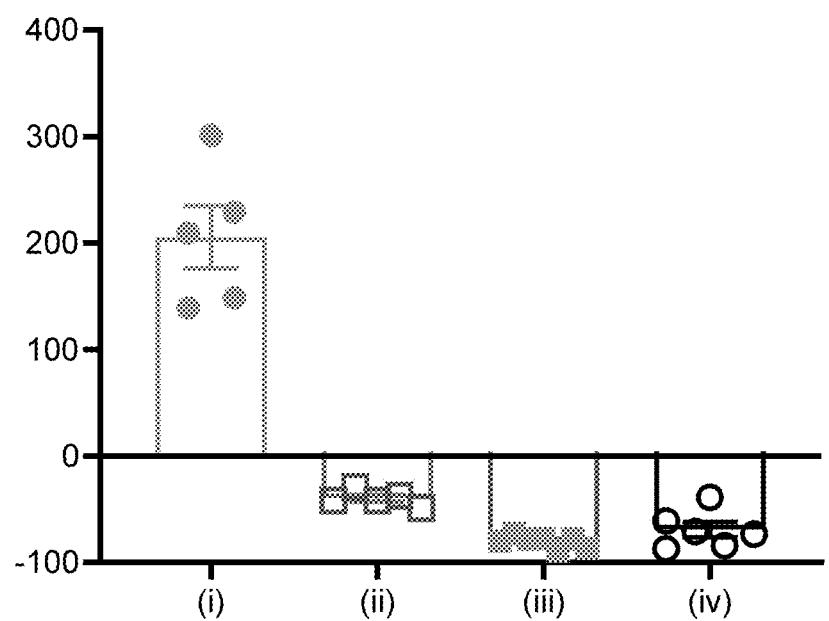

FIG. 11
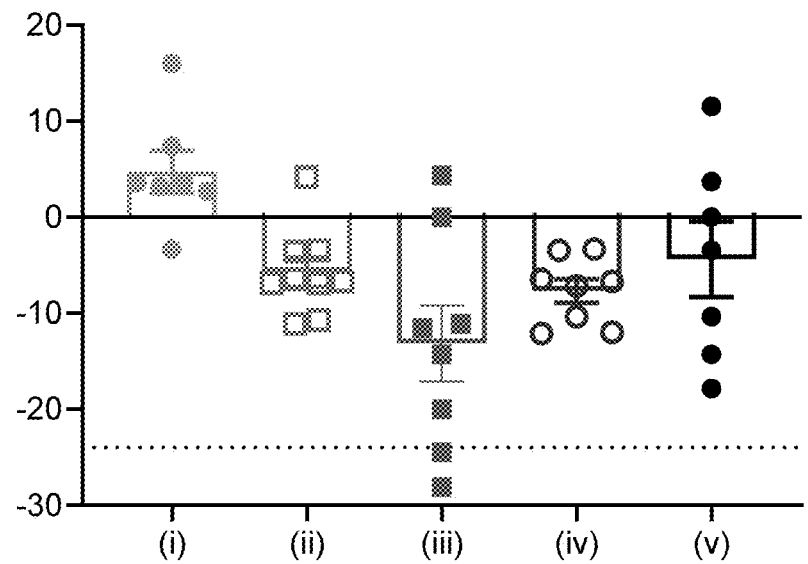
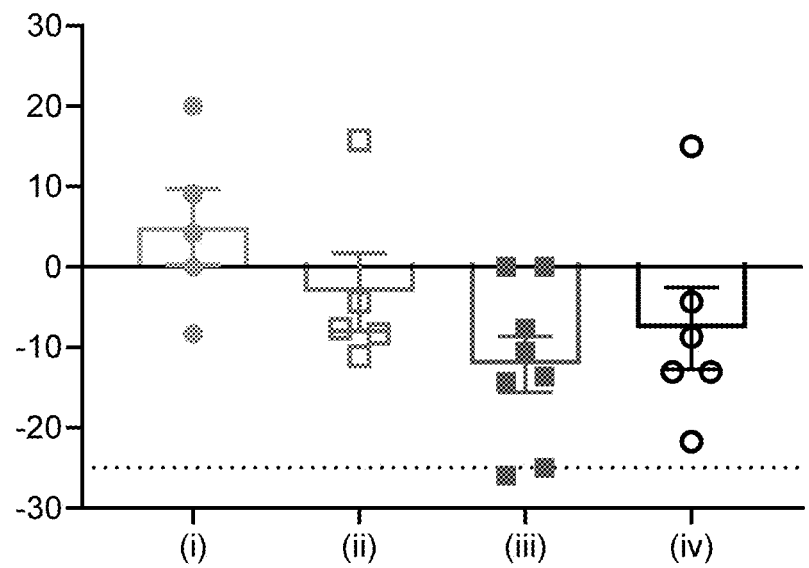

FIG. 12
(a)
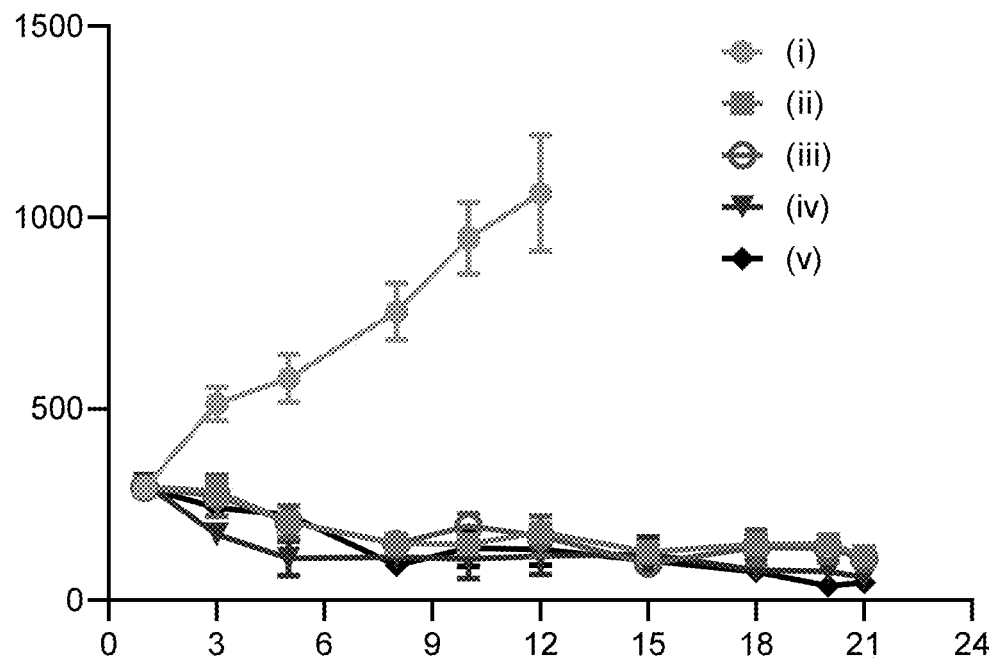
(b)
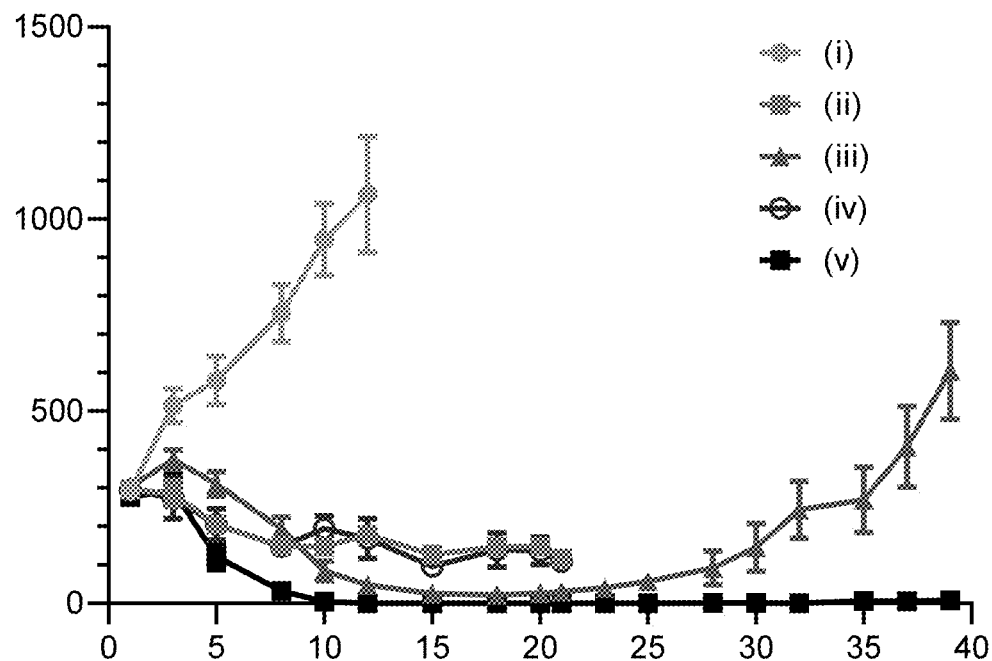

FIG. 13
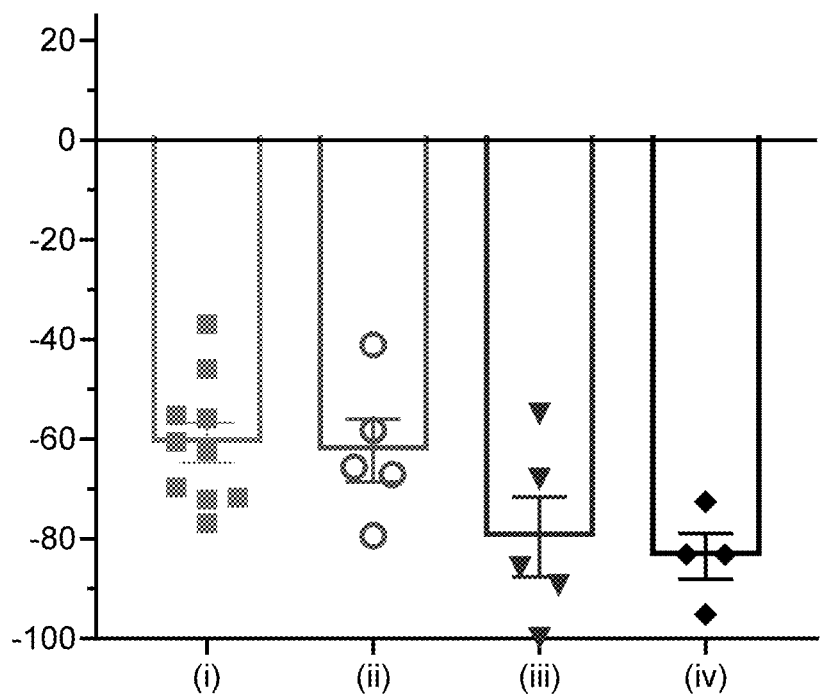
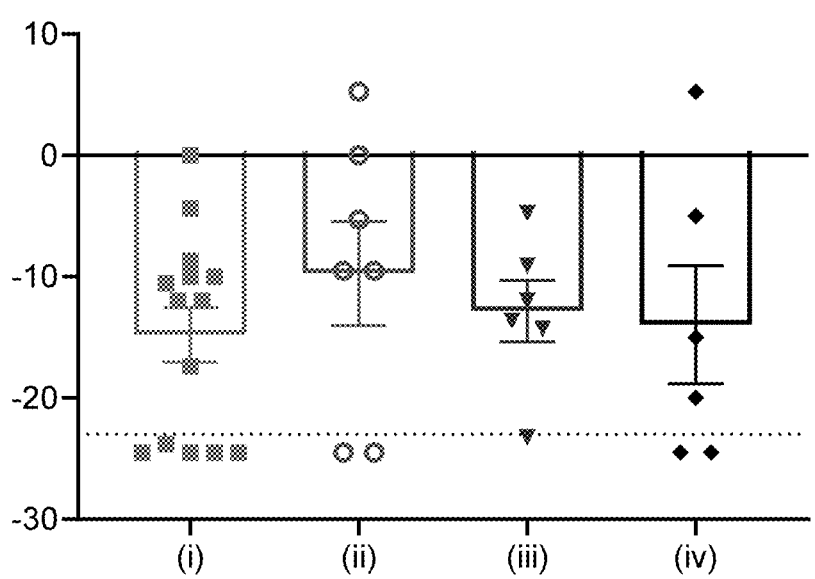

FIG. 16
(a)
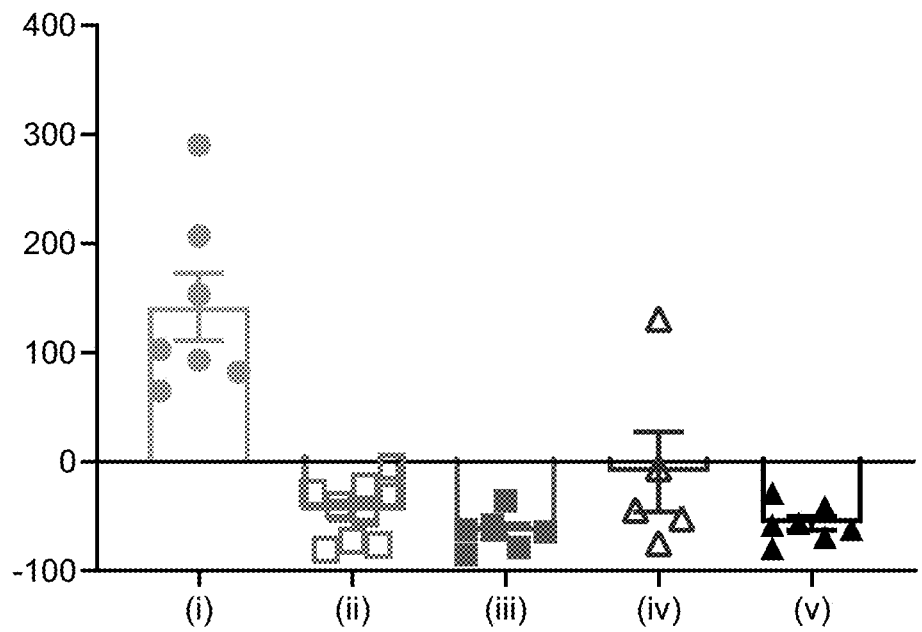
(b)
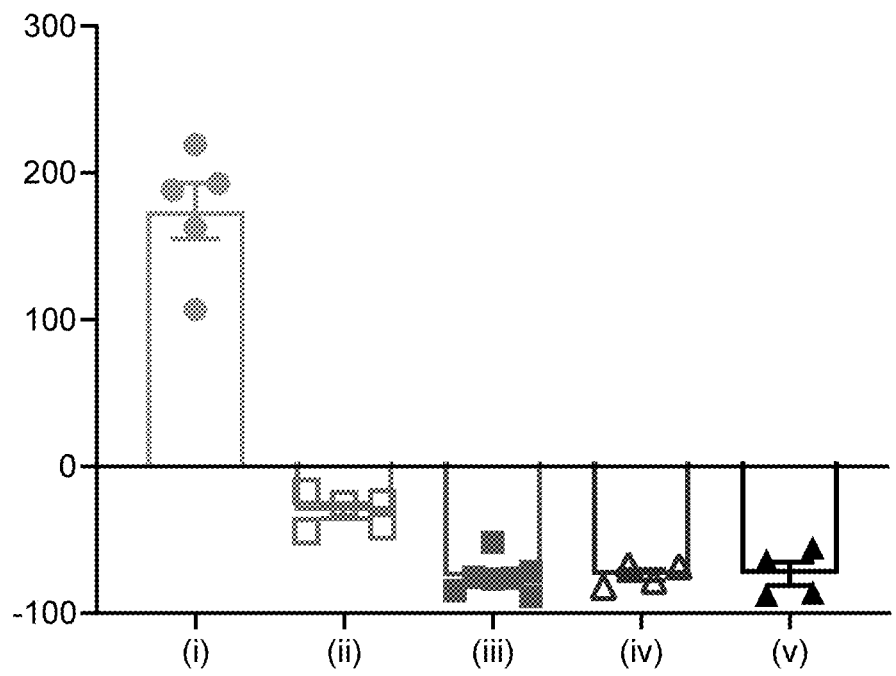

FIG. 17
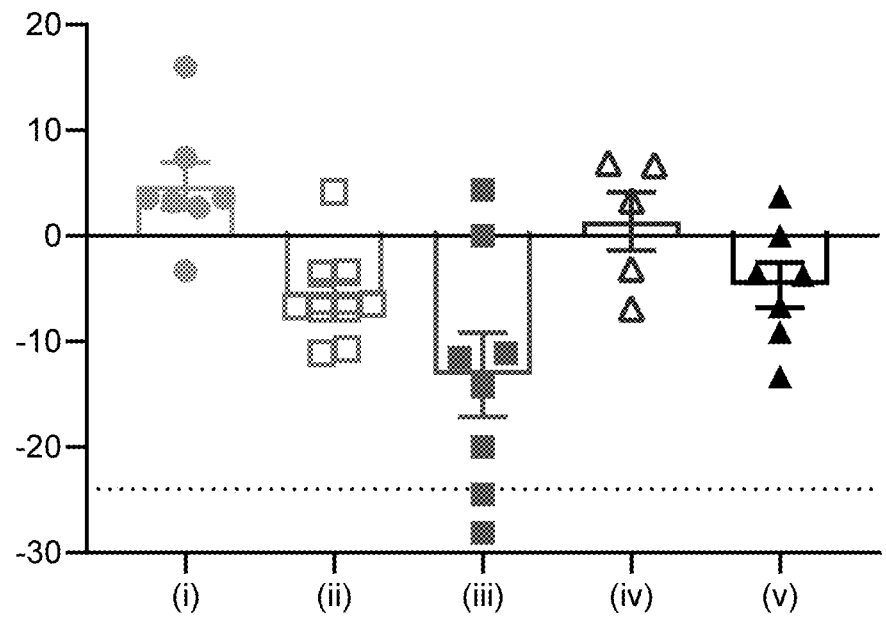
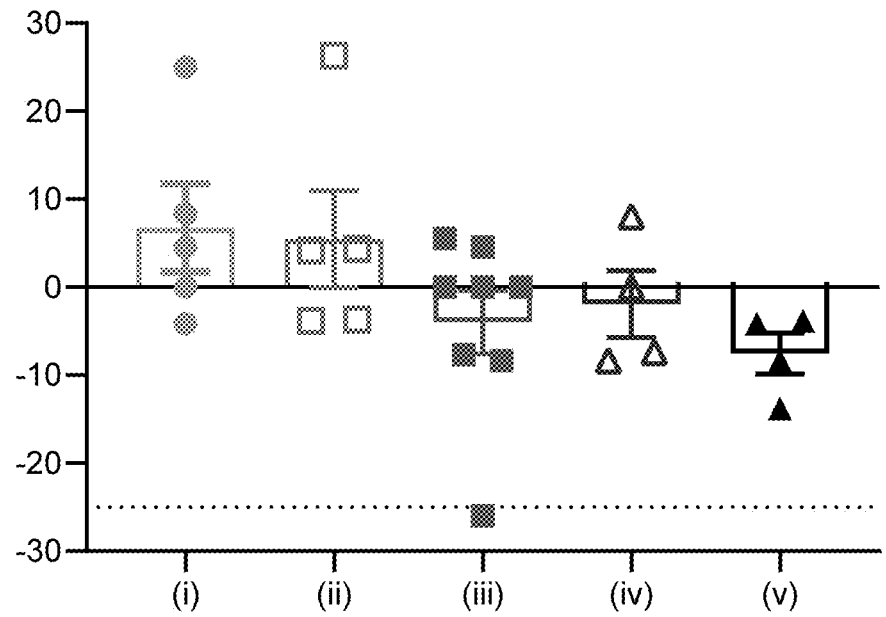

FIG. 19
(a)
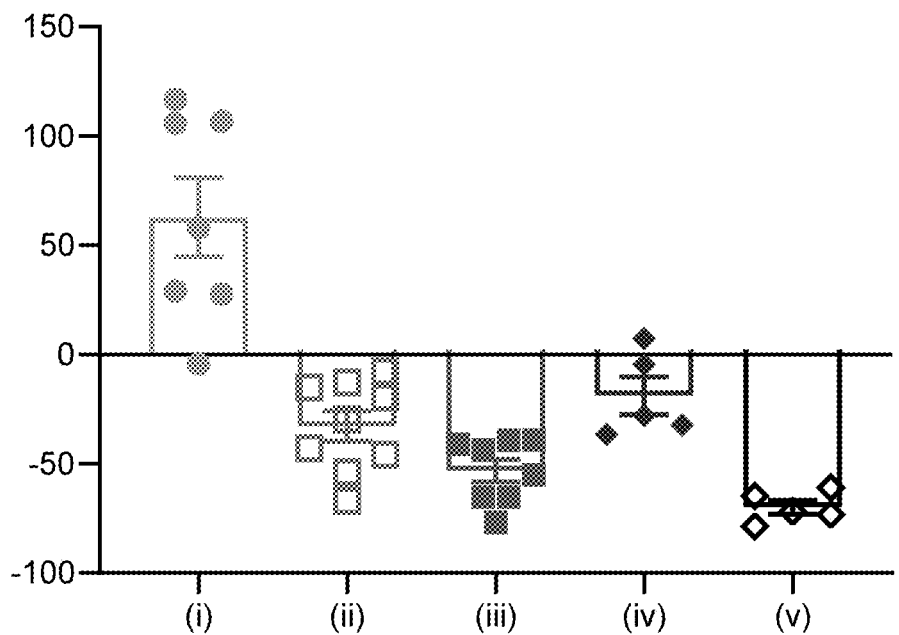
(b)
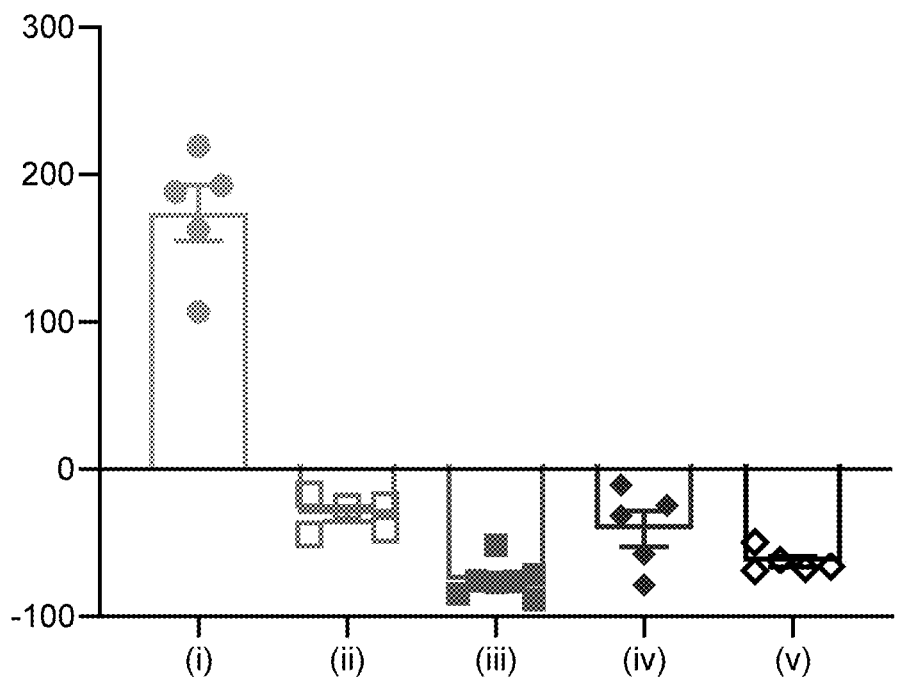

FIG. 20
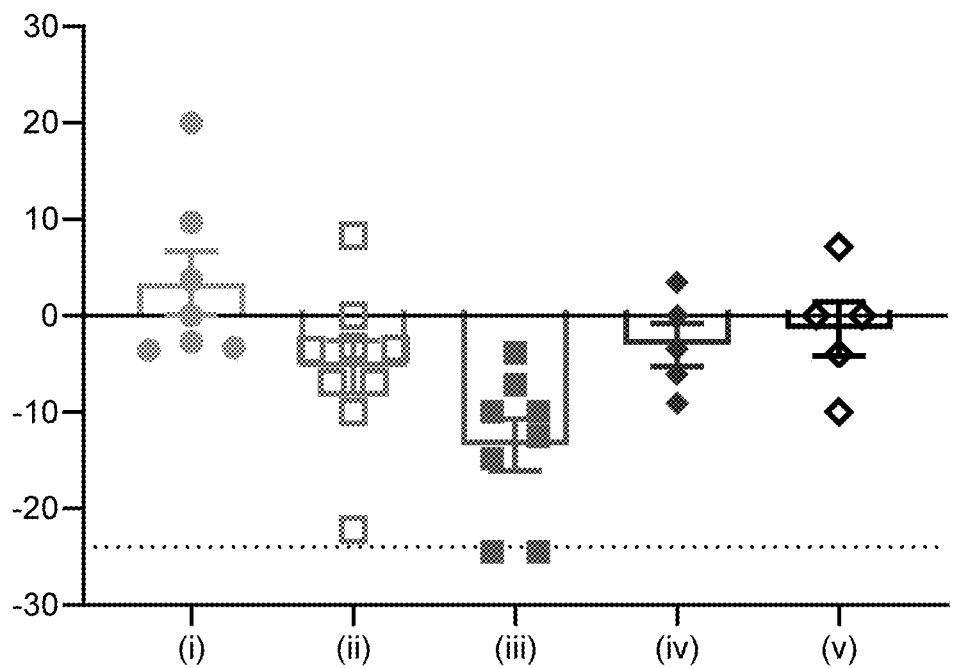
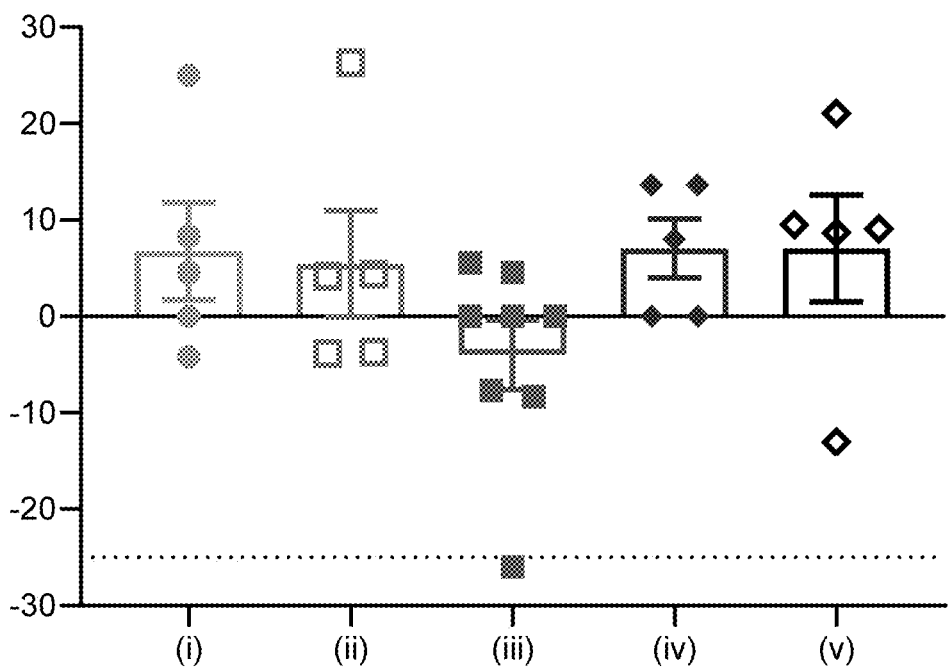

HETEROCYCLIC INHIBITORS OF TYROSINE KINASE

This application claims the benefit of priority of U.S. Provisional Application No. 62/838,696, filed Apr. 25, 2019, the disclosure of which is hereby incorporated by reference as if written herein in its entirety.

Disclosed herein are new heterocyclic compounds and compositions and their application as pharmaceuticals for the treatment of disease. Methods of inhibition of tyrosine kinase activity in a human or animal subject are also provided for the treatment diseases such as cancer.

Tyrosine kinases promote the phosphorylation of the phenolic hydroxyl of tyrosine, and this activity is commonly used to modulate the functionality of proteins. Mutations in tyrosine kinases are suspected in causing unregulated cell growth, leading to cancer. For this reason, tyrosine kinase inhibitors (TKIs) have been developed for their anticancer activity.

The ErbB family of proteins (named for the homologous erythroblastic leukemia viral oncogene) contains four tyrosine kinases, structurally related to the human epidermal growth factor receptor (EGFR, also termed Herl or ErbB1), discovered by Stanley Cohen. Abnormalities in EGFR have been identified as causative for cancer. The ErbB family also includes HER2 (Neu or ErbB2), HER3 (ErbB3) and HER4 (ErbB4).

ErbB receptors are overexpressed or mutated in many cancers, including cancers of the stomach, colon, rectum, head and neck, breast, ovary, pancreas, lung (NSCLC) and brain (glioblastoma). The overexpression and overactivation of ErbB receptors are correlated with poor prognosis, drug resistance, cancer metastasis, and lower survival rate. For this reason, ErbB receptors, especially EGFR and HER2 have been targeted for cancer chemotherapy.

The presence of mutations in an ErbB protein can influence the likelihood of successful treatment for certain cancers. Afatinib (GILOTRIF®), a TKI indicated for the treatment of certain NSCLC patients, inhibits WT EGFR and HER2 but does not effectively inhibit exon 20 mutant EGFR or HER2. Similarly, trastuzumab (HERCEPTIN®) is ineffective by itself against HER2 exon 20 insertions.

Beyond NSCLC, EGFR and HER2 exon 20 insertions are also observed in gastric cancer, breast cancer, glioblastomas, adenoid cystic carcinoma, and a number of gastrointestinal ailments. In fact, the number of non-lung cancer exon 20 mutations is larger than the number of lung cancer exon 20 mutations.

NSCLC patients harboring in-frame mutations (usually insertions) with exon 20 are resistant to FDA-approved EGFR TKIs, with an objective response rate of approximately 4-8% and a median progression-free survival (PFS) of <2 months, based on retrospective studies. Studies have shown that exon 20 insertions have a stabilized active conformation of EGFR, and lack affinity to currently available EGFR TKI. Other studies have reported that HER2 exon 20 mutations have heterogeneous responses to TKIs, but have not established an effective inhibitor of HER2 mutations. Furthermore, many patients experience dose limiting toxicities on currently available EGFR and HER2 targeted agents such as afatinib, dacomitinib, and neratinib due to off-target inhibition of wild-type (WT) EGFR. Additional agents with selective activity against exon 20 mutant EGFR and HER2 but not WT EGFR are required to reduce toxicity of targeted agents and improve clinical outcomes. Thus there is an unmet need to develop and identify inhibitors that target both EGFR and HER2 exon 20 mutations, as well as other EGFR and HER2 activating mutations.

Novel compounds and pharmaceutical compositions, certain of which have been found to inhibit mutant HER2 and EGFR have been discovered, together with methods of synthesizing and using the compounds including methods for the treatment of diseases mediated by HER2 or EGFR in a patient by administering the compounds. Certain compounds have been found to be effective against exon 20 insertion mutations of both HER2 and EGFR. In addition, certain compounds have been found to be effective against other mutations of HER2 and EGFR.

BRIEF DESCRIPTION OF THE SEVERAL VIEW OF THE DRAWINGS

FIG. 1 shows $IC_{50}$ values (nM) against (a) WT EGFR (+10 ng/mL EGF) and (b) HER2 mutants, and (c) selectivity indices for HER2 mutants over WT EGFR, for Example Compounds 1 and 2.

FIG. 4 shows $IC_{50}$ values (nM) against (a) WT EGFR (+10 ng/mL EGF), and (b) (i) EGFR Exon 20 and (ii) HER2 mutants, and (c) selectivity indices for (i) EGFR Exon 20 and (ii) HER2 mutants, for Example Compound 6.

FIG. 5 shows the effect, by day, on tumor volume ($mm^3$), upon treatment of (a) EGFR H773insNPH PDX and (b) Y772dupYVMA PDX implanted mice with Example Compound 6. (i) and (iv) vehicle (ii) 6 (2.5 mg/kg) (iii) 6 (5 mg/kg) (v) 6 (7.5 mg/kg) (vi) 6 (5 mg/kg).

FIG. 7 shows the percent change in tumor volume at (a) day 3, and (b) day 10 upon treatment of EGFR S768dupSVD (solid bars) and HER2 Y772dupYVMA (hashed bars) PDX implanted mice with (i) 10 mpk, (ii) 20 mpk, (iii) 40 mpk, and (iv) 60 mpk dosages of Example Compound 4.

FIG. 8 shows the percent change in mouse body weight at (a) day 3, and (b) day 10 upon treatment of EGFR S768dupSVD and HER2 Y772dupYVMA PDX implanted mice with (i) 10 mpk, (ii) 20 mpk, (iii) 40 mpk, and (iv) 60 mpk dosages of Example Compound 4.

FIG. 10 shows the percent change of PDX tumor volume upon treatment of (a) EGFR H773insNPH (day 28), and (b) EGFR S768dupSVD (day 17) PDX implanted mice, with Example Compound 1. (i) vehicle (ii) Poziotinib 1 mpk (iii) Poziotinib 2.5 mpk (iv) 130 mpk (v) 140 mpk.

FIG. 11 shows the percent change of mouse body weight upon treatment of (a) EGFR H773insNPH (day 28), and (b) EGFR S768dupSVD (day 17) PDX implanted mice, with Example Compound 1. (i) vehicle (ii) Poziotinib 1 mpk (iii) Poziotinib 2.5 mpk (iv) 1 30 mpk (v) 1 40 mpk, dotted line=Euthanized.

FIG. 12 shows the effect, by day, on PDX tumor volume (mm³) upon treatment of HER2 Y772dupYVMA PDX implanted mice with Example Compound 1, with and without coadministration of T-DM1. (a) (i) vehicle (ii) Poziotinib 2.5 mpk (iii) 130 mpk (iv) 1 50 mpk (v) 175 mpk (b) (i) vehicle (ii) Poziotinib 2.5 mpk (iii) T-DM1 10 mpk (iv) 130 mpk (v) 1+T-DM1.

FIG. 13 shows the percent changes at day 21 of (a) PDX tumor volume, and (b) mouse body weight, upon treatment of HER2 Y772dupYVMA PDX implanted mice with Example Compound 1. (i) Poziotinib 2.5 mpk (ii) 1 30 mpk (iii) 1 50 mpk (iv) 1 75 mpk; dotted line=Euthanized.

Figure 14:
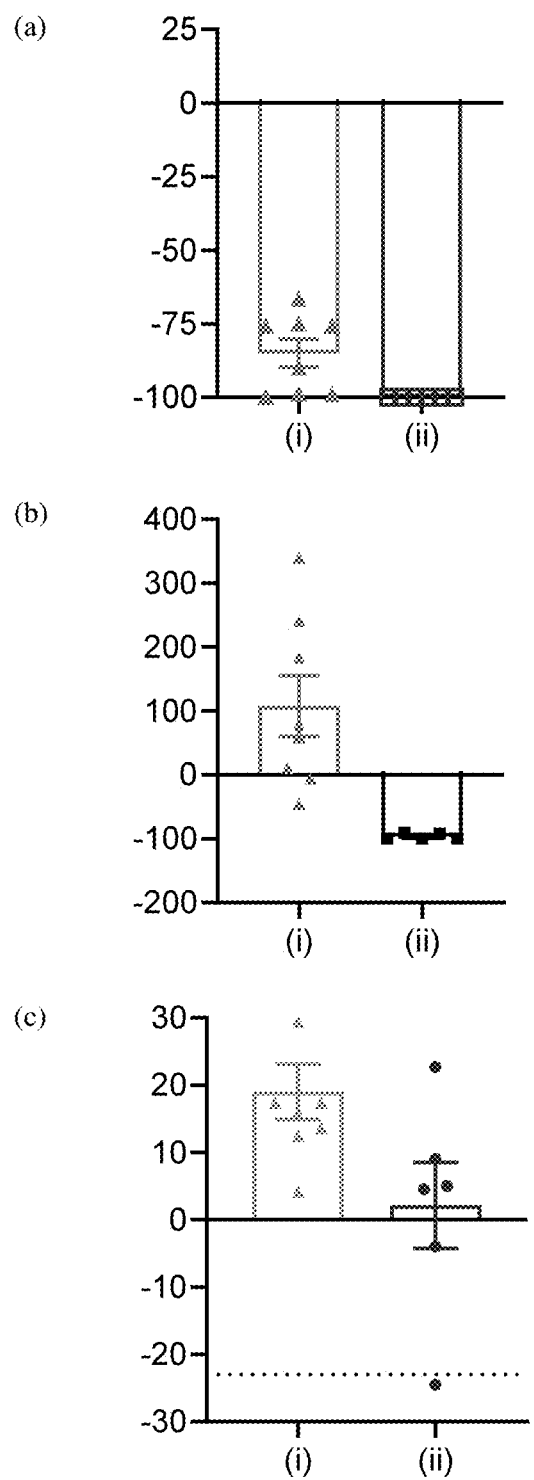

FIG. 14 shows the percent changes of (a) and (b) PDX tumor volume, and (c) mouse body weight, upon treatment of HER2 Y772dupYVMA PDX implanted mice with Example Compound 1, with and without coadministration of T-DM1. (a) day 23, p=0.02, (i) T-DM1 10 mpk, CR=3/8 (ii) 1+T-DM1, CR=6/6; (b) day 39, p=0.0031, (i) T-DM1 10 mpk (ii) 1+T-DM1; (c) day 39; (i) T-DM1 10 mpk (ii) 1+T-DM1, dotted line=Euthanized.

Figure 15:
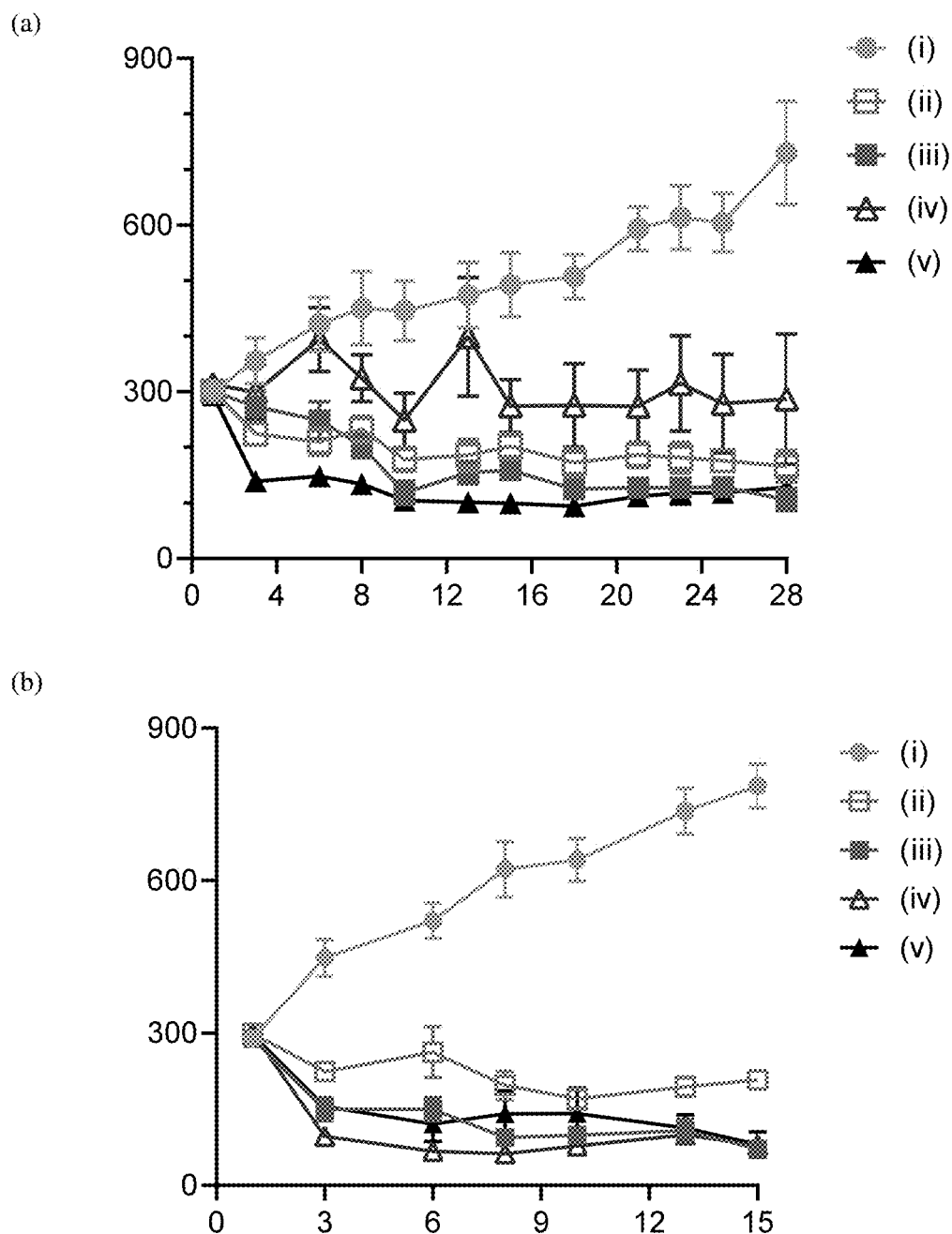

FIG. 15 shows the change, by day, of PDX tumor volume (mm³) upon treatment of (a) EGFR H773insNPH, and (b) EGFR S768dupSVD PDX implanted mice, with Example Compound 4. (i) vehicle (ii) Poziotinib 1 mpk (iii) Poziotinib 2.5 mpk (iv) 4 80 mpk (v) 4 120 mpk.

FIG. 16 shows the percent change of PDX tumor volume upon treatment of (a) EGFR H773insNPH (day 28), and (b) EGFR S768dupSVD (day 15) PDX implanted mice, with Example Compound 4. (i) vehicle (ii) Poziotinib 1 mpk (iii) Poziotinib 2.5 mpk (iv) 4 80 mpk (v) 4 120 mpk.

FIG. 17 the percent change of mouse body weight upon treatment of (a) EGFR H773insNPH (day 28), and (b) EGFR S768dupSVD (day 15) PDX implanted mice, with Example Compound 4. (i) vehicle (ii) Poziotinib 1 mpk (iii) Poziotinib 2.5 mpk (iv) 4 80 mpk (v) 4 120 mpk, dotted line=Euthanized.

Figure 18:
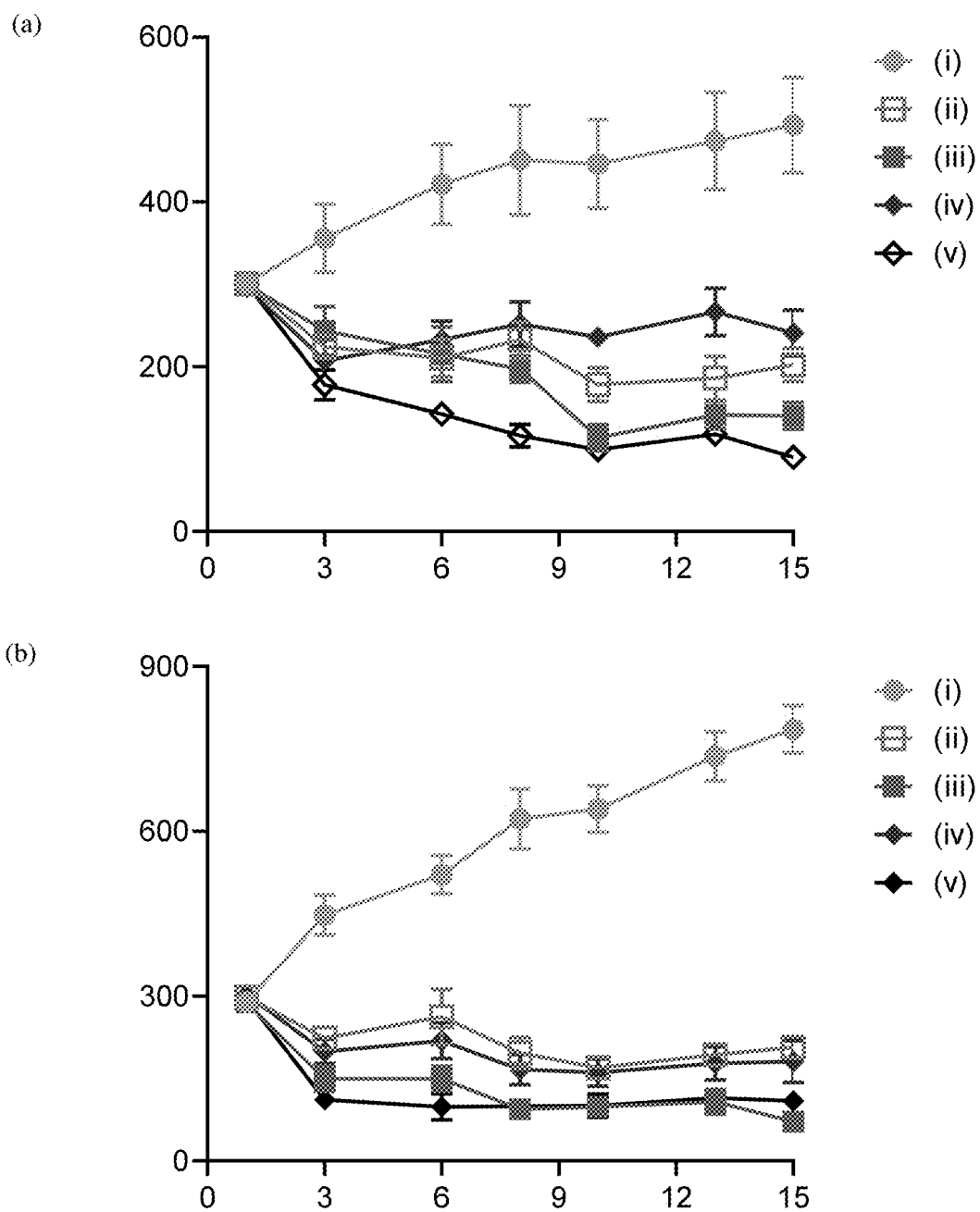

FIG. 18 shows the change, by day, of PDX tumor volume (mm³) upon treatment of (a) EGFR H773insNPH, and (b) EGFR S768dupSVD PDX implanted mice, with Example Compound 13. (i) vehicle (ii) Poziotinib 1 mpk (iii) Poziotinib 2.5 mpk (iv) 13 75 mpk (v) 13 150 mpk.

FIG. 19 shows the percent change of PDX tumor volume at day 15 upon treatment of (a) EGFR H773insNPH, and (b) EGFR S768dupSVD PDX implanted mice, with Example Compound 13. (i) vehicle (ii) Poziotinib 1 mpk (iii) Poziotinib 2.5 mpk (iv) 13 75 mpk (v) 13 150 mpk.

FIG. 20 shows the percent change of mouse body weight at day 15 upon treatment of (a) EGFR H773insNPH, and (b) EGFR S768dupSVD PDX implanted mice, with Example Compound 13. (i) vehicle (ii) Poziotinib 1 mpk (iii) Poziotinib 2.5 mpk (iv) 13 75 mpk (v) 13 150 mpk, dotted line=Euthanized.

Figure 21:
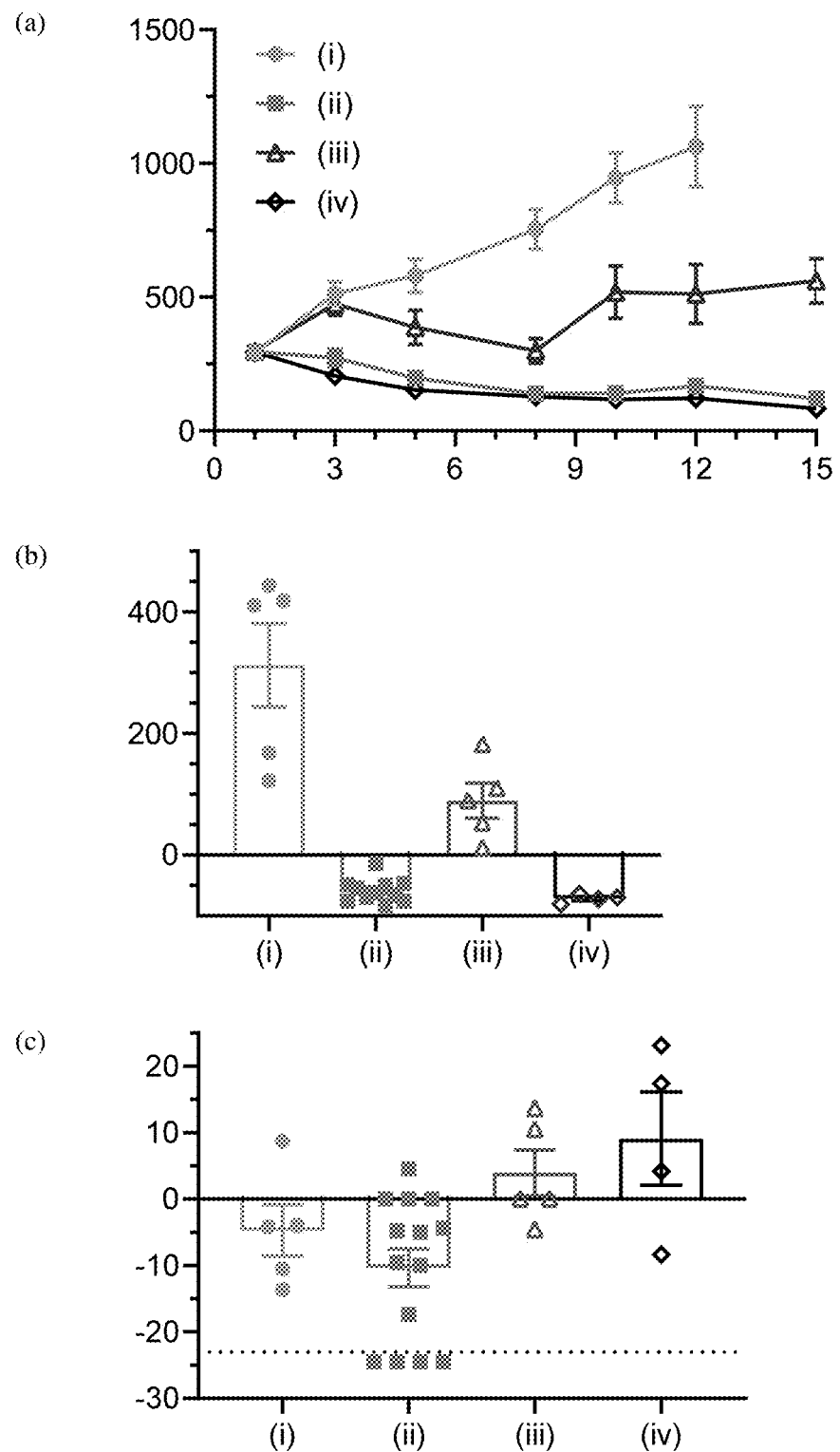

FIG. 21 shows (a) the change, by day, of PDX tumor volume (mm³), (b) the percent change of PDX tumor volume (day 15), and (c) the percent change of mouse body weight (day 15), upon treatment of HER2 Y772dupYVMA PDX implanted mice with Example Compounds 4 and 13. (i) vehicle (ii) Poziotinib 2.5 mpk (iii) 4 80 mpk (iv) 13 150 mpk.

Figure 22:
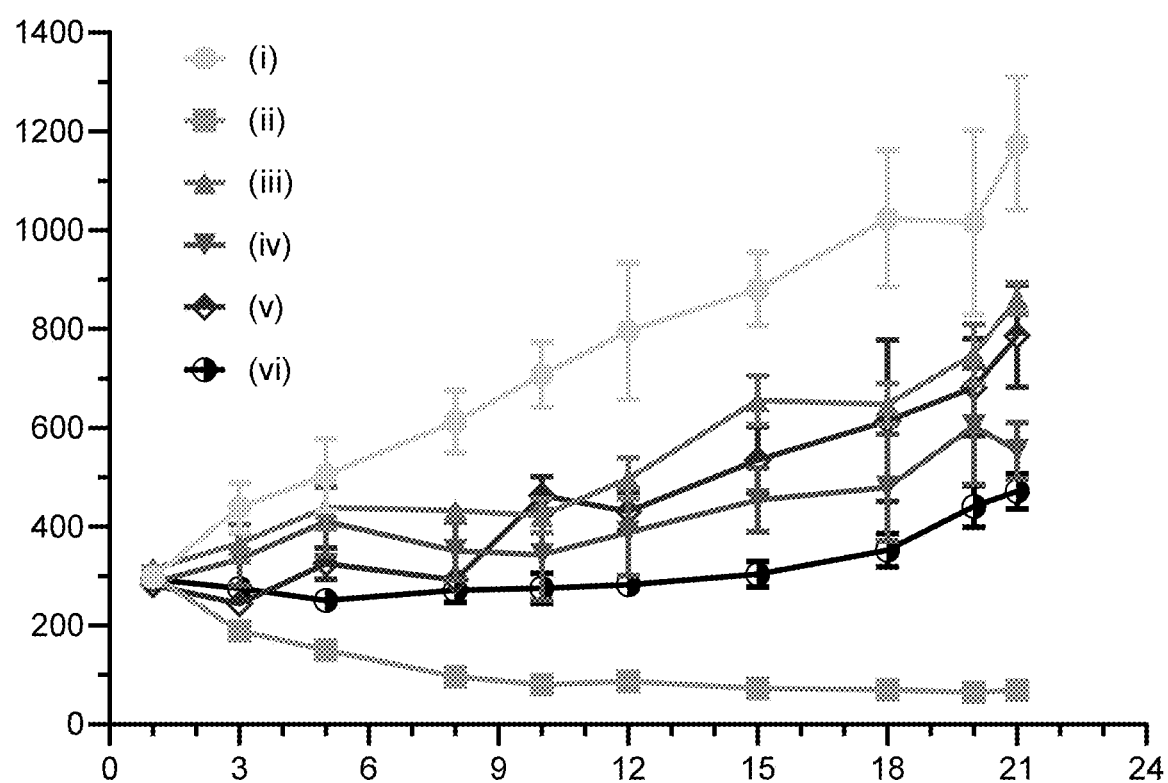

FIG. 22 shows the change, by day, of PDX tumor volume (mm³) upon treatment of EGFR S768dupSVD PDX implanted mice with Example Compounds 100 and 101. (i) vehicle (ii) Poziotinib 2.5 mpk (iii) osimertinib 5 mpk (iv) Osimertinib 25 mpk (v) 100 100 mpk.

Figure 23:
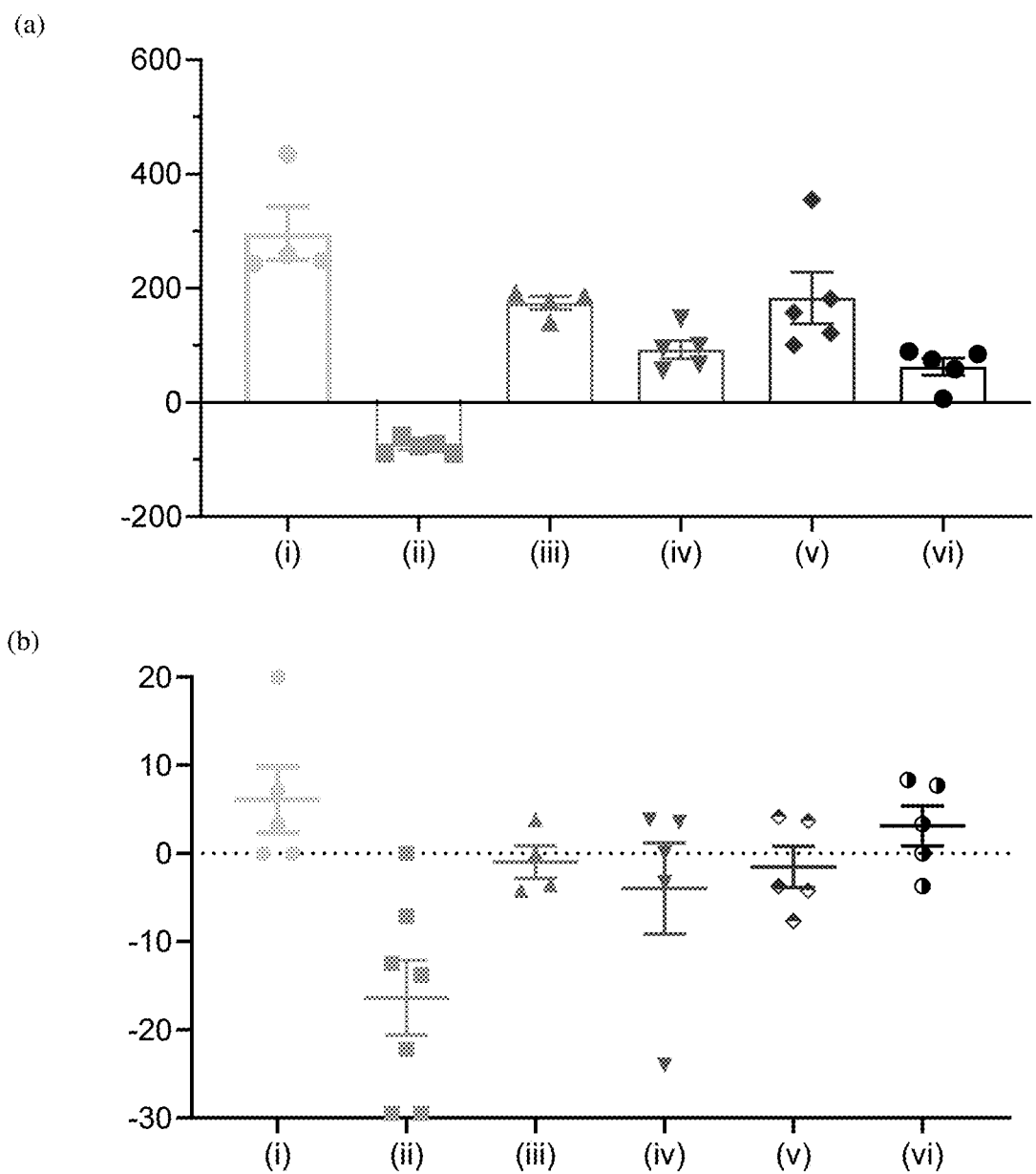

FIG. 23 shows (a) the percent change of PDX tumor volume (day 21), and (b) percent change of mouse body weight (day 21), upon treatment of EGFR S768dupSVD PDX implanted mice with Example Compounds 100 and 101. (i) vehicle (ii) Poziotinib 2.5 mpk (iii) Osimertinib 5 mpk (iv) Osimertinib 25 mpk (v) 100 100 mpk (vi) 101 100 mpk; (b)(ii) lowest two symbols=euthanized.

DETAILED DESCRIPTION

Provided herein is Embodiment 1: a compound having structural Formula (I):

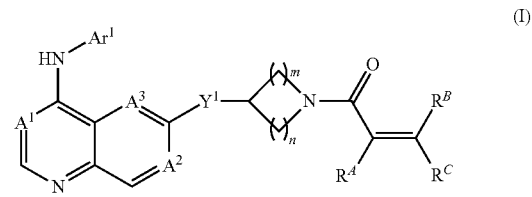

(I)

or a salt thereof, wherein:

$A^1$ is chosen from $C(R^1)$ and N;

$A^2$ is chosen from $C(R^2)$ and N;

$A^3$ is chosen from $C(R^3)$ and N;

$Ar^1$ is chosen from aryl and heteroaryl, either of which is optionally substituted with one or two $R^4$ groups, and either of which is optionally substituted with one, two, or three $R^5$ groups;

$R^A$ and $R^B$ are independently chosen from H and alkyl;

$R^C$ is chosen from H, $CH_3$, and $CH_2NR^{15}R^{16}$;

$R^1$ is chosen from halo, —CN, —$OR^6$, —$NR^{7a}R^{7b}$, —$COOR^8$, and —$CONR^{9a}R^{9b}$;

$R^2$ and $R^3$ are independently chosen from H, alkyl, and alkoxy;

each $R^4$ is independently chosen from alkyl, haloalkyl, cycloalkyl, heterocycloalkyl, aryl, and heteroaryl, any of which is optionally substituted with one or two $R^{10}$ groups;

each $R^5$ is independently chosen from halo, —CN, —$OR^{11}$, $NR^{12a}R^{12b}$, —$COOR^{13}$, and —$CONR^{14a}R^{14b}$;

each $R^6$, $R^{7a}$, and $R^{7b}$ is independently chosen from H, alkyl, haloalkyl, and C(=O)alkyl;

each $R^8$, $R^{9a}$, and $R^{9b}$ is independently chosen from H and alkyl;

each $R^{10}$ is independently chosen from halo, hydroxy, and alkoxy;

each $R^{11}$, $R^{12a}$, and $R^{12b}$ is independently chosen from H, $C_{1-6}$alkyl, $C_{1-6}$halolkyl, and C(=O)$C_{1-6}$alkyl;

each $R^{13}$, $R^{14a}$, and $R^{14b}$ is independently chosen from H and $C_{1-6}$alkyl;

$R^{15}$ and $R^{16}$ are independently chosen from H and $C_{1-6}$alkyl, or $R^{15}$ and $R^{16}$, together with the nitrogen to which that they are both attached, combine to form a 5-7 membered heterocycloalkyl;

m and n are independently chosen from 1, 2, and 3; and $Y^1$ is chosen from —NH— and —O—.

Certain compounds disclosed herein may possess useful HER2 inhibiting activity, and may be used in the treatment or prophylaxis of a disease or condition in which HER2 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting HER2. Certain embodiments provide selectivity for the inhibition of certain mutant forms of HER2 over wild type (WT) EGFR. Other embodiments provide methods for treating a HER2-mediated disorder in a patient in need of such treatment, comprising administering to said patient a therapeutically effective amount of a compound or composition according to the present disclosure. Also provided is the use of certain compounds disclosed herein for use in the manufacture of a medicament for the treatment of a disease or condition ameliorated by the inhibition of HER2.

Certain compounds disclosed herein may possess useful EGFR inhibiting activity, and may be used in the treatment or prophylaxis of a disease or condition in which EGFR plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting EGFR. Certain embodiments provide selectivity for the inhibition of certain mutant forms of EGFR over wild type (WT) EGFR. Other embodiments provide methods for treating an EGFR-mediated disorder in a patient in need of such treatment, comprising administering to said patient a therapeutically effective amount of a compound or composition according to the present disclosure. Also provided is the use of certain compounds disclosed herein for use in the manufacture of a medicament for the treatment of a disease or condition ameliorated by the inhibition of EGFR.

Also provided are the following embodiments:

Embodiment 2

The compound of Embodiment 1, wherein:
if m is 2 and n is 2,
and $A^1$ is $C(R^1)$, $A^2$ is $C(R^2)$, and $A^3$ is $C(R^3)$,
and $R^1$ is CN, $R^2$ is $C_1$-$C_2$ alkoxy, and $R^3$ is H,
then $Ar^1$ is not

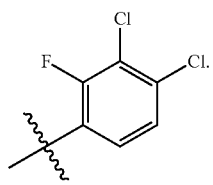 [SMILES: *c1ccc(Cl)c(Cl)c1F]

Embodiment 3

The compound of Embodiment 1, wherein:
if $A^1$ is C(CN), m is 2 and n is 2, then $Ar^1$ is not

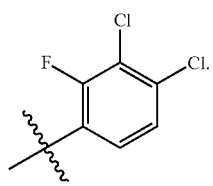 [SMILES: *c1ccc(Cl)c(Cl)c1F]

Embodiment 4

The compound of any one of Embodiments 1-3, wherein $A^1$ is $C(R^1)$.

Embodiment 5

The compound of Embodiment 4, wherein $R^1$ is —CN.

Embodiment 6

The compound of Embodiment 4, wherein $R^1$ is chosen from —$OR^6$ and —$NR^{7a}R^{7b}$.

Embodiment 7

The compound of Embodiment 6, wherein each $R^6$, $R^{7a}$, and $R^{7b}$ is H.

Embodiment 8

The compound of Embodiment 6, wherein each $R^6$, $R^{7a}$, and $R^{7b}$ is alkyl.

Embodiment 9

The compound of Embodiment 6, wherein each $R^6$, $R^{7a}$, and $R^{7b}$ is C(=O)alkyl.

Embodiment 10

The compound of any one of Embodiments 6-9, wherein $R^1$ is —$OR^6$.

Embodiment 11

The compound of any one of Embodiments 6-9, wherein $R^1$ is —$NR^{7a}R^{7b}$.

Embodiment 12

The compound of Embodiment 4, wherein $R^1$ is chosen from —$COOR^8$ and —$CONR^{9a}R^{9b}$.

Embodiment 13

The compound of Embodiment 12, wherein each $R^8$, $R^{9a}$, and $R^{9b}$ is H.

Embodiment 14

The compound of Embodiment 12, wherein each $R^8$, $R^{9a}$, and $R^{9b}$ is alkyl.

Embodiment 15

The compound of any one of Embodiments 12-14, wherein $R^1$ is —$COOR^8$.

Embodiment 16

The compound of any one of Embodiments 12-14, wherein $R^1$ is —$CONR^{9a}R^{9b}$.

Embodiment 17

The compound of either one of Embodiments 1 and 2, wherein $A^1$ is N.

Embodiment 18

The compound of any one of Embodiments 1-17, wherein $A^2$ is $C(R^2)$.

Embodiment 19

The compound of Embodiment 18, wherein $R^2$ is alkyl.

Embodiment 20

The compound of Embodiment 19, wherein $R^2$ is $C_{1-6}$alkyl.

Embodiment 21

The compound of Embodiment 20, wherein $R^2$ is methyl.

Embodiment 22

The compound of Embodiment 18, wherein $R^2$ is alkoxy.

Embodiment 23

The compound of Embodiment 22, wherein $R^2$ is $C_{1-6}$alkoxy.

Embodiment 24

The compound of Embodiment 23, wherein $R^2$ is methoxy.

Embodiment 25

The compound of Embodiment 18, wherein $R^2$ is H.

Embodiment 26

The compound of any one of Embodiments 1-17, wherein $A^2$ is N.

Embodiment 27

The compound of any one of Embodiments 1-26, wherein $A^3$ is $C(R^3)$.

Embodiment 28

The compound of Embodiment 27, wherein $R^3$ is alkyl.

Embodiment 29

The compound of Embodiment 28, wherein $R^3$ is $C_{1-6}$alkyl.

Embodiment 30

The compound of Embodiment 29, wherein $R^3$ is methyl.

Embodiment 31

The compound of Embodiment 27, wherein $R^3$ is alkoxy.

Embodiment 32

The compound of Embodiment 31, wherein $R^3$ is $C_{1-6}$alkoxy.

Embodiment 33

The compound of Embodiment 32, wherein $R^3$ is methoxy.

Embodiment 34

The compound of Embodiment 27, wherein $R^3$ is H.

Embodiment 35

The compound of any one of Embodiments 1-26, wherein $A^3$ is N.

Also provided is Embodiment 36: a compound having structural Formula (II):

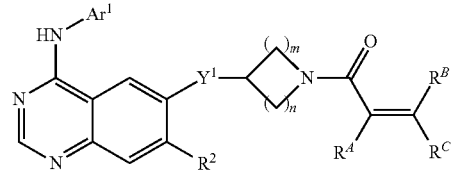

(II)

or a salt thereof, wherein:
- $Ar^1$ is chosen from aryl and heteroaryl, either of which is optionally substituted with one or two $R^4$ groups, and either of which is optionally substituted with one, two, or three $R^5$ groups;
- $R^A$ and $R^B$ are independently chosen from H and alkyl;
- $R^C$ is chosen from H, $CH_3$, and $CH_2NR^{15}R^{16}$;
- $R^2$ is chosen from H, alkyl, and alkoxy;
- each $R^4$ is independently chosen from alkyl, haloalkyl, cycloalkyl, heterocycloalkyl, aryl, and heteroaryl, any of which is optionally substituted with one or two $R^{10}$ groups;
- each $R^5$ is independently chosen from halo, —CN, —$OR^{11}$, —$NR^{12a}R^{12b}$, —$COOR^{13}$, and —$CONR^{14a}R^{14b}$;
- each $R^{10}$ is independently chosen from halo, hydroxy, and alkoxy;
- each $R^{11}$, $R^{12a}$, and $R^{12b}$ is independently chosen from H, $C_{1-6}$alkyl, $C_{1-6}$halolkyl, and $C(=O)C_{1-6}$alkyl;
- each $R^{13}$, $R^{14a}$, and $R^{14b}$ is independently chosen from H and $C_{1-6}$alkyl;
- $R^{15}$ and $R^{16}$ are independently chosen from H and $C_{1-6}$alkyl,
- or $R^{15}$ and $R^{16}$, together with the nitrogen to which that they are both attached, combine to form a 5-7 membered heterocycloalkyl;
- m and n are independently chosen from 1, 2, and 3; and
- $Y^1$ is chosen from —NH— and —O—.

Embodiment 37

The compound of Embodiment 36, wherein $R^2$ is alkyl.

Embodiment 38

The compound of Embodiment 37, wherein $R^2$ is $C_{1-6}$alkyl.

Embodiment 39

The compound of Embodiment 38, wherein $R^2$ is methyl.

Embodiment 40

The compound of Embodiment 36, wherein $R^2$ is alkoxy.

Embodiment 41

The compound of Embodiment 40, wherein $R^2$ is $C_{1-6}$alkoxy.

Embodiment 42

The compound of Embodiment 41, wherein $R^2$ is methoxy.

Embodiment 43

The compound of Embodiment 36, wherein $R^2$ is H.

Also provided is Embodiment 44: a compound having structural Formula (III):

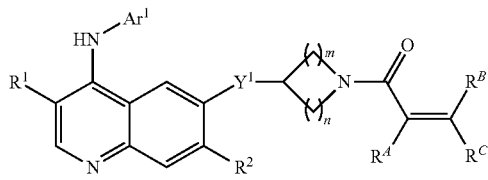

(III)

or a salt thereof, wherein:
- $Ar^1$ is chosen from aryl and heteroaryl, either of which is optionally substituted with one or two $R^4$ groups, and either of which is optionally substituted with one, two, or three $R^5$ groups;
- $R^A$ and $R^B$ are independently chosen from H and alkyl;
- $R^C$ is chosen from H, $CH_3$, and $CH_2NR^{15}R^{16}$;
- $R^1$ is chosen from halo, —CN, —$OR^6$, —$NR^{7a}R^{7b}$, —$COOR^8$, and —$CONR^{9a}R^{9b}$;
- $R^2$ is chosen from H, alkyl, and alkoxy;
- each $R^4$ is independently chosen from alkyl, haloalkyl, cycloalkyl, heterocycloalkyl, aryl, and heteroaryl, any of which is optionally substituted with one or two $R^{10}$ groups;
- each $R^5$ is independently chosen from halo, —CN, —$OR^{11}$, $NR^{12a}R^{12b}$, —$COOR^{13}$, and —$CONR^{14a}R^{14b}$;
- each $R^6$, $R^{7a}$, and $R^{7b}$ is independently chosen from H, alkyl, haloalkyl, and C(=O)alkyl;
- each $R^8$, $R^{9a}$, and $R^{9b}$ is independently chosen from H and alkyl;
- each $R^{10}$ is independently chosen from halo, hydroxy, and alkoxy;
- each $R^{11}$, $R^{12a}$, and $R^{12b}$ is independently chosen from H, $C_{1-6}$alkyl, $C_{1-6}$halolkyl, and C(=O)$C_{1-6}$alkyl;
- each $R^{13}$, $R^{14a}$, and $R^{14b}$ is independently chosen from H and $C_{1-6}$alkyl;
- $R^{15}$ and $R^{16}$ are independently chosen from H and $C_{1-6}$alkyl, or $R^{15}$ and $R^{16}$, together with the nitrogen to which that they are both attached, combine to form a 5-7 membered heterocycloalkyl;
- m and n are independently chosen from 1, 2, and 3; and
- $Y^1$ is chosen from —NH— and —O—.

Embodiment 45

The compound of Embodiment 44, wherein:
if m is 2 and n is 2,
and $A^1$ is $C(R^1)$, $A^2$ is $C(R^2)$, and $A^3$ is $C(R^3)$,
and $R^1$ is CN, $R^2$ is $C_1$-$C_2$ alkoxy, and $R^3$ is H,
then $Ar^1$ is not

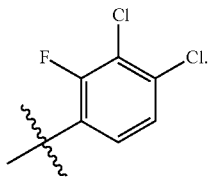 [SMILES: *c1ccc(Cl)c(Cl)c1F]

Embodiment 46

The compound of either one of Embodiments 44 and 45, wherein $R^1$ is —CN.

Embodiment 47

The compound of either one of Embodiments 44 and 45, wherein $R^1$ is chosen from —$OR^6$ and —$NR^{7a}R^{7b}$.

Embodiment 48

The compound of Embodiment 47, wherein each $R^6$, $R^{7a}$, and $R^{7b}$ is H.

Embodiment 49

The compound of Embodiment 47, wherein each $R^6$, $R^{7a}$, and $R^{7b}$ is alkyl.

Embodiment 50

The compound of Embodiment 47, wherein each $R^6$, $R^{7a}$, and $R^{7b}$ is C(=O)alkyl.

Embodiment 51

The compound of any one of Embodiments 47-50, wherein $R^1$ is —$OR^6$.

Embodiment 52

The compound of any one of Embodiments 47-50, wherein $R^1$ is —$NR^{7a}R^{7b}$.

Embodiment 53

The compound of either one of Embodiments 44 and 45, wherein $R^1$ is chosen from —$COOR^8$ and —$CONR^{9a}R^{9b}$.

Embodiment 54

The compound of Embodiment 53, wherein each $R^8$, $R^{9a}$, and $R^{9b}$ is H.

Embodiment 55

The compound of Embodiment 53, wherein each $R^8$, $R^{9a}$, and $R^{9b}$ is alkyl.

Embodiment 56

The compound of any one of Embodiments 53-55, wherein $R^1$ is —COOR$^8$.

Embodiment 57

The compound of any one of Embodiments 53-55, wherein $R^1$ is —CONR$^{9a}$R$^{9b}$.

Embodiment 58

The compound of any one of Embodiments 44-57, wherein $R^2$ is alkyl.

Embodiment 59

The compound of Embodiment 58, wherein $R^2$ is $C_{1-6}$alkyl.

Embodiment 60

The compound of Embodiment 59, wherein $R^2$ is methyl.

Embodiment 61

The compound of any one of Embodiments 44-57, wherein $R^2$ is alkoxy.

Embodiment 62

The compound of Embodiment 61, wherein $R^2$ is $C_{1-6}$alkoxy.

Embodiment 63

The compound of Embodiment 62, wherein $R^2$ is methoxy.

Embodiment 64

The compound of any one of Embodiments 44-57, wherein $R^2$ is H.

Also provided is Embodiment 65: a compound having structural Formula (IV):

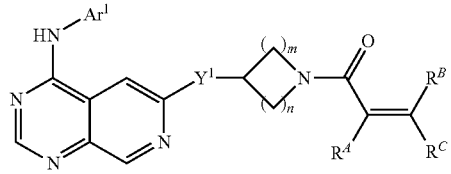

(IV)

or a salt thereof, wherein:
Ar$^1$ is chosen from aryl and heteroaryl, either of which is optionally substituted with one or two R$^4$ groups, and either of which is optionally substituted with one, two, or three R$^5$ groups;
R$^A$ and R$^B$ are independently chosen from H and alkyl;
R$^C$ is chosen from H, CH$_3$, and CH$_2$NR$^{15}$R$^{16}$;
each R$^4$ is independently chosen from alkyl, haloalkyl, cycloalkyl, heterocycloalkyl, aryl, and heteroaryl, any of which is optionally substituted with one or two R$^{10}$ groups;

each R$^5$ is independently chosen from halo, —CN, —OR$^{11}$, —NR$^{12a}$R$^{12b}$, —COOR$^{13}$, and —CONR$^{14a}$R$^{14b}$;
each R$^{10}$ is independently chosen from halo, hydroxy, and alkoxy;
each R$^{11}$, R$^{12a}$, and R$^{12b}$ is independently chosen from H, $C_{1-6}$alkyl, $C_{1-6}$halolkyl, and C(=O)$C_{1-6}$alkyl;
each R$^{13}$, R$^{14a}$, and R$^{14b}$ is independently chosen from H and $C_{1-6}$alkyl;
R$^{15}$ and R$^{16}$ are independently chosen from H and $C_{1-6}$alkyl,
or R$^{15}$ and R$^{16}$, together with the nitrogen to which that they are both attached, combine to form a 5-7 membered heterocycloalkyl;
m and n are independently chosen from 1, 2, and 3; and
Y$^1$ is chosen from —NH— and —O—.

Also provided is Embodiment 66: a compound having structural Formula (V):

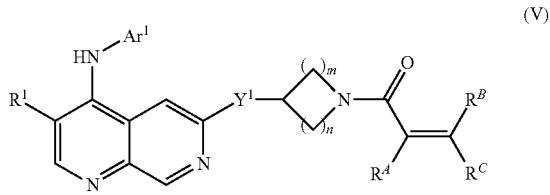

(V)

or a salt thereof, wherein:
Ar$^1$ is chosen from aryl and heteroaryl, either of which is optionally substituted with one or two R$^4$ groups, and either of which is optionally substituted with one, two, or three R$^5$ groups;
R$^A$ and R$^B$ are independently chosen from H and alkyl;
R$^C$ is chosen from H, CH$_3$, and CH$_2$NR$^{15}$R$^{16}$;
R$^1$ is chosen from halo, —CN, —OR$^6$, —NR$^{7a}$R$^{7b}$, —COOR$^8$, and —CONR$^{9a}$R$^{9b}$;
R$^2$ is chosen from H, alkyl, and alkoxy;
each R$^4$ is independently chosen from alkyl, haloalkyl, cycloalkyl, heterocycloalkyl, aryl, and heteroaryl, any of which is optionally substituted with one or two R$^{10}$ groups;
each R$^5$ is independently chosen from halo, —CN, —OR$^{11}$, NR$^{12a}$R$^{12b}$, —COOR$^{13}$, and —CONR$^{14a}$R$^{14b}$;
each R$^6$, R$^{7a}$, and R$^{7b}$ is independently chosen from H, alkyl, haloalkyl, and C(=O)alkyl;
each R$^8$, R$^{9a}$, and R$^{9b}$ is independently chosen from H and alkyl;
each R$^{10}$ is independently chosen from halo, hydroxy, and alkoxy;
each R$^{11}$, R$^{12a}$, and R$^{12b}$ is independently chosen from H, $C_{1-6}$alkyl, $C_{1-6}$halolkyl, and C(=O)$C_{1-6}$alkyl;
each R$^{13}$, R$^{14a}$, and R$^{14b}$ is independently chosen from H and $C_{1-6}$alkyl;
R$^{15}$ and R$^{16}$ are independently chosen from H and $C_{1-6}$alkyl,
or R$^{15}$ and R$^{16}$, together with the nitrogen to which that they are both attached, combine to form a 5-7 membered heterocycloalkyl;
m and n are independently chosen from 1, 2, and 3; and
Y$^1$ is chosen from —NH— and —O—.

Embodiment 67

The compound of Embodiment 66, wherein $R^1$ is —CN.

Embodiment 68

The compound of Embodiment 66, wherein $R^1$ is chosen from —$OR^6$ and —$NR^{7a}R^{7b}$.

Embodiment 69

The compound of Embodiment 68, wherein each $R^6$, $R^{7a}$, and $R^{7b}$ is H.

Embodiment 70

The compound of Embodiment 68, wherein each $R^6$, $R^{7a}$, and $R^{7b}$ is alkyl.

Embodiment 71

The compound of Embodiment 68, wherein each $R^6$, $R^{7a}$, and $R^{7b}$ is C(=O)alkyl.

Embodiment 72

The compound of any one of Embodiments 68-71, wherein $R^1$ is —$OR^6$.

Embodiment 73

The compound of any one of Embodiments 68-71, wherein $R^1$ is —$NR^{7a}R^{7b}$.

Embodiment 74

The compound of Embodiment 66, wherein $R^1$ is chosen from —$COOR^8$ and —$CONR^{9a}R^{9b}$.

Embodiment 75

The compound of Embodiment 74, wherein each $R^8$, $R^{9a}$, and $R^{9b}$ is H.

Embodiment 76

The compound of Embodiment 74, wherein each $R^8$, $R^{9a}$, and $R^{9b}$ is alkyl.

Embodiment 77

The compound of any one of Embodiments 74-76, wherein $R^1$ is —$COOR^8$.

Embodiment 78

The compound of any one of Embodiments 74-76, wherein $R^1$ is —$CONR^{9a}R^{9b}$.

Also provided are the following embodiments:

Embodiment 79

The compound of any one of Embodiments 1-78, wherein $Ar^1$ is chosen from phenyl and monocyclic heteroaryl, either of which is optionally substituted with one or two $R^4$ groups, and either of which is optionally substituted with one, two, or three $R^5$ groups.

Embodiment 80

The compound of Embodiment 79, wherein $Ar^1$ is chosen from phenyl and monocyclic 6-membered heteroaryl, either of which is optionally substituted with one or two $R^4$ groups, and either of which is optionally substituted with one, two, or three $R^5$ groups.

Embodiment 81

The compound of Embodiment 80, wherein $Ar^1$ is chosen from phenyl, pyridyl, pyrimidyl, pyridazyl, and pyrazyl, any of which is optionally substituted with one or two $R^4$ groups, and any of which is optionally substituted with one, two, or three $R^5$ groups.

Embodiment 82

The compound of Embodiment 81, wherein $Ar^1$ is phenyl, and is optionally substituted with one or two $R^4$ groups, and is optionally substituted with one, two, or three $R^5$ groups.

Embodiment 83

The compound of Embodiment 81, wherein $Ar^1$ is chosen from pyridyl, pyrimidyl, pyridazyl, and pyrazyl, any of which is optionally substituted with one or two $R^4$ groups, and any of which is optionally substituted with one, two, or three $R^5$ groups.

Embodiment 84

The compound of Embodiment 83, wherein $Ar^1$ is pyridyl, and is optionally substituted with one or two $R^4$ groups, and is optionally substituted with one, two, or three $R^5$ groups.

Embodiment 85

The compound of Embodiment 83, wherein $Ar^1$ is chosen from pyrimidyl, pyridazyl, and pyrazyl, any of which is optionally substituted with one or two $R^4$ groups, and any of which is optionally substituted with one, two, or three $R^5$ groups.

Embodiment 86

The compound of any one of Embodiments 1-78, wherein $Ar^1$ is chosen from naphthyl and bicyclic heteroaryl, either of which is optionally substituted with one or two $R^4$ groups, and either of which is optionally substituted with one, two, or three $R^5$ groups.

Embodiment 87

The compound of Embodiment 86, wherein $Ar^1$ is bicyclic heteroaryl, and is optionally substituted with one or two $R^4$ groups, and is optionally substituted with one, two, or three $R^5$ groups.

Embodiment 88

The compound of Embodiment 87, wherein $Ar^1$ is bicyclic 10-membered heteroaryl, and is optionally substituted with one or two $R^4$ groups, and is optionally substituted with one, two, or three $R^5$ groups.

Embodiment 89

The compound of Embodiment 88, wherein $Ar^1$ is chosen from quinolinyl and isoquinolinyl, either of which is optionally substituted with one or two $R^4$ groups, and either of which is optionally substituted with one, two, or three $R^5$ groups.

Embodiment 90

The compound of Embodiment 87, wherein $Ar^1$ is bicyclic 9-membered heteroaryl, and is optionally substituted with one or two $R^4$ groups, and is optionally substituted with one, two, or three $R^5$ groups.

Embodiment 91

The compound of Embodiment 90, wherein $Ar^1$ is chosen from indolyl, benzimidazolyl, benzopyrrolyl, benzoxazolyl, and benzisoxazolyl, any of which is optionally substituted with one or two $R^4$ groups, and any of which is optionally substituted with one, two, or three $R^5$ groups.

Embodiment 92

The compound of Embodiment 91, wherein $Ar^1$ is chosen from indolyl, benzimidazolyl, and benzopyrrolyl, any of which is optionally substituted with one or two $R^4$ groups, and any of which is optionally substituted with one, two, or three $R^5$ groups.

Embodiment 93

The compound of any one of Embodiments 1-92, wherein $Ar^1$ is optionally substituted with one $R^4$ group.

Embodiment 94

The compound of any one of Embodiments 1-92, wherein $Ar^1$ is substituted with one or two $R^4$ groups.

Embodiment 95

The compound of Embodiment 94, wherein $Ar^1$ is substituted with one $R^4$ group.

Embodiment 96

The compound of Embodiment 94, wherein $Ar^1$ is substituted with two $R^4$ groups.

Embodiment 97

The compound of any one of Embodiments 1-96, wherein each $R^4$ is independently chosen from $C_{1-6}$alkyl, $C_{3-7}$cycloalkyl, 4- to 7-membered heterocycloalkyl, $C_{6-10}$aryl, and 6- to 10-membered heteroaryl, any of which is optionally substituted with one or two $R^{10}$ groups.

Embodiment 98

The compound of Embodiment 97, wherein each $R^4$ is $C_{3-7}$cycloalkyl, and is optionally substituted with one or two $R^{10}$ groups.

Embodiment 99

The compound of Embodiment 97, wherein each $R^4$ is $C_{1-6}$alkyl, and is optionally substituted with one or two $R^{10}$ groups.

Embodiment 100

The compound of Embodiment 97, wherein each $R^4$ is $C_{1-6}$alkyl, and is optionally substituted with one or two $R^{10}$ groups.

Embodiment 101

The compound of Embodiment 97, wherein each $R^4$ is independently chosen from $C_{3-7}$cycloalkyl and 4- to 7-membered heterocycloalkyl, either of which is optionally substituted with one or two $R^{10}$ groups.

Embodiment 102

The compound of Embodiment 97, wherein each $R^4$ is independently chosen from $C_{6-10}$aryl and 6- to 10-membered heteroaryl, either of which is optionally substituted with one or two $R^{10}$ groups.

Embodiment 103

The compound of Embodiment 102, wherein each $R^4$ is 6- to 10-membered heteroaryl and is optionally substituted with one or two $R^{10}$ groups.

Embodiment 104

The compound of Embodiment 103, wherein each $R^4$ is monocyclic 5- to 7-membered heteroaryl and is optionally substituted with one or two $R^{10}$ groups.

Embodiment 105

The compound of Embodiment 104, wherein each $R^4$ is chosen from pyrrolyl, pyrazolyl, imidazolyl, triazolyl, oxazolyl, and isoxazolyl, and is optionally substituted with one or two $R^{10}$ groups.

Embodiment 106

The compound of Embodiment 105, wherein each $R^4$ is oxazolyl and is optionally substituted with one or two $R^{10}$ groups.

Embodiment 107

The compound of any one of Embodiments 1-106, wherein each $R^4$ is optionally substituted with one $R^{10}$ group.

Embodiment 108

The compound of any one of Embodiments 1-106, wherein each $R^4$ is substituted with one or two $R^{10}$ groups.

Embodiment 109

The compound of Embodiment 108, wherein each $R^4$ is substituted with one $R^{10}$ group.

Embodiment 110

The compound of any one of Embodiments 1-109, wherein $R^{10}$ is halo.

Embodiment 111

The compound of any one of Embodiments 1-109, wherein $R^{10}$ is hydroxy.

Embodiment 112

The compound of any one of Embodiments 1-109, wherein $R^{10}$ is alkoxy.

Embodiment 113

The compound of Embodiment 112, wherein $R^{10}$ is $C_{1-6}$alkoxy.

Embodiment 114

The compound of Embodiment 107, wherein each $R^4$ is not substituted with an $R^{10}$ group.

Embodiment 115

The compound of Embodiment 98, wherein each $R^4$ is cyclopropyl.

Embodiment 116

The compound of Embodiment 98, wherein each $R^4$ is cyclobutyl.

Embodiment 117

The compound of Embodiment 99, wherein each $R^4$ is $C_{1-6}$alkyl.

Embodiment 118

The compound of Embodiment 117, wherein each $R^4$ is methyl.

Embodiment 119

The compound of Embodiment 99, wherein each $R^4$ is hydroxyalkyl.

Embodiment 120

The compound of Embodiment 119, wherein each $R^4$ is hydroxymethyl.

Embodiment 121

The compound of Embodiment 93, wherein $Ar^1$ is not substituted with an $R^4$ group.

Embodiment 122

The compound of any one of Embodiments 1-121, wherein $Ar^1$ is optionally substituted with one or two $R^5$ groups.

Embodiment 123

The compound of Embodiment 122, wherein $Ar^1$ is optionally substituted with one $R^5$ group.

Embodiment 124

The compound of any one of Embodiments 1-121, wherein $Ar^1$ is optionally substituted with one, two, or three $R^5$ groups.

Embodiment 125

The compound of Embodiment 124, wherein $Ar^1$ is substituted with one or two $R^5$ groups.

Embodiment 126

The compound of Embodiment 125, wherein $Ar^1$ is substituted with one $R^5$ group.

Embodiment 127

The compound of any one of Embodiments 1-126, wherein each $R^5$ is independently chosen from halo and cyano.

Embodiment 128

The compound of Embodiment 127, wherein each $R^5$ is halo.

Embodiment 129

The compound of Embodiment 128, wherein each $R^5$ is independently chosen from fluoro and chloro.

Embodiment 130

The compound of Embodiment 129, wherein $R^5$ is chloro.

Embodiment 131

The compound of any one of Embodiments 1-126, wherein each $R^5$ is independently chosen from $—OR^{11}$ and $—NR^{12a}R^{12b}$.

Embodiment 132

The compound of Embodiment 131, wherein each $R^{11}$, $R^{12a}$, and $R^{12b}$ is H.

Embodiment 133

The compound of Embodiment 131, wherein each $R^5$ is $—OR^{11}$.

Embodiment 134

The compound of Embodiment 133, wherein each $R^{11}$ is alkyl.

Embodiment 135

The compound of Embodiment 131, wherein each $R^{11}$ is $C_{1-6}$alkyl.

Embodiment 136

The compound of Embodiment 131, wherein each $R^{11}$ is $C_{1-6}$haloalkyl.

Embodiment 137

The compound of Embodiment 136, wherein each $R^{11}$ is halomethyl.

Embodiment 138

The compound of Embodiment 137, wherein each $R^{11}$ is difluoromethyl.

Embodiment 139

The compound of Embodiment 137, wherein each $R^{11}$ is trifluoromethyl.

Embodiment 140

The compound of Embodiment 131, wherein each $R^{11}$, $R^{12a}$, and $R^{12b}$ is C(=O)alkyl.

Embodiment 141

The compound of Embodiment 140, wherein each $R^{11}$, $R^{12a}$, and $R^{12b}$ is C(=O)$C_{1-6}$alkyl.

Embodiment 142

The compound of any one of Embodiments 1-126, wherein each $R^5$ is independently chosen from —COOR$^{13}$, and —CONR$^{14a}$R$^{14b}$.

Embodiment 143

The compound of Embodiment 142, wherein each $R^{13}$, $R^{14a}$, and $R^{14b}$ is H.

Embodiment 144

The compound of Embodiment 142, wherein each $R^{13}$, $R^{14a}$, and $R^{14b}$ is alkyl.

Embodiment 145

The compound of Embodiment 144, wherein each $R^{13}$, $R^{14a}$, and $R^{14b}$ is $C_{1-6}$alkyl.

Embodiment 146

The compound of any one of Embodiments 142-145, wherein $R^5$ is —COOR$^{13}$.

Embodiment 147

The compound of any one of Embodiments 142-145, wherein $R^5$ is —CONR$^{14a}$R$^{14b}$.

Embodiment 148

The compound of Embodiment 123, wherein Ar$^1$ is not substituted with an $R^5$ group.

Embodiment 149

The compound of any one of Embodiments 1-148, wherein Ar$^1$ is not

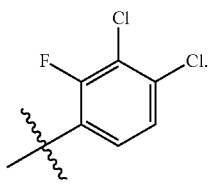 [SMILES: *c1ccc(Cl)c(Cl)c1F]

Embodiment 150

The compound of Embodiment 82, wherein Ar$^1$ is chosen from:

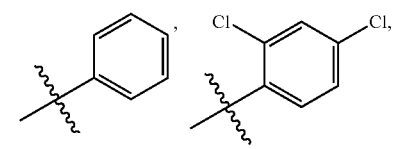

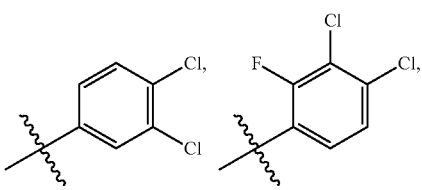

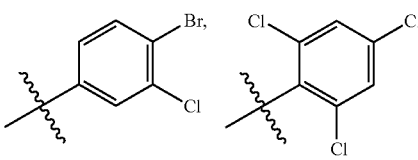

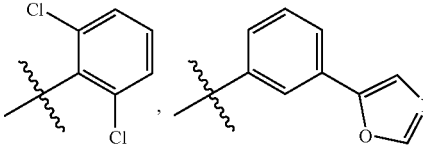

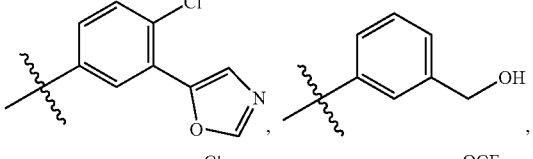

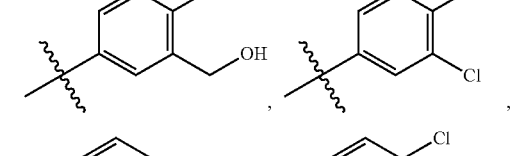

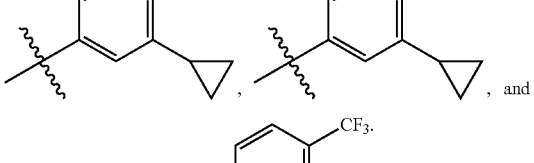

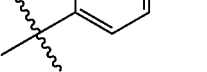

Embodiment 151

The compound of Embodiment 150, wherein Ar¹ is chosen from:

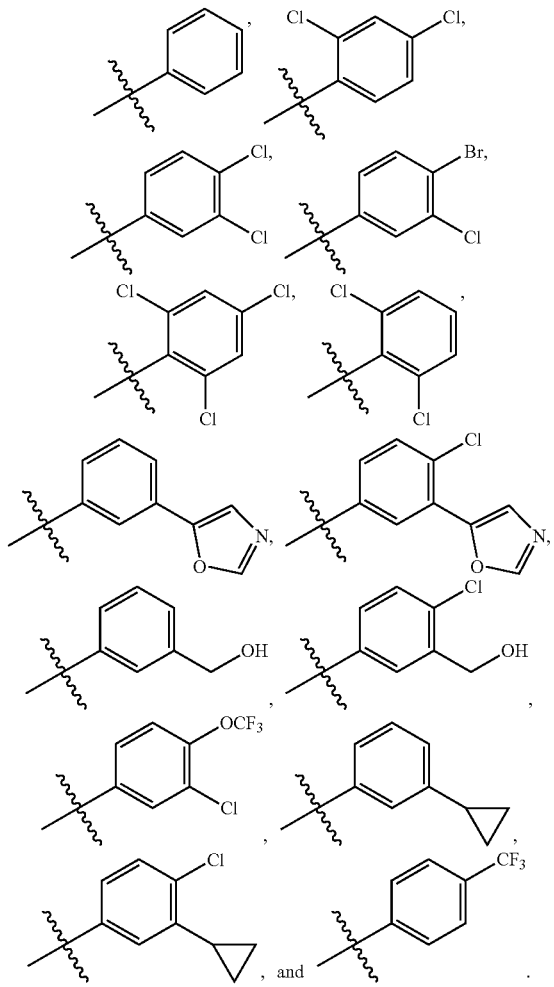

Embodiment 152

The compound of Embodiment 150, wherein Ar¹ is chosen from:

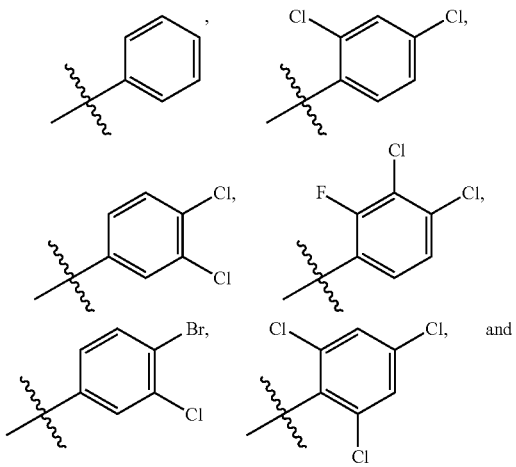

-continued

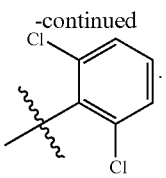

Embodiment 153

The compound of Embodiment 152, wherein Ar¹ is chosen from:

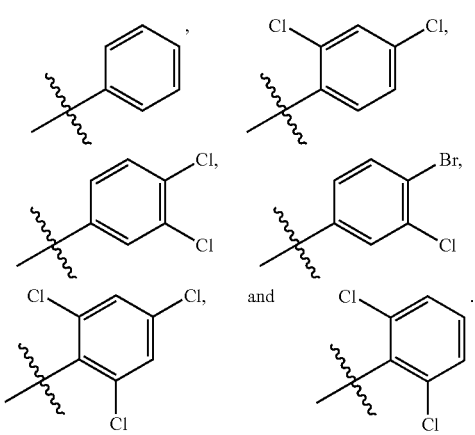

Embodiment 154

The compound of Embodiment 90, wherein Ar¹ is

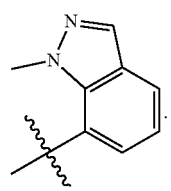

Embodiment 155

The compound of any one of Embodiments 1-154, wherein:
m is 1 and n is 1,
m is 2 and n is 2, or
m is 1 and n is 3.

Embodiment 156

The compound of any one of Embodiments 1-154, wherein:
m is 1 and n is 1, or
m is 1 and n is 3.

Embodiment 157

The compound of Embodiment 155, wherein:
m is 1 and n is 1, or
m is 2 and n is 2.

Embodiment 158

The compound of Embodiment 157, wherein m is 1 and n is 1.

Embodiment 159

The compound of any one of Embodiments 1-154, wherein m is 1.

Embodiment 160

The compound of any one of Embodiments 1-154, wherein m is 2.

Embodiment 161

The compound of any one of Embodiments 1-154, wherein m is 3.

Embodiment 162

The compound of any one of Embodiments 1-161, wherein n is 1.

Embodiment 163

The compound of any one of Embodiments 1-160, wherein n is 2.

Embodiment 164

The compound of any one of Embodiments 1-160, wherein n is 3.

Embodiment 165

The compound of any one of Embodiments 1-164, wherein $Y^1$ is —NH—.

Embodiment 166

The compound of any one of Embodiments 1-164, wherein $Y^1$ is —O—.

Embodiment 167

The compound of any one of Embodiments 1-166, wherein $R^A$ and $R^B$ are independently chosen from H and $C_{1-6}$alkyl.

Embodiment 168

The compound of any one of Embodiments 1-167, wherein $R^A$ is H.

Embodiment 169

The compound of any one of Embodiments 1-167, wherein $R^A$ is $C_{1-6}$alkyl.

Embodiment 170

The compound of any one of Embodiment 169, wherein $R^A$ is methyl.

Embodiment 171

The compound of any one of Embodiments 1-170, wherein $R^B$ is H.

Embodiment 172

The compound of any one of Embodiments 1-170, wherein $R^B$ is $C_{1-6}$alkyl.

Embodiment 173

The compound of any one of Embodiment 172, wherein $R^B$ is methyl.

Embodiment 174

The compound of any one of Embodiments 1-173, wherein $R^C$ is H.

Embodiment 175

The compound of any one of Embodiments 1-173, wherein $R^C$ is $CH_3$.

Embodiment 176

The compound of any one of Embodiments 1-173, wherein $R^C$ is $CH_2NR^{15}R^{16}$.

Embodiment 177

The compound of Embodiment 176, wherein $R^{15}$ and $R^{16}$ are independently chosen from H and $C_{1-6}$alkyl.

Embodiment 178

The compound of Embodiment 177, wherein $R^{15}$ and $R^{16}$ are independently chosen from H and methyl.

Embodiment 179

The compound of Embodiment 176, wherein $R^{15}$ and $R^{16}$ are $C_{1-6}$alkyl.

Embodiment 180

The compound of Embodiment 178, wherein $R^{15}$ and $R^{16}$ are methyl.

Embodiment 181

The compound of any one of Embodiments 176-178, wherein at least one of $R^{15}$ and $R^{16}$ is H.

Embodiment 182

The compound of Embodiment 181, wherein $R^{15}$ and $R^{16}$ are H.

Embodiment 183

The compound of Embodiment 176, wherein $R^{15}$ and $R^{16}$, together with the nitrogen to which that they are both attached, combine to form a 5-7 membered heterocycloalkyl.

Embodiment 184

The compound of Embodiment 183, wherein $R^{15}$ and $R^{16}$, together with the nitrogen to which that they are both attached, combine to form a 5-7 membered heterocycloalkyl chosen from pyrrolidine, piperidine, piperazine, and morpholine.

Also provided is Embodiment 185: a compound having structural Formula (VI):

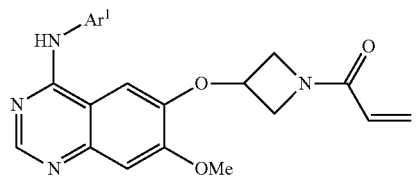

(VI)

or a salt thereof, wherein:
Ar$^1$ is chosen from aryl and heteroaryl, either of which is optionally substituted with one, two, or three R$^5$ groups;
each R$^5$ is independently chosen from halo, —CN, —OR$^{11}$, —NR$^{12a}$R$^{12b}$, —COOR$^{13}$, and —CONR$^{14a}$R$^{14b}$;
each R$^{11}$, R$^{12a}$, and R$^{12b}$ is independently chosen from H, C$_{1-6}$alkyl, C$_{1-6}$halolkyl, and C(=O)C$_{1-6}$alkyl; and
each R$^{13}$, R$^{14a}$, and R$^{14b}$ is independently chosen from H and C$_{1-6}$alkyl.

Embodiment 186

The compound of Embodiment 185, wherein Ar$^1$ is phenyl, and is substituted with one, two, or three R$^5$ groups.

Embodiment 187

The compound of Embodiment 186, wherein R$^5$ is halo.

Embodiment 188

The compound of Embodiment 185, wherein Ar$^1$ is chosen from

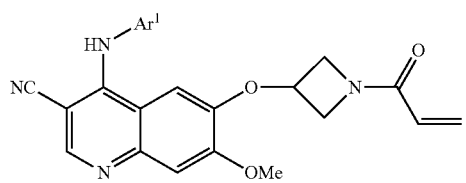

Also provided is Embodiment 189: a compound having structural Formula (VII):

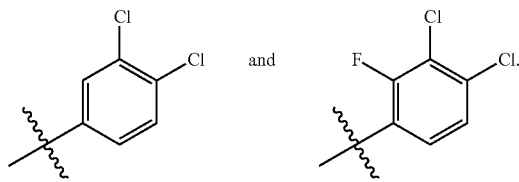 [SMILES: *c1ccc(Cl)c(Cl)c1 ; "and" ; *c1ccc(Cl)c(Cl)c1F]

(VII)

or a salt thereof, wherein:
Ar$^1$ is chosen from aryl and heteroaryl, either of which is optionally substituted with one, two, or three R$^5$ groups;
each R$^5$ is independently chosen from halo, —CN, —OR$^{11}$, —NR$^{12a}$R$^{12b}$, —COOR$^{13}$, and —CONR$^{14a}$R$^{14b}$;
each R$^{11}$, R$^{12a}$, and R$^{12b}$ is independently chosen from H, C$_{1-6}$alkyl, C$_{1-6}$halolkyl, and C(=O)C$_{1-6}$alkyl; and
each R$^{13}$, R$^{14a}$, and R$^{14b}$ is independently chosen from H and C$_{1-6}$alkyl.

Embodiment 190

The compound of Embodiment 189, wherein Ar$^1$ is phenyl, and is substituted with one, two, or three R$^5$ groups.

Embodiment 191

The compound of Embodiment 190, wherein R$^5$ is halo.

Embodiment 192

The compound of Embodiment 189, wherein Ar$^1$ is chosen from

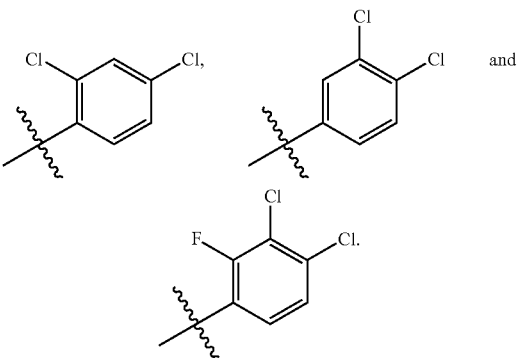

Also provided is Embodiment 193: a compound having structural Formula (VIII):

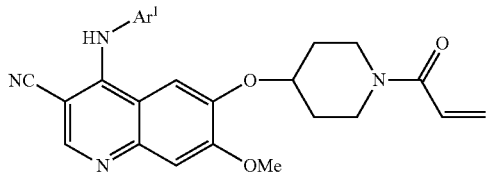

(VIII)

or a salt thereof, wherein:
Ar$^1$ is chosen from aryl and heteroaryl, either of which is optionally substituted with one, two, or three R$^5$ groups;
each R$^5$ is independently chosen from halo, —CN, —OR$^{11}$, —NR$^{12a}$R$^{12b}$, —COOR$^{13}$, and —CONR$^{14a}$R$^{14b}$;
each R$^{11}$, R$^{12a}$, and R$^{12b}$ is independently chosen from H, C$_{1-6}$alkyl, C$_{1-6}$halolkyl, and C(=O)C$_{1-6}$alkyl; and
each R$^{13}$, R$^{14a}$, and R$^{14b}$ is independently chosen from H and C$_{1-6}$alkyl.

Embodiment 194

The compound of Embodiment 193, wherein:
if m is 2 and n is 2,
and $A^1$ is $C(R^1)$, $A^2$ is $C(R^2)$, and $A^3$ is $C(R^3)$,
and $R^1$ is CN, $R^2$ is $C_1$-$C_2$ alkoxy, and $R^3$ is H,
then $Ar^1$ is not

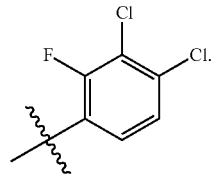 [SMILES: *c1ccc(Cl)c(Cl)c1F]

Embodiment 195

The compound of either one of Embodiments 193 and 194, wherein $Ar^1$ is phenyl, and is substituted with one, two, or three $R^5$ groups.

Embodiment 196

The compound of Embodiment 195, wherein $R^5$ is halo.

Embodiment 197

The compound of Embodiment 193, wherein $Ar^1$ is

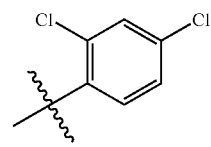 [SMILES: *c1ccc(Cl)cc1Cl]

Also provided are the following embodiments:

Embodiment 198

The compound of any one of Embodiments 185, 189, and 193, wherein each $R^5$ is independently chosen from halo, —CN, and —$OR^{11}$.

Embodiment 199

The compound of Embodiment 198, wherein each $R^5$ is independently chosen from halo and —CN.

Embodiment 200

The compound of Embodiment 199, wherein each $R^5$ is halo.

Embodiment 201

The compound of Embodiment 200, wherein each $R^5$ is chosen from fluoro and chloro.

Embodiment 202

The compound of Embodiment 201, wherein $R^5$ is chloro.

Embodiment 203

The compound of any one of Embodiments 185, 189, 193, and 198-202, wherein $Ar^1$ is chosen from phenyl and monocyclic heteroaryl, either of which is optionally substituted with one, two, or three $R^5$ groups.

Embodiment 204

The compound of Embodiment 203, wherein $Ar^1$ is chosen from phenyl, pyridyl, pyrimidyl, pyridazyl, and pyrazyl, any of which is optionally substituted with one, two, or three $R^5$ groups.

Embodiment 205

The compound of Embodiment 203, wherein $Ar^1$ is phenyl, and is substituted with one, two, or three $R^5$ groups.

Embodiment 206

The compound of Embodiment 205, wherein $Ar^1$ is not

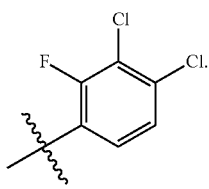

Embodiment 207

The compound of either one of Embodiments 204 and 205, wherein $Ar^1$ is substituted with one or two $R^5$ groups.

Embodiment 208

The compound of Embodiment 207, wherein $Ar^1$ is substituted with one $R^5$ group.

Embodiment 209

The compound of Embodiment 205, wherein $Ar^1$ is chosen from

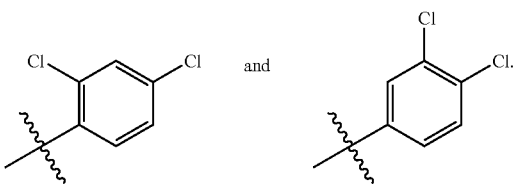 [SMILES: *c1ccc(Cl)cc1Cl ; *c1ccc(Cl)c(Cl)c1]

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is Embodiment 210: a compound chosen from:
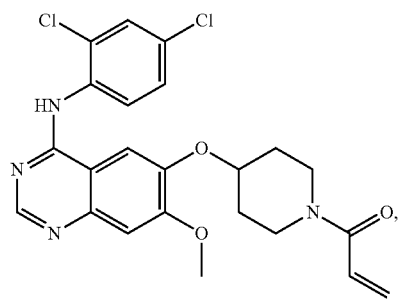
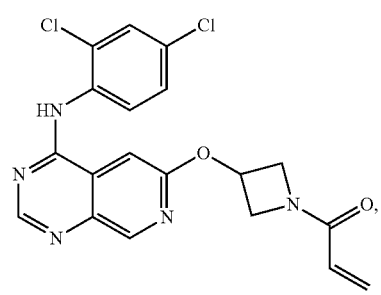
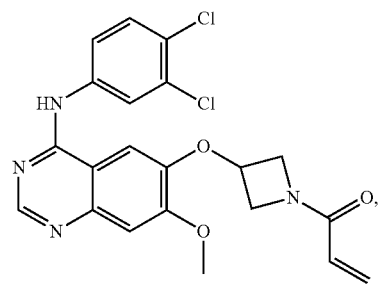
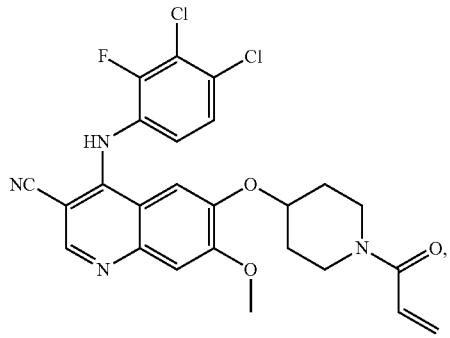
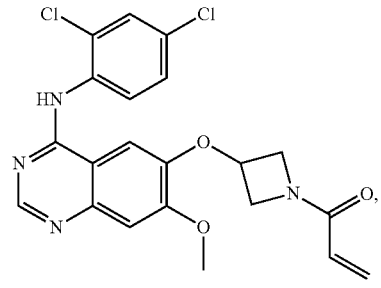
-continued
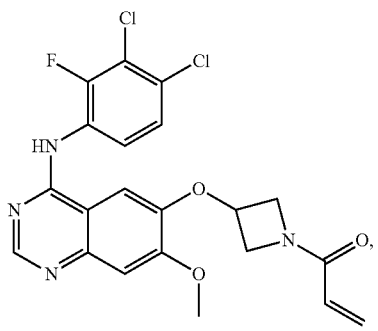
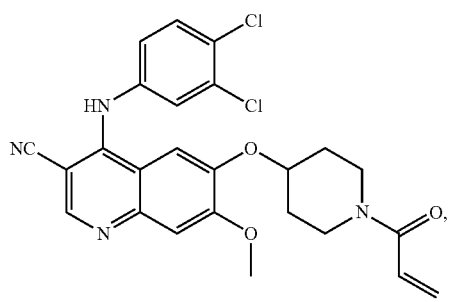
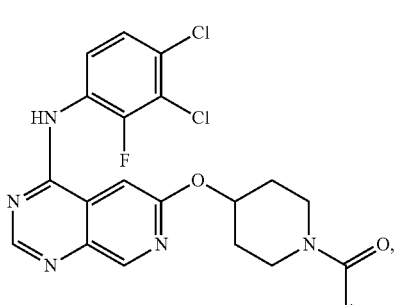
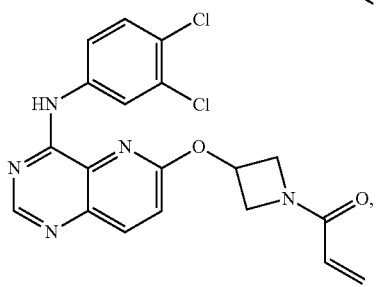
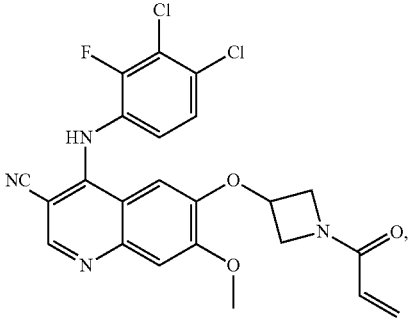

31
-continued
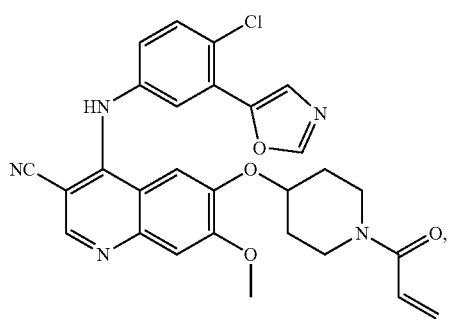
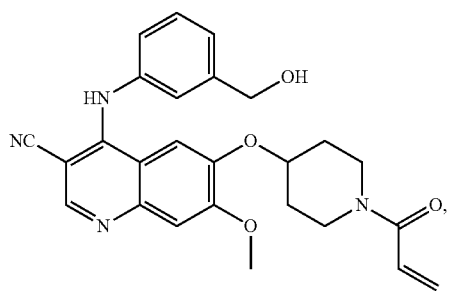
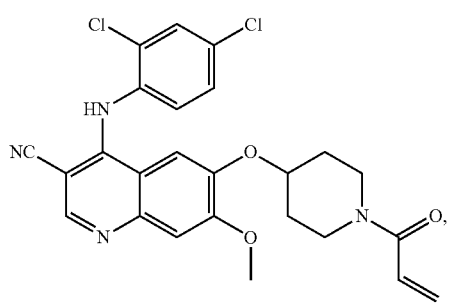
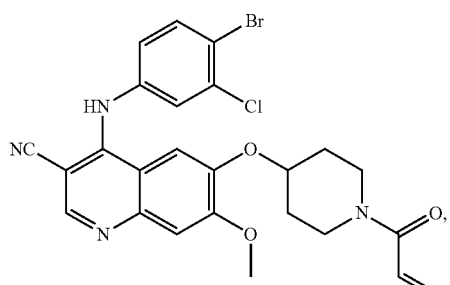
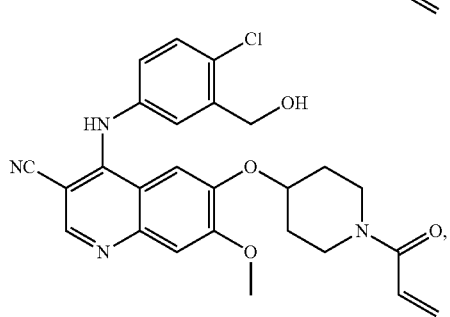
32
-continued
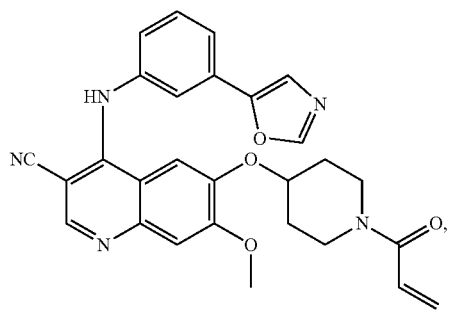
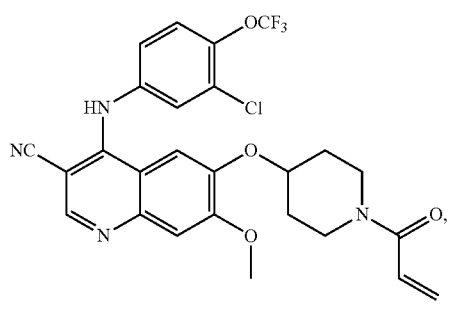
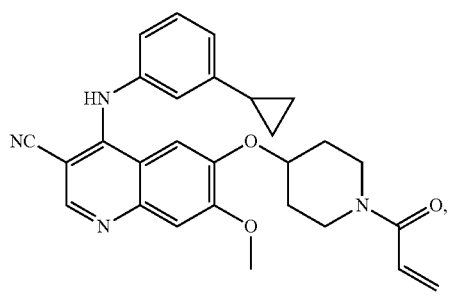
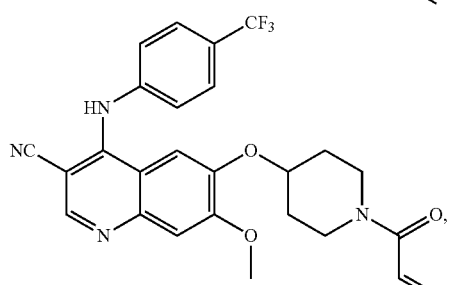
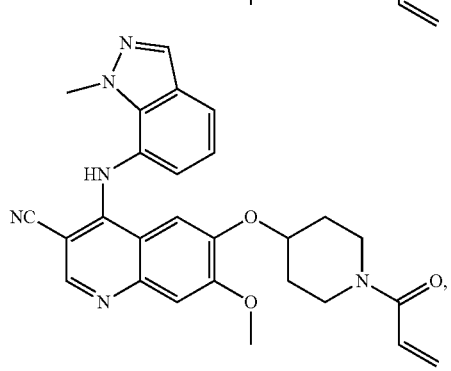

-continued
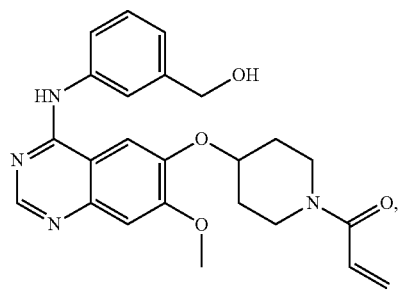
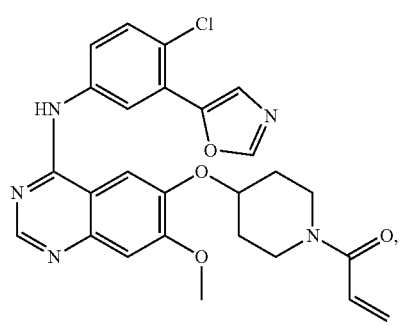
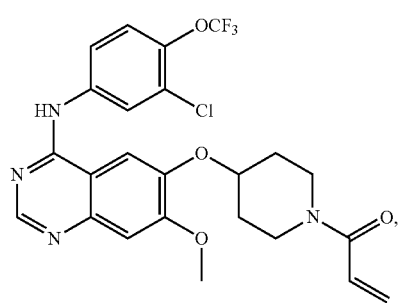
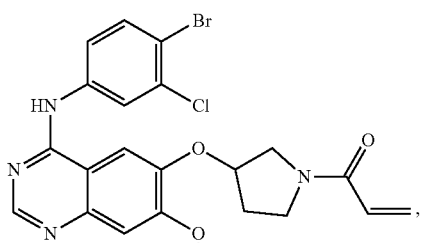
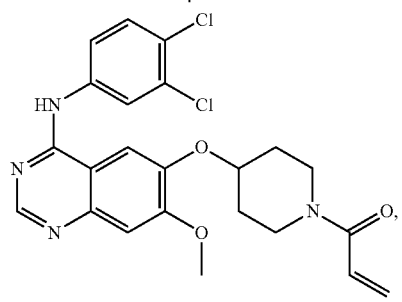
-continued
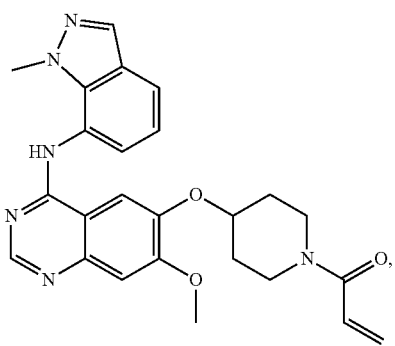
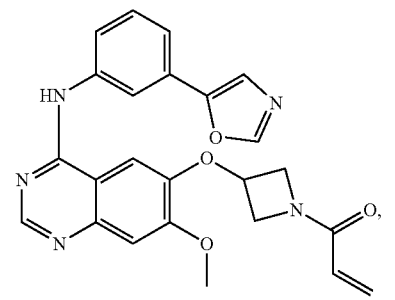
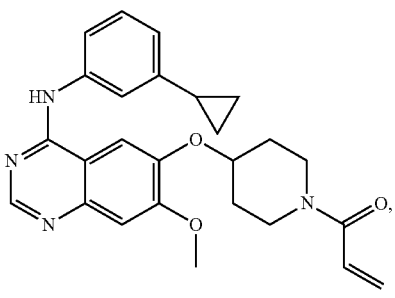
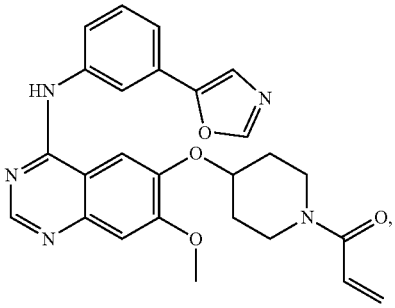
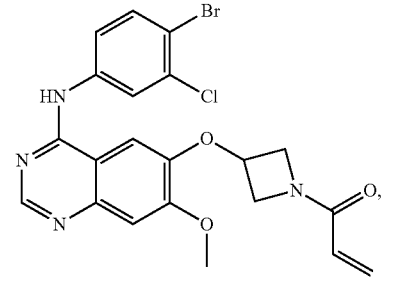

35
-continued
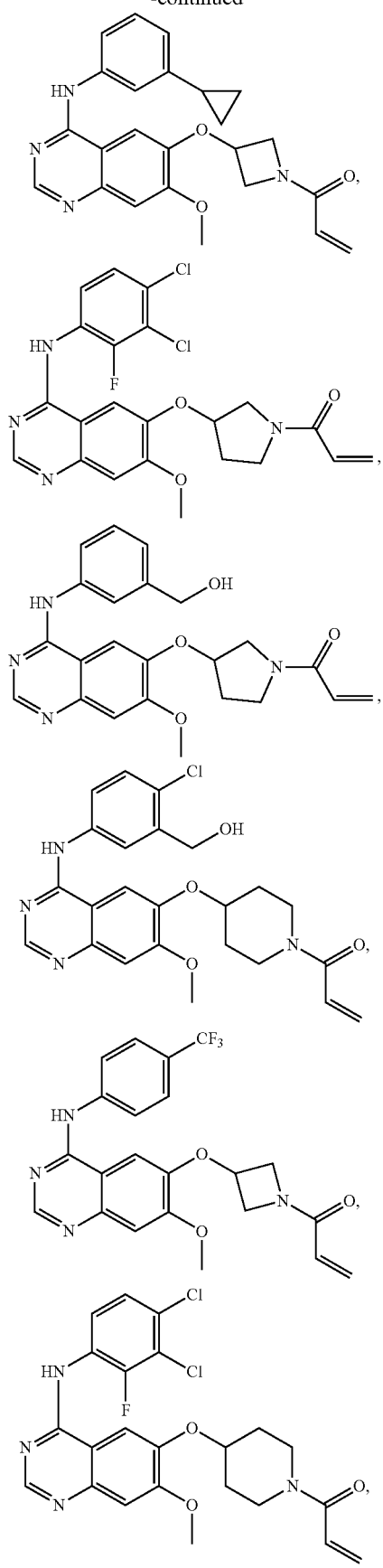
36
-continued
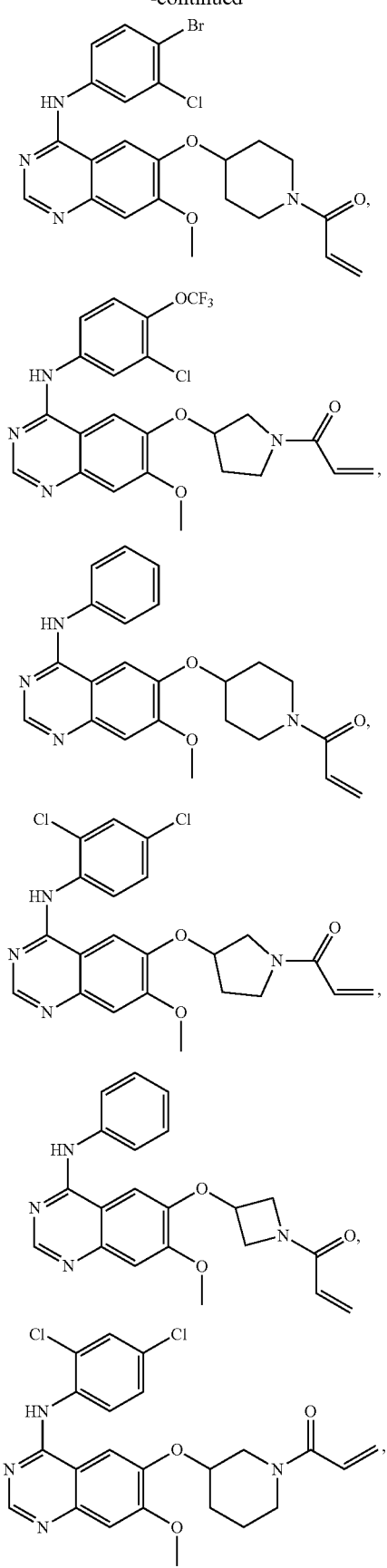

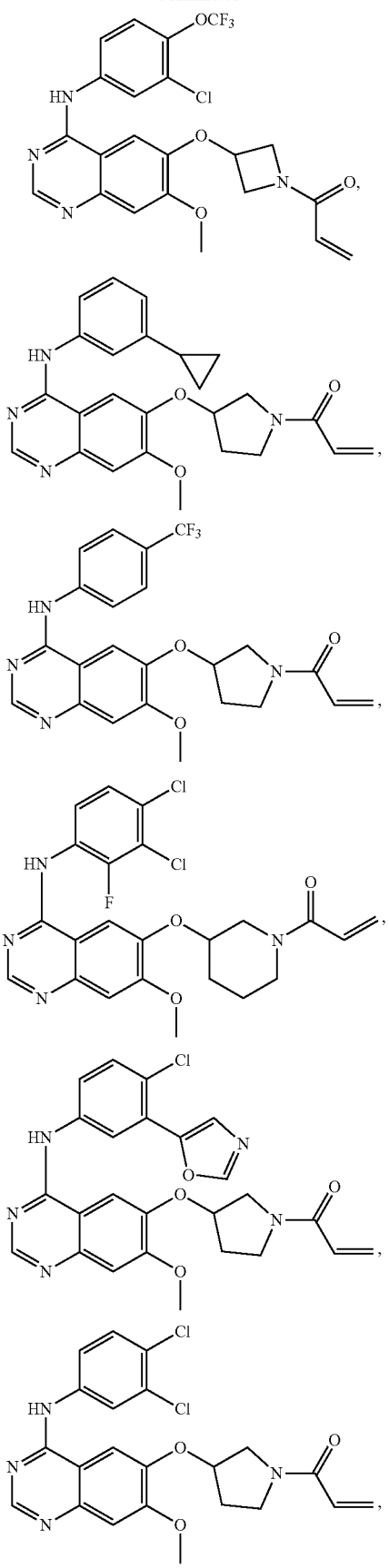
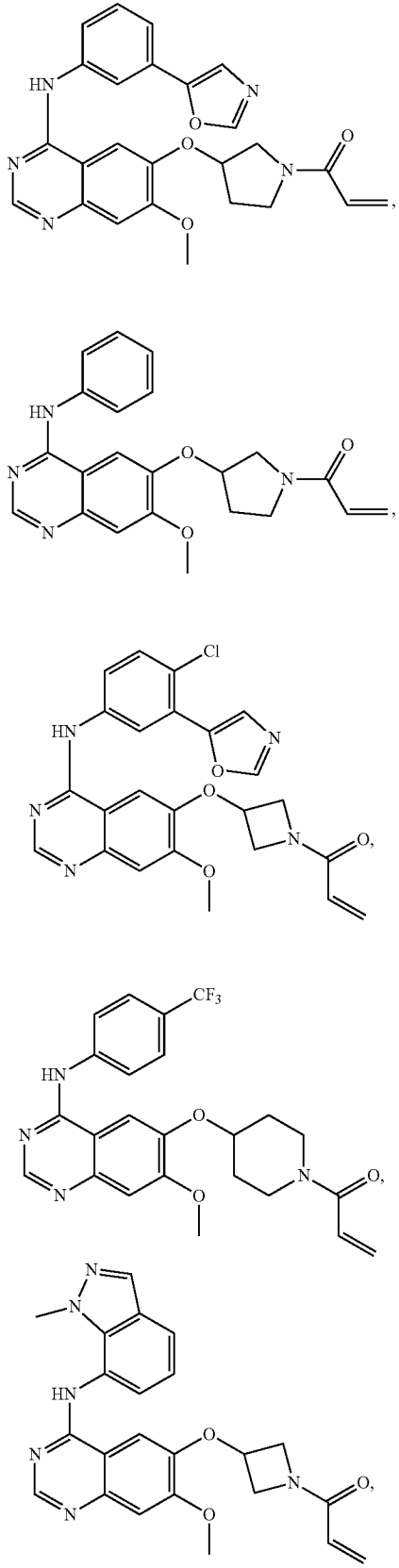

-continued
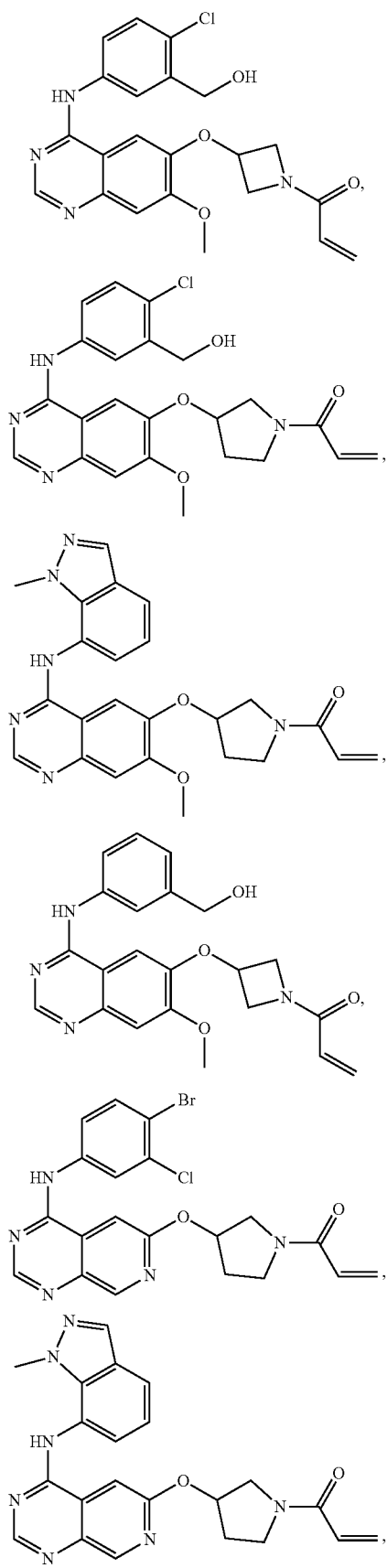
-continued
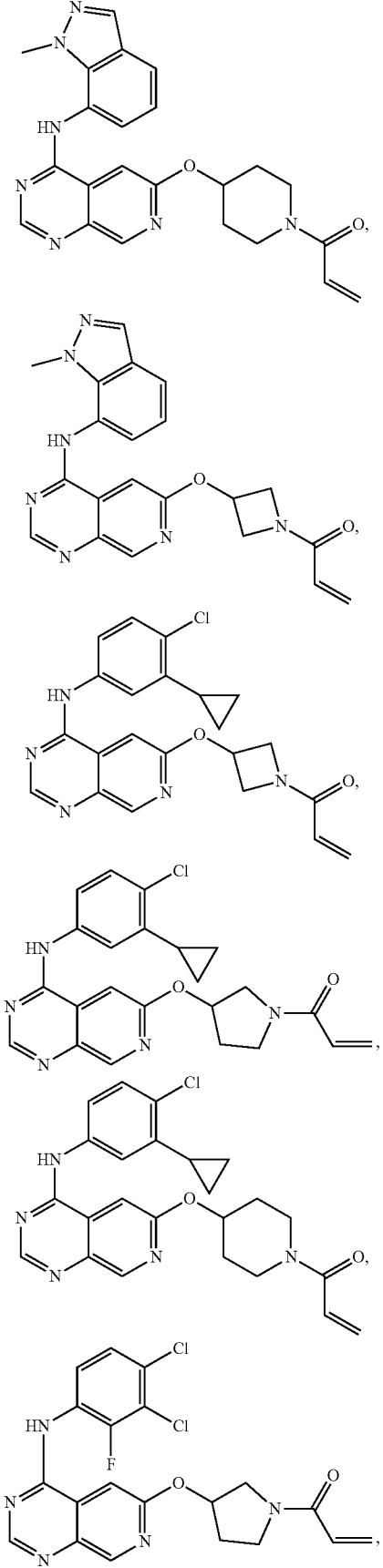

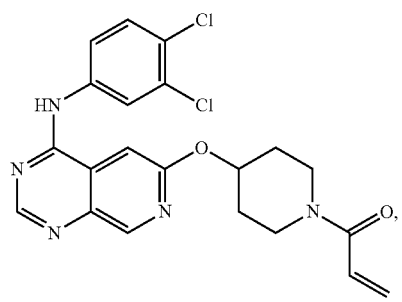
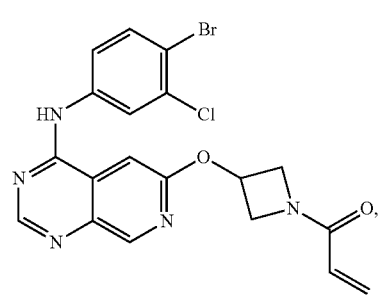
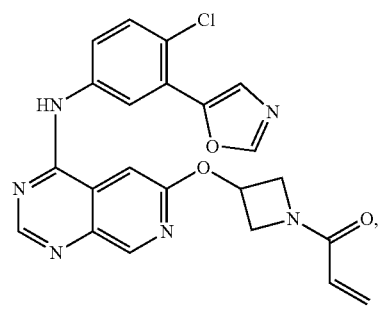
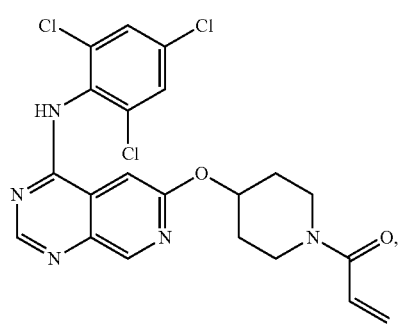
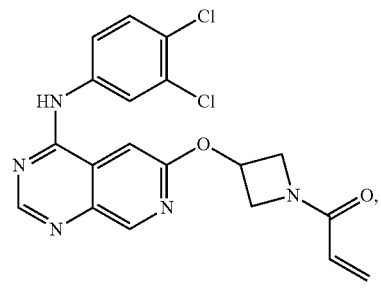
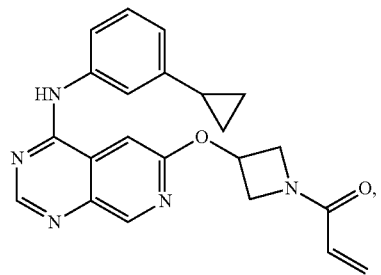
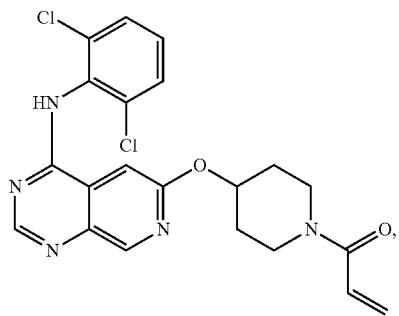
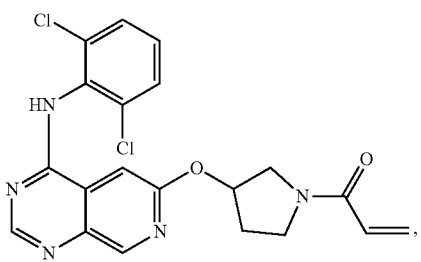
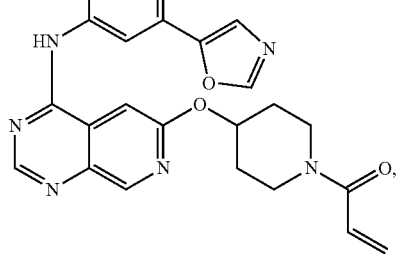
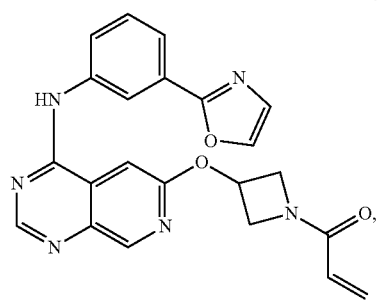
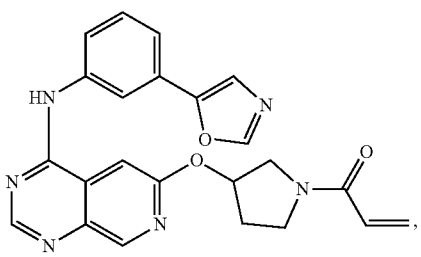

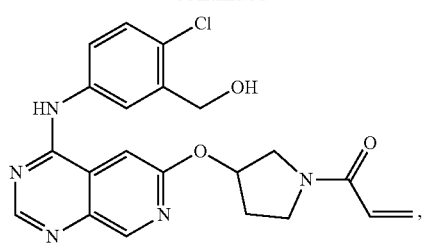
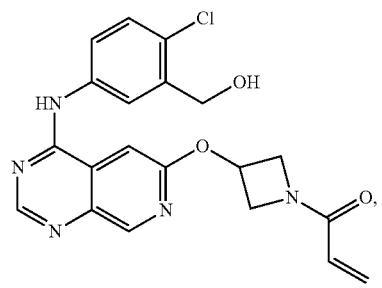
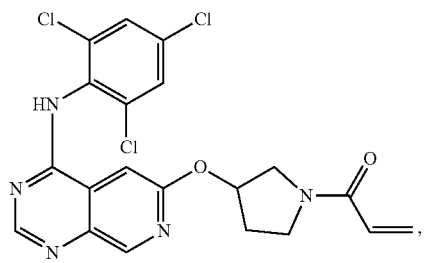
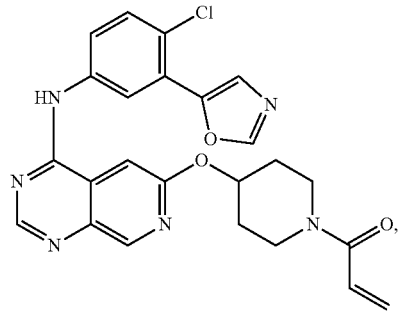
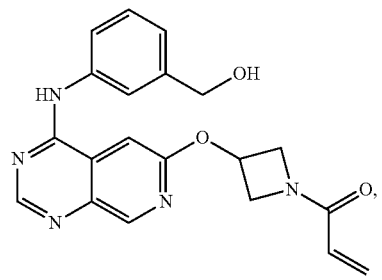
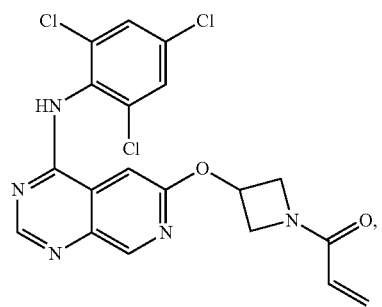
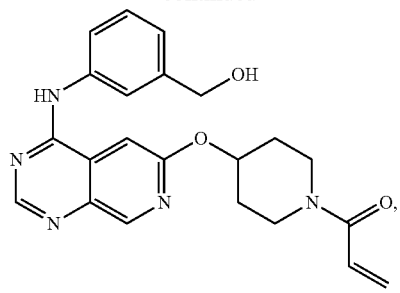
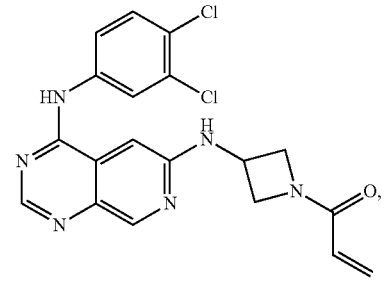
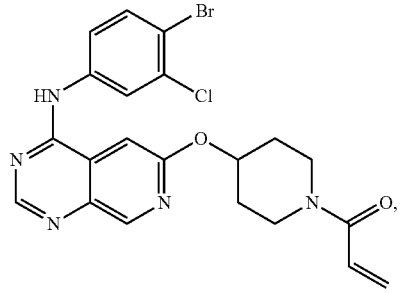
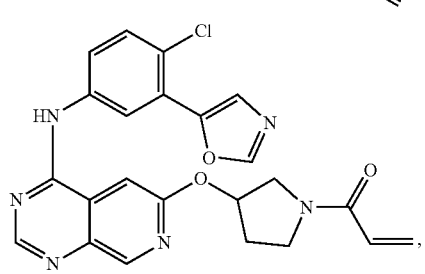
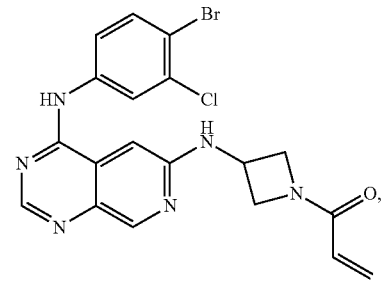
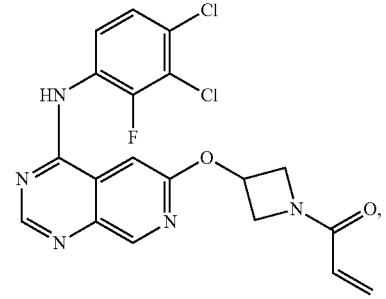

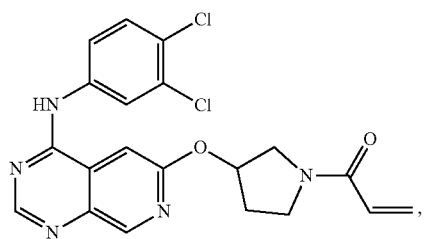
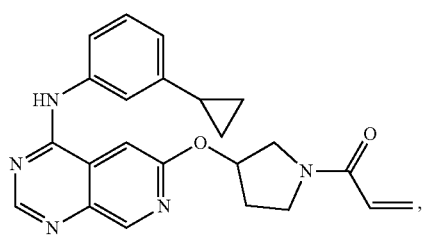
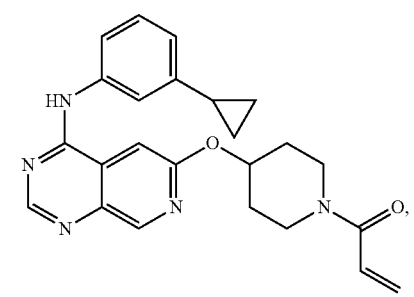
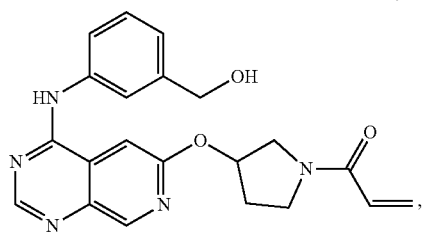
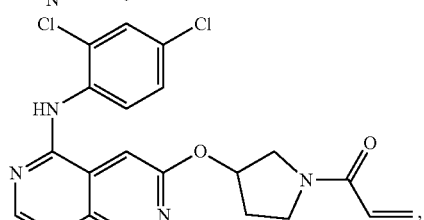
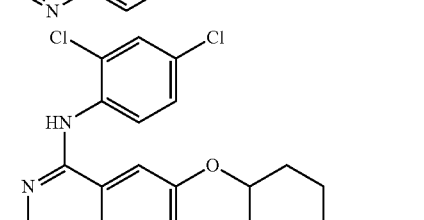
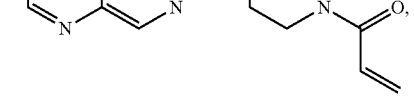
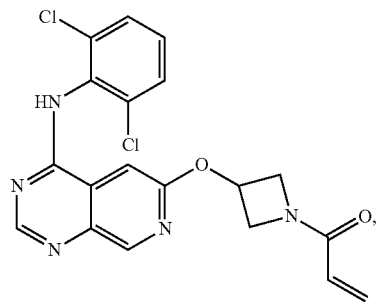
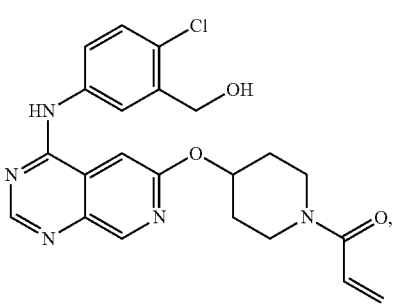
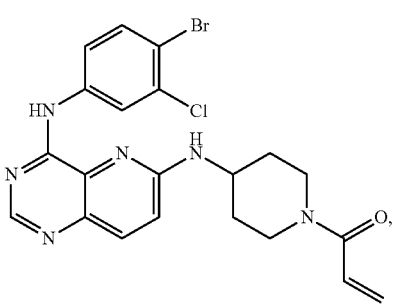
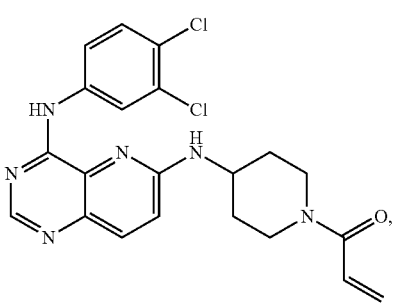
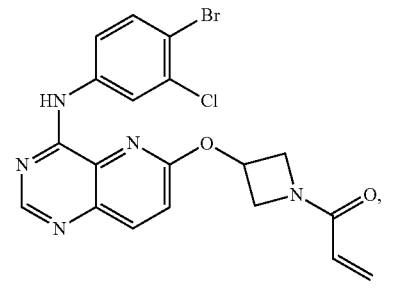

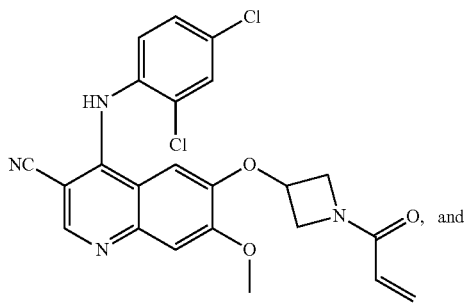
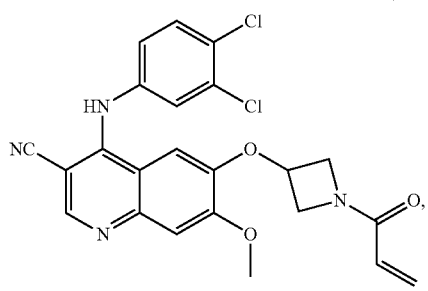
or a salt thereof.
Also provided is Embodiment 211: a compound chosen from:
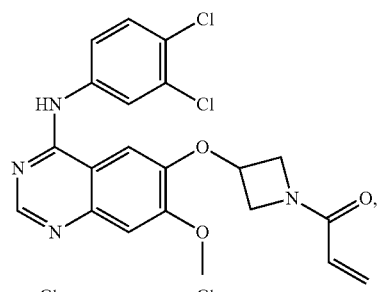
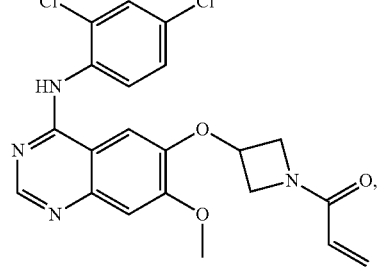
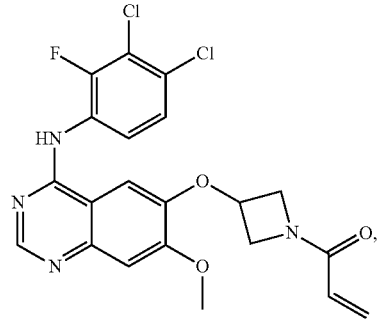
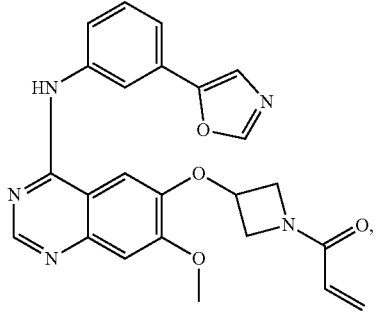
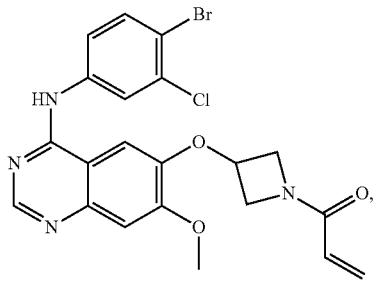
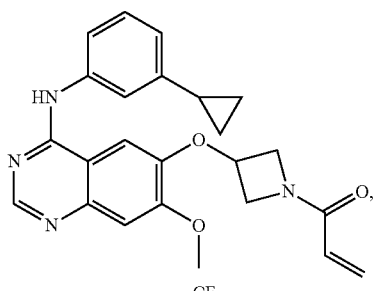
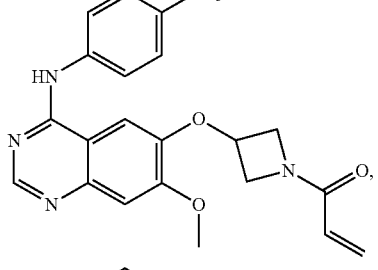
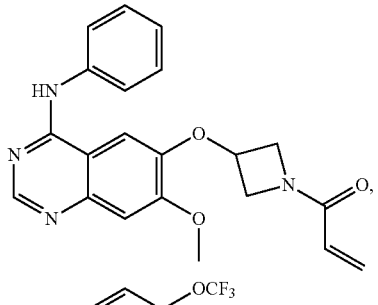
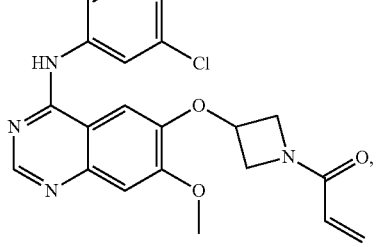

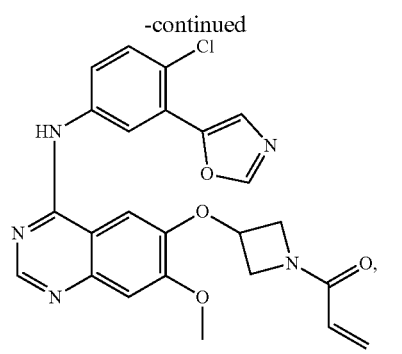
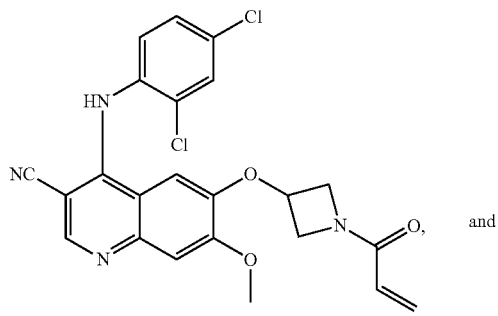
or a salt thereof.
Also provided is Embodiment 212: a compound chosen from:
or a salt thereof.
Also provided is Embodiment 213: a compound chosen from:
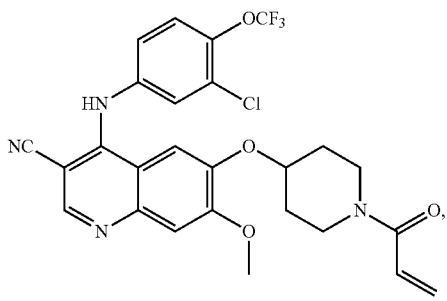
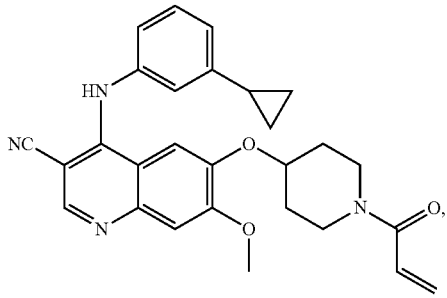
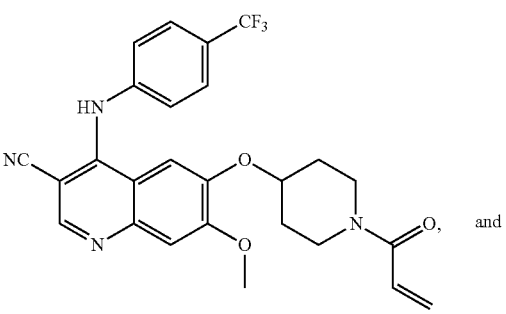

or a salt thereof.

Also provided are the following embodiments:

Embodiment 214

A method of inhibition of HER2 comprising contacting HER2 with a compound as recited in any one of Embodiments 1-213, or a salt thereof.

Embodiment 215

A method of inhibition of EGFR comprising contacting EGFR with a compound as recited in any one of Embodiments 1-213, or a salt thereof.

Embodiment 216

A method of treatment of a HER2-mediated disease comprising the administration of a therapeutically effective amount of a compound as recited in any one of Embodiments 1-213, or a salt thereof, to a patient in need thereof.

Embodiment 217

A method of treatment of an EGFR-mediated disease comprising the administration of a therapeutically effective amount of a compound as recited in any one of Embodiments 1-213, or a salt thereof, to a patient in need thereof.

Embodiment 218

The method as recited in either one of embodiments 216 and 217, wherein said disease is cancer.

Embodiment 219

The method as recited in Embodiment 218, wherein the cancer is chosen from small cell lung cancer, non small cell lung cancer, lung adenocarcinoma, colorectal cancer, pancreatic cancer, head and neck cancer, breast cancer, ovarian cancer, stomach cancer, and uterine cancer.

Embodiment 220

The method as recited in Embodiment 218, wherein the cancer is non small cell lung cancer.

Embodiment 221

A method of treatment of a HER2-mediated disease comprising the administration of:
a. a therapeutically effective amount of a compound as recited in any one of Embodiments 1-213, or a salt thereof; and
b. another therapeutic agent.

Embodiment 222

A method of treatment of an EGFR-mediated disease comprising the administration of:
a. a therapeutically effective amount of a compound as recited in any one of Embodiments 1-213, or a salt thereof; and
b. another therapeutic agent.

Embodiment 223

A method for treatment of an HER2-mediated disease in a population of subjects, characterized in that the population of subjects comprises a HER2 mutation, comprising administering a compound as recited in any one of Embodiments 1-213, or a salt thereof.

Embodiment 224

The method as recited in Embodiment 223, wherein the HER2-mediated disease is cancer.

Embodiment 225

The method as recited in either one of Embodiments 223 and 224, wherein the HER2 mutation is an exon 20 insertion mutation, excluding C805S.

Embodiment 226

The method as recited in either one of Embodiments 223 and 224, wherein the HER2 mutation is an activating mutation.

Embodiment 227

The method as recited in Embodiment 226, wherein the activating mutation is chosen from an extracellular mutation, an exon 19 point mutation, and an exon 21 point mutation.

Embodiment 228

The method as recited in Embodiment 226, wherein the activating mutation is chosen from L755 and D769.

Embodiment 229

The method as recited in Embodiment 226, wherein the activating mutation is chosen from V842I and L869R.

Embodiment 230

The method as recited in either one of Embodiments 223 and 224, wherein the HER2 mutation is chosen from YVMA, GSP, VC, V754M, L755S, L755P, D769H, D769N, Y772dupYVMA, V773M, G776del insVC, G776delinsVV, G776delinsLC, G778insLPS, G778dupGSP, V777L, G778insLPS, G778dupGSP, L786V, V842I, and L869R.

Embodiment 231

The method as recited in any one of Embodiments 223-230, wherein the selectivity of the compound or salt thereof for the HER2 mutation over WT EGFR is 0.5 or less.

Embodiment 232

The method as recited in Embodiment 231, wherein the selectivity of the compound or salt thereof for the HER2 mutation over WT EGFR is 0.1 or less.

Embodiment 233

A method for treatment of an EGFR-mediated disease in a population of subjects, characterized in that the population of subjects comprises an EGFR mutation, comprising administering a compound as recited in any one of Embodiments 1-213, or a salt thereof.

Embodiment 234

The method as recited in Embodiment 233, wherein the EGFR-mediated disease is cancer.

Embodiment 235

The method as recited in either one of Embodiments 233 and 234, wherein the EGFR mutation is an exon 20 insertion mutation excluding C797S.

Embodiment 236

The method as recited in either one of Embodiments 233 and 234, wherein the HER2 mutation is an atypical mutation.

Embodiment 237

The method as recited in Embodiment 236, wherein the atypical mutation is chosen from L719, G724, and L792.

Embodiment 238

The method as recited in either one of Embodiments 233 and 234, wherein the EGFR mutation is chosen from A763insFQEA, A767insASV, A767insTLA, S768dupSVD, S768dupSVD/C797S, S768dupSVD/T790M, S768I, S768I T790M, V769insASV, V769insGSV, V769insGVV, V769insMASVD, V769L, D770del insGY, D770insG, D770insNPG, D770insNPG/C797S, D770insNPG/T790M, D770insSVD, D770insY, H773Y, N771insHH, N771insSVDNR, P772insDNP, H773insAH, H773insH, H773insNPH, H773L/V774M, H773L V774M, and V774insHV.

Embodiment 239

The method as recited in any one of Embodiments 233-238, wherein the selectivity of the compound or salt thereof for the EGFR mutation over WT EGFR is 0.5 or less.

Embodiment 240

The method as recited in Embodiment 239, wherein the selectivity of the compound or salt thereof for the EGFR mutation over WT EGFR is 0.1 or less.

Embodiment 241

A method for treating a cancer or tumor in a subject in need of treatment comprising the steps of:
(a) determining the HER2 genotype of the subject,
(b) identifying the presence of an HER2 mutation in the genotype of the subject; and
(c) administering a compound of any one of Embodiments 1-213, or a salt thereof, wherein the compound or salt thereof is selective for the HER2 mutation over WT EGFR.

Embodiment 242

The method as recited in Embodiment 241, wherein the selectivity of the compound or salt thereof for the HER2 mutation over WT EGFR is 0.5 or less.

Embodiment 243

The method as recited in Embodiment 242, wherein the selectivity of the compound or salt thereof for the HER2 mutation over WT EGFR is 0.1 or less.

Embodiment 244

The method as recited in any one of Embodiments 241-243, wherein the HER2 mutation is chosen from YVMA, GSP, VC, V754M, L755S, L755P, D769H, D769N, Y772dupYVMA, V773M, G776del insVC, G776delinsVV, G776delinsLC, G778insLPS, G778dupGSP, V777L, G778insLPS, G778dupGSP, L786V, V842I, and L869R.

Embodiment 245

A method for treating a cancer or tumor in a subject in need of treatment comprising the steps of:
(a) determining the EGFR genotype of the subject,
(b) identifying the presence of an EGFR mutation in the genotype of the subject; and
(c) administering a compound of claim 1, or a salt thereof, wherein the compound or salt thereof is selective for the EGFR mutation over WT EGFR.

Embodiment 246

The method as recited in Embodiment 245, wherein the selectivity of the compound or salt thereof for the EGFR mutation over WT EGFR is 0.5 or less.

Embodiment 247

The method as recited in Embodiment 246, wherein the selectivity of the compound or salt thereof for the EGFR mutation over WT EGFR is 0.1 or less.

Embodiment 248

The method as recited in any one of Embodiments 245-247, wherein the EGFR mutation is chosen from A763insFQEA, A767insASV, A767insTLA, S768dupSVD, S768dupSVD/C797S, S768dupSVD/T790M, S768I, S768I T790M, V769insASV, V769insGSV, V769insGVV, V769insMASVD, V769L, D770del insGY, D770insG, D770insNPG, D770insNPG/C797S, D770insNPG/T790M, D770insSVD, D770insY H773Y, N771insHH, N771insSVDNR, P772insDNP, H773insAH, H773insH, H773insNPH, H773L/V774M, H773L V774M, and V774insHV.

In one aspect, the present disclosure provides methods of inhibiting at least one HER2 function comprising the step of contacting HER2 with a compound as described herein. The cell phenotype, cell proliferation, activity of HER2, change in biochemical output produced by active HER2, expression of HER2, or binding of HER2 with a natural binding partner may be monitored. Such methods may be modes of treatment of disease, biological assays, cellular assays, biochemical assays, or the like.

Also provided herein is a method of treatment of a HER2-mediated disease comprising the administration of a therapeutically effective amount of a compound as disclosed herein, or a salt thereof, to a patient in need thereof.

In certain embodiments, the HER2-mediated disease is cancer.

Also provided herein is a compound as disclosed herein for use as a medicament.

Also provided herein is a compound as disclosed herein for use as a medicament for the treatment of a HER2-mediated disease.

Also provided is the use of a compound as disclosed herein as a medicament.

Also provided is the use of a compound as disclosed herein as a medicament for the treatment of a HER2-mediated disease.

Also provided is a compound as disclosed herein for use in the manufacture of a medicament for the treatment of a HER2-mediated disease.

Also provided is the use of a compound as disclosed herein for the treatment of a HER2-mediated disease.

Also provided herein is a method of inhibition of HER2 comprising contacting HER2 with a compound as disclosed herein, or a salt thereof.

Compounds of the present disclosure may be selective for a mutant form of HER2 over WT EGFR in various ways. In one aspect, compounds described herein may be selective for a mutant form of HER2 over WT EGFR, wherein HER2 comprises an exon 20 insertion mutation (defined as insertions of 1-18 amino acids between amino acids E770-R786 in HER2). In another aspect, compounds described herein may be selective for a mutant form of HER2 over WT EGFR, wherein HER2 comprises a point mutation in exon 20 excluding C805S in HER2. In yet another aspect, compounds described herein may be selective for a mutant form of HER2 over WT EGFR, wherein HER2 comprises an activating mutation, including but not limited to an extracellular mutation, an exon 19 point mutation such as a mutation at L755 or D769, and an exon 21 point mutation such as a mutation at V842I or L869R. In yet another aspect, compounds described herein may be selective for a mutant form of HER2 over WT EGFR, wherein the mutant form of HER2 is chosen from YVMA, GSP, VC, V754M, L755S, L755P, D769H, D769N, Y772dupYVMA, V773M, G776del insVC, G776delinsVV, G776delinsLC, G778insLPS, G778dupGSP, V777L, G778insLPS, G778dupGSP, L786V, V842I, and L869R.

Certain compounds may display selectivity for a mutant HER2, quantified as the ratio IC50 (mutant HER2)/IC50 (wt EGFR) of 0.5 or less. Certain compounds may display selectivity for a mutant HER2 of 0.2 or less. Certain compounds may display selectivity for a mutant HER2 of 0.05 or less. Certain compounds may display selectivity for a mutant HER2 of 0.02 or less.

Also provided is a method of modulation of a HER2-mediated function in a subject comprising the administration of a therapeutically effective amount of a compound as disclosed herein.

Also provided is a method of treating a subject having a HER2-mediated disease or disorder, such as a cancer or tumor. The method comprises determining that the genotype of the subject comprises a mutant form of HER2, and administering a compound as disclosed herein, or a salt thereof, to the subject.

Also provided is a method for treating a HER2-mediated disease or disorder, such as a cancer or tumor, in a subpopulation of subjects, the subpopulation being characterized by the presence of a mutant form of HER2 in the genotype of the subjects of the subpopulation, and administering a compound as disclosed herein, or a salt thereof, to the subjects in the subpopulation.

Also provided is a method for stratifying a subject for response to therapy comprising administration of a compound as disclosed herein, or a salt thereof, the method comprising the steps of determining the presence of a mutant form of HER2 in the genotype of the subject, and administering a compound as disclosed herein, or a salt thereof.

In one aspect, the present disclosure provides methods of inhibiting at least one EGFR function comprising the step of contacting EGFR with a compound as described herein. The cell phenotype, cell proliferation, activity of EGFR, change in biochemical output produced by active EGFR, expression of EGFR, or binding of EGFR with a natural binding partner may be monitored. Such methods may be modes of treatment of disease, biological assays, cellular assays, biochemical assays, or the like.

Also provided herein is a method of treatment of an EGFR-mediated disease comprising the administration of a therapeutically effective amount of a compound as disclosed herein, or a salt thereof, to a patient in need thereof.

In certain embodiments, the EGFR-mediated disease is cancer.

Also provided herein is a compound as disclosed herein for use as a medicament.

Also provided herein is a compound as disclosed herein for use as a medicament for the treatment of an EGFR-mediated disease.

Also provided is the use of a compound as disclosed herein as a medicament.

Also provided is the use of a compound as disclosed herein as a medicament for the treatment of an EGFR-mediated disease.

Also provided is a compound as disclosed herein for use in the manufacture of a medicament for the treatment of an EGFR-mediated disease.

Also provided is the use of a compound as disclosed herein for the treatment of a HER2-mediated disease.

Also provided herein is a method of inhibition of EGFR comprising contacting EGFR with a compound as disclosed herein, or a salt thereof.

Compounds of the present disclosure may be selective for a mutant form of EGFR over WT EGFR in various ways. In one aspect, compounds described herein may be selective for a mutant form of EGFR over WT EGFR, wherein EGFR comprises an exon 20 insertion mutation (defined as insertions of 1-18 amino acids between amino acids A763-R776 in EGFR). In another aspect, compounds described herein may be selective for a mutant form of EGFR over WT EGFR, wherein EGFR comprises a point mutation in exon 20 excluding C797S in EGFR. In another aspect, compounds described herein may be selective for a mutant form of EGFR over WT EGFR, wherein EGFR comprises an atypical mutation, including but not limited to L719, G724, and L792. In yet another aspect, compounds described herein may be selective for a mutant form of EGFR over WT EGFR, wherein the mutant form of EGFR is chosen from A763insFQEA, A767insASV, A767insTLA, S768dupSVD, S768dupSVD/C797S, S768dupSVD/T790M, S768I, S768I T790M, V769insASV, V769insGSV, V769insGVV, V769insMASVD, V769L, D770del insGY, D770insG, D770insNPG, D770insNPG/C797S, D770insNPG/T790M, D770insSVD, D770insY H773Y, N771insHH, N771insSVDNR, P772insDNP, H773insAH, H773insH, H773insNPH, H773L/V774M, H773L V774M, and V774insHV.

Certain compounds may display selectivity for a mutant EGFR, quantified as the ratio IC50 (mutant EGFR)/IC50 (wt EGFR) of 0.5 or less. Certain compounds may display selectivity for a mutant EGFR of 0.2 or less. Certain compounds may display selectivity for a mutant EGFR of 0.05 or less. Certain compounds may display selectivity for a mutant EGFR of 0.02 or less.

Also provided is a method of modulation of an EGFR-mediated function in a subject comprising the administration of a therapeutically effective amount of a compound as disclosed herein.

Also provided is a method of treating a subject having an EGFR-mediated disease or disorder, such as a cancer or tumor. The method comprises determining that the genotype of the subject comprises a mutant form of EGFR, and administering a compound as disclosed herein, or a salt thereof, to the subject.

Also provided is a method for treating an EGFR-mediated disease or disorder, such as a cancer or tumor, in a subpopulation of subjects, the subpopulation being characterized by the presence of a mutant form of EGFR in the genotype of the subjects of the subpopulation, and administering a compound as disclosed herein, or a salt thereof, to the subjects in the subpopulation.

Also provided is a method for stratifying a subject for response to therapy comprising administration of a compound as disclosed herein, or a salt thereof, the method comprising the steps of determining the presence of a mutant form of EGFR in the genotype of the subject, and administering a compound as disclosed herein, or a salt thereof.

Thus, in another aspect, certain embodiments provide methods for treating disorders mediated by HER2 or EGFR in a human or animal subject in need of such treatment comprising administering to said subject an amount of a compound disclosed herein effective to reduce or prevent said disorder in the subject.

In certain embodiments, the disorder is a cancer. The cancer may be any cancer now known, or later discovered, including, but not limited to, Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma), Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, Low Malignant Potential Tumor and High Grade Serous Ovarian Cancer), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia and Wilms Tumor, or a variant thereof.

In certain embodiments, the cancer is chosen from small cell lung cancer, non small cell lung cancer, lung adenocarcinoma, colorectal cancer, pancreatic cancer, head and neck cancer, breast cancer, ovarian cancer, stomach cancer, and uterine cancer.

Also provided is a pharmaceutical composition comprising a compound as disclosed herein, together with a pharmaceutically acceptable carrier.

In certain embodiments, the pharmaceutical composition is formulated for oral administration. In certain embodiments, the pharmaceutical composition is formulated for parenteral administration. In certain embodiments, the pharmaceutical composition is formulated for intravenous administration. In certain embodiments, the pharmaceutical composition is formulated for intramuscular administration. In certain embodiments, the pharmaceutical composition is formulated for subcutaneous administration.

In certain embodiments, the oral pharmaceutical composition is chosen from a tablet and a capsule.

Definitions

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH$—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzindolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently chosen from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"HER2 inhibitor" is used herein to refer to a compound that exhibits an IC50 with respect to HER2 activity of no more than about 100 µM and more typically not more than about 50 µM, as measured in the HER2 assay described generally herein. "IC50" is that concentration of inhibitor which reduces the activity of an enzyme (e.g., HER2) to half-maximal level. Certain compounds disclosed herein have been discovered to exhibit inhibition against HER2. In certain embodiments, compounds will exhibit an IC50 with respect to HER2 of no more than about 10 µM; in further embodiments, compounds will exhibit an IC50 with respect to HER2 of no more than about 1 µM; in yet further embodiments, compounds will exhibit an IC50 with respect to HER2 of not more than about 200 nM; in yet further embodiments, compounds will exhibit an IC50 with respect to HER2 of not more than about 50 nM, as measured in the HER2 assay described herein.

Certain compounds display selectivity for certain mutant forms of HER2 over WT EGFR. For certain compounds and certain mutants, the mutant HER2 selectivity, quantified as the ratio $IC_{50}$ (HER2 mutant)/$IC_{50}$ (WT EGFR) is 0.5 or lower. For certain compounds and certain mutants, the mutant HER2 selectivity is 0.2 or lower. For certain compounds and certain mutants, the mutant HER2 selectivity is 0.1 or lower.

"EGFR inhibitor" is used herein to refer to a compound that exhibits an $IC_{50}$ with respect to EGFR activity of no more than about 100 µM and more typically not more than about 50 µM, as measured in the EGFR assay described generally herein. "$IC_{50}$" is that concentration of inhibitor which reduces the activity of an enzyme (e.g., EGFR) to half-maximal level. Certain compounds disclosed herein have been discovered to exhibit inhibition against EGFR. In certain embodiments, compounds will exhibit an $IC_{50}$ with respect to EGFR of no more than about 10 µM; in further embodiments, compounds will exhibit an $IC_{50}$ with respect to EGFR of no more than about 1 µM; in yet further embodiments, compounds will exhibit an $IC_{50}$ with respect to EGFR of not more than about 200 nM; in yet further embodiments, compounds will exhibit an $IC_{50}$ with respect to EGFR of not more than about 50 nM, as measured in the EGFR assay described herein.

Certain compounds display selectivity for certain mutant forms of EGFR over WT EGFR. For certain compounds and certain mutants, the mutant EGFR selectivity, quantified as the ratio $IC_{50}$ (EGFR mutant)/$IC_{50}$ (WT EGFR) is 0.5 or lower. For certain compounds and certain mutants, the mutant EGFR selectivity is 0.2 or lower. For certain compounds and certain mutants, the mutant EGFR selectivity is 0.1 or lower.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Oral Administration

The compounds of the present disclosure may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules, solutions or suspensions in an aqueous liquid or a non-aqueous liquid, or as an oil-in-water liquid emulsion or a water-in-oil liquid emulsion. The active ingredient may also be presented as a bolus, electuary or paste.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Parenteral Administration

Compounds of the present disclosure may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions. Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present disclosure may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

Rectal, Buccal, and Sublingual Administration

Suppositories for rectal administration of the compounds of the present disclosure can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Administration by Inhalation

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the disclosure may be prepared by any of the well-known techniques of pharmacy, such as effective formulation and administration procedures. Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Combinations and Combination Therapy

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

In another aspect, a compound with EGFR or HER2 inhibitory properties, as disclosed herein, is optionally used in combination with procedures that provide additional benefit to the patient. The inhibitor and any additional therapies are optionally administered before, during, or after the occurrence of a disease or condition, and the timing of administering the composition containing the inhibitor varies in some embodiments. Thus, for example, the inhibitor may be used as a prophylactic and is administered continuously to subjects with a propensity to develop conditions or diseases in order to prevent the occurrence of the disease or condition. The inhibitor and compositions are optionally administered to a subject during or as soon as possible after the onset of the symptoms.

A compound with EGFR or HER2 inhibitory properties, as disclosed herein, can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in the treatment or attenuation of cancer and neoplastic diseases, a compound with EGFR or HER2 inhibitory properties, as disclosed herein, may be optimally used together with one or more of the following non-limiting examples of anti-cancer agents, including, but not limited to:

1) inhibitors or modulators of a protein involved in one or more of the DNA damage repair (DDR) pathways such as:
   a. PARP1/2, including, but not limited to: olaparib, niraparib, rucaparib;
   b. checkpoint kinase 1 (CHK1), including, but not limited to: UCN-01, AZD7762, PF477736, SCH900776, MK-8776, LY2603618, V158411, and EXEL-9844;
   c. checkpoint kinase 2 (CHK2), including, but not limited to: PV1019, NSC 109555, and VRX0466617;
   d. dual CHK1/CHK2, including, but not limited to: XL-844, AZD7762, and PF-473336;
   e. WEE1, including, but not limited to: MK-1775 and PD0166285;
   f. ATM, including, but not limited to KU-55933,
   g. DNA-dependent protein kinase, including, but not limited to NU7441 and M3814; and
   h. Additional proteins involved in DDR;

2) Inhibitors or modulators of one or more immune checkpoints, including, but not limited to:
   a. PD-1 inhibitors such as nivolumab (OPDIVO), pembrolizumab (KEYTRUDA), pidilizumab (CT-011), and AMP-224 (AMPLIMMUNE);
   b. PD-L1 inhibitors such as Atezolizumab (TECENTRIQ), Avelumab (Bavencio), Durvalumab (Imfinzi), MPDL3280A (Tecentriq), BMS-936559, and MEDI4736;
   c. anti-CTLA-4 antibodies such as ipilimumab (YERVOY) and CP-675,206 (TREMELIMUMAB);
   d. inhibitors of T-cell immunoglobulin and mucin domain 3 (Tim-3);
   e. inhibitors of V-domain Ig suppressor of T cell activation (Vista);
   f. inhibitors of band T lymphocyte attenuator (BTLA);
   g. inhibitors of lymphocyte activation gene 3 (LAG3); and
   h. inhibitors of T cell immunoglobulin and immunoreceptor tyrosine-based inhibitory motif domain (TIGIT);

3) telomerase inhibitors or telomeric DNA binding compounds;

4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;

5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);

6) anti-metabolites, including, but not limited to: cladribine (LEUSTATIN), cytarbine, (ARA-C), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSI-LEV), methotrexate (RHEUMATREX), and raltitrexed;

7) antimitotics, which are often plant alkaloids and terpenoids, or derivatives thereof including but limited to: taxanes such as docetaxel (TAXITERE), paclitaxel (ABRAXANE, TAXOL), *vinca* alkaloids such as vincristine (ONCOVIN), vinblastine, vindesine, and vinorelbine (NAVELBINE);

8) topoisomerase inhibitors, including, but not limited to: amsacrine, camptothecin (CTP), genistein, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VUMON), mitoxantrone (NOVANTRONE), and etoposide (EPOSIN);

9) DNA replication inhibitors, including, but not limited to: fludarabine (FLUDARA), aphidicolin, ganciclovir, and cidofovir;

10) ribonucleoside diphosphate reductase inhibitors, including, but not limited to: hydroxyurea;

11) transcription inhibitors, including, but not limited to: actinomycin D (dactinomycin, COSMEGEN) and plicamycin (mithramycin);

12) DNA cleaving agents, including, but not limited to: bleomycin (BLENOXANE), idarubicin, 13) cytotoxic antibiotics, including, but not limited to: actinomycin D (dactinomycin, COSMEGEN), 14) aromatase inhibitors, including, but not limited to: aminoglutethimide, anastrozole (ARIMIDEX), letrozole (FEMARA), vorozole (RIVIZOR), and exemestane (AROMASIN);

15) angiogenesis inhibitors, including, but not limited to: genistein, sunitinib (SUTENT), ramucirumab (CYRAMZA), and bevacizumab (AVASTIN);

16) anti-steroids and anti-androgens, including, but not limited to: aminoglutethimide (CYTADREN), bicalutamide (CASODEX), cyproterone, flutamide (EULEXIN), nilutamide (NILANDRON);

17) tyrosine kinase inhibitors, including, but not limited to: imatinib (GLEEVEC), erlotinib (TARCEVA), lapatinib (TYKERB), sorafenib (NEXAVAR), and axitinib (INLYTA);

18) mTOR inhibitors, including, but not limited to: everolimus, temsirolimus (TORISEL), and sirolimus;

19) monoclonal antibodies, including, but not limited to: trastuzumab (HERCEPTIN) and rituximab (RITUXAN);

20) drug-antibody conjugates, including but not limited to trastuzumab emtansine (T-DM1 or KADCYLA™), lorvotuzumab mertansine, cantuzumab mertansine, bivatuzumab mertansine, cantuzumab mertansine, lorvotuzumab mertansine, gemtuzumab ozogamicin, brentuximab vedotin, trastuzumab deruxtecan, enfortumab vedotin, polatuzumab vedotin-piiq, and inotuzumab ozogamicin;

21) apoptosis inducers such as cordycepin;

22) protein synthesis inhibitors, including, but not limited to: clindamycin, chloramphenicol, streptomycin, anisomycin, and cycloheximide;

23) antidiabetics, including, but not limited to: metformin and phenformin;

24) antibiotics, including, but not limited to:
    a. tetracyclines, including, but not limited to: doxycycline;
    b. erythromycins, including, but not limited to: azithromycin;
    c. glycylglycines, including, but not limited to: tigecyline;
    d. antiparasitics, including, but not limited to: pyrvinium pamoate;
    e. beta-lactams, including, but not limited to the penicillins and cephalosporins;
    f. anthracycline antibiotics, including, but not limited to: daunorubicin and doxorubicin;
    g. other antibiotics, including, but not limited to: chloramphenicol, mitomycin C, and actinomycin;

25) antibody therapeutic agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and 26) other agents, such as *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

Where a subject is suffering from or at risk of suffering from an inflammatory condition, a compound with EGFR or HER2 inhibitory properties, as disclosed herein, is optionally used together with one or more agents or methods for treating an inflammatory condition in any combination. Therapeutic agents/treatments for treating an autoimmune and/or inflammatory condition include, but are not limited to any of the following examples:

1) corticosteroids, including but not limited to cortisone, dexamethasone, and methylprednisolone;

2) nonsteroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE);

3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN);

4) CD20 blockers, including but not limited to rituximab (RITUXAN);

5) Tumor Necrosis Factor (TNF) blockers, including but not limited to etanercept (ENBREL), infliximab (REMICADE) and adalimumab (HUMIRA);
6) interleukin-1 receptor antagonists, including but not limited to anakinra (KINERET);
7) interleukin-6 inhibitors, including but not limited to tocilizumab (ACTEMRA);
8) interleukin-17 inhibitors, including but not limited to AIN457;
9) Janus kinase inhibitors, including but not limited to tasocitinib; and
10) syk inhibitors, including but not limited to fostamatinib.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Compound Synthesis

Compounds of the present disclosure can be prepared using methods illustrated in general synthetic schemes and experimental procedures detailed below. General synthetic schemes and experimental procedures are presented for purposes of illustration and are not intended to be limiting. Starting materials used to prepare compounds of the present disclosure are commercially available or can be prepared using routine methods known in the art.

Abbreviations $Ac_2O$=acetic anhydride; AcCl=acetyl chloride; AcOH=acetic acid; AIBN=azobisisobutyronitrile; aq.=aqueous; $Bu_3SnH$=tributyltin hydride; $CD_3OD$=deuterated methanol; $CDCl_3$=deuterated chloroform; CDI=1,1'-Carbonyldiimidazole; CR=complete response (no palpable tumor); DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; EDC.HCl=EDCI.HCl=1-ethyl-3-(3-dimethylaminopropyl)carbodiimide hydrochloride; EGFR=HER1=ErbB1=human epidermal growth factor receptor); $Et_2O$=diethyl ether; EtOAc=ethyl acetate; EtOH=ethanol; h=hour; FACS=fluorescence activated cell sorting; FBS=fetal bovine serum; FITC=fluorescein isothiocyanate; HATU=2-(1H-7-azabenzotriazol-1-yl)-1,1,3,3-tetramethyl uronium hexafluorophosphate methanaminium; HER2=Neu=ErbB2=human epidermal growth factor receptor 2; HMDS=hexamethyldisilazane; HOBT=1-hydroxybenzotriazole; i-PrOH=isopropanol; IL-3=interleukin-3; LAH=$LiAlH_4$=lithium aluminium hydride; LiHMDS=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; MW=microwave irradiation; n-BuLi=n-butyllithium; NaHMDS=Sodium bis(trimethylsilyl)amide; NaOMe=sodium methoxide; NaOtBu=sodium t-butoxide; NBS=N-bromosuccinimide; NCS=N-chlorosuccinimide; NMP=N-Methyl-2-pyrrolidone; PDF=patient-derived xenograft; $Pd(Ph_3)_4$=tetrakis(triphenylphosphine)-palladium(0); $Pd_2(dba)_3$=tris(dibenzylideneacetone)dipalladium(0); $PdCl_2(PPh_3)_2$=bis(triphenylphosphine)palladium(II) dichloride; PE=phycoerythrin; PG=protecting group; prep-HPLC=preparative high-performance liquid chromatography; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; t-BuOH=tert-butanol; T3P=Propylphosphonic Anhydride; TBS=TBDMS=tert-butyldimethylsilyl; TBSCl=TBDMSCl=tert-butyldimethylchlorosilane; TEA=$Et_3N$=triethylamine; TFA=trifluoroacetic acid; TFAA=trifluoroacetic anhydride; THF=tetrahydrofuran; Tol=toluene; TsCl=p-toluenesulfonyl chloride=tosyl chloride; XPhos=2-dicyclohexylphosphino-2',4',6'-triisopropylbiphenyl.

General Synthetic Methods for Preparing Compounds

The following schemes can be used to practice the present disclosure.

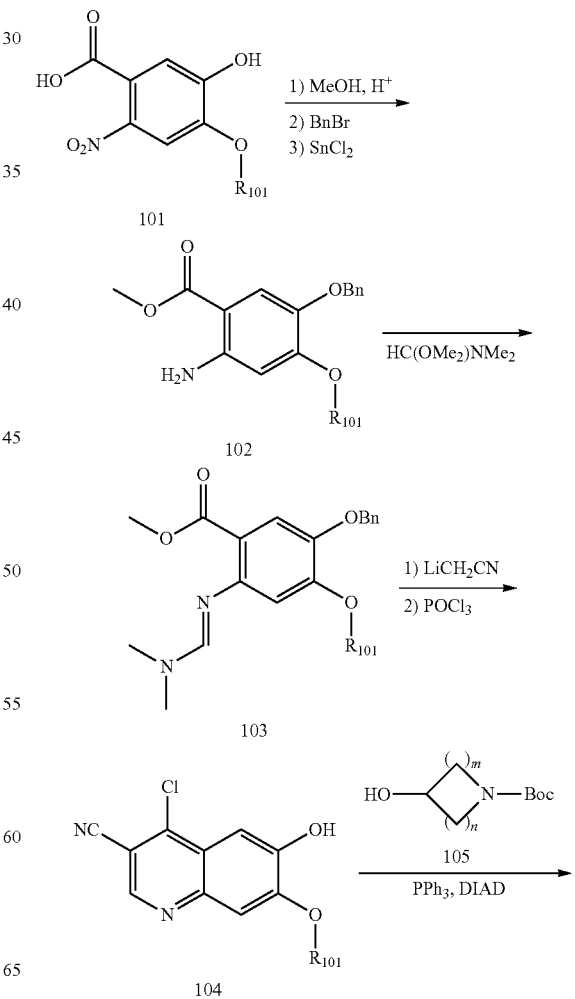

Scheme I

Scheme II

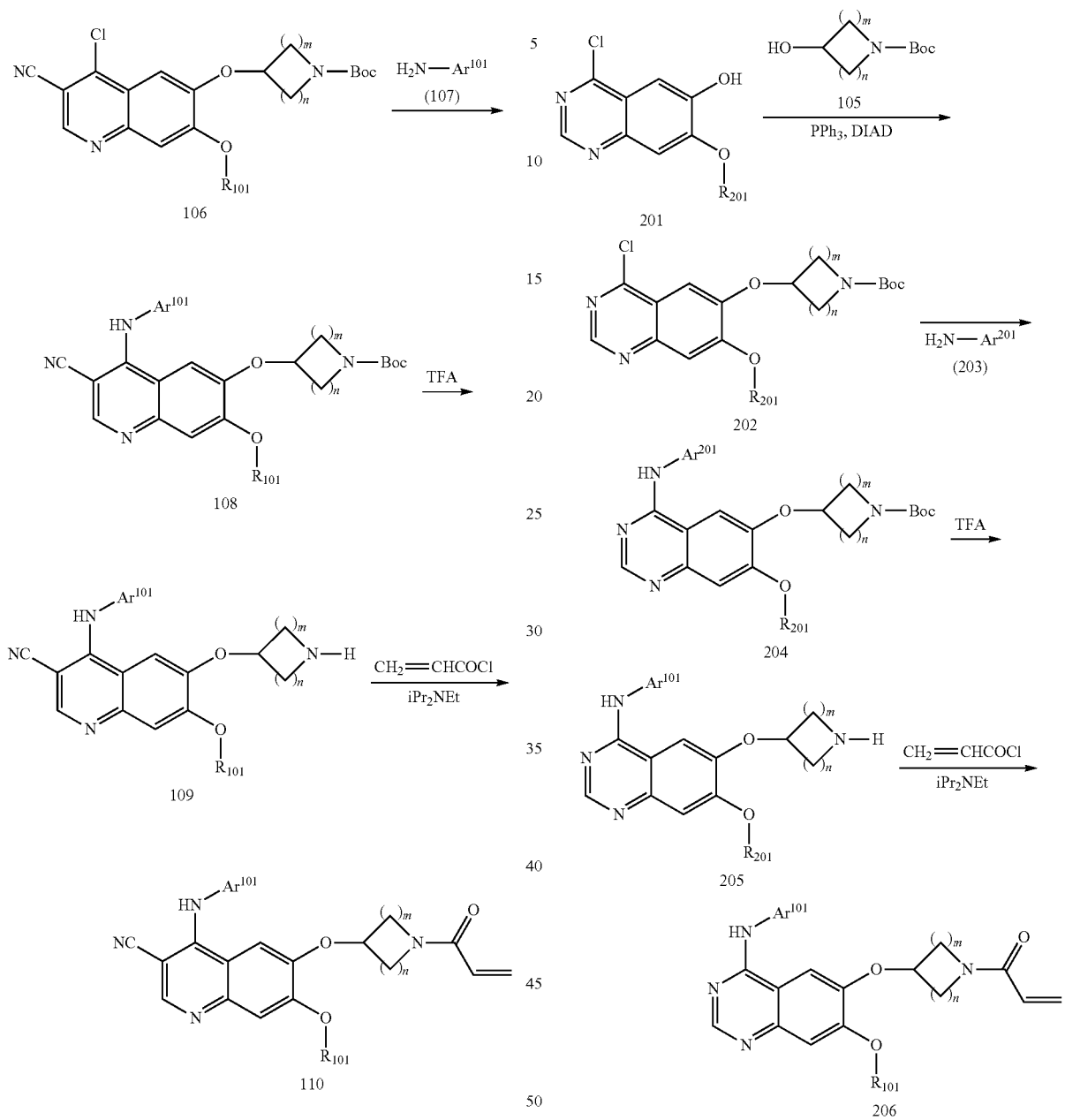

Certain examples disclosed herein can be synthesized using the following general synthetic procedure set forth in Scheme I. The functional groups of starting material 101 are manipulated via sequential Fisher esterification, Williamson ether formation, and nitro group reduction to give functionalized benzene 102. Condensation with DMF dimethyl acetal gives amidine 103, which is converted to chloro quinoline 104 via ring formation with acetonitrile anion, followed by chlorination of the intermediate quinolone compound (not shown). Mitsunobu-type coupling of secondary alcohol 105 with phenol 104 provides ether 106. $S_N Ar$ reaction with arylamine 107 gives the substitution product 108. After removal of the Boc protecting group, secondary amine 109 is reacted with acryloyl chloride to give amide 110.

Certain examples disclosed herein can be synthesized using the following general synthetic procedure set forth in Scheme II. Synthesis proceeds as for Scheme I, with the difference being the choice of quinazoline starting material 201.

Scheme III

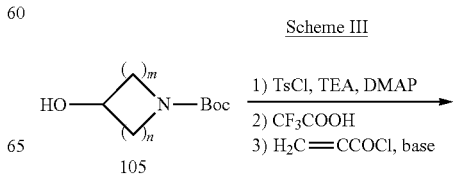

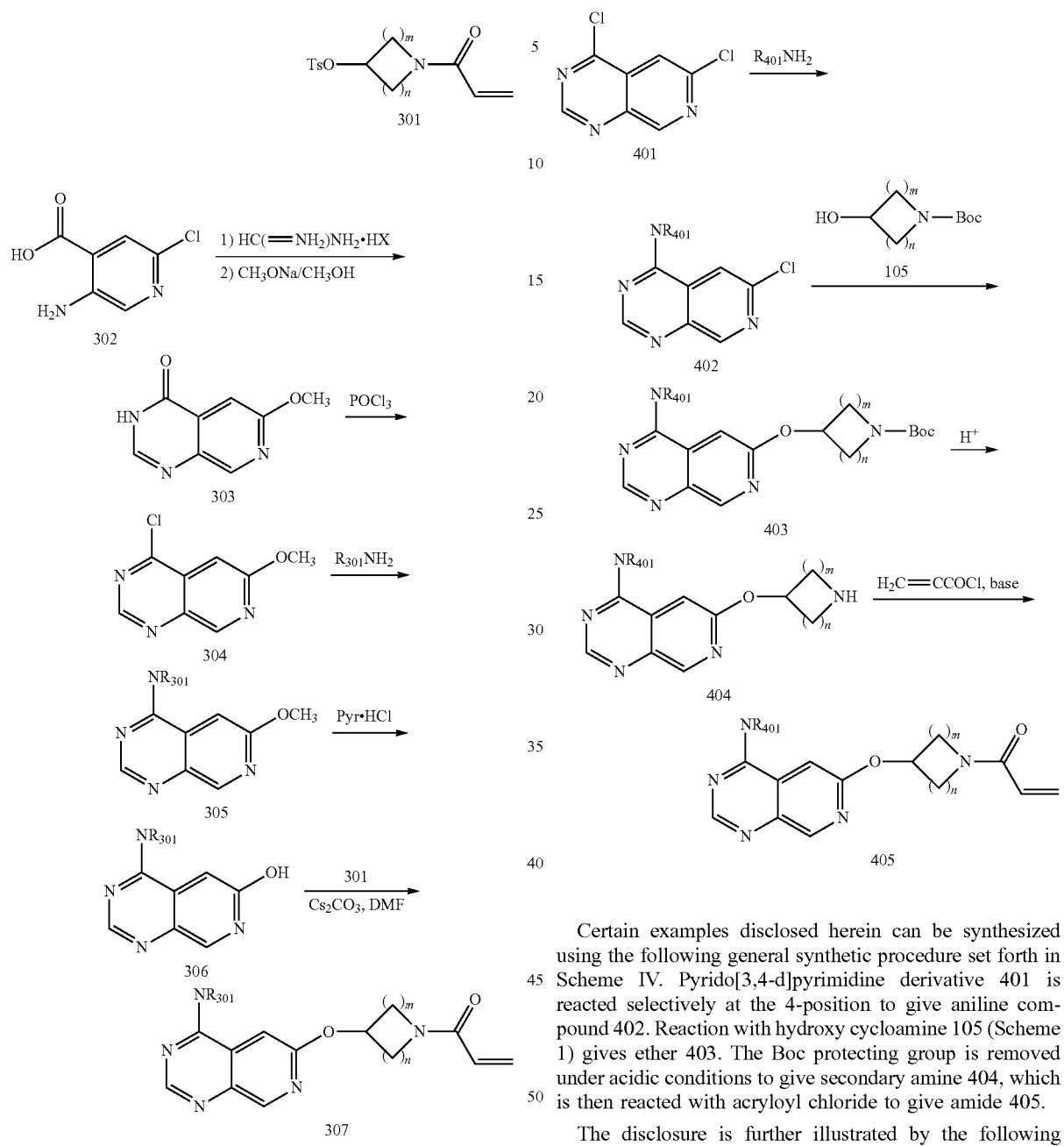

Certain examples disclosed herein can be synthesized using the following general synthetic procedure set forth in Scheme III. Heterocyclic tosylate 301 is prepared in three steps from Boc-protected hydroxy cycloamine 105 (Scheme I). Anthranilic acid analogue 302 is converted into a bicyclic arene with formamidine, followed by displacement of the choride to form phenolic ether 303. Reaction with phosphorus oxychloride converts the amide functionality to chloro compound 304. Reaction with $R_{301}NH_2$ gives aminoarene 305. The methoxy group is removed under acidic conditions to give phenol 306. Finally, reaction of the phenol with tosylate 301 under Williamson ether synthesis conditions gives 307.

Certain examples disclosed herein can be synthesized using the following general synthetic procedure set forth in Scheme IV. Pyrido[3,4-d]pyrimidine derivative 401 is reacted selectively at the 4-position to give aniline compound 402. Reaction with hydroxy cycloamine 105 (Scheme 1) gives ether 403. The Boc protecting group is removed under acidic conditions to give secondary amine 404, which is then reacted with acryloyl chloride to give amide 405.

The disclosure is further illustrated by the following examples.

Intermediate A

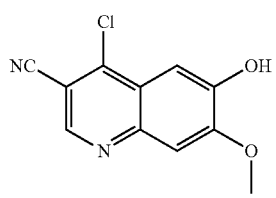 [SMILES: COc1cc2ncc(C#N)c(Cl)c2cc1O]

4-chloro-6-hydroxy-7-methoxyquinoline-3-carbonitrile

Step 1

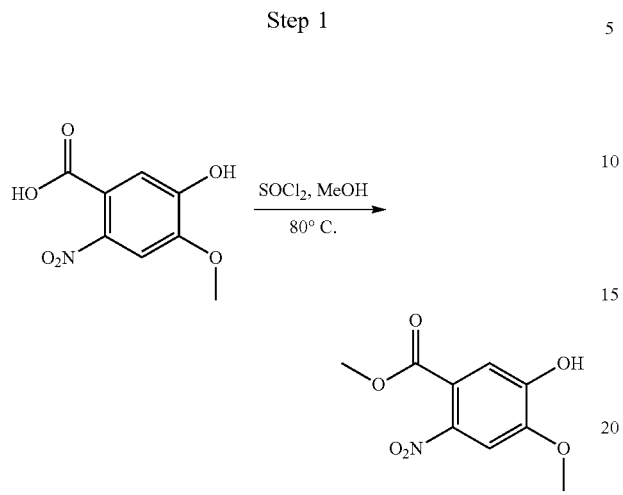

Methyl 5-hydroxy-4-methoxy-2-nitrobenzoate

A solution of 5-hydroxy-4-methoxy-2-nitrobenzoic acid (5.3 g, 24.9 mmol) and SOCl$_2$ (2 ml, 28 mmol) in MeOH (50 mL) was stirred at 80° C. for 16 h. The solvent was removed to give the title compound as a white solid (5.3 g, 94%). MS (ES+) C$_9$H$_9$NO$_6$ requires: 227, found: 228 [M+H]$^+$.

Step 2

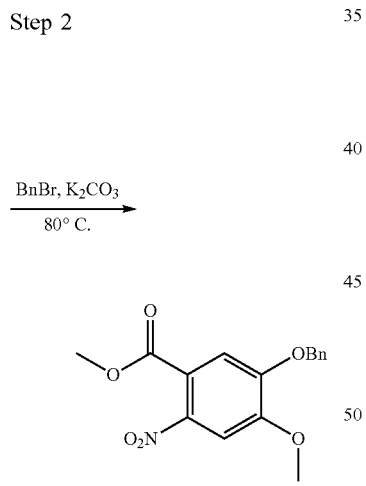

Methyl 5-(benzyloxy)-4-methoxy-2-nitrobenzoate

A solution of the product from the previous step (5.3 g, 23 mmol), (bromomethyl)benzene (6.0 g, 35 mmol) and K$_2$CO$_3$ (6.3 g, 46 mmol) in MeCN (100 mL) was stirred at 80° C. for 4 h. The solvent was removed, the residue taken up in water, and the product extracted with EtOAc. The combined organics were washed with brine, dried over Na$_2$SO$_4$, filtered and concentrated to give the title compound as a yellow solid (7 g, 97%). MS (ES+) C$_{16}$H$_{15}$NO$_6$ requires: 317, found: 318[M+H]$^+$.

Step 3

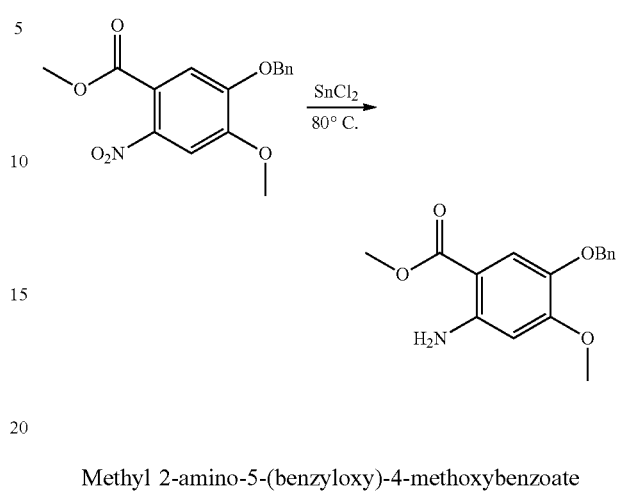

Methyl 2-amino-5-(benzyloxy)-4-methoxybenzoate

To a solution of the product from the previous step (3.17 g, 10 mmol) in EtOH (100 mL) was added SnCl$_2$.H$_2$O (11.3 g, 55 mmol) and the mixture was stirred at 80° C. overnight. The mixture was quenched with sat. NaHCO$_3$ solution. The insoluble material was removed by filtration and the filtrate was extracted with EtOAc. The organic layer was washed with brine, dried over MgSO$_4$, filtered and concentrated to give the title compound as a white solid (4.2 g, crude 70%). MS (ES+) C$_{11}$H$_{10}$BrN requires: 287, found: 288 [M+H]$^+$.

Step 4

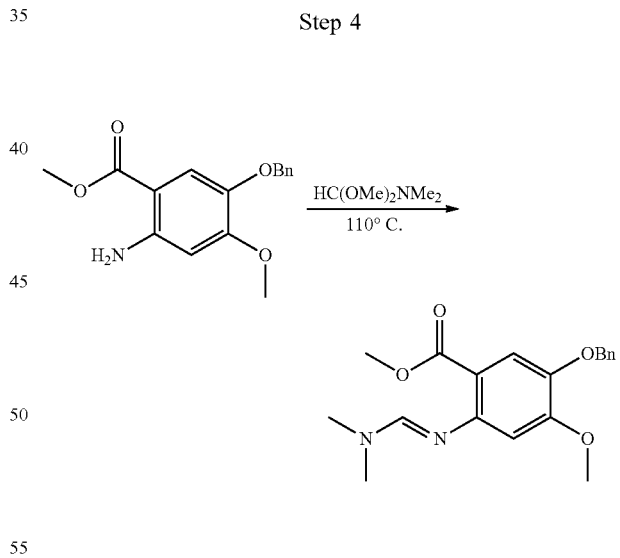

(E)-Methyl 5-(benzyloxy)-2-(((dimethylamino)methyleneamino)-4-methoxybenzoate

A solution of the product from the previous step (4.1 g, 14.3 mmol) and DMF dimethyl acetal (10 ml) in DMF (20 mL) was heated at 110° C. for 3 h, diluted with water, and extracted with EtOAc. The combined organic layers were washed with brine, dried over Na$_2$SO$_4$, filtered and concentrated to give the title compound as a yellow solid (4.5 g, 87.%). MS (ES+) C$_{19}$H$_{22}$N$_2$O$_4$ requires: 342, found: 343 [M+H]$^+$.

Step 5

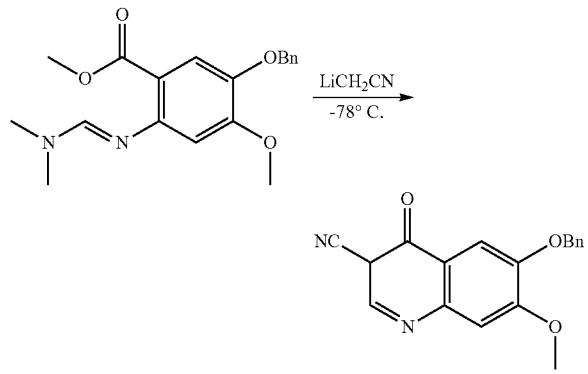

6-(Benzyloxy)-7-methoxy-4-oxo-3,4-dihydroquinoline-3-carbonitrile

To a solution of MeCN (180 mg, 4.38 mmol) in THF (6 ml) at −78° C. was slowly added n-BuLi (2.2 ml, 4.38 mmol). The solution was stirred at −78° C. for 30 min and then a solution of the product from the previous step (600 mg, 1.75 mmol) in THF (4 ml) was slowly added. The mixture was stirred at −78° C. for 1 h. AcOH (0.2 ml) was added, the mixture was diluted with water and CHCl$_3$, filtered and dried in vacuo to give the title compound as a yellow solid (260 mg, 48%). MS (ES+) $C_{18}H_{14}N_2O_3$ requires: 306, found: 307 [M+H]$^+$.

Step 6

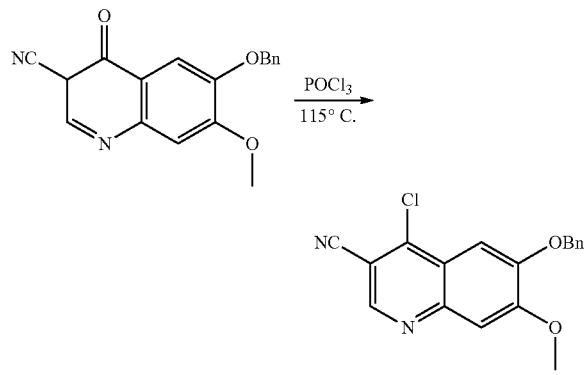

6-(Benzyloxy)-4-chloro-7-methoxyquinoline-3-carbonitrile

A mixture of the product from the previous step in POCl$_3$ (5 ml) was stirred at 115° C. for 2 h. The solvent was evaporated and the residue was taken up in aqueous NaHCO$_3$ and extracted with DCM. The combined organic layers were washed with brine, dried over Na$_2$SO$_4$, filtered and concentrated to give the title compound as a yellow solid (300 mg, 92%). MS (ES+) $C_{18}H_{13}ClN_2O_2$ requires: 324, found: 325 [M+H]$^+$.

Step 7

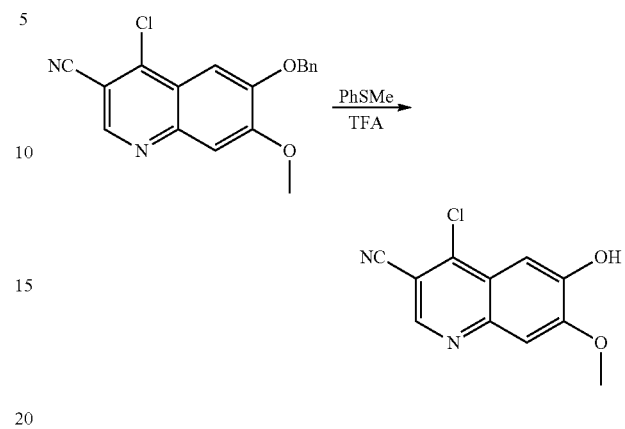

4-Chloro-6-hydroxy-7-methoxyquinoline-3-carbonitrile (Intermediate A)

A mixture of the product from the previous step (300 mg, 0.93 mmol) and PhSMe (2 ml, 17.0 mmol) in TFA (15 ml) was stirred at 80° C. for 2 h. The solvent was removed and the residue was stirred with ice water and NH$_4$OH was slowly added. The reaction mixture was filtered and the solids were washed with EtOAc to give the title compound as a yellow solid (180 mg, 83%). MS (ES+) $C_{11}H_7ClN_2O_2$ requires: 234, found: 235 [M+H]$^+$.

Intermediate B tert-Butyl 4-((4-chloro-3-cyano-7-methoxyquinolin-6-yl)oxy)piperidine-1-carboxylate

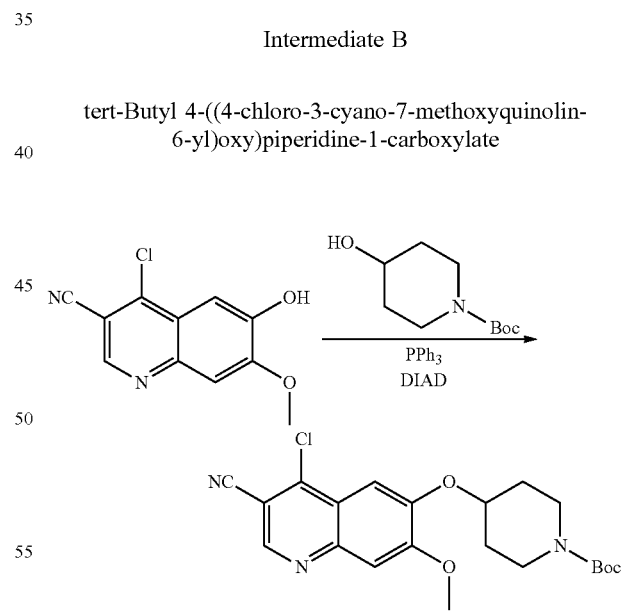

To a mixture of Intermediate A, (235 mg, 1 mmol), PPh$_3$ (393 mg, 1.5 mmol) and tert-butyl 4-hydroxypiperidine-1-carboxylate (201 mg, 1 mmol) in THF (8 ml) at 0° C. was slowly added DIAD (303 mg, 1.5 mmol) in THF (2 ml). The mixture was stirred at RT for 16 h and then purified by silica gel column (0-30% EtOAc in PE) to give a white solid (300 mg, 72%). MS (ES+) $C_{21}H_{24}ClN_3O_4$ requires: 417, found: 418 [M+H]$^+$.

Intermediate C tert-Butyl 3-((4-chloro-7-methoxyquinazolin-6-yl)oxy)azetidine-1-carboxylate

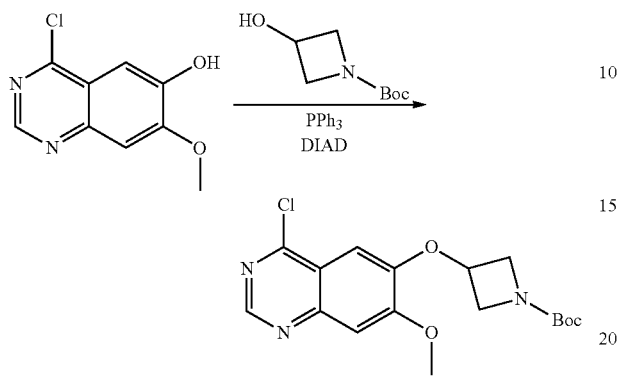

To a suspension of PPh$_3$ (4.23 g, 16.14 mmol) in dioxane (60 ml) was added diisopropyl (E)-diazene-1,2-dicarboxylate (2.88 g, 14.24 mmol) and the resulting mixture was stirred at room temperature for 20 minutes. tert-Butyl 3-hydroxyazetidine-1-carboxylate (1.809 g, 10.45 mmol) was added and the reaction was stirred at room temperature for an additional 20 minutes. 4-Chloro-7-methoxyquinazolin-6-ol (2.00 g, 9.50 mmol) was then added and the reaction was heated at 70° C. overnight. The volatiles were removed under reduced pressure. The residue was purified via silica gel chromatography (20-100% EtOAc in hexanes) to give the title compound (3.00 g, 8.20 mmol, 86% yield) as a white solid. Product was a mixture of desired product and tert-Butyl 3-hydroxyazetidine-1-carboxylate and was carried through to the next reaction. MS (ES+) C$_{17}$H$_{20}$ClN$_3$O$_4$ requires: 365, found: 366 [M+H]$^+$.

Intermediate D tert-Butyl 3-((4-chloro-3-cyano-7-methoxyquinolin-6-yl)oxy)azetidine-1-carboxylate

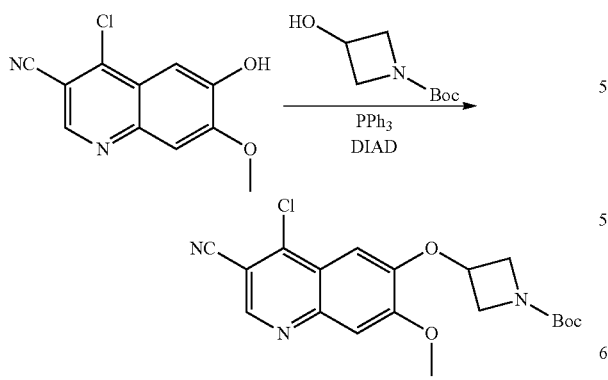

To a mixture of Intermediate A, (235 mg, 1 mmol), PPh$_3$ (393 mg, 1.5 mmol) and tert-butyl 3-hydroxyazetidine-1-carboxylate (173 mg, 1 mmol) in THF (8 ml) at 0° C. was slowly added DIAD (303 mg, 1.5 mmol) in THF (2 ml). The mixture was stirred at RT for 16 h and then purified by silica gel column (0-30% EtOAc in PE) to give a white solid (260 mg, 67%). MS (ES+) C$_{19}$H$_{20}$ClN$_3$O$_4$ requires: 389, found: 390 [M+H]$^+$.

Example 1

1-(4-((4-((2,4-dichlorophenyl)amino)-7-methoxyquinazolin-6-yl)oxy)piperidin-1-yl)-prop-2-en-1-one

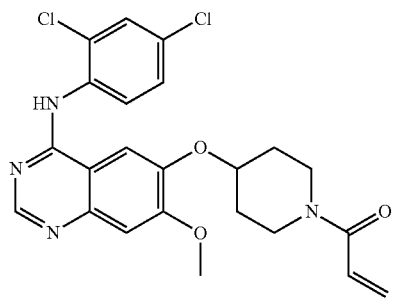 [SMILES: C=CC(=O)N1CCC(Oc2cc3c(Nc4ccc(Cl)cc4Cl)ncnc3cc2OC)CC1]

Step 1

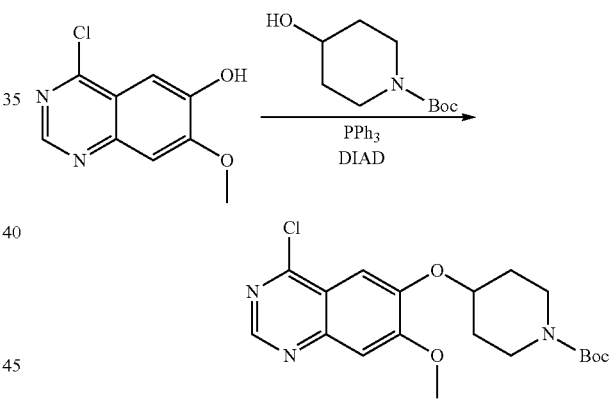

tert-butyl 4-((4-chloro-7-methoxyquinazolin-6-yl)oxy)piperidine-1-carboxylate

To a suspension of PPh$_3$ (210 mg, 0.80 mmol) in dioxane (3 ml) was added diisopropyl (E)-diazene-1,2-dicarboxylate (140 µL, 0.72 mmol) and the resulting mixture was stirred at room temperature for 20 minutes. tert-butyl 4-hydroxypiperidine-1-carboxylate (143 mg, 0.72 mmol) was added and the reaction was stirred at room temperature for an additional 20 minutes. 4-Chloro-7-methoxyquinazolin-6-ol (100 mg, 0.48 mmol) was then added and the reaction was heated at 70° C. overnight. The volatiles were removed under reduced pressure. The residue was purified via silica gel chromatography (25-100% EtOAc in hexanes) to give the title compound (144 mg, 0.37 mmol, 77% yield) as a white solid. MS (ES+) C$_{19}$H$_{24}$ClN$_3$O$_4$ requires: 393, found: 394 [M+H]$^+$.

91

Step 2

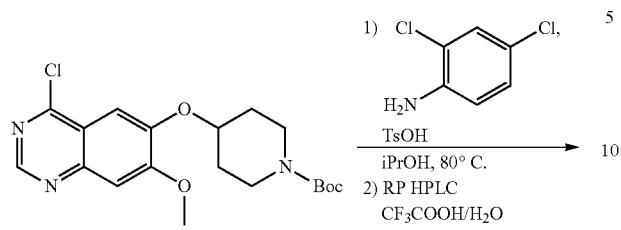

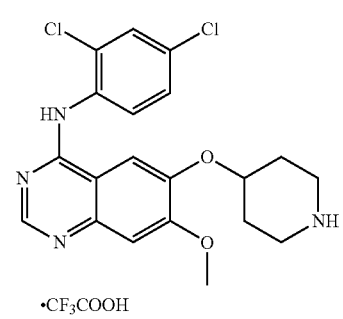

•CF₃COOH

N-(2,4-dichlorophenyl)-7-methoxy-6-(piperidin-4-yloxy)quinazolin-4-amine Trifluoroacetate To a solution of tert-butyl 4-((4-chloro-7-methoxyquinazolin-6-yl)oxy)piperidine-1-carboxylate (50 mg, 0.127 mmol) and 2,4-dichloroaniline (41 mg, 0.254 mmol) in 2-propanol (3 ml) was added toluenesulfonic acid (2.2 mg, 0.0127 mmol) and the resulting mixture was stirred at 80° C. for 16 hours. The volatiles were removed under reduced pressure. The residue was purified by mass-triggered preparative HPLC (Mobile phase: A=0.1% TFA/H₂O, B=0.1% TFA/MeCN; Gradient: B=10-60%; 12 min; Column: C18) to give the title compound (impure) as a brown amorphous material that was carried on to the next step. MS (ES+) $C_{20}H_{20}Cl_2N_4O_2$ requires: 418, found: 419 [M+H]⁺.

Step 3

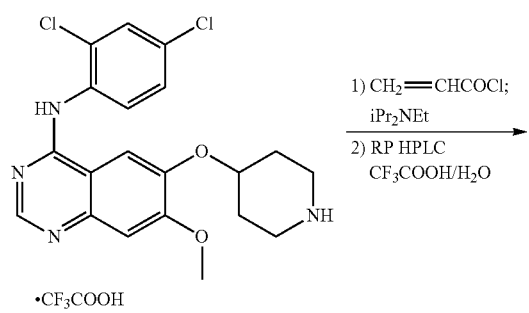

•CF₃COOH

92

-continued

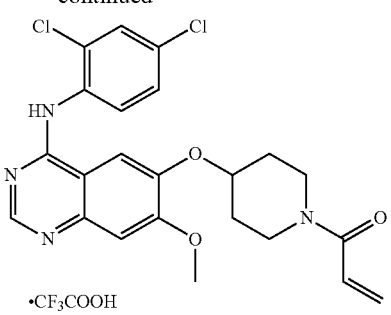

•CF₃COOH 1-(4-((4-((2,4-Dichlorophenyl)amino)-7-methoxy-quinazolin-6-yl)oxy)piperidin-1-yl)prop-2-en-1-one Trifluoroacetate To a solution of the product from the previous step in CH₂Cl₂ (3 ml) was added iPr₂NEt (67 μL, 0.382 mmol) and acryloyl chloride (10.2 μL, 0.129 mmol). The resulting mixture was stirred at room temperature for 30 minutes and then concentrated under reduced pressure. The residue was purified by mass-triggered preparative HPLC (Mobile phase: A=0.1% TFA/H₂O, B=0.1% TFA/MeCN; Gradient: B=30-70%; 12 min; Column: C18) to give the title compound (8.2 mg, 0.014 mmol, 11% yield) as a brown amorphous solid. MS (ES+) $C_{23}H_{22}Cl_2N_4O_3$ requires: 472, found: 473 [M+H]⁺.

Example 2

1-(3-((4-((2,4-dichlorophenyl)amino)pyrido[3,4-d]pyrimidin-6-yl)oxy)azetidin-1-yl)-prop-2-en-1-one

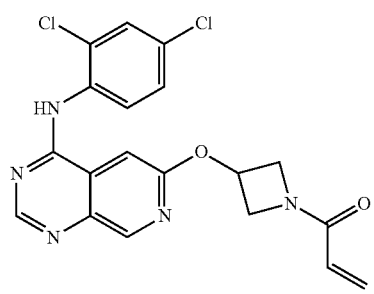 [SMILES: C=CC(=O)N1CC(Oc2cc3c(Nc4ccc(Cl)cc4Cl)ncnc3cn2)C1]

Step 1

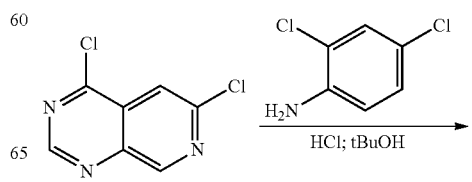

-continued

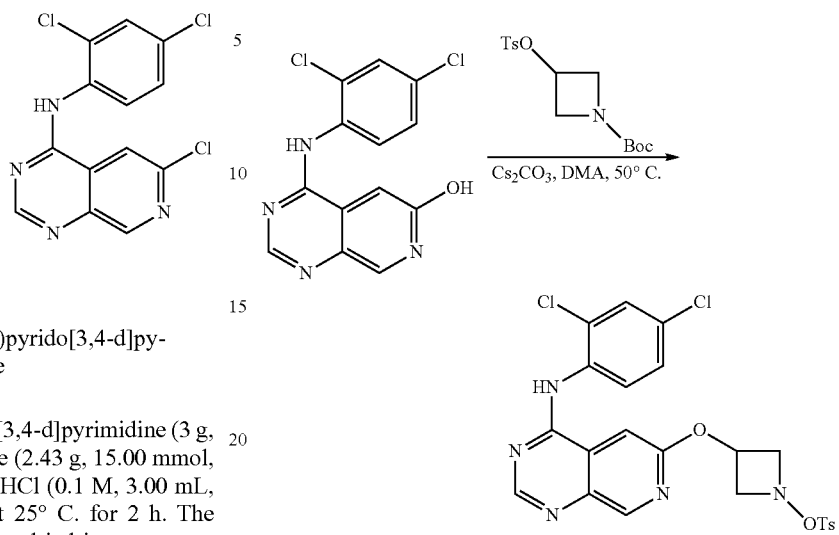

6-Chloro-N-(2,4-dichlorophenyl)pyrido[3,4-d]pyrimidin-4-amine

To a solution of 4,6-dichloropyrido[3,4-d]pyrimidine (3 g, 15.00 mmol, 1 eq), 2,4-dichloroaniline (2.43 g, 15.00 mmol, 1 eq) in t-BuOH (30 mL) was added HCl (0.1 M, 3.00 mL, 0.02 eq). The mixture was stirred at 25° C. for 2 h. The mixture was filtered and the cake was dried in vacuum to afford the title compound (3.7 g, crude) as a yellow solid.

Step 2

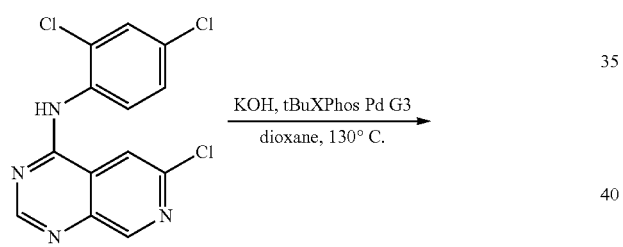

4-((2,4-Dichlorophenyl)amino)pyrido[3,4-d]pyrimidin-6-ol

To a solution of the product from the previous step (3 g, 9.21 mmol, 1 eq), KOH (1.55 g, 27.64 mmol, 3 eq) in dioxane (30 mL) was added tBuXPhos Pd G3 (365.98 mg, 460.72 umol, 0.05 eq). The mixture was stirred at 130° C. for 16 h under $N_2$. The mixture was filtered and the cake was dried in vacuum to afford the title compound (1.6 g, crude) as yellow solid. MS (ES$^+$) $C_{13}H_8Cl_2N_4O$ requires: 306 and 308, found: 307 and 309 [M+H]$^+$.

Step 3

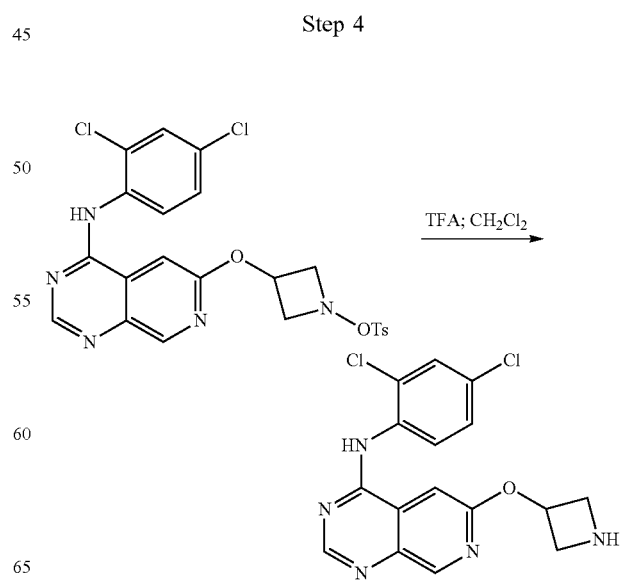

tert-Butyl 3-((4-((2,4-dichlorophenyl)amino)pyrido[3,4-d]pyrimidin-6-yl)oxy)azetidine-1-carboxylate To a mixture of the product from the previous step (0.5 g, 1.24 mmol, 1 eq) and tert-butyl 3-(tosyloxy)azetidine-1-carboxylate (810.13 mg, 2.47 mmol, 2 eq) in DMA (10 mL) was added $Cs_2CO_3$ (1.21 g, 3.71 mmol, 3 eq). The mixture was stirred at 50° C. for 5 h. The mixture was diluted with $H_2O$ (50 mL) and extracted with EtOAc (100 mL×3). The combined organic phase was washed with brine (100 mL×2), dried over $Na_2SO_4$, filtered and concentrated in vacuum. The residue was purified by silica gel chromatography (SiO$_2$, Petroleum ether:Ethyl acetate=10:1 to 3:1) to afford the title compound (130 mg, 0.281 mmol, 22.7% yield) as a yellow solid.

Step 4

6-(Azetidin-3-yloxy)-N-(2,4-dichlorophenyl)pyrido[3,4-d]pyrimidin-4-amine trifluoroacetate To a mixture of the product from the previous step (160 mg, 0.346 mmol, 1 eq) in DCM (3 mL) was added TFA (1 mL). The mixture was stirred at 25° C. for 2 h. The mixture was concentrated in vacuum to afford the title compound (150 mg, crude) as a yellow oil. MS (ES+) $C_{16}H_{13}Cl_2N_5O$ requires: 361 and 363, found: 362 and 364 [M+H]+.

Step 5

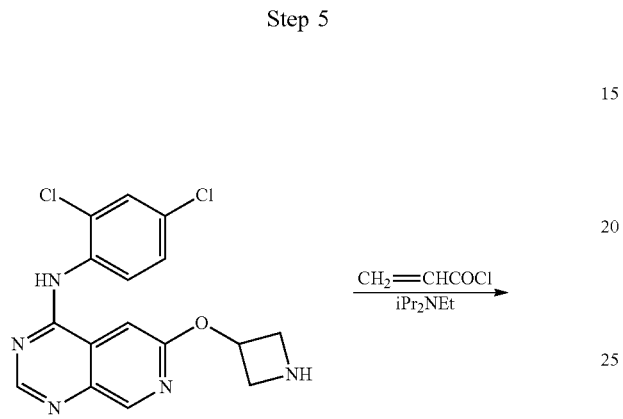

1-(3-((4-((2,4-Dichlorophenyl)amino)pyrido[3,4-d]pyrimidin-6-yl)oxy)azetidin-1-yl)prop-2-en-1-one To a mixture of the product from the previous step (150 mg, 0.314 mmol, 1 eq) and DIEA (161 mg, 1.24 mmol, 216 uL, 3 eq) in DCM (3 mL) was added acryloyl chloride (45 mg, 0.497 mmol, 41 uL, 1.2 eq). The mixture was stirred at 25° C. for 2 h. The mixture was concentrated in vacuum. The residue was purified by prep-HPLC (column: Shim-pack $C_{18}$ 150×25×10 um; mobile phase: [water (0.225% FA)-ACN]; B %: 36%-56%, 8 min) to afford the title compound (25.8 mg, 0.062 mmol, 19.7% yield, 100% purity) as a yellow solid.

MS (ES+) $C_{19}H_{15}Cl_2N_5O_2$ requires: 415 and 417, found: 416 and 418[M+H]+.

$^1$H NMR (400 MHz, DMSO-$d_6$) δ 10.37 (bs, 1H), 8.86 (bs, 1H), 8.34 (bs, 1H), 7.73-7.83 (m, 2H), 7.45-7.59 (m, 2H), 6.36 (dd, J=16.9, 10.3 Hz, 1H), 6.13 (dd, J=16.9, 2.1 Hz, 1H), 5.69 (dd, J=10.3, 2.0 Hz, 1H), 5.42-5.53 (m, 1H), 4.67-4.78 (m, 1H), 4.42 (dd, J=10.8, 6.8 Hz, 1H), 4.27 (dd, J=9.6, 3.1 Hz, 1H), 3.97 (dd, J=10.9, 3.1 Hz, 1H).

Example 3

1-(3-((4-((3,4-dichlorophenyl)amino)-7-methoxyquinazolin-6-yl)oxy)azetidin-1-yl)-prop-2-en-1-one

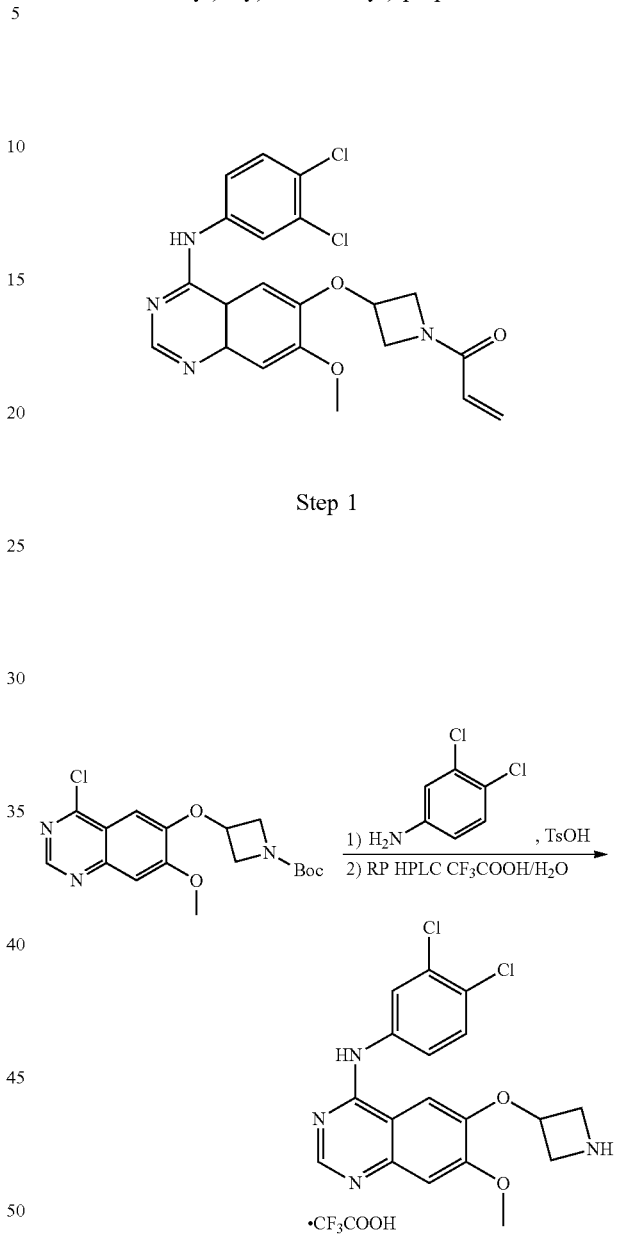

Step 1

6-(Azetidin-3-yloxy)-N-(3,4-dichlorophenyl)-7-methoxyquinazolin-4-amine trifluoroacetate To a solution of Intermediate C (50 mg, 0.137 mmol) and 3,4-dichloroaniline (44 mg, 0.274 mmol) in 2-propanol (3 ml) was added toluenesulfonic acid (2.4 mg, 0.0137 mmol) and the resulting mixture was stirred at 80° C. for 16 hours. The volatiles were removed under reduced pressure. The residue was purified by mass-triggered preparative HPLC (Mobile phase: A=0.1% TFA/$H_2O$, B=0.1% TFA/MeCN; Gradient: B=10-30%; 12 min; Column: C18) to give the title compound (28.6 mg, 0.0566 mmol, 41.3%) as a brown amorphous material. MS (ES+) $C_{18}H_{16}Cl_2N_4O_2$ requires: 390, found: 391 [M+H]+.

Step 2

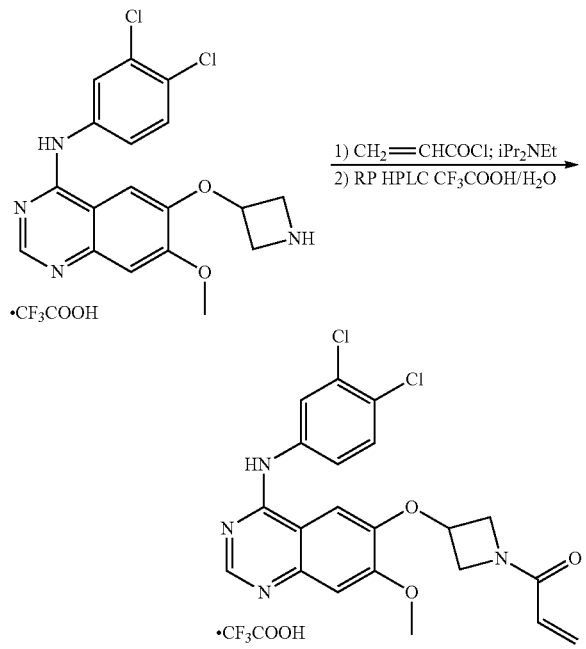

1-(3-((4-((3,4-Dichlorophenyl)amino)-7-methoxy-quinazolin-6-yl)oxy)azetidin-1-yl)prop-2-en-1-one trifluoroacetate To a solution of the product from the previous step (28.6 mg, 0.0566 mmol) in $CH_2Cl_2$ (3 ml) was added $iPr_2NEt$ (29.6 µL, 0.170 mmol) and acryloyl chloride (4.55 µL, 0.0566 mmol). The resulting mixture was stirred at room temperature for 30 minutes and then concentrated under reduced pressure. The residue was purified by mass-triggered preparative HPLC (Mobile phase: A=0.1% TFA/$H_2O$, B=0.1% TFA/MeCN; Gradient: B=20-50%; 12 min; Column: C18) to give the title compound (18.8 mg, 0.034 mmol, 59% yield) as a brown amorphous solid. MS (ES+) $C_{21}H_{18}Cl_2N_4O_3$ requires: 444, found: 445 $[M+H]^+$.

Example 4

6-((1-acryloylpiperidin-4-yl)oxy)-4-((3,4-dichloro-2-fluorophenyl)amino)-7-methoxy-quinoline-3-carbonitrile

Step 1

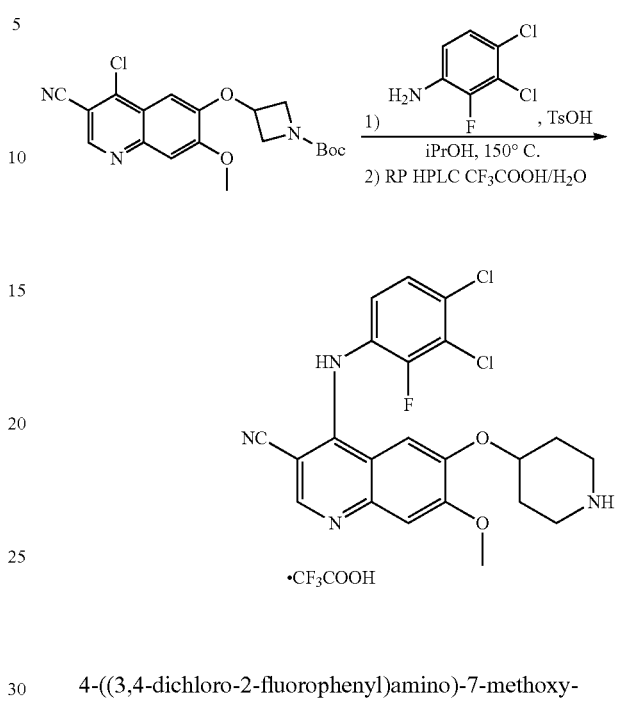

4-((3,4-dichloro-2-fluorophenyl)amino)-7-methoxy-6-(piperidin-4-yloxy)-quinoline-3-carbonitrile To a solution of Intermediate B (425 mg, 1.02 mmol) in 2-propanol (18 ml) was added 3,4-dichloro-2-fluoroaniline (366 mg, 2.03 mmol) and toluenesulfonic acid (19.34 mg, 0.102 mmol). The resulting mixture was stirred at 80° C. for 16 hours. The volatiles were removed under reduced pressure. The residue was purified by mass-triggered preparative HPLC (Mobile phase: A=0.1% TFA/$H_2O$, B=0.1% TFA/MeCN; Gradient: B=10-50%; 16 min; Column: C18) to give the title compound (433 mg, 0.753 mmol, 74.0% yield) as a yellow amorphous material. MS (ES+) $C_{22}H_{19}Cl_2N_4O_2$ requires: 460, found: 461 $[M+H]^+$.

Step 2

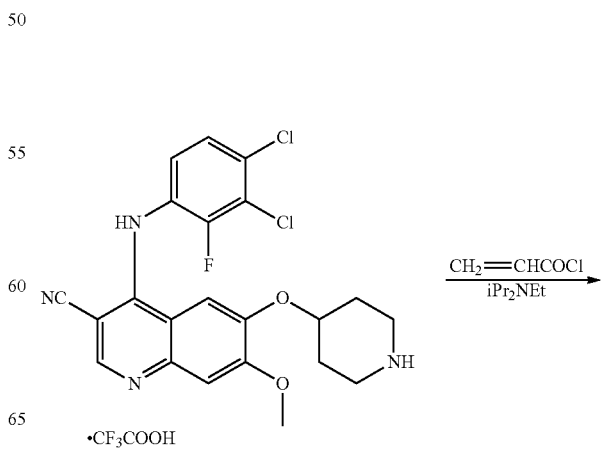

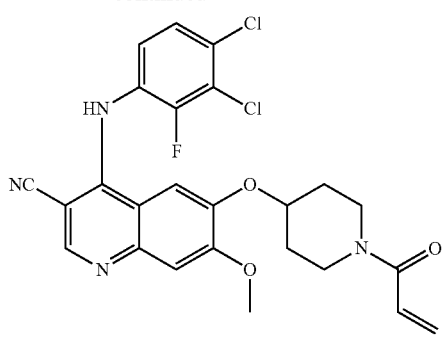

6-((1-Acryloylpiperidin-4-yl)oxy)-4-((3,4-dichloro-2-fluorophenyl)amino)-7-methoxyquinoline-3-carbonitrile To a solution of the product from the previous step (433 mg, 0.753 mmol) in CH$_2$Cl$_2$ (10 ml) was added iPr$_2$NEt (0.657 ml, 3.76 mmol) and acryloyl chloride (0.073 ml, 0.903 mmol). The resulting mixture was stirred at room temperature for 30 minutes and then concentrated under reduced pressure. The residue was purified via silica gel chromatography (0-7% MeOH in DCM) to give the title compound (145 mg, 0.281 mmol, 37.4% yield) as a yellow solid. MS (ES+) C$_{25}$H$_{21}$Cl$_2$FN$_4$O$_3$ requires: 514, found: 515 [M+H]$^+$.

Example 5

1-(3-((4-((2,4-dichlorophenyl)amino)-7-methoxyquinazolin-6-yl)oxy)azetidin-1-yl)-prop-2-en-1-one

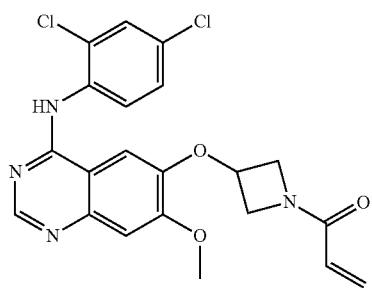 [SMILES: C=CC(=O)N1CC(Oc2cc3c(Nc4ccc(Cl)cc4Cl)ncnc3cc2OC)C1]

Step 1

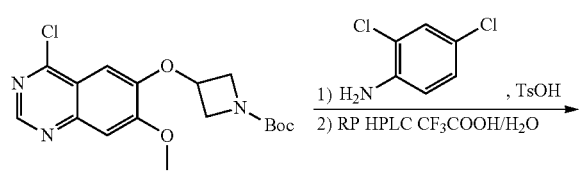

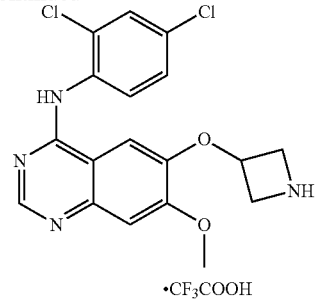

6-(Azetidin-3-yloxy)-N-(2,4-dichlorophenyl)-7-methoxyquinazolin-4-amine trifluoroacetate To a solution of Intermediate C (50 mg, 0.137 mmol) and 2,4-dichloroaniline (44 mg, 0.274 mmol) in 2-propanol (3 ml) was added toluenesufonic acid (2.4 mg, 0.0137 mmol) and the resulting mixture was stirred at 80° C. for 16 hours. The volatiles were removed under reduced pressure. The residue was purified by mass-triggered preparative HPLC (Mobile phase: A=0.1% TFA/H$_2$O, B=0.1% TFA/MeCN; Gradient: B=10-30%; 12 min; Column: C18) to give the title compound (13.9 mg, 0.0275 mmol, 20.1%) as a brown amorphous material. MS (ES+) C$_{18}$H$_{16}$Cl$_2$N$_4$O$_2$ requires: 390, found: 391 [M+H]$^+$.

Step 2

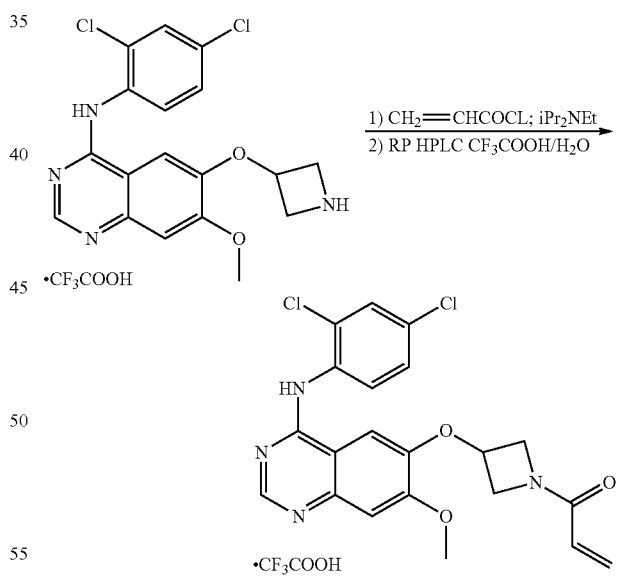

1-(3-((4-((2,4-Dichlorophenyl)amino)-7-methoxyquinazolin-6-yl)oxy)azetidin-1-yl)prop-2-en-1-one trifluoroacetate To a solution of the product from the previous step (13.9 mg, 0.0275 mmol) in CH$_2$Cl$_2$ (3 ml) was added iPr$_2$NEt (13.9 μL, 0.0800 mmol) and acryloyl chloride (2.21 μL, 0.0275 mmol). The resulting mixture was stirred at room temperature for 30 minutes and then concentrated under reduced pressure. The residue was purified by mass-triggered preparative HPLC (Mobile phase: A=0.1% TFA/H₂O, B=0.1% TFA/MeCN; Gradient: B=20-50%; 12 min; Column: C18) to give the title compound (6.6 mg, 0.012 mmol, 43% yield) as a brown amorphous solid. MS (ES+) C$_{21}$H$_{18}$Cl$_2$N$_4$O$_3$ requires: 444, found: 445 [M+H]⁺.

Example 6

1-(3-((4-((3,4-dichloro-2-fluorophenyl)amino)-7-methoxyquinazolin-6-yl)oxy)azetidin-1-yl)prop-2-en-1-one panol (90 ml) was added p-toluenesulfonic acid (0.624 g, 3.28 mmol), and the resulting mixture was stirred at 80° C. for 36 hours. The volatiles were removed under reduced pressure. The residue was purified by mass-triggered preparative HPLC (Mobile phase: A=0.1% TFA/H₂O, B=0.1% TFA/MeCN; Gradient: B=10-50%; 16 min; Column: C18) to give the title compound (2.86 g, 5.47 mmol, 66.6% yield) as a white solid. MS (ES+) C$_{18}$H$_{15}$Cl$_2$FN$_4$O$_2$ requires: 408, found: 409 [M+H]⁺.

Step 2

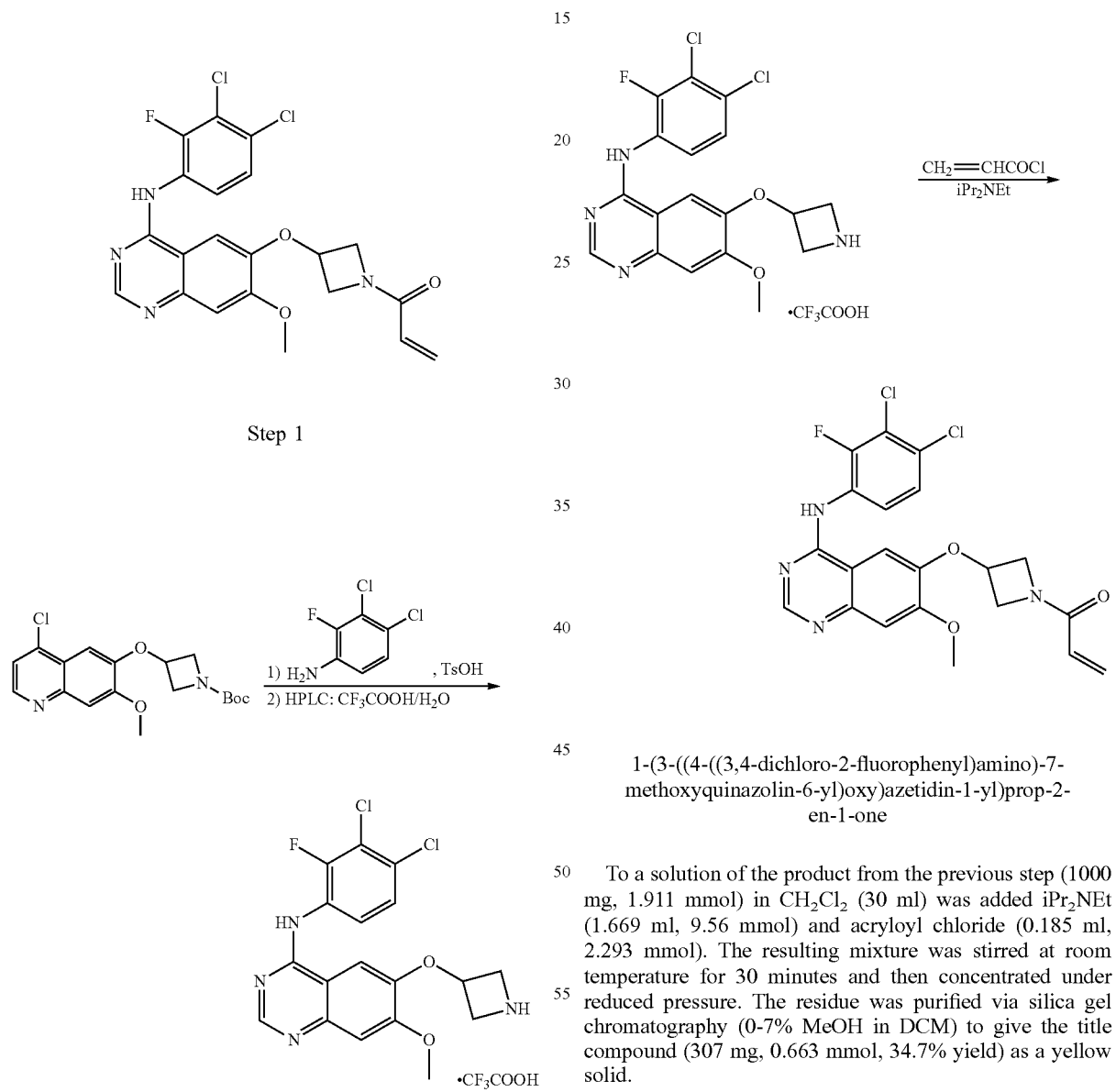

Step 1

1-(3-((4-((3,4-dichloro-2-fluorophenyl)amino)-7-methoxyquinazolin-6-yl)oxy)azetidin-1-yl)prop-2-en-1-one To a solution of the product from the previous step (1000 mg, 1.911 mmol) in CH₂Cl₂ (30 ml) was added iPr₂NEt (1.669 ml, 9.56 mmol) and acryloyl chloride (0.185 ml, 2.293 mmol). The resulting mixture was stirred at room temperature for 30 minutes and then concentrated under reduced pressure. The residue was purified via silica gel chromatography (0-7% MeOH in DCM) to give the title compound (307 mg, 0.663 mmol, 34.7% yield) as a yellow solid.

MS (ES+) C$_{21}$H$_{17}$Cl$_2$FN$_4$O$_3$ requires: 462, found: 463 [M+H]⁺.

¹H NMR (600 MHz, d$_6$-DMSO) δ 9.67 (s, 1H), 8.42 (s, 1H), 7.64-7.56 (m, 2H), 7.50 (s, 1H), 7.28 (s, 1H), 6.37 (dd, J=10.3, 16.9 Hz, 1H), 6.14 (dd, J=1.7, 16.9 Hz, 1H), 5.70 (dd, J=1.7, 10.3 Hz, 1H), 5.24-5.16 (m, 1H), 4.83-4.76 (m, 1H), 4.60-4.52 (m, 1H), 4.34-4.25 (m, 1H), 4.01-3.92 (m, 1H), 3.97 (s, 3H).

6-(azetidin-3-yloxy)-N-(3,4-dichloro-2-fluorophenyl)-7-methoxyquinazolin-4-amine Trifluoroacetate Salt To a solution of Intermediate C (3.00 g, 8.20 mmol) and 3,4-dichloro-2-fluoroaniline (1.919 g, 10.66 mmol) in 2-pro-

Example 7

6-((1-acryloylpiperidin-4-yl)oxy)-4-((3,4-dichloro-phenyl)amino)-7-methoxyquinoline-3-carbonitrile

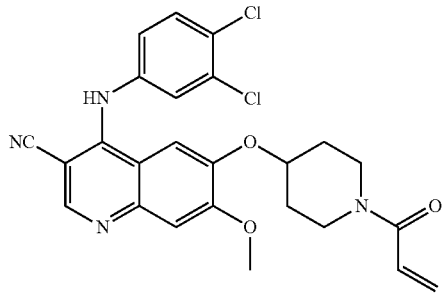 [SMILES: C=CC(=O)N1CCC(Oc2cc3c(Nc4ccc(Cl)c(Cl)c4)c(C#N)cnc3cc2OC)CC1]

Step 1

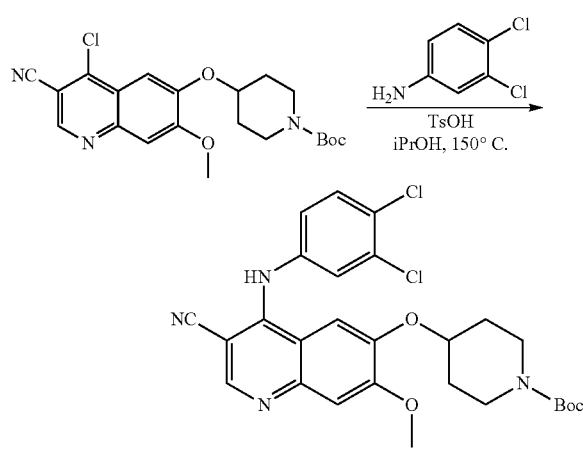

tert-Butyl 4-(3-cyano-4-(3,4-dichlorophenylamino)-7-methoxyquinolin-6-yloxy)piperidine-1-carboxylate A mixture of Intermediate B (100 mg, 0.24 mmol), 3,4-dichloroaniline (78 mg, 0.48 mmol), and TsOH (5 mg, 0.024 mmol) in i-PrOH (3 ml) was stirred at 150° C. for 4 h. The solvent was removed to give a white solid (182 mg, crude 100%). MS (ES+) $C_{27}H_{28}Cl_2N_4O_4$ requires: 542, found: 543 [M+H]$^+$.

Step 2

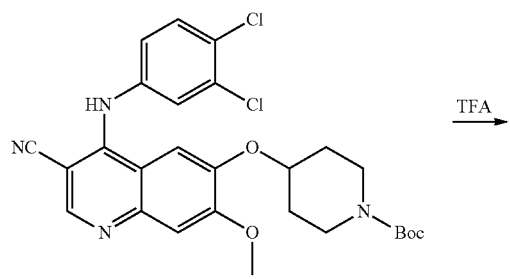

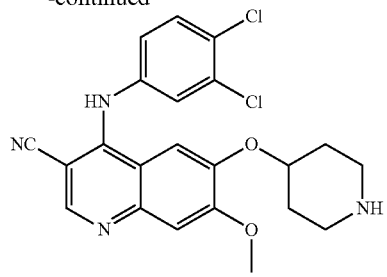

4-(3,4-Dichloro-phenylamino)-7-methoxy-6-(piperidin-4-yloxy)-quinoline-3-carbonitrile A mixture of the product from the previous step (182 mg, 0.24 mmol) and TFA (3 ml) in DCM (3 ml) was stirred at RT for 4 h. The solvent was removed to give a yellow oil (100 mg, 100%). MS (ES+) $C_{22}H_{20}Cl_2N_4O_2$ requires: 442, found: 443 [M+H]$^+$.

Step 3

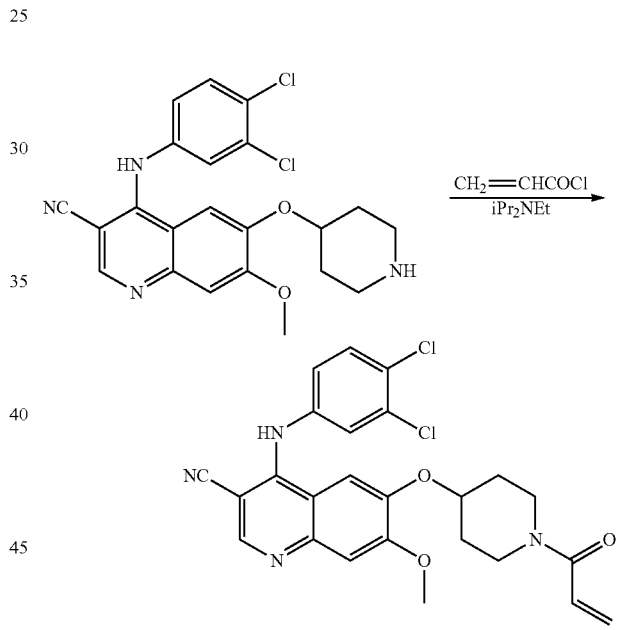

6-(1-Acryloyl-piperidin-4-yloxy)-4-(3,4-dichloro-phenylamino)-7-methoxy-quinoline-3-carbonitrile To a mixture of the product from the previous step (45 mg, 0.1 mmol) and iPr$_2$NEt (39 mg, 0.3 mmol) in DCM (3 ml) was added acryloyl chloride (10 mg, 0.1 mmol). The mixture was stirred at 0° C. for 30 min. The solvent was removed and the residue was purified by Prep-HPLC to give a white solid (5 mg, 10%).

MS (ES+) $C_{25}H_{22}Cl_2N_4O_3$ requires: 496, found: 497 [M+H]$^+$.

$^1$H NMR (500 MHz, d$_6$-DMSO) δ 9.56 (s, 1H), 8.59 (s, 1H), 7.69 (s, 1H), 7.61 (d, J=8.7 Hz, 1H), 7.43 (d, J=23.1 Hz, 2H), 7.19 (d, J=11.1 Hz, 1H), 6.82 (dd, J=16.7, 10.5 Hz, 1H), 6.10 (dd, J=16.7, 2.4 Hz, 1H), 5.68 (dd, J=10.4, 2.4 Hz, 1H), 4.73 (m, 1H), 3.84 (m, 2H), 3.45 (m, 2H), 1.95 (m, 2H), 1.63 (m, 2H).

Example 8

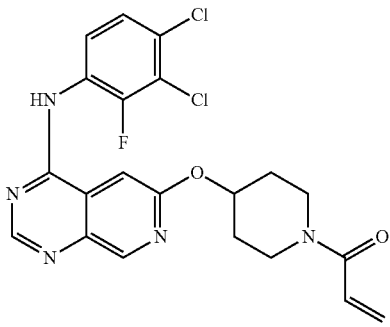 [SMILES: C=CC(=O)N1CCC(Oc2cc3c(Nc4ccc(Cl)c(Cl)c4F)ncnc3cn2)CC1]

1-(4-((4-((3,4-dichloro-2-fluorophenyl)amino)pyrido[3,4-d]pyrimidin-6-yl)oxy)-piperidin-1-yl)prop-2-en-1-one

Step 1

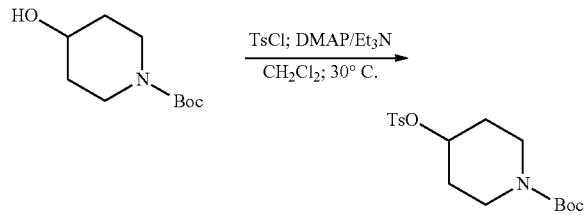

tert-Butyl 4-(tosyloxy)piperidine-1-carboxylate

A mixture of tert-butyl 4-hydroxypiperidine-1-carboxylate (10 g, 49.7 mmol, 1 eq), p-toluenesulfonyl chloride (10.4 g, 54.6 mmol, 1.1 eq), DMAP (607 mg, 5.0 mmol, 0.1 eq) and Et$_3$N (12.6 g, 124.2 mmol, 17.3 mL, 2.5 eq) in DCM (100 mL) was stirred at 25° C. for 12 h. The reaction mixture was diluted with DCM (200 mL), washed with 0.5 M HCl (200 mL×2), and washed with brine (200 mL). The organic layer was dried over anhydrous Na$_2$SO$_4$ and concentrated in vacuum. The residue was triturated with (Petroleum ether: Ethyl acetate=5:1, 60 mL), filtered, and the filter cake was collected to afford two batches of the title compound (8.0 g, 22.5 mmol, 45.3% yield) as an off-white solid.

Step 2

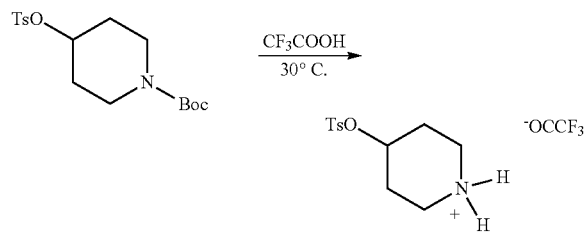

Piperidin-4-yl 4-methylbenzenesulfonate Trifluoroacetate

To a solution of the product from the previous step (8 g, 22.5 mmol, 1 eq) in DCM (5 mL) was added TFA (16.00 mL) and the mixture was stirred at 30° C. for 2 h. The mixture was concentrated under reduced pressure to afford the title compound (5.9 g, 16.0 mmol, 71.0% yield) as a yellow oil which was used in the next step without further purification.

Step 3

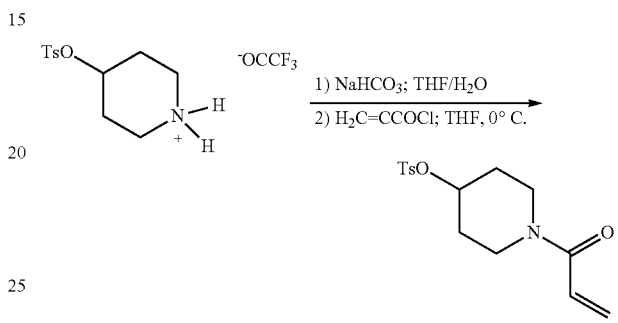

1-Acryloylpiperidin-4-yl 4-methylbenzenesulfonate

To a mixture of the product from the previous step (5.9 g, 16.0 mmol, 1 eq) in THF (20 mL) and H$_2$O (25 mL) was added NaHCO$_3$ (4.03 g, 47.9 mmol, 1.86 mL, 3 eq) and the mixture was cooled to 0° C. A solution of acryloyl chloride (1.45 g, 16.0 mmol, 1.30 mL, 1 eq) in THF (5 mL) was added into the reaction mixture over 5 min and the reaction was then stirred at 0° C. for 1 h. The reaction mixture was poured into H$_2$O (100 mL) and extracted with EtOAc (100 mL×3). The combined organic layers were washed with brine (200 mL), dried over Na$_2$SO$_4$, filtered, and concentrated. The residue was purified by silica gel chromatography (Petroleum ether:Ethyl acetate=10/1 5/1) to afford the title compound (3.3 g, 10.7 mmol, 66.8% yield) as a colorless oil.

Step 4

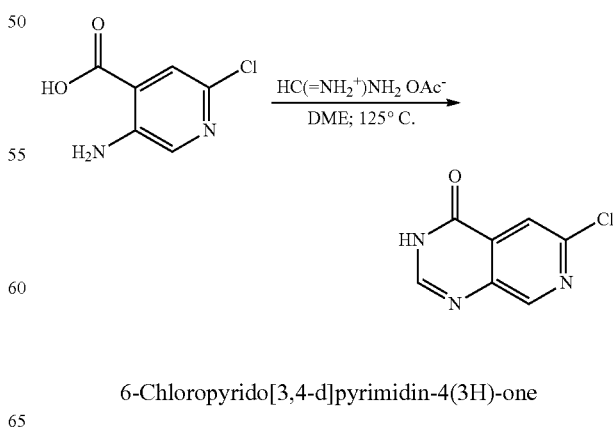

6-Chloropyrido[3,4-d]pyrimidin-4(3H)-one

A mixture of 5-amino-2-chloro-isonicotinic acid (30 g, 173.8 mmol, 1 eq) and formimidamide acetate (36.20 g, 347.7 mmol, 2 eq) in 1,2-dimethoxyethane (100 mL) was stirred at 125° C. for 16 h. The mixture was filtered, the filtered cake washed with ethyl acetate (60 mL×2), and dried in vacuum to afford the title compound (25 g, crude) as a white solid. MS (ES⁺) C₇H₄ClN₃O requires: 181, found: 182 [M+H]⁺.

Step 5

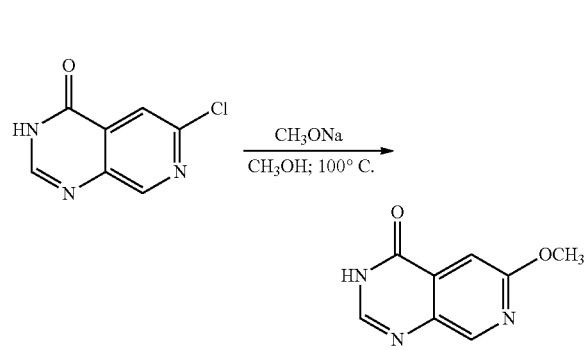

6-Methoxypyrido[3,4-d]pyrimidin-4(3H)-one

A solution of the product from the previous step (3 g, 16.5 mmol, 1 eq) in MeONa/MeOH (16.5 mmol, 60 mL, 30% purity, 1 eq) was stirred at 100° C. for 16 h in a 100 mL sealed tube. The reaction mixture was concentrated under reduced pressure, the residue was diluted with H₂O (100 mL), acidified with 4 M HCl (pH=4-6), filtered, and the filter cake was dried in vacuum to afford the title compound (1.36 g, 7.14 mmol, 43.21% yield, 93% purity) as a white solid. The filtrate was extracted with EtOAc (150 mL×3), the combined organic layers were dried over Na₂SO₄, filtered, and concentrated in vacuum to afford another batch of the title compound (1.72 g, 9.32 mmol, 56.4% yield, 96% purity) as a white solid. MS (ES⁺) C₈H₇N₃O₂ requires: 177, found: 178 [M+H]⁺.

Step 6

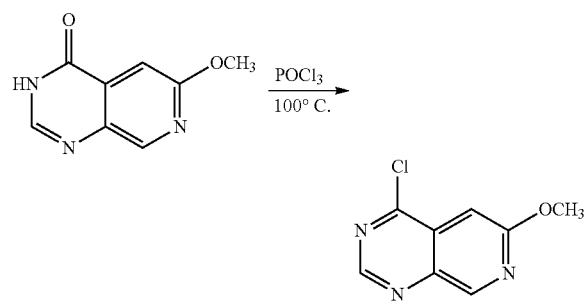

4-Chloro-6-methoxypyrido[3,4-d]pyrimidine

A mixture of the product from the previous step (2.4 g, 13.5 mmol, 1 eq) in POCl₃ (49.5 g, 322.8 mmol, 30 mL, 23.8 eq) was heated at 100° C. for 4 h. The reaction mixture was concentrated in vacuum. The residue was diluted with EtOAc (80 mL) and added slowly to a 0° C. saturated solution of NaHCO₃ (100 mL). The mixture was then extracted with EtOAc (80 mL×2), and the combined organic layers were washed with brine (60 mL×2), dried over Na₂SO₄, filtered, and concentrated in vacuum to afford the title compound (2.3 g, crude) as a yellow solid which was used in the next step without further purification.

Step 7

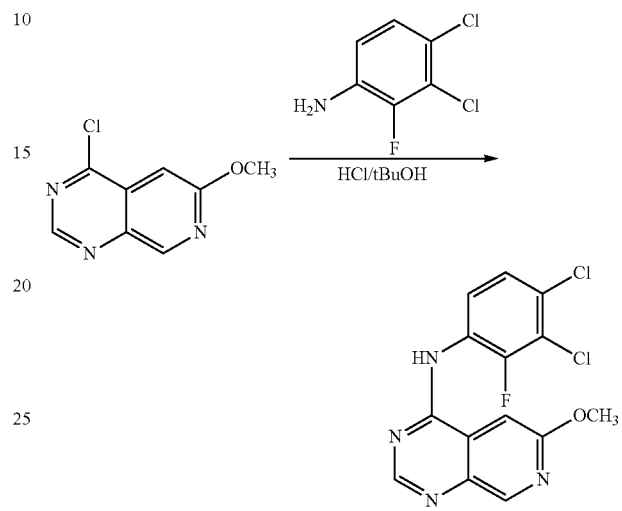

N-(3,4-Dichloro-2-fluorophenyl)-6-methoxypyrido[3,4-d]pyrimidin-4-amine

To a mixture of the product from the previous step (2.3 g, 11.76 mmol, 1 eq) and 3,4-dichloro-2-fluoroaniline (2.12 g, 11.76 mmol, 1 eq) in t-BuOH (23 mL) was added HCl (0.1 M, 5.88 mL, 0.05 eq) and the mixture was stirred at 25° C. for 16 h. The reaction mixture was filtered, the filter cake was washed with methyl tert-butyl ether (40 mL), and dried in vacuum to afford the title compound (2.4 g, 6.9 mmol, 59.0% yield, 98% purity) as a yellow solid. MS (ES⁺) C₁₄H₉Cl₂FN₄O requires: 338, found: 339 [M+H]⁺.

Step 8

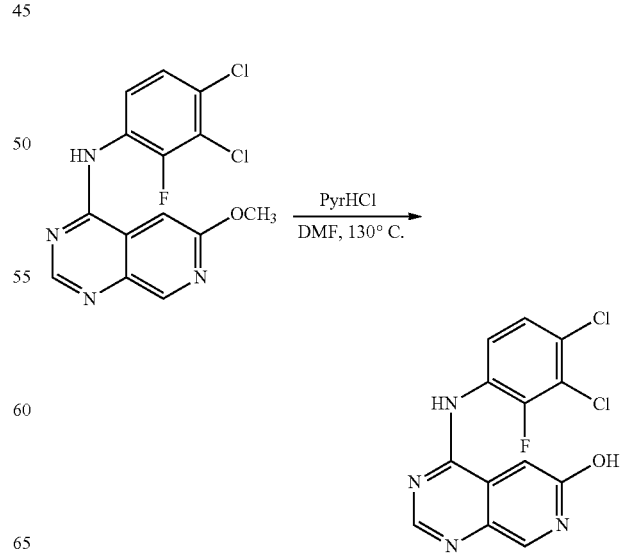

4-((3,4-Dichloro-2-fluorophenyl)amino)pyrido[3,4-d]pyrimidin-6-ol

To a mixture of the product from the previous step (600 mg, 1.77 mmol, 1 eq) in DMF (6 mL) was added pyridine hydrochloride salt (5.11 g, 44.23 mmol, 25 eq). Four batches of the mixture were stirred at 130° C. for 20 h. The four batches of the reaction mixture were poured into H$_2$O (100 mL), filtrated, the filter cake was washed with ethyl acetate (50 mL), dried in vacuum, and the crude product was purified by prep-HPLC (column: Xbridge BEH C18, 250× 50 mm, 10 um; mobile phase: [water (0.05% ammonia hydroxide v/v)-ACN]; B %: 5%-30%, 43 min) to afford the title compound (760 mg, 2.06 mmol, 29.1% yield, 88% purity) as a yellow solid. MS (ES$^+$) C$_{13}$H$_7$Cl$_2$FN$_4$O requires: 324, found: 325 [M+H]$^+$.

Step 9

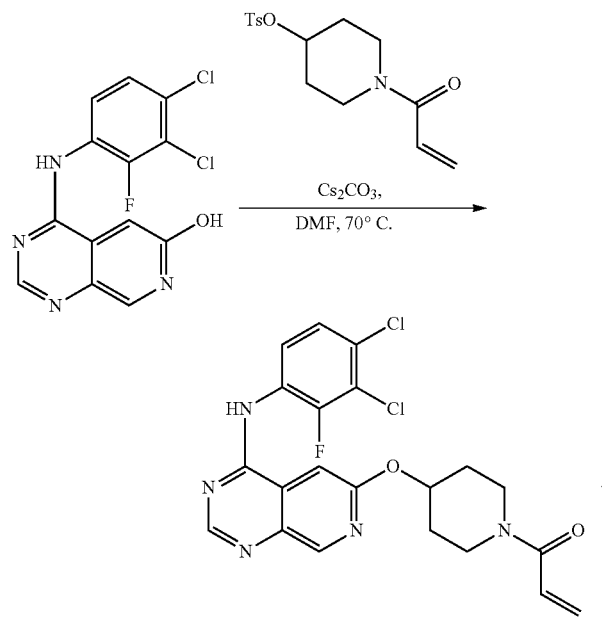

1-(4-((4-((3,4-Dichloro-2-fluorophenyl)amino)pyrido[3,4-d]pyrimidin-6-yl)oxy)piperidin-1-yl)prop-2-en-1-one To a mixture of the product from the previous step (100 mg, 307.6 umol, 1 eq) and 1-acryloylpiperidin-4-yl 4-methylbenzenesulfonate (114.2 mg, 369.1 umol, 1.2 eq) in DMF (4 mL) was added Cs$_2$CO$_3$ (300.64 mg, 922.7 umol, 3 eq) at 25° C. under N$_2$. The mixture was stirred at 70° C. for 16 h. The reaction mixture was poured into H$_2$O (20 mL) and extracted with EtOAc (20 mL×3). The combined organic layers were washed with brine (15 mL×2), dried over Na$_2$SO$_4$, filtered, and concentrated in vacuum. The residue was purified by prep-TLC (SiO$_2$, Petroleum ether:Ethyl acetate=1:1) followed by prep-HPLC (column: Phenomenex Synergi C18 150*30 mm*4 um; mobile phase: [water (0.225% FA)-ACN]; B %: 40%-70%, 10 min) to afford the title compound (9.1 mg, 18.7 umol, 3.0% yield, 95% purity) as a yellow solid.

MS (ES$^+$) C$_{21}$H$_{18}$Cl$_2$FN$_5$O$_2$ requires: 461, found: 462 [M+H]$^+$.

$^1$H NMR (400 MHz, MeOD) δ 8.92 (s, 1H), 8.46 (s, 1H), 7.71-7.58 (m, 2H), 7.47 (br d, J=7.6 Hz, 1H), 6.82 (dd, J=10.6, 16.9 Hz, 1H), 6.22 (dd, J=2.0, 16.8 Hz, 1H), 5.76 (dd, J=2.0, 10.6 Hz, 1H), 5.48-5.37 (m, 1H), 4.06-3.90 (m, 2H), 3.71-3.59 (m, 2H), 2.30-2.05 (m, 2H), 1.95-1.75 (m, 2H).

Example 9

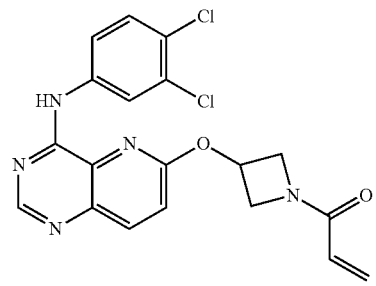

1-(3-((4-((3,4-dichlorophenyl)amino)pyrido[3,2-d]pyrimidin-6-yl)oxy)azetidin-1-yl)-prop-2-en-1-one Step 1

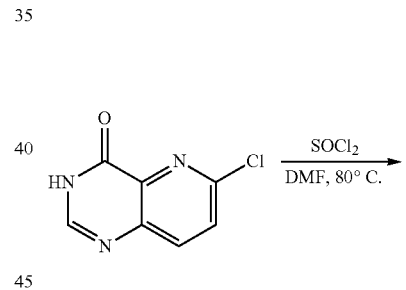

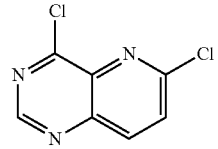

4,6-Dichloropyrido[3,2-d]pyrimidine

To a mixture of 6-chloropyrido[3,2-d]-pyrimidin-4(1H)-one (4.5 g, 24.8 mmol, 1 eq) in SOCl$_2$ (49.20 g, 413.55 mmol, 30 mL, 16.69 eq) was added DMF (90.57 mg, 1.24 mmol, 95.34 uL, 0.05 eq). The mixture was stirred at 80° C. for 2 h. The solvent was evaporated. The residue was dissolved in EtOAc (300 mL), washed with saturated NaHCO$_3$ aqueous solution (100 mL), the organic layer was dried over Na$_2$SO$_4$, and concentrated to afford the title compound (4.6 g, 23.00 mmol, 92.8% yield) as yellow solid which was used directly in the next step without further purification.

Step 2

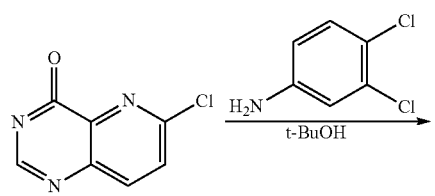

6-Chloro-N-(3,4-dichlorophenyl)pyrido[3,2-d]pyrimidin-4-amine

To a mixture of the product from the previous step (0.5 g, 2.50 mmol, 1 eq) and 3,4-dichloroaniline (405.04 mg, 2.50 mmol, 1 eq) in t-BuOH (5 mL) was added HCl (0.1 M, 2.50 mL, 0.1 eq). The mixture was stirred at 25° C. for 3 h. The solvent was evaporated. The residue was triturated with EtOAc (10 mL) at 25° C. for 30 minutes and then the mixture was filtered and the filter cake was collected to afford the title compound (0.75 g, 2.30 mmol, 92.1% yield) as a yellow solid which was used in the next step without further purification.

Step 3

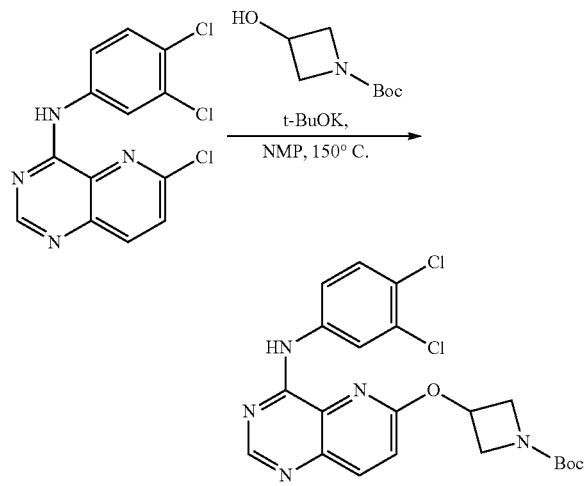

tert-Butyl 3-((4-((3,4-dichlorophenyl)amino)pyrido[3,2-d]pyrimidin-6-yl)oxy)-azetidine-1-carboxylate To a mixture of tert-butyl 3-hydroxyazetidine-1-carboxylate (425.60 mg, 2.46 mmol, 4 eq) and the product from the previous step (0.2 g, 614.3 umol, 1 eq) in NMP (3 mL) was added t-BuOK (275.72 mg, 2.46 mmol, 4 eq). The mixture was heated at 150° C. and stirred for 1 h in a microwave reactor. The mixture was poured into water (20 mL) and extracted with EtOAc (20 mL×2). The combined organic layers were dried over $Na_2SO_4$, concentrated, and the residue was purified by silica gel chromatography (petroleum ether: ethyl acetate=10:1 3:1) to afford the title compound (262 mg, 512.29 umol, 83.4% yield, 90.4% purity) as light yellow solid. MS (ES+) $C_{21}H_{21}Cl_2N_5O_3$ requires: 461 and 463, found: 462 and 464[M+H]+.

Step 4

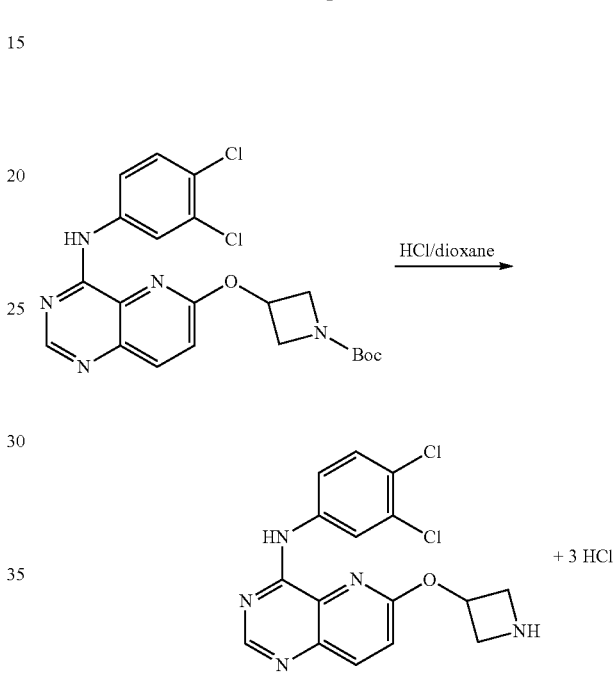

6-(Azetidin-3-yloxy)-N-(3,4-dichlorophenyl)pyrido[3,2-d]pyrimidin-4-amine Trihydrochloride A mixture of the product from the previous step (262 mg, 512.3 umol, 1 eq) and HCl/dioxane (4 M, 5 mL, 39.0 eq) was stirred at 25° C. for 1 h. The solvent was evaporated to afford the title compound (241 mg, 511.0 umol, 99.8% yield,) as a yellow solid which was used directly in the next step without further purification. MS (ES+) $C_{16}H_{13}Cl_2N_5O$ requires: 361 and 363, found: 362 and 364 [M+H]+.

Step 5

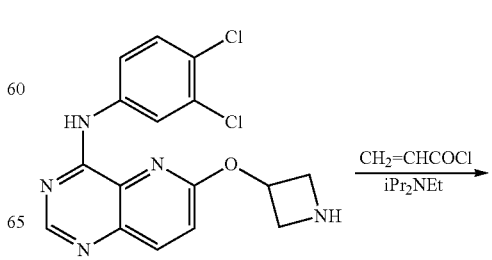

113

-continued

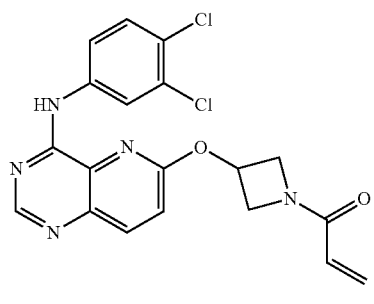

1-(3-((4-((3,4-Dichlorophenyl)amino)pyrido[3,2-d]pyrimidin-6-yl)oxy)azetidin-1-yl)prop-2-en-1-one To a mixture of the product from the previous step (241 mg, 511.0 umol, 1 eq) in DCM (2 mL) were added iPr$_2$NEt (264.18 mg, 2.04 mmol, 356.0 uL, 4 eq) and acryloyl chloride (50.88 mg, 562.1 umol, 45.8 uL, 1.1 eq). The mixture was stirred at 25° C. for 1 h. The solvent was evaporated. The residue was purified by prep-HPLC (column: Shim-pack C18 150×25, 10 um; mobile phase: [water (0.225% FA)-ACN]; B %: 40%-70%, 10 min) to afford the title compound (67.6 mg, 157.36 umol, 30.8% yield, 96.9% purity) as a white solid.

MS (ES$^+$) C$_{19}$H$_{15}$Cl$_2$N$_5$O$_2$ requires: 415 and 417, found: 416 and 418 [M+H]$^+$.

$^1$H NMR (400 MHz, MeOD) δ 8.63 (s, 1H), 8.35 (d, J=2.7 Hz, 1H), 8.13 (d, J=9.0 Hz, 1H), 7.86 (dd, J=2.4, 8.8 Hz, 1H), 7.51 (d, J=8.8 Hz, 1H), 7.45 (d, J=9.0 Hz, 1H), 6.48-6.38 (m, 1H), 6.35-6.27 (m, 1H), 5.88 (s, 1H), 5.79 (dd, J=2.0, 10.3 Hz, 1H), 4.93 (ddd, J=1.3, 6.7, 10.0 Hz, 1H), 4.72-4.64 (m, 1H), 4.42 (dd, J=2.9, 10.3 Hz, 1H), 4.19 (dd, J=3.2, 11.7 Hz, 1H).

Example 10

6-((1-acryloylazetidin-3-yl)oxy)-4-((3,4-dichloro-2-fluorophenyl)amino)-7-methoxyquinoline-3-carbonitrile

114

Step 1

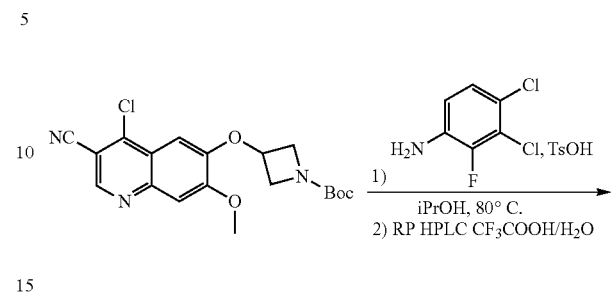

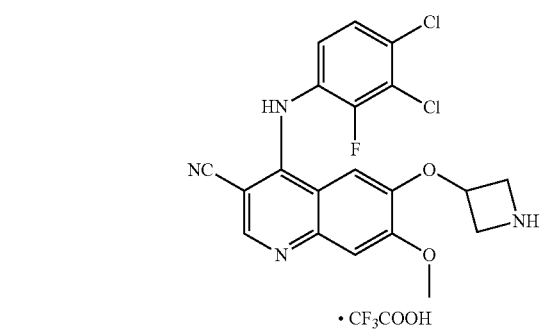

6-(Azetidin-3-yloxy)-4-((3,4-dichloro-2-fluorophenyl)amino)-7-methoxyquinoline-3-carbonitrile To a solution of Intermediate D (200 mg, 0.513 mmol) in 2-propanol (12 ml) was added 3,4-dichloro-2-fluoroaniline (185 mg, 1.03 mmol) and p-toluenesulfonic acid (9.76 mg, 0.051 mmol). The resulting mixture was stirred at 80° C. for 16 hours. The volatiles were removed under reduced pressure. The residue was purified by mass-triggered preparative HPLC (Mobile phase: A=0.1% TFA/H$_2$O, B=0.1% TFA/MeCN; Gradient: B=10-50%; 16 min; Column: C18) to give the title compound (256 mg, 0.468 mmol, 91.0% yield) as a yellow amorphous material. MS (ES+) C$_{20}$H$_{15}$Cl$_2$FN$_4$O$_2$ requires: 432, found: 433 [M+H]$^+$.

Step 2

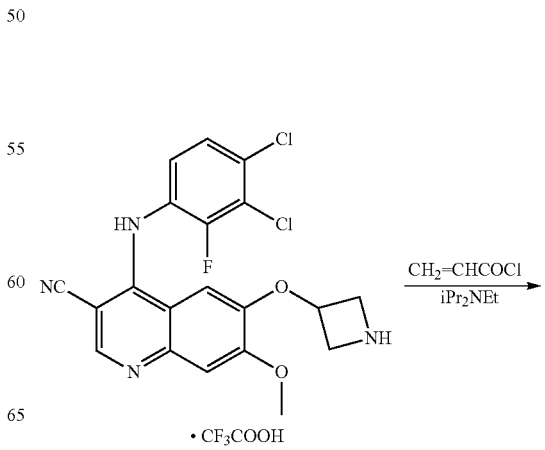

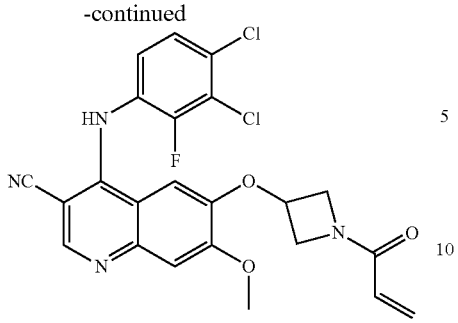

6-((1-Acryloylazetidin-3-yl)oxy)-4-((3,4-dichloro-2-fluorophenyl)amino)-7-methoxyquinoline-3-carbonitrile To a solution of the product from the previous step (256 mg, 0.426 mmol) in $CH_2Cl_2$ (12 ml) was added $iPr_2NEt$ (0.223 ml, 1.28 mmol) and acryloyl chloride (0.034 ml, 0.426 mmol). The resulting mixture was stirred at room temperature for 30 minutes and then concentrated under reduced pressure. The residue was purified via silica gel chromatography (0-7% MeOH in DCM) to give the title compound (121 mg, 0.248 mmol, 58.3% yield) as a yellow solid.

MS (ES+) $C_{23}H_{17}Cl_2FN_4O_3$ requires: 486, found: 487 $[M+H]^+$.

$^1$H NMR (600 MHz, $d_6$-DMSO) δ 9.57 (s, 1H), 8.55 (s, 1H), 7.64-7.52 (m, 1H), 7.52-7.33 (m, 3H), 6.35 (dd, J=10.3, 16.9 Hz, 1H), 6.12 (dd, J=1.7, 16.9 Hz, 1H), 5.69 (dd, J=1.7, 10.3 Hz, 1H), 5.26-5.16 (m, 1H), 4.78-4.66 (m, 1H), 4.57-4.43 (m, 1H), 4.31-4.21 (m, 1H), 3.99 (s, 3H), 3.98-3.91 (m, 1H).

TABLE 1

Examples 11-101

| Ex. No | Structure | IUPAC Name | MWt | M + H | Ex. Meth. |
|---|---|---|---|---|---|
| 11 | *(structure)* | 6-((1-acryloylpiperidin-4-yl)oxy)-4-((4-chloro-3-(oxazol-5-yl)phenyl)amino)-7-methoxyquinoline-3-carbonitrile | 529 | 530 | 1 |
| 12 | *(structure)* | 6-((1-acryloylpiperidin-4-yl)oxy)-4-((3-(hydroxymethyl)phenyl)amino)-7-methoxyquinoline-3-carbonitrile | 458 | 459 | 1 |
| 13 | *(structure)* | 6-((1-acryloylpiperidin-4-yl)oxy)-4-((2,4-dichlorophenyl)amino)-7-methoxyquinoline-3-carbonitrile | 496 | 497 | 1 |

TABLE 1-continued

Examples 11-101

| Ex. No | Structure | IUPAC Name | MWt | M + H | Ex. Meth. |
|---|---|---|---|---|---|
| 14 | 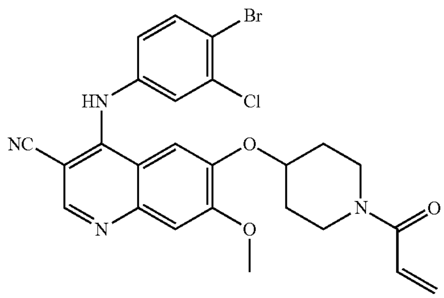 [SMILES: C=CC(=O)N1CCC(Oc2cc3c(Nc4ccc(Br)c(Cl)c4)c(C#N)cnc3cc2OC)CC1] | 6-((1-acryloylpiperidin-4-yl)oxy)-4-((4-bromo-3-chlorophenyl)amino)-7-methoxyquinoline-3-carbonitrile | 540 | 541 | 1 |
| 15 | 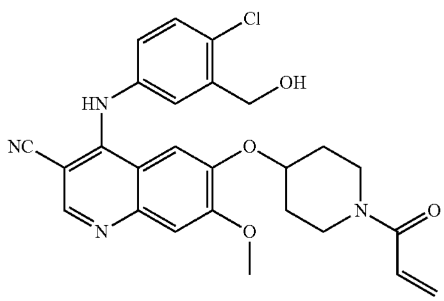 [SMILES: C=CC(=O)N1CCC(Oc2cc3c(Nc4ccc(Cl)c(CO)c4)c(C#N)cnc3cc2OC)CC1] | 6-((1-acryloylpiperidin-4-yl)oxy)-4-((4-chloro-3-(hydroxymethyl)phenyl)-amino)-7-methoxy-quinoline-3-carbonitrile | 492 | 493 | 1 |
| 16 | 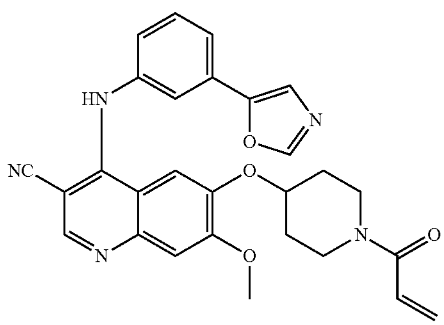 [SMILES: C=CC(=O)N1CCC(Oc2cc3c(Nc4cccc(-c5cnco5)c4)c(C#N)cnc3cc2OC)CC1] | 6-((1-acryloylpiperidin-4-yl)oxy)-7-methoxy-4-((3-(oxazol-5-yl)phenyl)-amino)quinoline-3-carbonitrile | 495 | 496 | 1 |
| 17 | 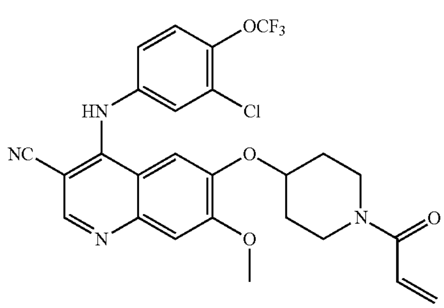 [SMILES: C=CC(=O)N1CCC(Oc2cc3c(Nc4ccc(OC(F)(F)F)c(Cl)c4)c(C#N)cnc3cc2OC)CC1] | 6-((1-acryloylpiperidin-4-yl)oxy)-4-((3-chloro-4-(trifluoromethoxy)phenyl)-amino)-7-methoxy-quinoline-3-carbonitrile | 546 | 547 | 1 |
| 18 | 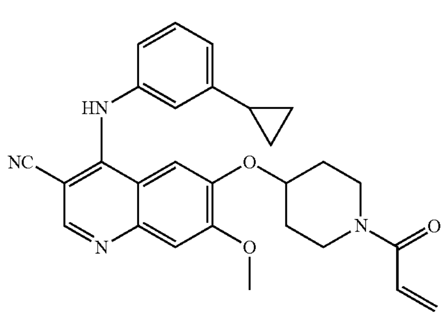 [SMILES: C=CC(=O)N1CCC(Oc2cc3c(Nc4cccc(C5CC5)c4)c(C#N)cnc3cc2OC)CC1] | 6-((1-acryloylpiperidin-4-yl)oxy)-4-((3-cyclopropyl-phenyl)amino)-7-methoxy-quinoline-3-carbonitrile | 68 | 469 | 1 |

TABLE 1-continued

Examples 11-101

| Ex. No | Structure | IUPAC Name | MWt | M + H | Ex. Meth. |
|---|---|---|---|---|---|
| 19 | 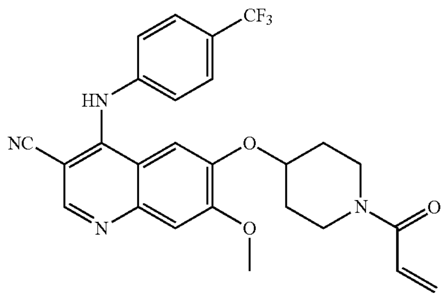 [SMILES: C=CC(=O)N1CCC(Oc2cc3c(Nc4ccc(C(F)(F)F)cc4)c(C#N)cnc3cc2OC)CC1] | 6-((1-acryloylpiperidin-4-yl)oxy)-7-methoxy-4-((4-(trifluoromethyl)phenyl)-amino)quinoline-3-carbonitrile | 496 | 497 | 1 |
| 20 | 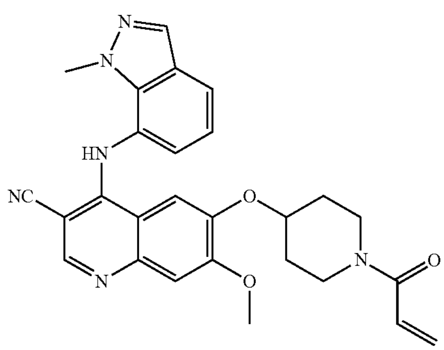 [SMILES: C=CC(=O)N1CCC(Oc2cc3c(Nc4cccc5cnn(C)c45)c(C#N)cnc3cc2OC)CC1] | 6-((1-acryloylpiperidin-4-yl)oxy)-7-methoxy-4-((1-methyl-1H-indazol-7-yl)-amino)quinoline-3-carbonitrile | 481 | 482 | 1 |
| 21 | 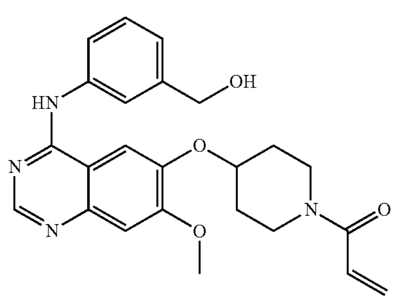 [SMILES: C=CC(=O)N1CCC(Oc2cc3c(Nc4cccc(CO)c4)ncnc3cc2OC)CC1] | 1-(4-((4-((3-(hydroxy-methyl)phenyl)amino)-7-methoxyquinazolin-6-yl)-oxy)piperidin-1-yl)prop-2-en-1-one | 434 | 435 | 2 |
| 22 | 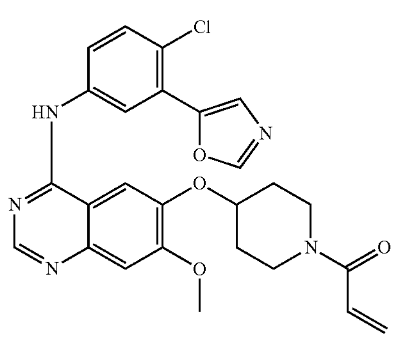 [SMILES: C=CC(=O)N1CCC(Oc2cc3c(Nc4ccc(Cl)c(-c5cnco5)c4)ncnc3cc2OC)CC1] | 1-(4-((4-((4-chloro-3-(oxazol-5-yl)phenyl)-amino)-7-methoxy-quinazolin-6-yl)oxy)-piperidin-1-yl)prop-2-en-1-one | 505 | 506 | 2 |

TABLE 1-continued

Examples 11-101

| Ex. No | Structure | IUPAC Name | MWt | M + H | Ex. Meth. |
|---|---|---|---|---|---|
| 23 | 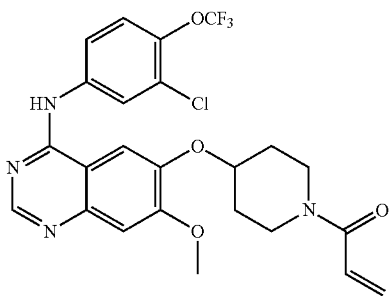 [SMILES: C=CC(=O)N1CCC(Oc2cc3c(Nc4ccc(OC(F)(F)F)c(Cl)c4)ncnc3cc2OC)CC1] | 1-(4-((4-((3-chloro-4-(trifluoromethoxy)phenyl)-amino)-7-methoxy-quinazolin-6-yl)oxy)-piperidin-1-yl)prop-2-en-1-one | 522 | 523 | 2 |
| 24 | 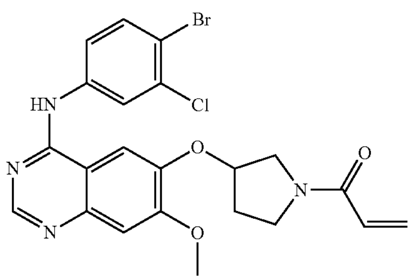 [SMILES: C=CC(=O)N1CCC(Oc2cc3c(Nc4ccc(Br)c(Cl)c4)ncnc3cc2OC)C1] | 1-(3-((4-((4-bromo-3-chlorophenyl)amino)-7-methoxyquinazolin-6-yl)-oxy)pyrrolidin-1-yl)prop-2-en-1-one | 502 | 503 | 2 |
| 25 | 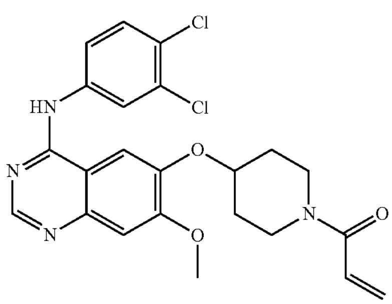 [SMILES: C=CC(=O)N1CCC(Oc2cc3c(Nc4ccc(Cl)c(Cl)c4)ncnc3cc2OC)CC1] | 1-(4-((4-((3,4-dichloro-phenyl)amino)-7-methoxy-quinazolin-6-yl)oxy)-piperidin-1-yl)prop-2-en-1-one | 472 | 473 | 2 |
| 26 | 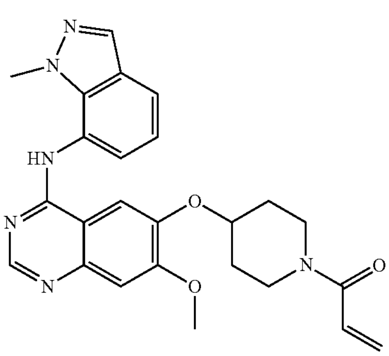 [SMILES: C=CC(=O)N1CCC(Oc2cc3c(Nc4cccc5cnn(C)c45)ncnc3cc2OC)CC1] | 1-(4-((7-methoxy-4-((1-methyl-1H-indazol-7-yl)-amino)quinazolin-6-yl)-oxy)piperidin-1-yl)prop-2-en-1-one | 458 | 459 | 2 |
| 27 | 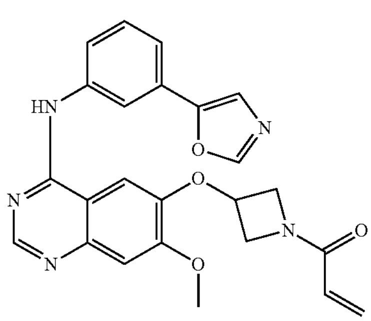 [SMILES: C=CC(=O)N1CC(Oc2cc3c(Nc4cccc(-c5cnco5)c4)ncnc3cc2OC)C1] | 1-(3-((7-methoxy-4-((3-(oxazol-5-yl)phenyl)-amino)quinazolin-6-yl)-oxy)azetidin-1-yl)prop-2-en-1-one | 443 | 444 | 2 |

TABLE 1-continued

Examples 11-101

| Ex. No | Structure | IUPAC Name | MWt | M + H | Ex. Meth. |
|---|---|---|---|---|---|
| 28 | 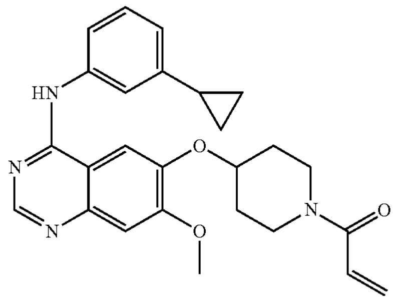 [SMILES: C=CC(=O)N1CCC(Oc2cc3c(Nc4cccc(C5CC5)c4)ncnc3cc2OC)CC1] | 1-(4-((4-((3-cyclopropyl-phenyl)amino)-7-methoxy-quinazolin-6-yl)oxy)-piperidin-1-yl)prop-2-en-1-one | 444 | 445 | 2 |
| 29 | 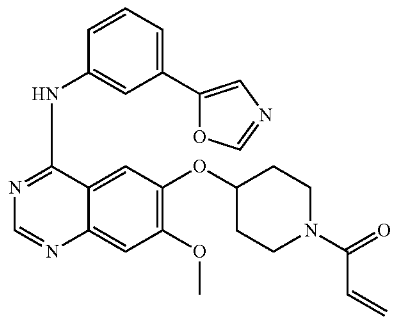 [SMILES: C=CC(=O)N1CCC(Oc2cc3c(Nc4cccc(-c5cnco5)c4)ncnc3cc2OC)CC1] | 1-(4-((7-methoxy-4-((3-(oxazol-5-yl)phenyl)-amino)quinazolin-6-yl)-oxy)piperidin-1-yl)prop-2-en-1-one | 471 | 472 | 2 |
| 30 | 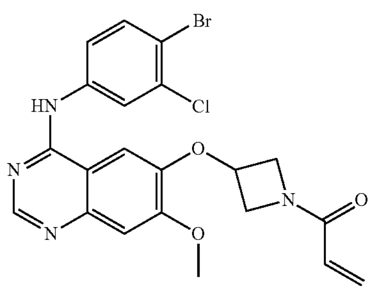 [SMILES: C=CC(=O)N1CC(Oc2cc3c(Nc4ccc(Br)c(Cl)c4)ncnc3cc2OC)C1] | 1-(3-((4-((4-bromo-3-chlorophenyl)amino)-7-methoxyquinazolin-6-yl)oxy)azetidin-1-yl)prop-2-en-1-one | 488 | 489 | 2 |
| 31 | 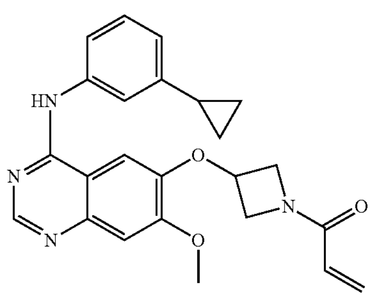 [SMILES: C=CC(=O)N1CC(Oc2cc3c(Nc4cccc(C5CC5)c4)ncnc3cc2OC)C1] | 1-(3-((4-((3-cyclopropyl-phenyl)amino)-7-methoxy-quinazolin-6-yl)oxy)-azetidin-1-yl)prop-2-en-1-one | 416 | 417 | 2 |
| 32 | 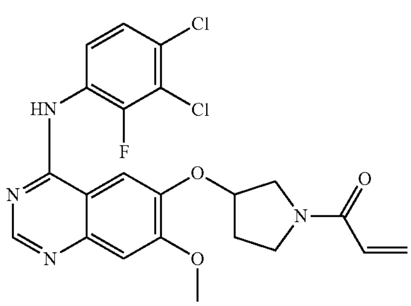 [SMILES: C=CC(=O)N1CCC(Oc2cc3c(Nc4ccc(Cl)c(Cl)c4F)ncnc3cc2OC)C1] | 1-(3-((4-((3,4-dichloro-2-fluorophenyl)amino)-7-methoxyquinazolin-6-yl)-oxy)pyrrolidin-1-yl)prop-2-en-1-one | 476 | 477 | 2 |

TABLE 1-continued

Examples 11-101

| Ex. No | Structure | IUPAC Name | MWt | M + H | Ex. Meth. |
|---|---|---|---|---|---|
| 33 | 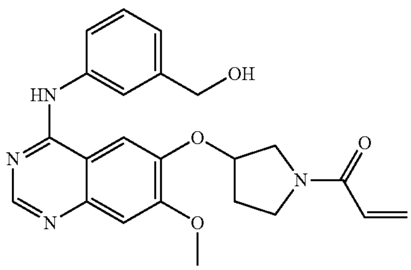 [SMILES: C=CC(=O)N1CCC(Oc2cc3c(Nc4cccc(CO)c4)ncnc3cc2OC)C1] | 1-(3-((4-((3-(hydroxy-methyl)phenyl)amino)-7-methoxyquinazolin-6-yl)-oxy)pyrrolidin-1-yl)prop-2-en-1-one | 420 | 421 | 2 |
| 34 | 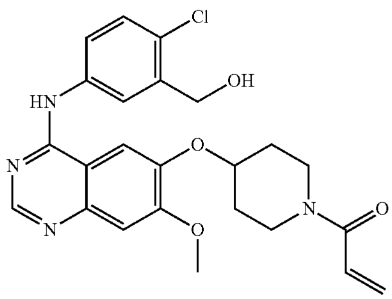 [SMILES: C=CC(=O)N1CCC(Oc2cc3c(Nc4ccc(Cl)c(CO)c4)ncnc3cc2OC)CC1] | 1-(4-((4-((4-chloro-3-(hydroxymethyl)phenyl)-amino)-7-methoxy-quinazolin-6-yl)oxy)-piperidin-1-yl)prop-2-en-1-one | 468 | 469 | 2 |
| 35 | 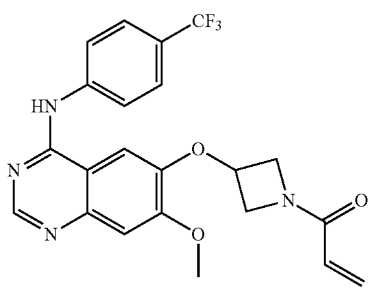 [SMILES: C=CC(=O)N1CC(Oc2cc3c(Nc4ccc(C(F)(F)F)cc4)ncnc3cc2OC)C1] | 1-(3-((7-methoxy-4-((4-(trifluoromethyl)phenyl)-amino)quinazolin-6-yl)-oxy)azetidin-1-yl)prop-2-en-1-one | 444 | 445 | 2 |
| 36 | 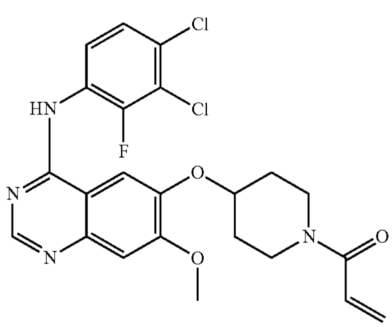 [SMILES: C=CC(=O)N1CCC(Oc2cc3c(Nc4ccc(Cl)c(Cl)c4F)ncnc3cc2OC)CC1] | 1-(4-((4-((3,4-dichloro-2-fluorophenyl)amino)-7-methoxyquinazolin-6-yl)-oxy)piperidin-1-yl)prop-2-en-1-one | 490 | 491 | 2 |
| 37 | 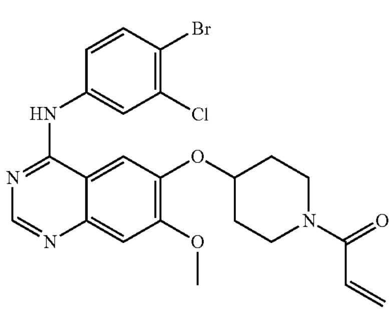 [SMILES: C=CC(=O)N1CCC(Oc2cc3c(Nc4ccc(Br)c(Cl)c4)ncnc3cc2OC)CC1] | 1-(4-((4-((4-bromo-3-chlorophenyl)amino)-7-methoxyquinazolin-6-yl)-oxy)piperidin-1-yl)prop-2-en-1-one | 516 | 517 | 2 |

TABLE 1-continued

Examples 11-101

| Ex. No | Structure | IUPAC Name | MWt | M + H | Ex. Meth. |
|---|---|---|---|---|---|
| 38 | 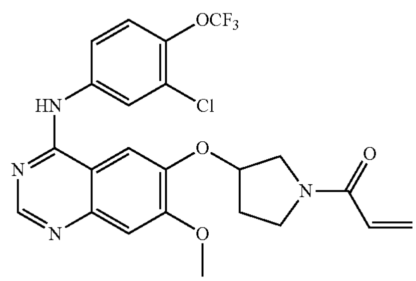 [SMILES: C=CC(=O)N1CCC(Oc2cc3c(Nc4ccc(OC(F)(F)F)c(Cl)c4)ncnc3cc2OC)C1] | 1-(3-((4-((3-chloro-4-(trifluoromethoxy)phenyl)-amino)-7-methoxy-quinazolin-6-yl)oxy)-pyrrolidin-1-yl)prop-2-en-1-one | 508 | 509 | 2 |
| 39 | 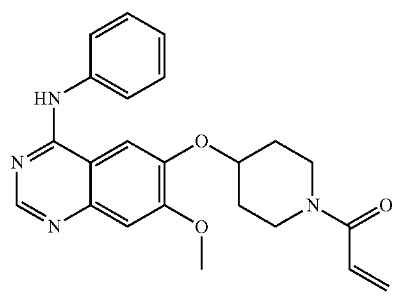 [SMILES: C=CC(=O)N1CCC(Oc2cc3c(Nc4ccccc4)ncnc3cc2OC)CC1] | 1-(4-((7-methoxy-4-(phenylamino)quinazolin-6-yl)oxy)piperidin-1-yl)prop-2-en-1-one | 404 | 405 | 2 |
| 40 | 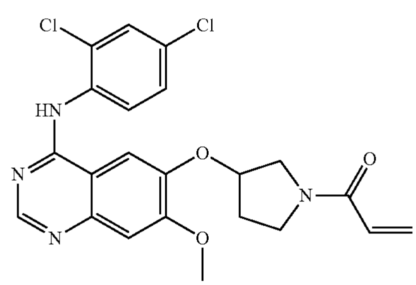 [SMILES: C=CC(=O)N1CCC(Oc2cc3c(Nc4ccc(Cl)cc4Cl)ncnc3cc2OC)C1] | 1-(3-((4-((2,4-dichloro-phenyl)amino)-7-methoxy-quinazolin-6-yl)oxy)-pyrrolidin-1-yl)prop-2-en-1-one | 458 | 459 | 2 |
| 41 | 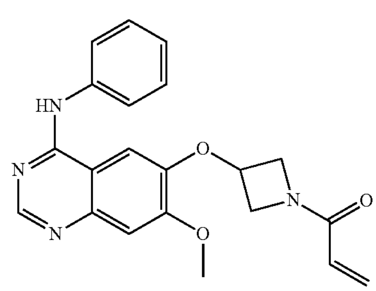 [SMILES: C=CC(=O)N1CC(Oc2cc3c(Nc4ccccc4)ncnc3cc2OC)C1] | 1-(3-((7-methoxy-4-(phenylamino)quinazolin-6-yl)oxy)azetidin-1-yl)prop-2-en-1-one | 376 | 377 | 2 |
| 42 | 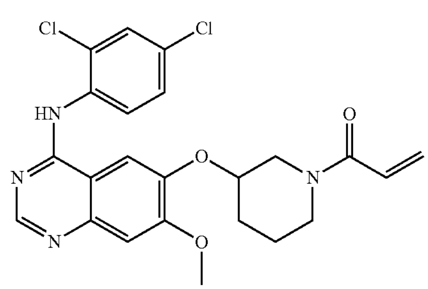 [SMILES: C=CC(=O)N1CCCC(Oc2cc3c(Nc4ccc(Cl)cc4Cl)ncnc3cc2OC)C1] | 1-(3-((4-((2,4-dichloro-phenyl)amino)-7-methoxy-quinazolin-6-yl)oxy)-piperidin-1-yl)prop-2-en-1-one | 472 | 473 | 2 |

TABLE 1-continued

Examples 11-101

| Ex. No | Structure | IUPAC Name | MWt | M + H | Ex. Meth. |
|---|---|---|---|---|---|
| 43 | 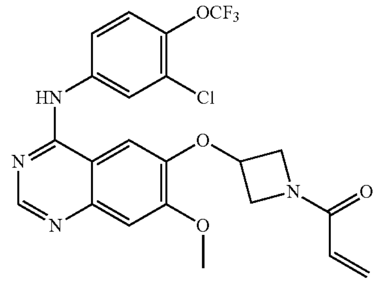 [SMILES: C=CC(=O)N1CC(Oc2cc3c(Nc4ccc(OC(F)(F)F)c(Cl)c4)ncnc3cc2OC)C1] | 1-(3-((4-((3-chloro-4-(trifluoromethoxy)phenyl)-amino)-7-methoxy-quinazolin-6-yl)oxy)-azetidin-1-yl)prop-2-en-1-one | 494 | 494 | 2 |
| 44 | 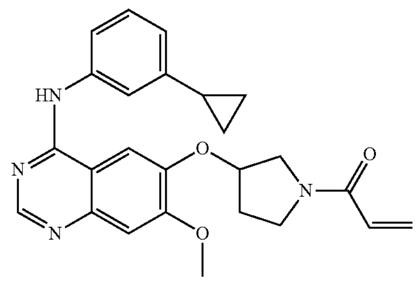 [SMILES: C=CC(=O)N1CCC(Oc2cc3c(Nc4cccc(C5CC5)c4)ncnc3cc2OC)C1] | 1-(3-((4-((3-cyclopropyl-phenyl)amino)-7-methoxy-quinazolin-6-yl)oxy)-pyrrolidin-1-yl)prop-2-en-1-one | 430 | 430 | 2 |
| 45 | 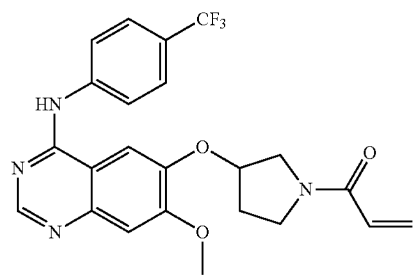 [SMILES: C=CC(=O)N1CCC(Oc2cc3c(Nc4ccc(C(F)(F)F)cc4)ncnc3cc2OC)C1] | 1-(3-((7-methoxy-4-((4-(trifluoromethyl)phenyl)-amino)quinazolin-6-yl)-oxy)pyrrolidin-1-yl)prop-2-en-1-one | 458 | 459 | 2 |
| 46 | 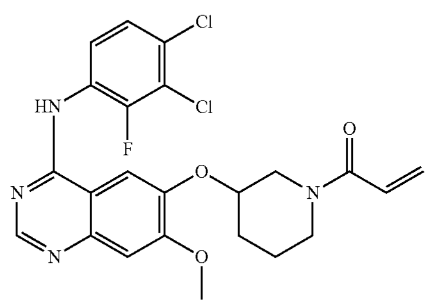 [SMILES: C=CC(=O)N1CCCC(Oc2cc3c(Nc4ccc(Cl)c(Cl)c4F)ncnc3cc2OC)C1] | 1-(3-((4-((3,4-dichloro-2-fluorophenyl)amino)-7-methoxyquinazolin-6-yl)oxy)piperidin-1-yl)prop-2-en-1-one | 490 | 491 | 2 |
| 47 | 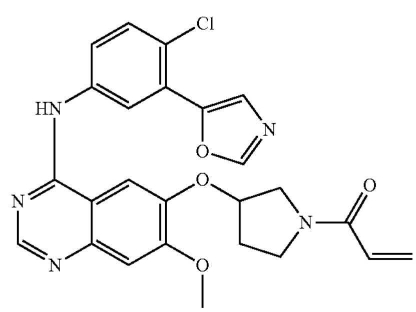 [SMILES: C=CC(=O)N1CCC(Oc2cc3c(Nc4ccc(Cl)c(-c5cnco5)c4)ncnc3cc2OC)C1] | 1-(3-((4-((4-chloro-3-(oxazol-5-yl)phenyl)-amino)-7-methoxy-quinazolin-6-yl)oxy)-pyrrolidin-1-yl)prop-2-en-1-one | 491 | 492 | 2 |

TABLE 1-continued

Examples 11-101

| Ex. No | Structure | IUPAC Name | MWt | M + H | Ex. Meth. |
|---|---|---|---|---|---|
| 48 | 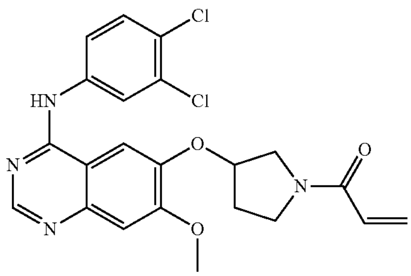 | 1-(3-((4-((3,4-dichloro-phenyl)amino)-7-methoxy-quinazolin-6-yl)oxy)-pyrrolidin-1-yl)prop-2-en-1-one | 458 | 459 | 2 |
| 49 | 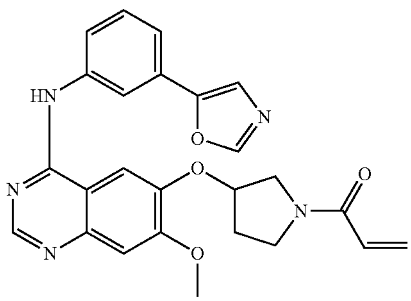 [SMILES: C=CC(=O)N1CCC(Oc2cc3c(Nc4cccc(-c5cnco5)c4)ncnc3cc2OC)C1] | 1-(3-((7-methoxy-4-((3-(oxazol-5-yl)phenyl)-amino)quinazolin-6-yl)-oxy)pyrrolidin-1-yl)prop-2-en-1-one | 457 | 458 | 2 |
| 50 | 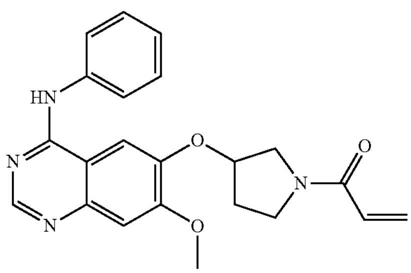 [SMILES: C=CC(=O)N1CCC(Oc2cc3c(Nc4ccccc4)ncnc3cc2OC)C1] | 1-(3-((7-methoxy-4-(phenylamino)quinazolin-6-yl)oxy)pyrrolidin-1-yl)prop-2-en-1-one | 390 | 390 | 2 |
| 51 | 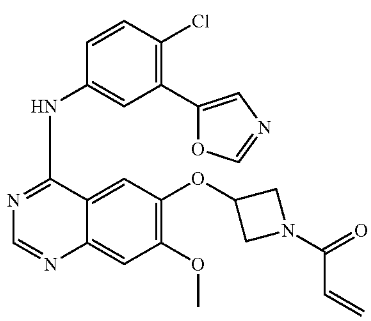 [SMILES: C=CC(=O)N1CC(Oc2cc3c(Nc4ccc(Cl)c(-c5cnco5)c4)ncnc3cc2OC)C1] | 1-(3-((4-((4-chloro-3-(oxazol-5-yl)phenyl)-amino)-7-methoxy-quinazolin-6-yl)oxy)-azetidin-1-yl)prop-2-en-1-one | 477 | 478 | 2 |
| 52 | 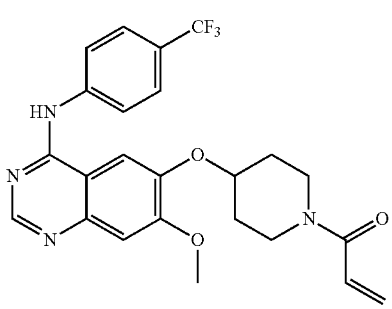 [SMILES: C=CC(=O)N1CCC(Oc2cc3c(Nc4ccc(C(F)(F)F)cc4)ncnc3cc2OC)CC1] | 1-(4-((7-methoxy-4-((4-(trifluoromethyl)phenyl)-amino)quinazolin-6-yl)-oxy)piperidin-1-yl)prop-2-en-1-one | 472 | 473 | 2 |

TABLE 1-continued

Examples 11-101

| Ex. No | Structure | IUPAC Name | MWt | M + H | Ex. Meth. |
|---|---|---|---|---|---|
| 53 | 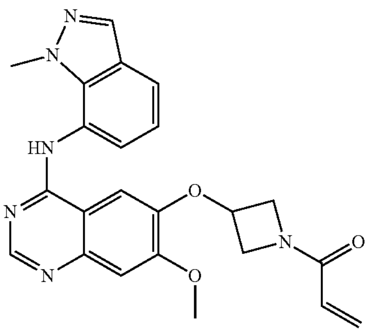 [SMILES: C=CC(=O)N1CC(Oc2cc3c(Nc4cccc5cnn(C)c45)ncnc3cc2OC)C1] | 1-(3-((7-methoxy-4-((1-methyl-1H-indazol-7-yl)-amino)quinazolin-6-yl)-oxy)azetidin-1-yl)prop-2-en-1-one | 430 | 431 | 2 |
| 54 | 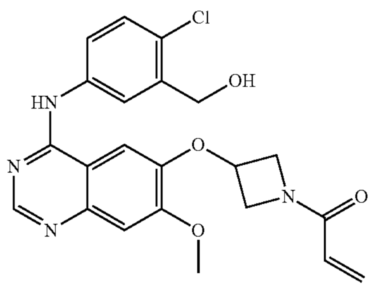 [SMILES: C=CC(=O)N1CC(Oc2cc3c(Nc4ccc(Cl)c(CO)c4)ncnc3cc2OC)C1] | 1-(3-((4-((4-chloro-3-(hydroxymethyl)phenyl)-amino)-7-methoxy-quinazolin-6-yl)oxy)-azetidin-1-yl)prop-2-en-1-one | 440 | 441 | 2 |
| 55 | 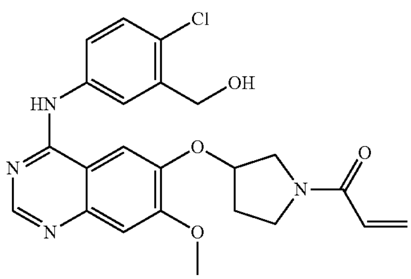 [SMILES: C=CC(=O)N1CCC(Oc2cc3c(Nc4ccc(Cl)c(CO)c4)ncnc3cc2OC)C1] | 1-(3-((4-((4-chloro-3-(hydroxymethyl)phenyl)-amino)-7-methoxy-quinazolin-6-yl)oxy)-pyrrolidin-1-yl)prop-2-en-1-one | 454 | 455 | 2 |
| 56 | 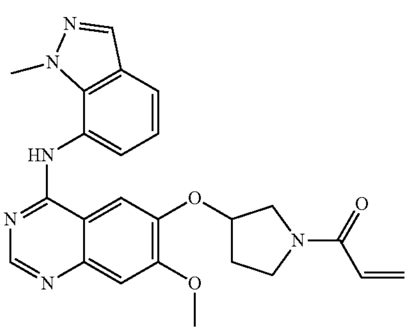 [SMILES: C=CC(=O)N1CCC(Oc2cc3c(Nc4cccc5cnn(C)c45)ncnc3cc2OC)C1] | 1-(3-((7-methoxy-4-((1-methyl-1H-indazol-7-yl)-amino)quinazolin-6-yl)-oxy)pyrrolidin-1-yl)prop-2-en-1-one | 444 | 445 | 2 |
| 57 | 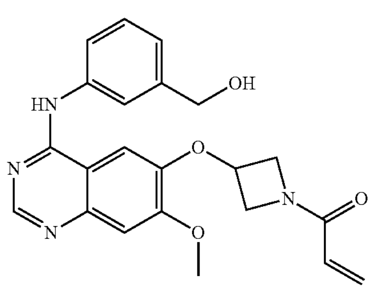 [SMILES: C=CC(=O)N1CC(Oc2cc3c(Nc4cccc(CO)c4)ncnc3cc2OC)C1] | 1-(3-((4-((3-(hydroxy-methyl)phenyl)amino)-7-methoxyquinazolin-6-yl)-oxy)azetidin-1-yl)prop-2-en-1-one | 406 | 407 | 2 |

TABLE 1-continued

Examples 11-101

| Ex. No | Structure | IUPAC Name | MWt | M + H | Ex. Meth. |
|---|---|---|---|---|---|
| 58 | 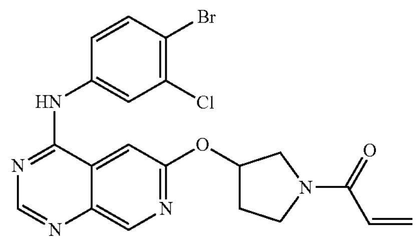 [SMILES: C=CC(=O)N1CCC(Oc2cc3c(Nc4ccc(Br)c(Cl)c4)ncnc3cn2)C1] | 1-(3-((4-((4-bromo-3-chlorophenyl)amino)-pyrido[3,4-d]pyrimidin-6-yl)oxy)pyrrolidin-1-yl)prop-2-en-1-one | 473 | 474 | 3 |
| 59 | 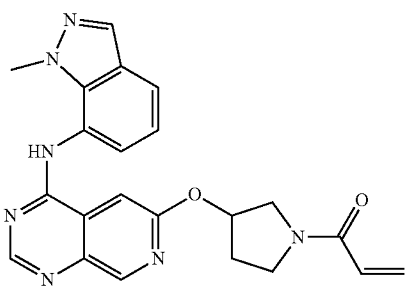 [SMILES: C=CC(=O)N1CCC(Oc2cc3c(Nc4cccc5cnn(C)c45)ncnc3cn2)C1] | 1-(3-((4-((1-methyl-1H-indazol-7-yl)amino)pyrido-[3,4-d]pyrimidin-6-yl)oxy)-pyrrolidin-1-yl)prop-2-en-1-one | 415 | 416 | 3 |
| 60 | 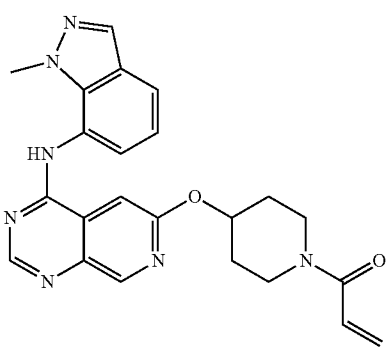 [SMILES: C=CC(=O)N1CCC(Oc2cc3c(Nc4cccc5cnn(C)c45)ncnc3cn2)CC1] | 1-(4-((4-((1-methyl-1H-indazol-7-yl)amino)pyrido-[3,4-d]pyrimidin-6-yl)oxy)-piperidin-1-yl)prop-2-en-1-one | 429 | 430 | 3 |
| 61 | 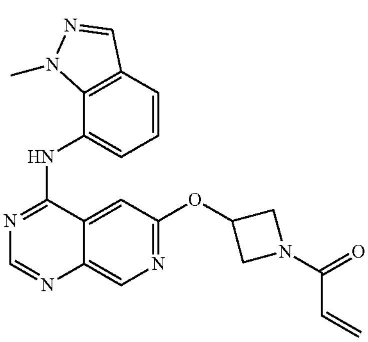 [SMILES: C=CC(=O)N1CC(Oc2cc3c(Nc4cccc5cnn(C)c45)ncnc3cn2)C1] | 1-(3-((4-((1-methyl-1H-indazol-7-yl)amino)pyrido-[3,4-d]pyrimidin-6-yl)oxy)-azetidin-1-yl)prop-2-en-1-one | 401 | 402 | 3 |
| 62 | 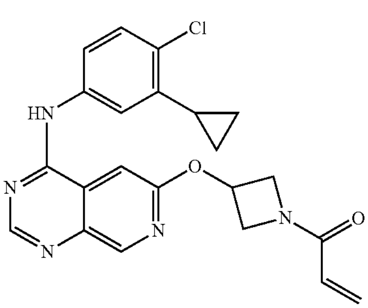 [SMILES: C=CC(=O)N1CC(Oc2cc3c(Nc4ccc(Cl)c(C5CC5)c4)ncnc3cn2)C1] | 1-(3-((4-((4-chloro-3-cyclopropylphenyl)amino)-pyrido[3,4-d]pyrimidin-6-yl)oxy)azetidin-1-yl)prop-2-en-1-one | 421 | 422 | 3 |

TABLE 1-continued

Examples 11-101

| Ex. No | Structure | IUPAC Name | MWt | M + H | Ex. Meth. |
|---|---|---|---|---|---|
| 63 | 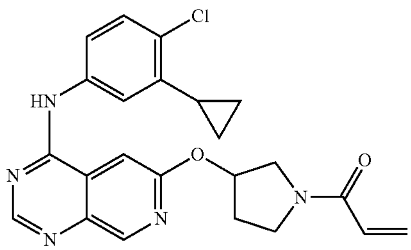 [SMILES: C=CC(=O)N1CCC(Oc2cc3c(Nc4ccc(Cl)c(C5CC5)c4)ncnc3cn2)C1] | 1-(3-((4-((4-chloro-3-cyclo-propylphenyl)amino)-pyrido[3,4-d]pyrimidin-6-yl)oxy)pyrrolidin-1-yl)prop-2-en-1-one | 435 | 436 | 3 |
| 64 | 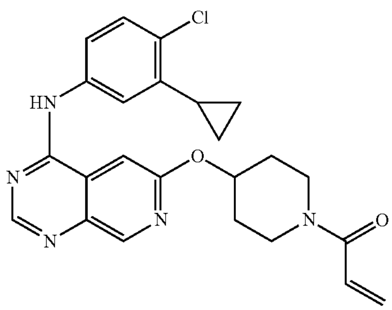 [SMILES: C=CC(=O)N1CCC(Oc2cc3c(Nc4ccc(Cl)c(C5CC5)c4)ncnc3cn2)CC1] | 1-(4-((4-((4-chloro-3-cyclo-propylphenyl)amino)-pyrido[3,4-d]pyrimidin-6-yl)oxy)piperidin-1-yl)prop-2-en-1-one | 449 | 450 | 3 |
| 65 | 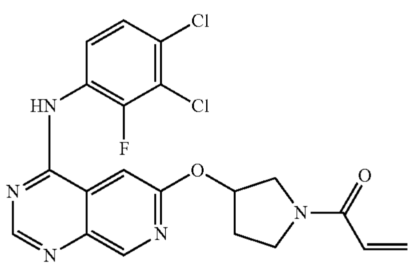 [SMILES: C=CC(=O)N1CCC(Oc2cc3c(Nc4ccc(Cl)c(Cl)c4F)ncnc3cn2)C1] | 1-(3-((4-((3,4-dichloro-2-fluorophenyl)amino)-pyrido[3,4-d]pyrimidin-6-yl)oxy)pyrrolidin-1-yl)prop-2-en-1-one | 447 | 448 | 3 |
| 66 | 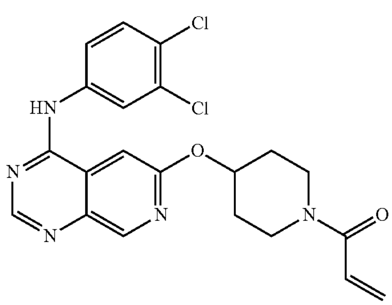 | 1-(4-((4-((3,4-dichloro-phenyl)amino)pyrido[3,4-d]pyrimidin-6-yl)oxy)-piperidin-1-yl)prop-2-en-1-one | 443 | 444 | 3 |
| 67 | 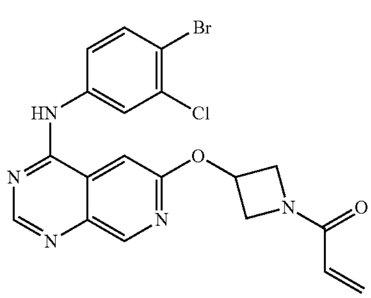 [SMILES: C=CC(=O)N1CC(Oc2cc3c(Nc4ccc(Br)c(Cl)c4)ncnc3cn2)C1] | 1-(3-((4-((4-bromo-3-chlorophenyl)amino)pyrido-[3,4-d]pyrimidin-6-yl)oxy)-azetidin-1-yl)prop-2-en-1-one | 459 | 460 | 3 |

TABLE 1-continued

Examples 11-101

| Ex. No | Structure | IUPAC Name | MWt | M + H | Ex. Meth. |
|---|---|---|---|---|---|
| 68 | 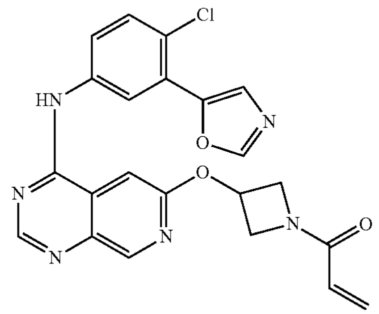 [SMILES: C=CC(=O)N1CC(Oc2cc3c(Nc4ccc(Cl)c(-c5cnco5)c4)ncnc3cn2)C1] | 1-(3-((4-((4-chloro-3-(oxazol-5-yl)phenyl)-amino)pyrido[3,4-d]-pyrimidin-6-yl)oxy)-azetidin-1-yl)prop-2-en-1-one | 448 | 449 | 3 |
| 69 | 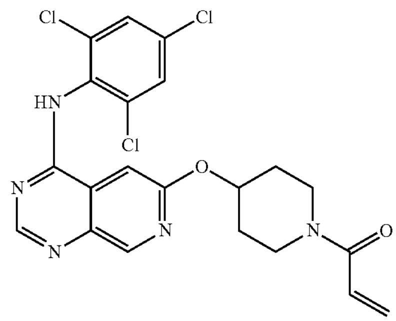 [SMILES: C=CC(=O)N1CCC(Oc2cc3c(Nc4c(Cl)cc(Cl)cc4Cl)ncnc3cn2)CC1] | 1-(4-((4-((2,4,6-trichloro-phenyl)amino)pyrido[3,4-d]pyrimidin-6-yl)oxy)-piperidin-1-yl)prop-2-en-1-one | 477 | 478 | 3 |
| 70 | 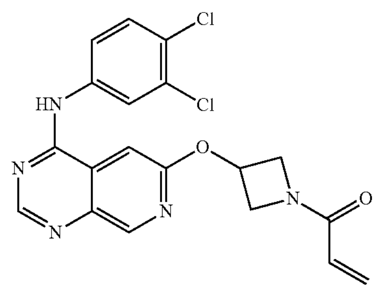 [SMILES: C=CC(=O)N1CC(Oc2cc3c(Nc4ccc(Cl)c(Cl)c4)ncnc3cn2)C1] | 1-(3-((4-((3,4-dichloro-phenyl)amino)pyrido[3,4-d]pyrimidin-6-yl)oxy)-azetidin-1-yl)prop-2-en-1-one | 415 | 416 | 3 |
| 71 | 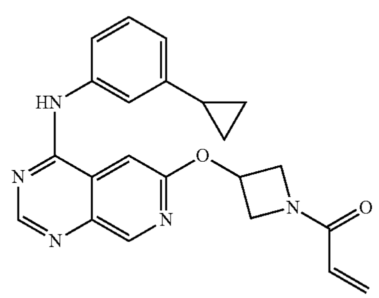 [SMILES: C=CC(=O)N1CC(Oc2cc3c(Nc4cccc(C5CC5)c4)ncnc3cn2)C1] | 1-(3-((4-((3-cyclopropyl-phenyl)amino)pyrido[3,4-d]pyrimidin-6-yl)oxy)-azetidin-1-yl)prop-2-en-1-one | 387 | 388 | 3 |
| 72 | 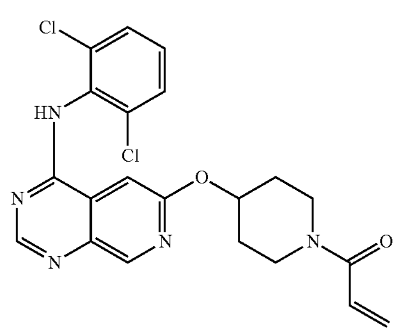 [SMILES: C=CC(=O)N1CCC(Oc2cc3c(Nc4c(Cl)cccc4Cl)ncnc3cn2)CC1] | 1-(4-((4-((2,6-dichloro-phenyl)amino)pyrido[3,4-d]pyrimidin-6-yl)oxy)-piperidin-1-yl)prop-2-en-1-one | 443 | 444 | 3 |

TABLE 1-continued

Examples 11-101

| Ex. No | Structure | IUPAC Name | MWt | M + H | Ex. Meth. |
|---|---|---|---|---|---|
| 73 | 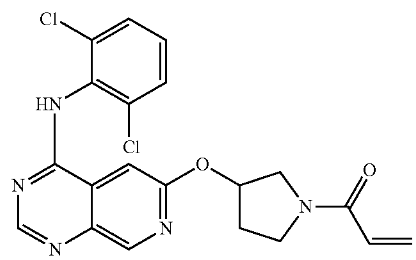 [SMILES: C=CC(=O)N1CCC(Oc2cc3c(Nc4c(Cl)cccc4Cl)ncnc3cn2)C1] | 1-(3-((4-((2,6-dichloro-phenyl)amino)pyrido[3,4-d]pyrimidin-6-yl)oxy)-pyrrolidin-1-yl)prop-2-en-1-one | 429 | 430 | 3 |
| 74 | 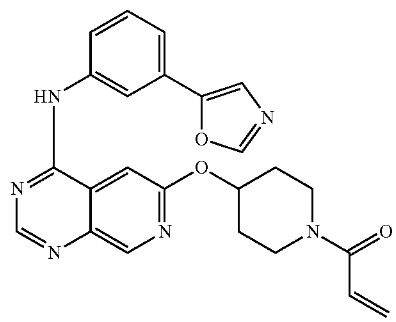 [SMILES: C=CC(=O)N1CCC(Oc2cc3c(Nc4cccc(-c5cnco5)c4)ncnc3cn2)CC1] | 1-(4-((4-((3-(oxazol-5-yl)-phenyl)amino)pyrido[3,4-d]pyrimidin-6-yl)oxy)-piperidin-1-yl)prop-2-en-1-one | 442 | 443 | 3 |
| 75 | 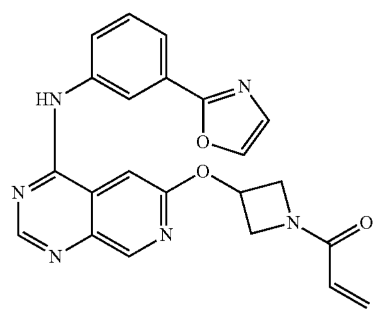 [SMILES: C=CC(=O)N1CC(Oc2cc3c(Nc4cccc(-c5ncco5)c4)ncnc3cn2)C1] | 1-(3-((4-((3-(oxazol-5-yl)-phenyl)amino)pyrido[3,4-d]pyrimidin-6-yl)oxy)-azetidin-1-yl)prop-2-en-1-one | 414 | 415 | 3 |
| 76 | 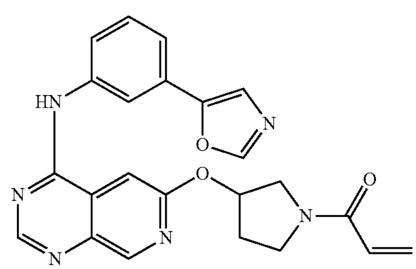 [SMILES: C=CC(=O)N1CCC(Oc2cc3c(Nc4cccc(-c5cnco5)c4)ncnc3cn2)C1] | 1-(3-((4-((3-(oxazol-5-yl)-phenyl)amino)pyrido[3,4-d]pyrimidin-6-yl)oxy)-pyrrolidin-1-yl)prop-2-en-1-one | 428 | 429 | 3 |
| 77 | 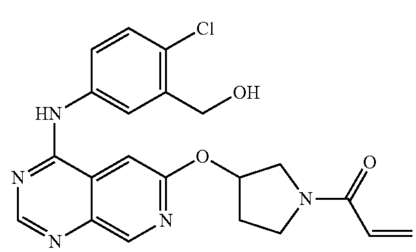 [SMILES: C=CC(=O)N1CCC(Oc2cc3c(Nc4ccc(Cl)c(CO)c4)ncnc3cn2)C1] | 1-(3-((4-((4-chloro-3-(hydroxymethyl)phenyl)-amino)pyrido[3,4-d]-pyrimidin-6-yl)oxy)-pyrrolidin-1-yl)prop-2-en-1-one | 425 | 426 | 3 |

TABLE 1-continued

Examples 11-101

| Ex. No | Structure | IUPAC Name | MWt | M + H | Ex. Meth. |
|---|---|---|---|---|---|
| 78 | 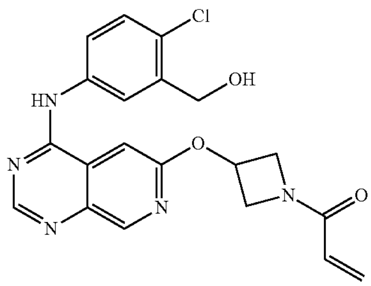 [SMILES: C=CC(=O)N1CC(Oc2cc3c(Nc4ccc(Cl)c(CO)c4)ncnc3cn2)C1] | 1-(3-((4-((4-chloro-3-(hydroxymethyl)phenyl)-amino)pyrido[3,4-d]-pyrimidin-6-yl)oxy)-azetidin-1-yl)prop-2-en-1-one | 411 | 412 | 3 |
| 79 | 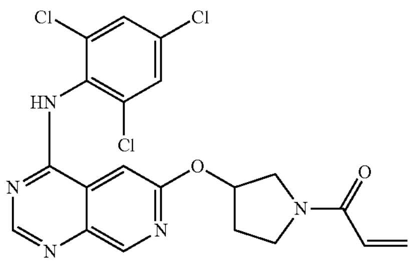 [SMILES: C=CC(=O)N1CCC(Oc2cc3c(Nc4c(Cl)cc(Cl)cc4Cl)ncnc3cn2)C1] | 1-(3-((4-((2,4,6-trichloro-phenyl)amino)pyrido[3,4-d]pyrimidin-6-yl)oxy)-pyrrolidin-1-yl)prop-2-en-1-one | 463 | 464 | 3 |
| 80 | 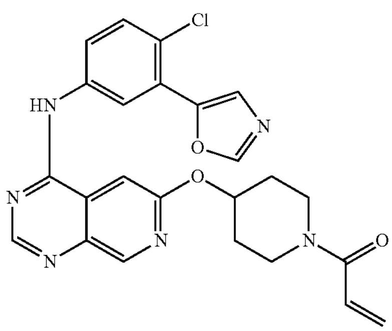 [SMILES: C=CC(=O)N1CCC(Oc2cc3c(Nc4ccc(Cl)c(-c5cnco5)c4)ncnc3cn2)CC1] | 1-(4-((4-((4-chloro-3-(oxazol-5-yl)phenyl)-amino)pyrido[3,4-d]-pyrimidin-6-yl)oxy)-piperidin-1-yl)prop-2-en-1-one | 476 | 477 | 3 |
| 81 | 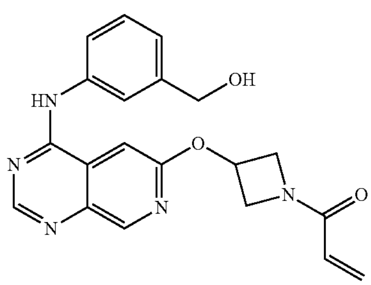 [SMILES: C=CC(=O)N1CC(Oc2cc3c(Nc4cccc(CO)c4)ncnc3cn2)C1] | 1-(3-((4-((3-(hydroxy-methyl)phenyl)amino)-pyrido[3,4-d]pyrimidin-6-yl)oxy)azetidin-1-yl)prop-2-en-1-one | 377 | 378 | 3 |
| 82 | 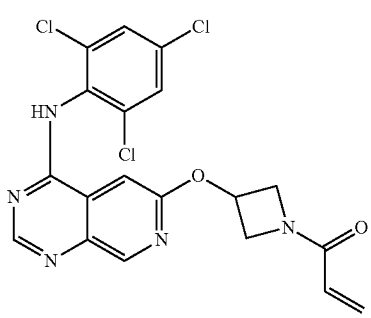 [SMILES: C=CC(=O)N1CC(Oc2cc3c(Nc4c(Cl)cc(Cl)cc4Cl)ncnc3cn2)C1] | 1-(3-((4-((2,4,6-trichloro-phenyl)amino)pyrido[3,4-d]pyrimidin-6-yl)oxy)-azetidin-1-yl)prop-2-en-1-one | 449 | 450 | 3 |

TABLE 1-continued

Examples 11-101

| Ex. No | Structure | IUPAC Name | MWt | M + H | Ex. Meth. |
|---|---|---|---|---|---|
| 83 | 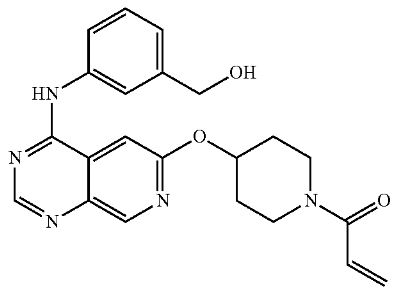 [SMILES: C=CC(=O)N1CCC(Oc2cc3c(Nc4cccc(CO)c4)ncnc3cn2)CC1] | 1-(4-((4-((3-(hydroxymethyl)phenyl)amino)-pyrido[3,4-d]pyrimidin-6-yl)oxy)piperidin-1-yl)prop-2-en-1-one | 405 | 406 | 3 |
| 84 | 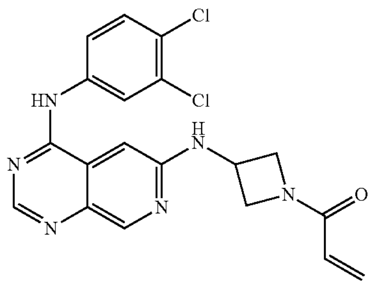 | 1-(3-((4-((3,4-dichlorophenyl)amino)pyrido[3,4-d]pyrimidin-6-yl)amino)-azetidin-1-yl)prop-2-en-1-one | 414 | 415 | 3 |
| 85 | 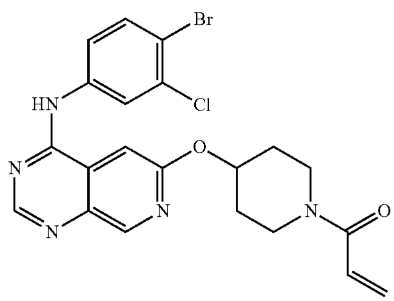 [SMILES: C=CC(=O)N1CCC(Oc2cc3c(Nc4ccc(Br)c(Cl)c4)ncnc3cn2)CC1] | 1-(4-((4-((4-bromo-3-chlorophenyl)amino)pyrido-[3,4-d]pyrimidin-6-yl)oxy)-piperidin-1-yl)prop-2-en-1-one | 487 | 488 | 3 |
| 86 | 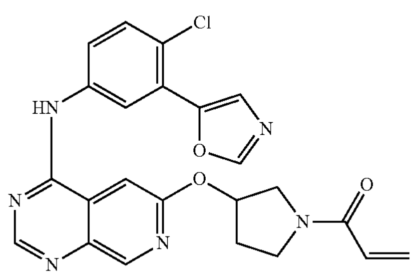 [SMILES: C=CC(=O)N1CCC(Oc2cc3c(Nc4ccc(Cl)c(-c5cnco5)c4)ncnc3cn2)C1] | 1-(3-((4-((4-chloro-3-(oxazol-5-yl)phenyl)-amino)pyrido[3,4-d]-pyrimidin-6-yl)oxy)-pyrrolidin-1-yl)prop-2-en-1-one | 462 | 463 | 3 |
| 87 | 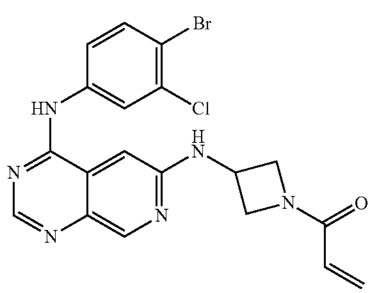 [SMILES: C=CC(=O)N1CC(Nc2cc3c(Nc4ccc(Br)c(Cl)c4)ncnc3cn2)C1] | 1-(3-((4-((4-bromo-3-chlorophenyl)amino)pyrido-[3,4-d]pyrimidin-6-yl)-amino)azetidin-1-yl)prop-2-en-1-one | 458 | 458 | 3 |

TABLE 1-continued

Examples 11-101

| Ex. No | Structure | IUPAC Name | MWt | M + H | Ex. Meth. |
|---|---|---|---|---|---|
| 88 | 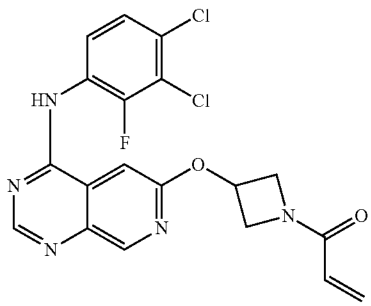 [SMILES: C=CC(=O)N1CC(Oc2cc3c(Nc4ccc(Cl)c(Cl)c4F)ncnc3cn2)C1] | 1-(3-((4-((3,4-dichloro-2-fluorophenyl)amino)pyrido-[3,4-d]pyrimidin-6-yl)oxy)-azetidin-1-yl)prop-2-en-1-one | 433 | 444 | 3 |
| 89 | 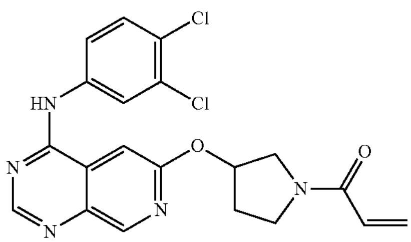 | 1-(3-((4-((3,4-dichloro-phenyl)amino)pyrido[3,4-d]pyrimidin-6-yl)oxy)-pyrrolidin-1-yl)prop-2-en-1-one | 429 | 430 | 3 |
| 90 | 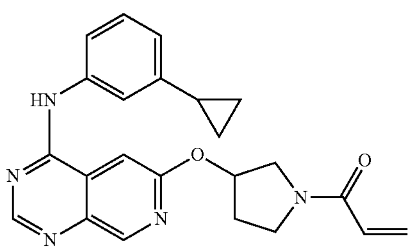 [SMILES: C=CC(=O)N1CCC(Oc2cc3c(Nc4cccc(C5CC5)c4)ncnc3cn2)C1] | 1-(3-((4-((3-cyclopropyl-phenyl)amino)pyrido[3,4-d]pyrimidin-6-yl)oxy)-pyrrolidin-1-yl)prop-2-en-1-one | 401 | 402 | 3 |
| 91 | 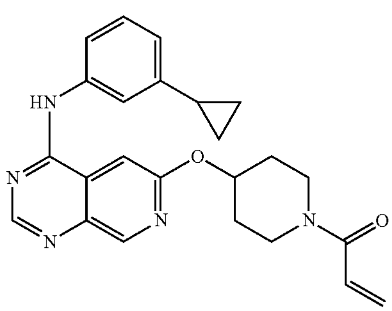 [SMILES: C=CC(=O)N1CCC(Oc2cc3c(Nc4cccc(C5CC5)c4)ncnc3cn2)CC1] | 1-(4-((4-((3-cyclopropyl-phenyl)amino)pyrido[3,4-d]pyrimidin-6-yl)oxy)-piperidin-1-yl)prop-2-en-1-one | 415 | 416 | 3 |
| 92 | 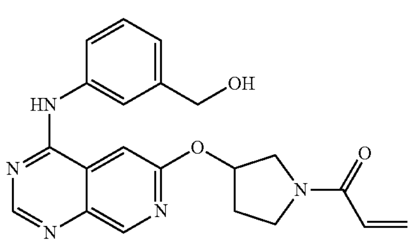 [SMILES: C=CC(=O)N1CCC(Oc2cc3c(Nc4cccc(CO)c4)ncnc3cn2)C1] | 1-(3-((4-((3-(hydroxy-methyl)phenyl)amino)-pyrido[3,4-d]pyrimidin-6-yl)oxy)pyrrolidin-1-yl)prop-2-en-1-one | 391 | 392 | 3 |

TABLE 1-continued

Examples 11-101

| Ex. No | Structure | IUPAC Name | MWt | M + H | Ex. Meth. |
|---|---|---|---|---|---|
| 93 | 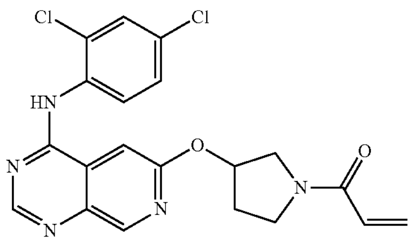 [SMILES: C=CC(=O)N1CCC(Oc2cc3c(Nc4ccc(Cl)cc4Cl)ncnc3cn2)C1] | 1-(3-((4-((2,4-dichloro-phenyl)amino)pyrido[3,4-d]pyrimidin-6-yl)oxy)-pyrrolidin-1-yl)prop-2-en-1-one | 429 | 430 | 3 |
| 94 | 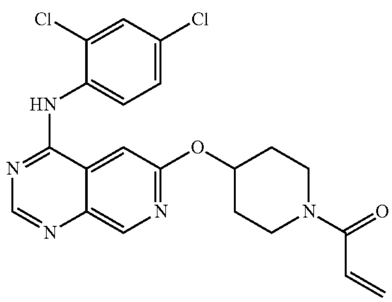 [SMILES: C=CC(=O)N1CCC(Oc2cc3c(Nc4ccc(Cl)cc4Cl)ncnc3cn2)CC1] | 1-(4-((4-((2,4-dichloro-phenyl)amino)pyrido[3,4-d]pyrimidin-6-yl)oxy)-piperidin-1-yl)prop-2-en-1-one | 443 | 444 | 3 |
| 95 | 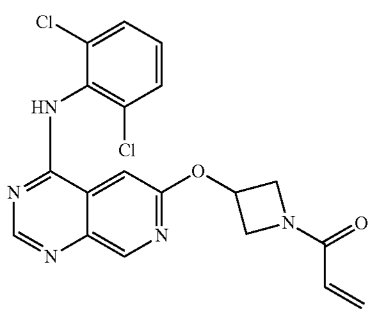 [SMILES: C=CC(=O)N1CC(Oc2cc3c(Nc4c(Cl)cccc4Cl)ncnc3cn2)C1] | 1-(3-((4-((2,6-dichloro-phenyl)amino)pyrido[3,4-d]pyrimidin-6-yl)oxy)-azetidin-1-yl)prop-2-en-1-one | 415 | 416 | 3 |
| 96 | 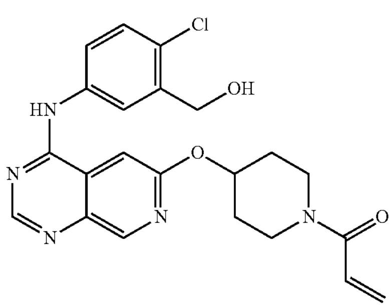 [SMILES: C=CC(=O)N1CCC(Oc2cc3c(Nc4ccc(Cl)c(CO)c4)ncnc3cn2)CC1] | 1-(4-((4-((4-chloro-3-(hydroxymethyl)phenyl)-amino)pyrido[3,4-d]-pyrimidin-6-yl)oxy)-piperidin-1-yl)prop-2-en-1-one | 439 | 440 | 3 |
| 97 | 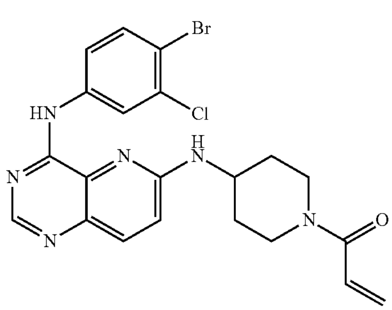 [SMILES: C=CC(=O)N1CCC(Nc2ccc3ncnc(Nc4ccc(Br)c(Cl)c4)c3n2)CC1] | 1-(4-((4-((4-bromo-3-chlorophenyl)amino)pyrido[3,2-d]pyrimidin-6-yl)-amino)piperidin-1-yl)prop-2-en-1-one | 486 | 487 | 4 |

TABLE 1-continued

Examples 11-101

| Ex. No | Structure | IUPAC Name | MWt | M + H | Ex. Meth. |
|---|---|---|---|---|---|
| 98 | 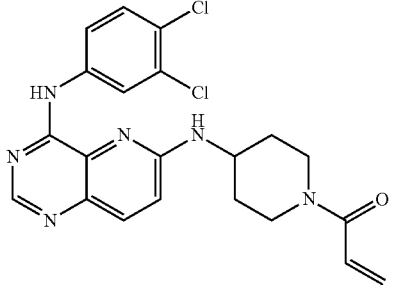 [SMILES: C=CC(=O)N1CCC(Nc2ccc3ncnc(Nc4ccc(Cl)c(Cl)c4)c3n2)CC1] | 1-(4-((4-((3,4-dichloro-phenyl)amino)pyrido[3,2-d]pyrimidin-6-yl)amino)-piperidin-1-yl)prop-2-en-1-one | 442 | 443 | 4 |
| 99 | 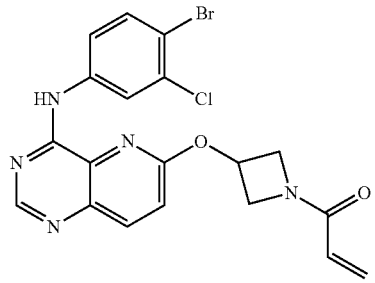 [SMILES: C=CC(=O)N1CC(Oc2ccc3ncnc(Nc4ccc(Br)c(Cl)c4)c3n2)C1] | 1-(3-((4-((4-bromo-3-chlorophenyl)amino)-pyrido[3,2-d]pyrimidin-6-yl)oxy)azetidin-1-yl)prop-2-en-1-one | 459 | 460 | 4 |
| 100 | 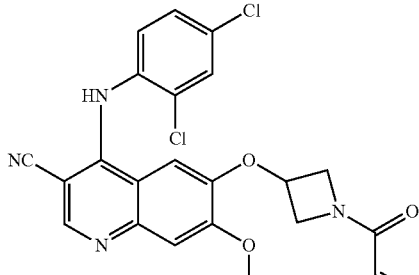 | 6-((1-acryloylazetidin-3-yl)oxy)-4-((2,4-dichloro-phenyl)amino)-7-methoxyquinoline-3-carbonitrile | 468 | 469 | 10 |
| 101 | 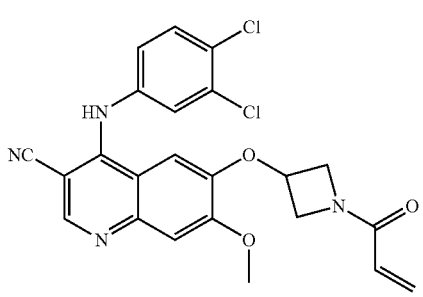 [SMILES: C=CC(=O)N1CC(Oc2cc3c(Nc4ccc(Cl)c(Cl)c4)c(C#N)cnc3cc2OC)C1] | 6-((1-acryloylazetidin-3-yl)oxy)-4-((3,4-dichloro-phenyl)amino)-7-methoxyquinoline-3-carbonitrile | 468 | 469 | 10 |

The activity of the compounds in Examples 1-101 as HER2 and EGFR inhibitors is illustrated in the following assays.

Biological Activity Assay

Ba/F3 Cell Line Generation and IL-3 Deprivation

The Ba/F3 cell line was cultured using incomplete RPMI-1640 medium (R8758; Sigma Life Science) supplemented with L-glutamine, 10% heat-inactivated FBS (Gibco), 1% penicillin-streptomycin (Sigma Life Science), and 10 ng/ml mouse IL-3 (R&D systems) under sterile conditions. Stable cell lines were generated through retroviral transduction of the Ba/F3 cell line for 12 hours. Retroviruses were generated through transfecting pBABE-Puro-based vectors into the Phoenix 293 T Ampho packaging cell line (Orbigen) using Lipofectamine 2000 (Invitrogen). 72 hours after transduction, 2 g/ml puromycin (Invitrogen) was added to the medium. After 5 days of selection, cells were stained with FITC-conjugated HER2 (Biolegend) or phycoerythrin (PE)-conjugated EGFR (Biolegend) and sorted via FACS. Cell lines were then grown in the absence of IL-3 for 15 days, and cell viability was determined every 3 days using the Cell Titer Glo assay (Promega). Resulting stable cell lines were maintained in the complete RPMI-1640 medium described above without IL-3.

Cell Viability Assay and $IC_{50}$ Estimation

Cell viability was determined using the Cell Titer Glo assay (Promega) as previously described. Briefly, 2000-3000 cells per well were plated in 384-well plates (Greiner Bio-One) in technical triplicate. Cells were treated with seven different concentrations of tyrosine kinase inhibitors or vehicle alone at a final volume of 40 µL per well. After 3 days hours, 11 µL of Cell Titer Glo was added to each well. Plates were shaken for 15 minutes, and bioluminescence was determined using a FLUOstar OPTIMA multi-mode micro-plate reader (BMG LABTECH). Bioluminescence values were normalized to DMSO treated cells, and normalized values were plotted in GraphPad Prism using non-linear regression fit to normalized data with a variable slope. $IC_{50}$ values were calculated by GraphPad Prism at 50% inhibition.

Inhibition of HER2 Mutations $IC_{50}$ estimation was performed for selected Examples against three common HER2 mutations: A775_G776insYVMA(YVMA), P780_Y781insGSP(GSP), and G776delinsVC(VC). Results are disclosed in Table 2.

TABLE 2

HER2 Log($IC_{50}$, nm)

| Ex. No. | YVMA | GSP | VC |
|---|---|---|---|
| 1 | 1.93 | 1.34 | 1.74 |
| 2 | 2.99 | 2.88 | 3.24 |
| 3 | 0.85 | 0.50 | 0.96 |
| 4 | 1.48 | 1.40 | 1.68 |
| 5 | 1.75 | 1.17 | 1.49 |
| 6 | 0.69 | 0.98 | 1.08 |
| 7 | 1.30 | 2.00 | N.D. |
| 9 | 1.95 | 1.90 | 2.19 |
| 11 | 3.29 | 3.95 | N.D. |
| 12 | 3.65 | 2.41 | N.D. |
| 13 | 2.15 | 1.31 | N.D. |
| 14 | 1.60 | 3.51 | N.D. |
| 15 | 2.55 | 2.47 | N.D. |
| 16 | 2.67 | 3.11 | N.D. |
| 20 | 4.09 | N.D. | N.D. |
| 25 | 1.39 | 0.81 | 1.05 |
| 27 | 2.96 | 2.85 | 2.12 |
| 29 | 2.60 | 2.31 | 2.01 |
| 30 | 0.98 | 1.24 | 1.56 |
| 31 | 2.78 | 1.90 | 2.20 |
| 32 | 1.70 | 1.34 | 1.78 |
| 35 | 1.92 | 2.04 | 1.87 |
| 37 | 1.49 | 1.07 | 1.38 |
| 39 | 1.72 | 1.70 | 1.62 |
| 40 | 2.92 | 2.71 | 3.02 |
| 41 | 1.61 | 1.27 | 1.39 |
| 43 | 2.64 | 2.19 | 2.46 |
| 49 | 2.65 | 2.51 | 2.34 |
| 50 | 2.57 | 2.54 | 2.52 |
| 53 | 4.34 | 3.96 | 3.78 |
| 54 | 2.84 | 2.47 | 2.68 |
| 99 | 2.88 | 2.43 | 2.72 |

Selectivity for Mutated HER2 Over WT EGFR

A panel of 16 Ba/F3 cell lines was generated expressing HER2 activating mutations, including mutations within the tyrosine kinase domain (spanning exons 19-21) of HER2. Mutations were then evaluated for transforming capability, as demonstrated by cell viability against IL-3 deprivation. $IC_{50}$ estimation was then performed for Examples 1, 2, 5, and 6. Results are presented in Table 3.

TABLE 3

Ba/F3 HER2 Log($IC_{50}$, nM)

| Mutation | Ex. 1 | Ex. 2 | Ex. 5 | Ex. 6 |
|---|---|---|---|---|
| WT EGFR | 2.65 | 3.42 | 2.01 | 0.87 |
| V754M | 0.64 | 1.67 | 0.41 | 0.29 |
| L755S | 1.96 | 3.09 | 1.84 | 2.83 |
| L755P | 1.91 | 3.03 | 1.80 | 3.64 |
| D769H | 1.03 | 2.17 | 0.82 | 0.42 |
| D769N | 1.79 | 2.89 | 1.51 | 3.35 |
| Y772dupYVMA | 1.91 | 2.99 | 1.58 | 4.85 |
| V773M | 1.44 | 2.57 | 1.27 | 1.16 |
| G776del insVC | 1.72 | 3.10 | 1.35 | 2.34 |
| G776delinsVV | 1.61 | 2.74 | 1.43 | 3.23 |
| G776delinsLC | 1.71 | 2.93 | 1.57 | 5.51 |
| V777L | 0.67 | 1.85 | 0.49 | 0.51 |
| G778insLPS | 1.82 | 2.91 | 1.64 | 5.24 |
| G778dupGSP | 1.32 | 2.77 | 1.13 | 2.82 |
| L786V | 1.51 | 2.61 | 1.26 | 1.60 |
| V842I | 1.08 | 2.25 | 0.89 | 0.75 |
| L869R | 1.41 | 2.56 | 1.27 | 1.78 |

A selectivity index, defined as the ratio: (HER2 mutant $IC_{50}$ value/WT EGFR $IC_{50}$ value) were calculated for each combination of mutant and inhibitor. For a given mutant and inhibitor pairing, therefore, a selectivity ratio less than 1 reflects inhibition of the mutant by inhibitor at a concentration less than inhibition by WT EGFR by the same inhibitor. Selectivity ratios for the HER2 mutants are disclosed in Table 4.

TABLE 4

Ba/F3 HER2 selectivity index

| Mutation | Ex. 1 | Ex. 2 | Ex. 5 | Ex. 6 |
|---|---|---|---|---|
| V754M | 0.0112 | 0.0197 | 0.0302 | 0.0389 |
| L755S | 0.2036 | 0.4683 | 0.6732 | 0.3780 |
| L755P | 0.1847 | 0.4155 | 0.6217 | 0.4862 |
| D769H | 0.0248 | 0.0563 | 0.0666 | 0.0556 |
| D769N | 0.1386 | 0.2969 | 0.3199 | 0.4472 |
| Y772dupYVMA | 0.1897 | 0.3697 | 0.3715 | 0.6469 |
| V773M | 0.0613 | 0.1437 | 0.1834 | 0.1548 |
| G776del insVC | 0.1242 | 0.6585 | 0.2050 | 0.3116 |
| G776delinsVV | 0.0918 | 0.2095 | 0.2642 | 0.4307 |
| G776delinsLC | 0.1160 | 0.3211 | 0.3672 | 0.7354 |
| G778insLPS | 0.1469 | 0.3059 | 0.0305 | 0.0674 |
| G778dupGSP | 0.0487 | 0.2873 | 0.4383 | 0.6990 |
| V777L | 0.0106 | 0.0271 | 0.1460 | 0.2415 |
| L786V | 0.0720 | 0.1552 | 0.1776 | 0.2128 |
| V842I | 0.0269 | 0.0674 | 0.0756 | 0.0998 |
| L869R | 0.0573 | 0.1391 | 0.1825 | 0.2373 |

Inhibition of Mutated EGFR Over WT EGFR

TABLE 5

EGFR log($IC_{50}$, nM)

| | WT | S768I | S768dupSVD | D770insNPG | D770insSVD | V774insHV |
|---|---|---|---|---|---|---|
| 1 | 2.65 | 0.70 | 2.19 | 1.89 | 2.26 | 4.53 |
| 2 | 3.42 | 1.69 | 3.37 | 3.24 | 3.54 | 3.48 |
| 3 | 1.04 | −0.29 | 0.36 | 0.31 | 0.56 | 0.48 |
| 4 | 1.78 | −0.90 | 1.04 | 0.86 | 1.04 | (b) |

TABLE 5-continued

| | EGFR log(IC$_{50}$, nM) | | | | | |
|---|---|---|---|---|---|---|
| | WT | S768I | S768dupSVD | D770insNPG | D770insSVD | V774insHV |
| 5 | 2.01 | 0.40 | 1.64 | 1.38 | 1.61 | 1.77 |
| 6 | 0.87 | −0.46 | 0.04 | 0.06 | 0.30 | 0.22 |
| 9 | 2.11 | 1.07 | 2.17 | 2.29 | 2.27 | 2.46 |
| 11 | (b) | 1.91 | 2.93 | 2.96 | 2.96 | (b) |
| 12 | (b) | 2.81 | 3.43 | 3.37 | 3.59 | (b) |
| 14 | 1.57 | 0.60 | 1.35 | 1.08 | 1.32 | (b) |
| 15 | (b) | 1.82 | 3.14 | 2.17 | 2.44 | (b) |
| 16 | (b) | 1.30 | 2.66 | 2.60 | 2.70 | (b) |
| 17 | 2.12 | 1.98 | (a) | 1.85 | (a) | (a) |
| 18 | 3.13 | 1.83 | 3.26 | 3.19 | 3.30 | 3.29 |
| 19 | 2.73 | 4.40 | (a) | (a) | (a) | (a) |
| 20 | (b) | 3.26 | 3.42 | 3.32 | 3.49 | (b) |
| 21 | 3.83 | 2.87 | 4.03 | 3.61 | 4.05 | 4.03 |
| 22 | 2.48 | 1.73 | 2.84 | 4.12 | 3.01 | 2.86 |
| 23 | 2.07 | 2.04 | 2.42 | 2.17 | 2.40 | 2.50 |
| 24 | 1.71 | 1.00 | 1.88 | 1.54 | 2.03 | 3.31 |
| 25 | 0.62 | 0.31 | 1.03 | 1.01 | 1.10 | 1.15 |
| 26 | 4.21 | 3.43 | (b) | 4.53 | (b) | (b) |
| 27 | 2.37 | 1.31 | 2.66 | 2.54 | 2.74 | 2.57 |
| 28 | 2.43 | 1.18 | 2.84 | 2.61 | 2.88 | 2.90 |
| 29 | 2.45 | 0.81 | 2.85 | 2.85 | 2.92 | 2.63 |
| 30 | 1.15 | 0.68 | 1.29 | 1.39 | 1.40 | 1.33 |
| 31 | 1.93 | 0.91 | 1.99 | 1.93 | 2.56 | 2.34 |
| 32 | 1.41 | 0.59 | 1.14 | 1.12 | 1.14 | 1.45 |
| 33 | 4.27 | 3.65 | (b) | (b) | (b) | (b) |
| 34 | 2.82 | 2.03 | 2.95 | 2.82 | 3.03 | 3.33 |
| 35 | 1.98 | 2.01 | 2.34 | 2.10 | 2.36 | 3.89 |
| 36 | 0.72 | −0.04 | 0.22 | 0.36 | 0.48 | 0.87 |
| 37 | 1.33 | 0.70 | 1.47 | 1.31 | 1.60 | 1.33 |
| 38 | 3.05 | 2.71 | 2.90 | 2.74 | 2.95 | 3.31 |
| 39 | 1.91 | 1.52 | 2.70 | 2.59 | 2.72 | 2.67 |
| 40 | 3.02 | 2.12 | 2.62 | 2.50 | 2.79 | 3.16 |
| 41 | 1.22 | 0.46 | 1.56 | 1.47 | 1.58 | 1.50 |
| 43 | 2.48 | 2.11 | 2.15 | 2.24 | 2.33 | 2.44 |
| 44 | 3.15 | 2.40 | 3.08 | 2.87 | 3.22 | 3.39 |
| 45 | 3.23 | (a) | (a) | (a) | (a) | 2.53 |
| 47 | 2.58 | 1.82 | 2.87 | 2.74 | 2.96 | 3.10 |
| 48 | 1.37 | 0.82 | 1.42 | 1.50 | 1.43 | 1.81 |
| 49 | 2.68 | 1.31 | 2.74 | 2.65 | 2.83 | 2.84 |
| 50 | 2.65 | 1.54 | 2.64 | 2.56 | 2.70 | 2.87 |
| 51 | 1.96 | 1.16 | 2.20 | 2.21 | 2.38 | 2.28 |
| 52 | 2.52 | 2.34 | 4.37 | 4.59 | 3.14 | 2.80 |
| 53 | 4.34 | 3.34 | (b) | 3.97 | (b) | 4.42 |
| 54 | 2.80 | 1.84 | 2.55 | 2.45 | 2.64 | 2.66 |
| 55 | 3.03 | 2.32 | 2.89 | 2.78 | 2.94 | 3.57 |
| 56 | 4.27 | 3.59 | (b) | 3.25 | (b) | (b) |
| 57 | 3.43 | 2.69 | 3.75 | 3.62 | 3.86 | 4.16 |
| 59 | 4.19 | (b) | (b) | (b) | (b) | 4.39 |
| 60 | 4.33 | 4.46 | (b) | (b) | (b) | 5.17 |
| 61 | 4.01 | 3.73 | (b) | 4.26 | (b) | 4.22 |
| 62 | 3.54 | 3.40 | 4.33 | 3.85 | (b) | 3.73 |
| 93 | 3.94 | (a) | (a) | (a) | (a) | 2.50 |
| 94 | 3.53 | 4.14 | 5.00 | 3.19 | (b) | (b) |
| 99 | 2.63 | 1.55 | 2.68 | 2.80 | 2.85 | 3.24 |

(a) IC$_{50}$ >1000
(b) IC$_{50}$ >10,000

TABLE 6

| | Inhibition of EGFR resistance mutations, log(IC$_{50}$, nM) | | | | |
|---|---|---|---|---|---|
| | H773L/V774M | D770insNPG/ C797S | D770insNPG/ T790M | S768dupSVD/ C797S | S768dupSVD/ T790M |
| 1 | 2.64 | N.D. | N.D. | 2.81 | 2.81 |
| 2 | 3.32 | N.D. | N.D. | 4.00 | 4.14 |
| 3 | 1.10 | 2.50 | 1.49 | 2.92 | 2.07 |
| 4 | 1.83 | N.D. | N.D. | 3.12 | 3.13 |
| 5 | 2.32 | N.D. | N.D. | 3.38 | 3.51 |
| 6 | 0.58 | 2.19 | 1.51 | 3.06 | 2.73 |

TABLE 7

Selected EGFR Log(IC$_{50}$, nM)

| | 1 | 2 | 3 | 4 | 5 | 6 |
|---|---|---|---|---|---|---|
| A763insFQEA | 0.31 | 1.00 | −0.30 | −0.13 | −0.06 | −0.44 |
| A767insASV | 2.09 | 2.97 | 0.79 | 1.04 | 1.59 | 0.42 |
| S768I T790M | 1.72 | 2.59 | 0.33 | 0.59 | 1.27 | 0.03 |
| V769L | 1.41 | 2.18 | −0.13 | 0.14 | 0.79 | −0.51 |
| A767insTLA | 1.61 | 2.53 | 0.00 | 0.28 | 1.03 | −0.34 |
| V769insMASVD | 1.81 | 2.77 | 0.37 | 0.70 | 1.32 | −0.04 |
| V769insGSV | N.D. | N.D. | 0.46 | N.D. | N.D. | 0.19 |
| V769insGVV | N.D. | N.D. | 0.06 | N.D. | N.D. | −0.20 |
| V769insASV | N.D. | N.D. | 0.45 | N.D. | N.D. | 0.12 |
| D770del insGY | N.D. | N.D. | 0.30 | N.D. | N.D. | −0.11 |
| D770insY H773Y | N.D. | N.D. | 0.58 | N.D. | N.D. | 0.38 |
| D770insG | N.D. | N.D. | 1.24 | N.D. | N.D. | 1.28 |
| N771insSVDNR | N.D. | N.D. | 0.32 | N.D. | N.D. | 0.07 |
| N771insHH | N.D. | N.D. | 0.33 | N.D. | N.D. | 0.04 |
| P772insDNP | N.D. | N.D. | 0.13 | N.D. | N.D. | −0.17 |
| H773insAH | N.D. | N.D. | −0.22 | N.D. | N.D. | −0.46 |

TABLE 8

EGFR H773insNPH log(IC$_{50}$, nM)

| Ex. No | H773insNPH log(IC$_{50}$, nM) |
|---|---|
| 1 | 1.69 |
| 2 | 2.59 |
| 3 | 0.38 |
| 4 | 0.77 |
| 5 | 1.21 |
| 6 | 0.45 |
| 11 | 2.61 |
| 12 | 3.41 |
| 14 | 1.18 |
| 15 | 2.39 |
| 16 | 2.29 |
| 20 | 3.47 |

Selectivity for Mutated EGFR Over WT EGFR

A panel of Ba/F3 cell lines was generated expressing EGFR exon 20 mutations. Mutations were then evaluated for transforming capability, as demonstrated by cell viability against IL-3 deprivation. IC$_{50}$ estimation was then performed for Examples 3, 4, 5, and 6. Results are disclosed in Table 9.

TABLE 9

Ba/F3 EGFR Exon 20 Log(IC$_{50}$, nM)

| Mutation | Ex. 3 | Ex. 4 | Ex. 5 | Ex. 6 |
|---|---|---|---|---|
| WT | 1.036 | 1.779 | 2.01 | 0.87 |
| A763insFQEA | −0.470 | −0.133 | −0.06 | 0.37 |
| A767insASV | N.D. | N.D. | 1.59 | N.D. |
| A767insTLA | 0.357 | 0.984 | N.D. | 1.56 |
| S768I | −0.233 | −0.898 | 0.40 | 0.43 |
| S768dupSVD | 0.262 | 1.044 | 1.64 | 1.10 |
| V769L | −0.143 | −0.644 | N.D. | 0.35 |
| V769insASV | 0.357 | 0.700 | 1.32 | 0.90 |
| V769insGSV | 0.289 | 0.610 | N.D. | 1.18 |
| V769insGVV | 0.268 | 0.885 | N.D. | 1.09 |
| V769insMASVD | 0.120 | 1.258 | N.D. | 0.67 |
| D770del insGY | 0.028 | 0.856 | N.D. | 0.63 |
| D770insY H773Y | 0.153 | 0.141 | 0.79 | 0.70 |
| D770insNPG | 0.234 | 0.858 | 1.38 | 1.16 |
| D770insG | 0.317 | 0.588 | 1.27 | 1.08 |
| D770insSVD | 0.549 | 1.045 | 1.61 | 1.99 |
| N771insSVDNR | −0.001 | 0.277 | 1.03 | 0.31 |
| N771insHH | 0.284 | 0.869 | N.D. | 0.78 |
| P772insDNP | 0.571 | 1.104 | N.D. | 2.37 |
| H773insAH | 0.400 | 1.276 | N.D. | 1.31 |
| H773insNPH | 0.612 | 0.771 | 1.21 | 2.79 |
| H773insH | N/D | N/D | N.D. | 11.14 |
| H773L V774M | N/D | N/D | N.D. | 3.82 |
| V774insHV | 0.457 | 1.274 | 1.77 | 1.67 |

A selectivity index, defined as the ratio: (EGFR mutant IC$_{50}$ value/WT EGFR IC$_{50}$ value) were calculated for each combination of mutant and inhibitor. For a given mutant and inhibitor pairing, therefore, a selectivity ratio less than 1 reflects inhibition of the mutant by inhibitor at a concentration less than inhibition by WT EGFR by the same inhibitor. Selectivity ratios for the EGFR mutants are disclosed in Table 10.

TABLE 10

EGFR Selectivity Index

| Mutation | Ex. 3 | Ex. 4 | Ex. 5 | Ex. 6 |
|---|---|---|---|---|
| A763insFQEA | 0.046 | 0.012 | 0.01 | 0.05 |
| A767insASV | N.D. | N.D. | 0.38 | N.D. |
| A767insTLA | 0.263 | 0.160 | N.D. | 0.20 |
| S768I | 0.057 | 0.002 | 0.02 | 0.05 |
| S768dupSVD | 0.212 | 0.184 | 0.43 | 0.14 |
| V769L | 0.055 | 0.004 | N.D. | 0.04 |
| V769insASV | 0.215 | 0.083 | 0.21 | 0.11 |
| V769insGSV | 0.194 | 0.068 | N.D. | 0.15 |
| V769insGVV | 0.195 | 0.128 | N.D. | 0.14 |
| V769insMASVD | 0.125 | 0.301 | N.D. | 0.08 |
| D770del insGY | 0.105 | 0.119 | N.D. | 0.08 |
| D770insY H773Y | 0.140 | 0.023 | 0.06 | 0.09 |
| D770insNPG | 0.190 | 0.120 | 0.24 | 0.15 |
| D770insG | 0.196 | 0.064 | 0.18 | 0.14 |
| D770insSVD | 0.338 | 0.184 | 0.40 | 0.25 |
| N771insSVDNR | 0.092 | 0.031 | 0.10 | 0.06 |
| N771insHH | 0.183 | 0.123 | N.D. | 0.10 |
| P772insDNP | 0.351 | 0.211 | N.D. | 0.30 |
| H773insAH | 0.259 | 0.314 | N.D. | 0.17 |
| H773insNPH | 0.386 | 0.098 | 0.16 | 0.35 |
| H773insH | N/D | N/D | N.D. | 1.41 |
| H773L V774M | N/D | N/D | N.D. | 0.48 |
| V774insHV | 0.281 | 0.313 | 0.57 | 0.21 |

EGFR IC$_{50}$ values for example compounds 10, 100, and 101 are disclosed in Table 11.

TABLE 11

EGFR IC50, nM

| Average IC$_{50}$ nM | 10 | 100 | 101 |
|---|---|---|---|
| S768dupSVD | 2.53 | 9.57 | 2.71 |
| V769L | 0.26 | 3.51 | 0.35 |
| V769insGVV | 7.06 | 34.43 | 7.62 |
| V769insGSV | 1.49 | 8.99 | 1.74 |
| V769insMASVD | 2.03 | 11.44 | 2.72 |
| N771insHH | 2.07 | 19.09 | 3.33 |
| P772insDNP | 4.87 | 23.90 | 6.63 |
| H773insAH | 2.23 | 10.54 | 3.34 |
| H773insH | 6.39 | 16.84 | 6.52 |
| H773insNPH | 5.97 | 19.83 | 5.50 |
| V774insHV | 2.74 | 12.75 | 3.42 |

TABLE 12

Average IC50, nM

|  | 10 | 100 | 101 |
|---|---|---|---|
| WT | 49.488 | 526.308 | 47.187 |
| A763insFQEA | 0.320 | 0.111 | 0.320 |
| A763insLQEA | 1.490 | 6.224 | 1.650 |
| A767insASV | 24.073 | 71.267 | 24.083 |
| S768I | 4.259 | 43.897 | 3.806 |
| S768I V774M | 2.694 | 77.290 | 2.985 |
| S768I V769L | 0.705 | 8.185 | 1.147 |
| S768dupSVD | 2.531 | 9.567 | 2.707 |
| S768dupSVD V769M | 2.513 | 19.773 | 3.080 |
| V769L | 0.255 | 3.512 | 0.349 |
| V769insGSV | 1.492 | 8.989 | 1.738 |
| V769insMASVD | 2.360 | 11.438 | 2.720 |
| V769insASV | 9.610 | 56.187 | 10.787 |
| V769insGVV | 7.057 | 34.430 | 7.615 |
| D770insSVD | 17.427 | 39.100 | 13.623 |
| D770insNPG | 13.787 | 36.590 | 11.130 |
| N771insHH | 2.402 | 19.090 | 3.328 |
| N771del insSVDNR | 8.261 | 40.210 | 10.514 |
| P772insDNP | 4.875 | 23.897 | 6.628 |
| H773insAH | 2.231 | 10.537 | 3.344 |
| H773insNPH | 5.966 | 19.825 | 5.497 |
| H773insH | 6.393 | 16.837 | 6.525 |
| V774M | 0.296 | 20.810 | 0.503 |
| V774insHV | 2.743 | 12.750 | 3.419 |

TABLE 13

Mutant/WT ratio

|  | 10 | 100 | 101 |
|---|---|---|---|
| WT | 1 | 1 | 1 |
| A763insFQEA | 0.006466 | 0.000211 | 0.006782 |
| A763insLQEA | 0.030109 | 0.011827 | 0.034975 |
| A767insASV | 0.486452 | 0.135409 | 0.510384 |
| S768I | 0.086069 | 0.083405 | 0.080665 |
| S768I V774M | 0.054438 | 0.146853 | 0.063259 |
| S768I V769L | 0.014251 | 0.015552 | 0.024308 |
| S768dupSVD | 0.051144 | 0.018177 | 0.057357 |
| S768dupSVD V769M | 0.05078 | 0.03757 | 0.065273 |
| V769L | 0.005162 | 0.006674 | 0.007388 |
| V769insGSV | 0.030142 | 0.017079 | 0.036832 |
| V769insMASVD | 0.047685 | 0.021732 | 0.05765 |
| V769insASV | 0.19419 | 0.106756 | 0.228596 |
| V769insGVV | 0.142595 | 0.065418 | 0.161387 |
| D770insSVD | 0.352142 | 0.074291 | 0.288712 |
| D770insNPG | 0.278588 | 0.069522 | 0.235865 |
| N771insHH | 0.048533 | 0.036272 | 0.070521 |
| N771del insSVDNR | 0.166924 | 0.0764 | 0.22281 |
| P772insDNP | 0.098503 | 0.045404 | 0.14047 |
| H773insAH | 0.045082 | 0.020021 | 0.070875 |
| H773insNPH | 0.120545 | 0.037668 | 0.116495 |
| H773insH | 0.129184 | 0.03199 | 0.138274 |
| V774M | 0.005991 | 0.03954 | 0.010651 |
| V774insHV | 0.055421 | 0.024225 | 0.072457 |

In Vivo Activity Assay

In Vivo Patient Derived Xenograft (PDX) Studies

HER2 Y772dupYVMA PDX mice were purchased from Jax Labs (Model # TM01446), and EGFR H773insNPH mice were generated as part of the MD Anderson Cancer Center Lung Cancer Moon shot. Fragments from tumors expressing HER2 Y772dupYVMA or EGFR H773insNPH were inoculated into 5- to 6-week old female NSG mice (Jax Labs #005557). Mice were measured three times per week, and when tumors reached a volume of 275-325 mm³ mice were randomized into treatment groups: vehicle control (0.5% Methylcellulose, 0.05% Tween-80 in dH₂O), or the indicated dose of the tyrosine kinase inhibitor compound. Tumor volumes and body weight were measured three times per week. Mice received drug orally Monday-Friday (5 days per week). Experiments were completed in agreement with Good Animal Practices and with approval from MD Anderson Cancer Center Institutional Animal Care and Use Committee (Houston, Tex.). Mice with acute body weight loss greater than 15% or sustained body weight loss than 25% were humanely euthanized in accordance with good animal practices and excluded from tumor volume assessments.

Tumor Inhibition of PDX by Example Compound 6

Figure 2:
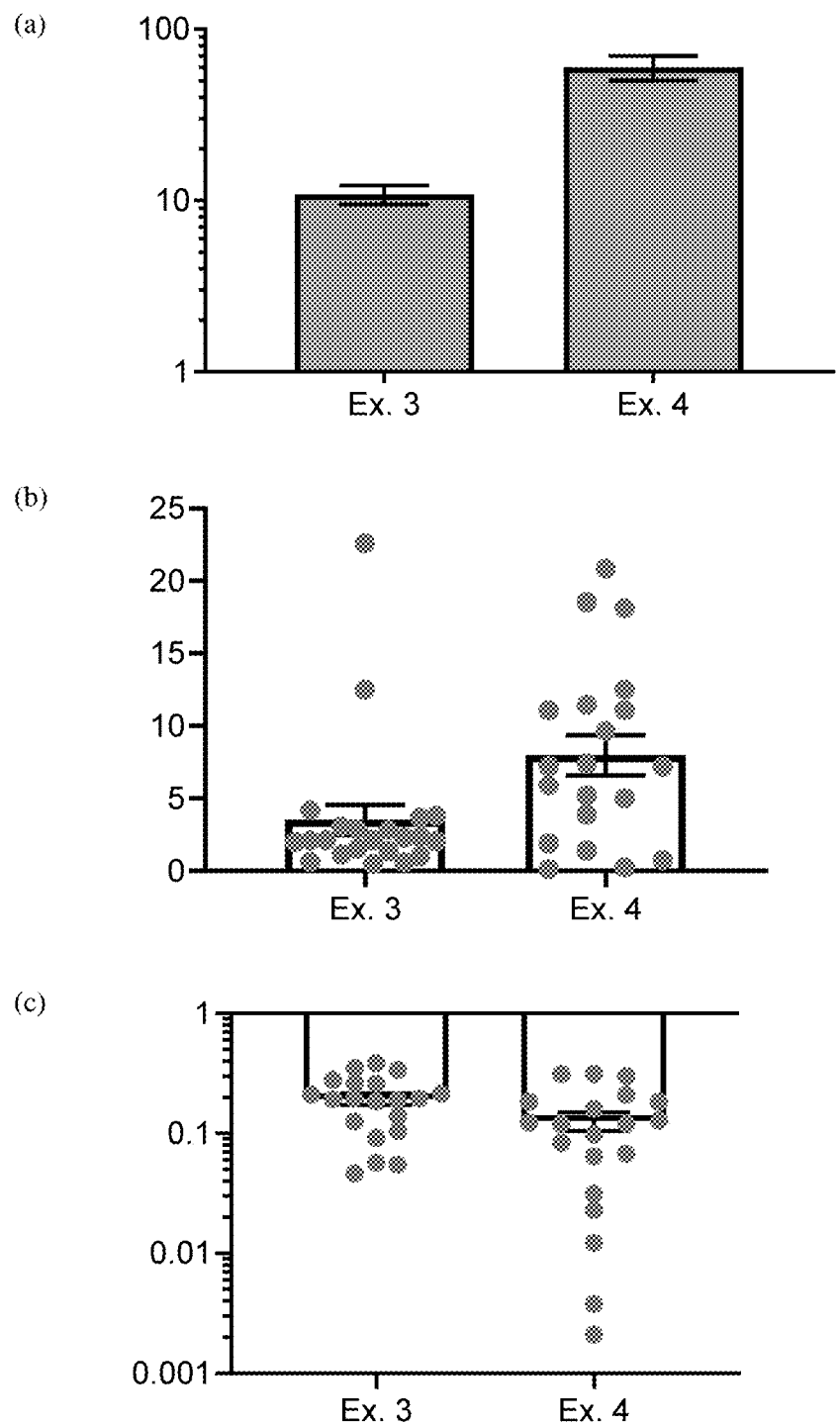
FIG. 2 shows $IC_{50}$ values (nM) against (a) WT EGFR (+10 ng/mL EGF) and (b) EGFR Exon 20 mutants, and (c) selectivity indices for EGFR Exon 20 mutants over WT EGFR, for Example Compounds 3 and 4.
Figure 3:
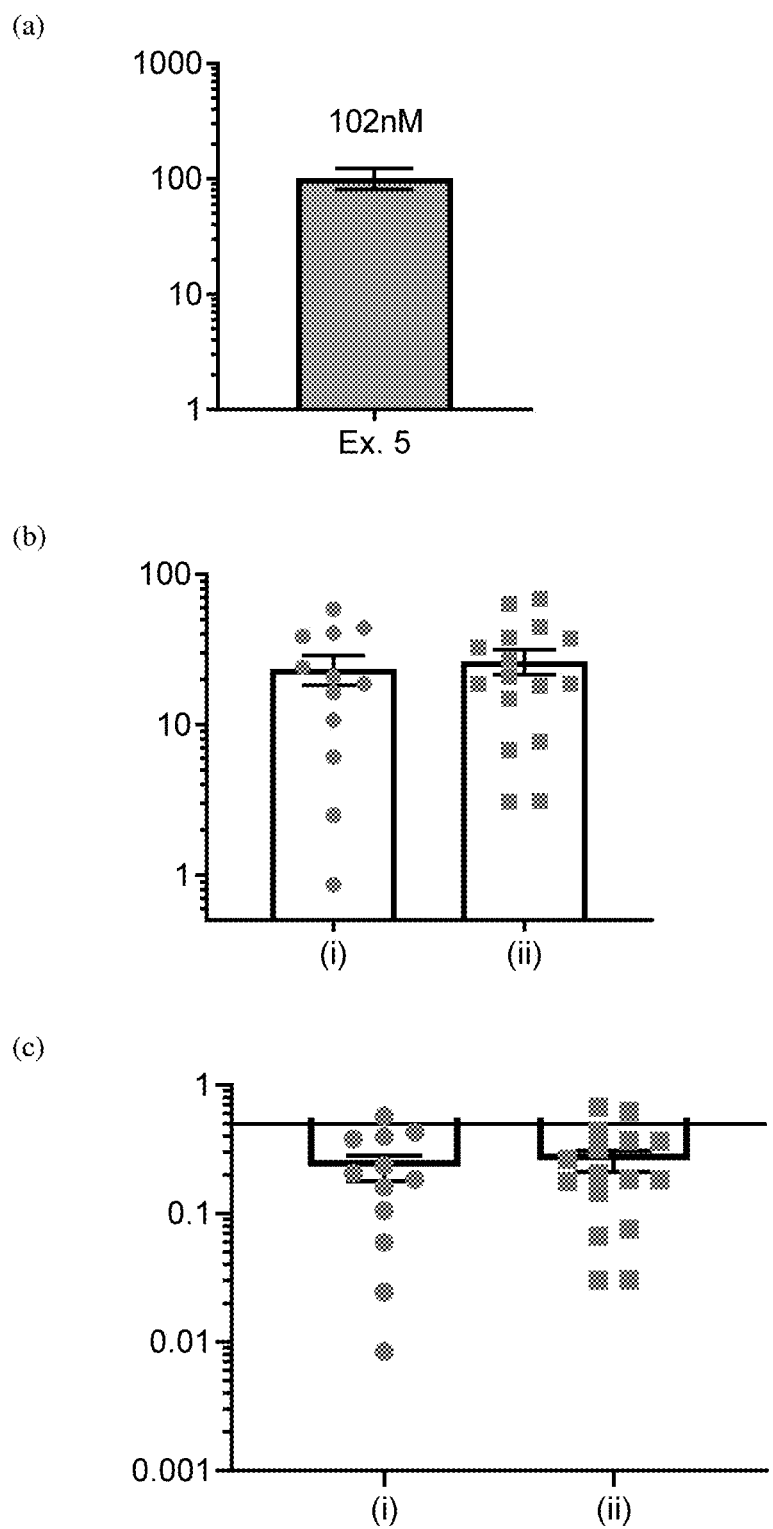
FIG. 3 shows $IC_{50}$ values (nM) against (a) WT EGFR (+10 ng/mL EGF), and (b) (i) EGFR Exon 20 and (ii) HER2 mutants, and (c) selectivity indices for (i) EGFR Exon 20 and (ii) HER2 mutants, for Example Compound 5.
Figure 6:
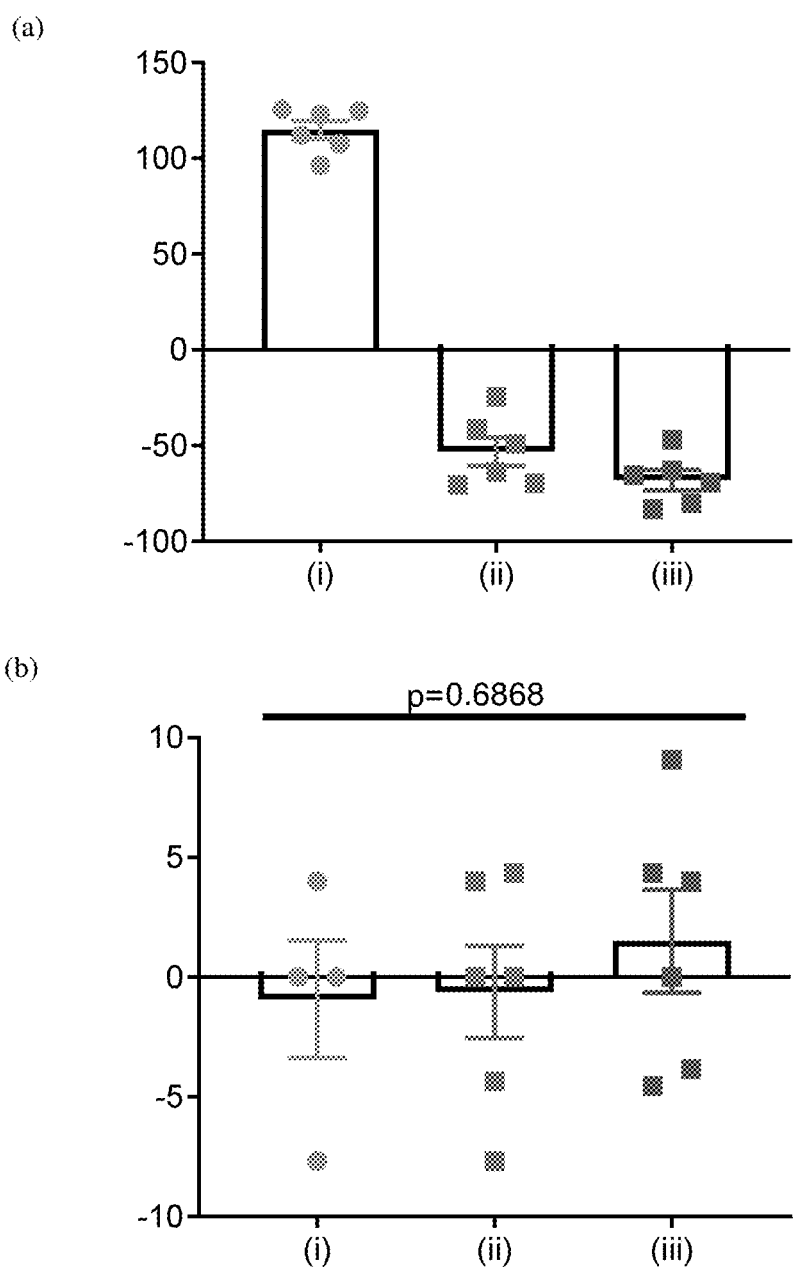
FIG. 6 shows the percent changes of (a) tumor volume and (b) mouse body weight upon treatment of EGFR H773insNPH PDX implanted mice with Example Compound 6. (i) vehicle (ii) 6 (2.5 mg/kg) (iii) 6 (5 mg/kg).
Figure 9:
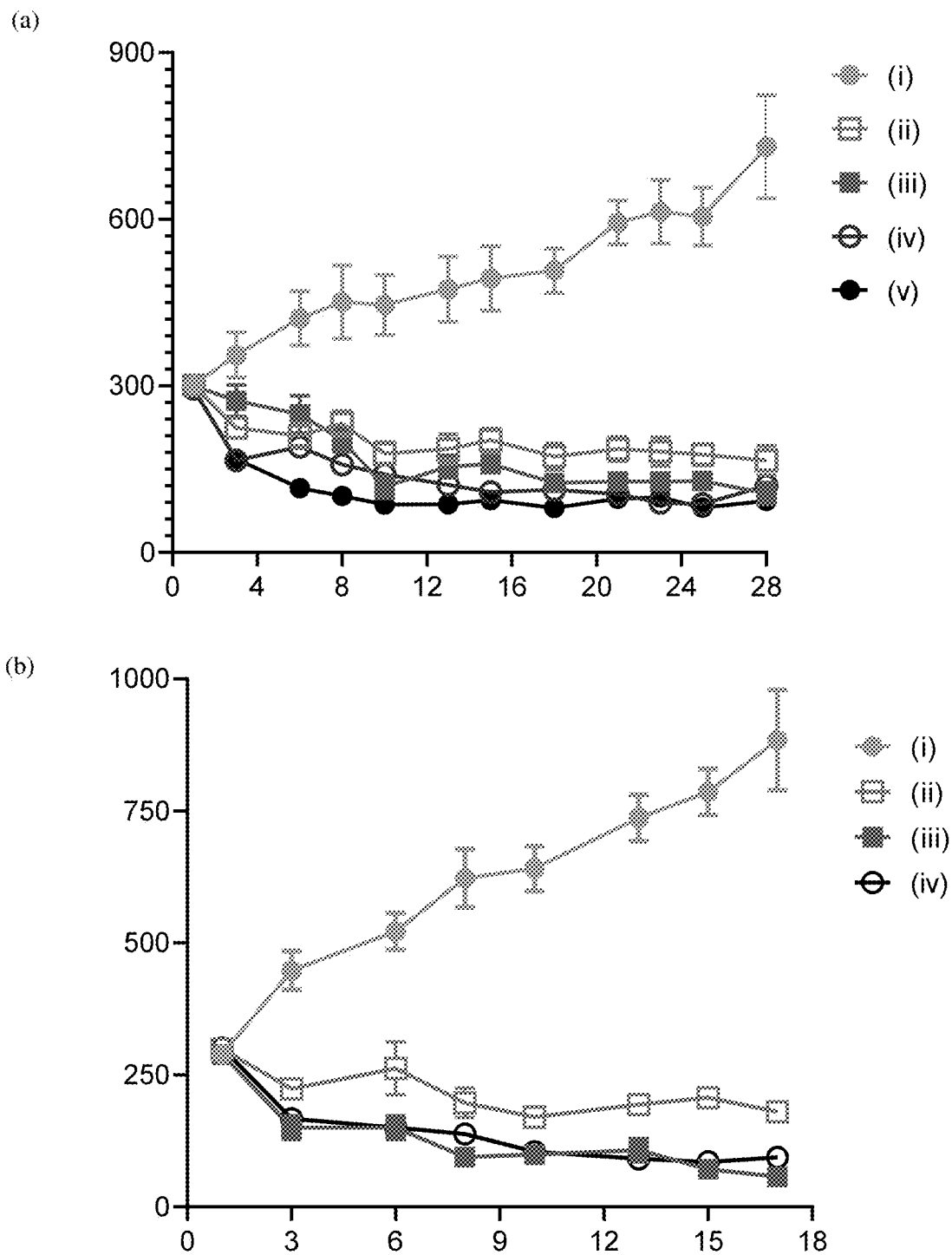
FIG. 9 shows the effect, by day, on PDX tumor volume ($mm^3$) upon treatment of (a) EGFR H773insNPH, and (b) EGFR S768dupSVD PDX implanted mice, with Example Compound 1. (i) vehicle (ii) poziotinib 1 mpk (iii) Poziotinib 2.5 mpk (iv) 130 mpk (v) 140 mpk.

EGFR H773insNPH and HER2 Y772dupYVMA mice were treated with (a) vehicle, (b) 2.5 mg/kg or (c) 5 mg/kg of Example Compound 6. Tumor volumes for the EGFR and HER2 PDX mice are disclosed in FIG. 5. Percent change of tumor volume for the EGFR mice at day 17 is disclosed in FIG. 6(a). Percent change in body weight for the EGFR mice at day 17 is disclosed in FIG. FIG. 6(b).

EGFR S768dupSVD and HER2 Y772dupYVMA mice were treated with (a) vehicle, (b) 2.5 mg/kg or (c) 5 mg/kg of Example Compound 6. Tumor volumes for the EGFR (solid bars) and HER2 (hashed bars) mice are disclosed in FIGS. 7(a) and (b) (days 3 and 10, respectively). FIGS. 8 (a) and (b) show the change in body weight in both EGFR and HER2 mice treated with indicated doses of inhibitor at days 3 and 10, respectively.

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:

1. A compound of structural Formula I

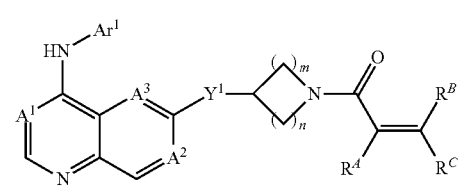

(I)

or a salt thereof, wherein:
$A^1$ is chosen from $C(R^1)$ and N;
$A^2$ is chosen from $C(R^2)$ and N;
$A^3$ is chosen from $C(R^3)$ and N;
$Ar^1$ is

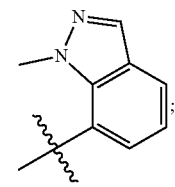 [SMILES: *c1cccc2cnn(C)c12]

$R^A$ and $R^B$ are independently chosen from H and alkyl;
$R^C$ is chosen from H, $CH_3$, and $CH_2NR^{15}R^{16}$;
$R^1$ is chosen from halo, —CN, —$OR^6$, —$NR^{7a}R^{7b}$, —$COOR^8$, and —$CONR^{9a}R^{9b}$;

$R^2$ is chosen from H, alkyl, and alkoxy;
$R^3$ is chosen from H and alkyl;
each $R^6$, $R^{7a}$, and $R^{7b}$ is independently chosen from H, alkyl, and C(=O)alkyl;
each $R^8$, $R^{9a}$, and $R^{9b}$ is independently chosen from H and alkyl;
$R^{15}$ and $R^{16}$ are independently chosen from H and $C_{1-6}$alkyl,
or $R^{15}$ and $R^{16}$, together with the nitrogen to which that they are both attached, combine to form a 5-7 membered heterocycloalkyl;
m and n are independently chosen from 1 and 2; and
$Y^1$ is chosen from —NH— and —O—.

2. The compound as recited in claim 1, or a salt thereof, wherein Y is —O—.

3. The compound as recited in claim 1, or a salt thereof, wherein $Y^1$ is —NH—.

4. The compound as recited in claim 1, or a salt thereof, wherein m is 1 and n is 1.

5. The compound as recited in claim 1, or a salt thereof, wherein m is 2 and n is 2.

6. The compound as recited in claim 1, or a salt thereof, wherein:
$A^2$ is $C(OCH_3)$; and
$A^3$ is C(H).

7. A compound having the formula

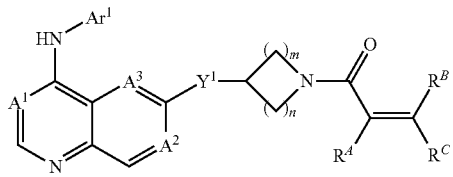

[[(I)]]

or a salt thereof, wherein:
$A^1$ is N;
$A^2$ is C(H);
$A^3$ is N;
$Ar^1$ is chosen from aryl and heteroaryl, either of which is optionally substituted with one or two $R^4$ groups, and either of which is optionally substituted with one, two, or three $R^5$ groups;
$R^A$ and $R^B$ are independently chosen from H and alkyl;
$R^C$ is chosen from H, $CH_3$, and $CH_2NR^{15}R^{16}$;
each $R^4$ is independently chosen from alkyl, cycloalkyl, heterocycloalkyl, aryl, and heteroaryl, any of which is optionally substituted with one or two $R^{10}$ groups;
each $R^5$ is independently chosen from halo, —CN, —$OR^{11}$, —$NR^{12a}R^{12b}$, —$COOR^{13}$, and —$CONR^{14a}R^{14b}$;
each $R^{10}$ is independently chosen from halo, hydroxy, and alkoxy;
each $R^{11}$, $R^{12a}$, and $R^{12b}$ is independently chosen from H, $C_{1-6}$alkyl, $C_{1-6}$halolkyl, and C(=O)$C_{1-6}$alkyl;
each $R^1$, $R^{14a}$ and $R^{14b}$ is independently chosen from H and $C_{1-6}$alkyl;
$R^{15}$ and $R^{16}$ are independently chosen from H and $C_{1-6}$alkyl,
or $R^{15}$ and $R^{16}$, together with the nitrogen to which that they are both attached, combine to form a 5-7 membered heterocycloalkyl;
m and n are independently chosen from 1 and 2; and
$Y^1$ is chosen from —NH— and —O—.

8. A compound of structural Formula (VI):

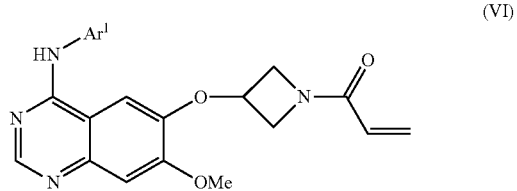

(VI)

or a salt thereof, wherein:
$Ar^1$ is chosen from

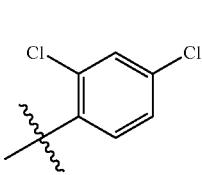 and 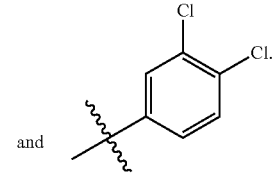

9. A compound of structural Formula (VII):

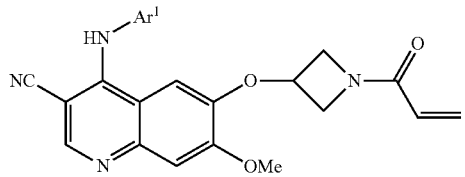

(VII)

or a salt thereof, wherein:
$Ar^1$ is chosen from aryl and heteroaryl, either of which is optionally substituted with one, two, or three $R^5$ groups;
each $R^5$ is independently chosen from halo, —CN, —$OR^{11}$, —$NR^{12a}R^{12b}$, —$COOR^{13}$, and —$CONR^{14a}R^{14b}$;
each $R^{11}$, $R^{12a}$, and $R^{12b}$ is independently chosen from H, $C_{1-6}$alkyl, $C_{1-6}$halolkyl, and C(=O)$C_{1-6}$alkyl; and
each $R^{13}$, $R^{14a}$, and $R^{14b}$ is independently chosen from H and $C_{1-6}$alkyl.

10. A compound of structural Formula (VIII):

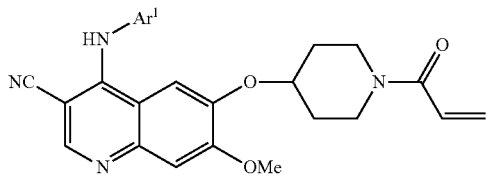

(VIII)

or a salt thereof, wherein:
$Ar^1$ is chosen from aryl and heteroaryl, either of which is optionally substituted with one, two, or three $R^5$ groups;
each $R^5$ is independently chosen from halo, —CN, —$OR^{11}$, —$NR^{12a}R^{12b}$, —$COOR^{13}$, and —$CONR^{14a}R^{14b}$;
each $R^{11}$, $R^{12a}$, and $R^{12b}$ is independently chosen from H, $C_{1-6}$alkyl, $C_{1-6}$halolkyl, and C(=O)$C_{1-6}$alkyl; and each $R^{13}$, $R^{14a}$, and $R^{14b}$ is independently chosen from H and $C_{1-6}$alkyl; and, with the proviso that:

Ar¹ is not

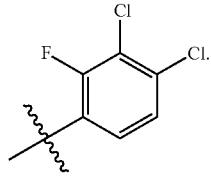 [SMILES: *c1ccc(Cl)c(Cl)c1F]

11. The compound as recited in claim 10, or a salt thereof, wherein Ar¹ is chosen from

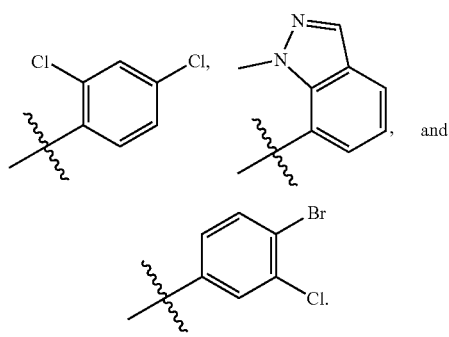

12. The compound as recited in claim 8, or a salt thereof, wherein Ar¹ is phenyl, and is substituted with one, two, or three R⁵ groups chosen from halo and —CN.

13. The compound as recited in claim 12, or a salt thereof, wherein Ar¹ is substituted with two or three R⁵ groups chosen from F and Cl.

14. The compound as recited in claim 13, or a salt thereof, wherein Ar¹ is chosen from

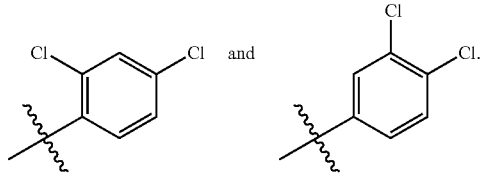 [SMILES: *c1ccc(Cl)cc1Cl ; "and" ; *c1ccc(Cl)c(Cl)c1]

15. The compound as recited in claim 14, or a salt thereof, wherein Ar¹ is

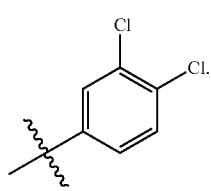 [SMILES: *c1ccc(Cl)c(Cl)c1]

16. The compound as recited in claim 14, or a salt thereof, wherein Ar¹ is

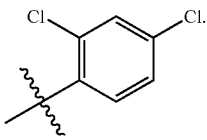

17. A pharmaceutical composition comprising a compound as recited in claim 1, a salt thereof, together with a pharmaceutically acceptable carrier.

18. A compound as recited in claim 1, chosen from:

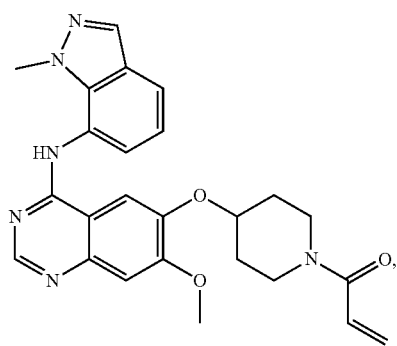

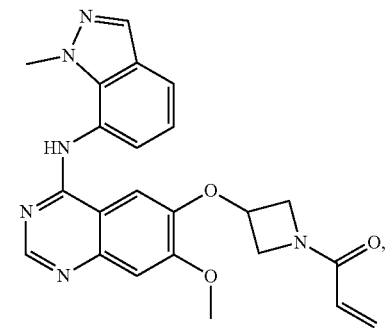

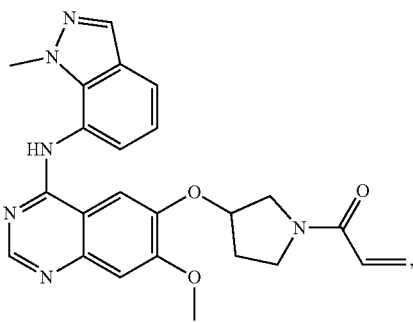

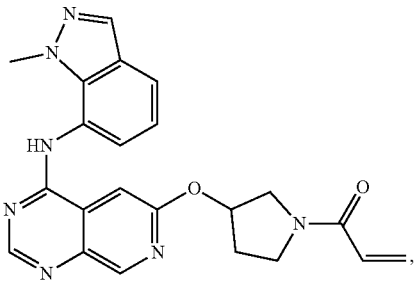

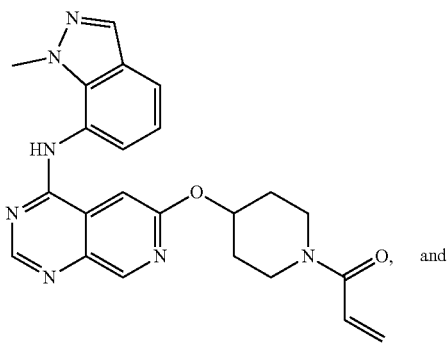
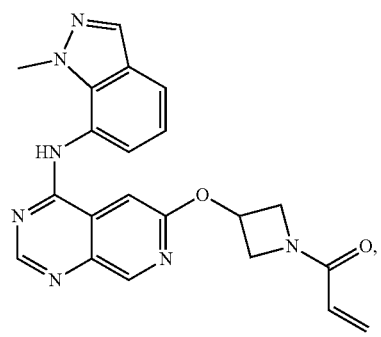 [SMILES: C=CC(=O)N1CC(Oc2cc3c(Nc4cccc5cnn(C)c45)ncnc3cn2)C1]
or a salt thereof.
19. A compound as recited in claim 7, chosen from:
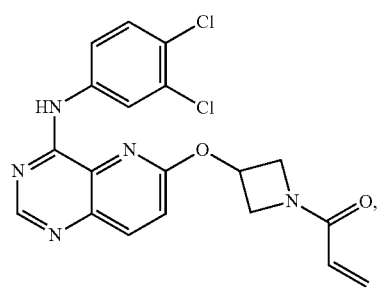
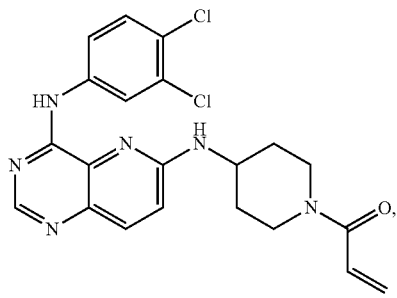
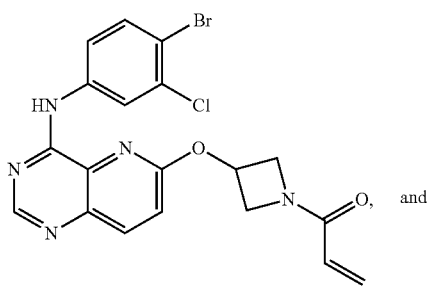
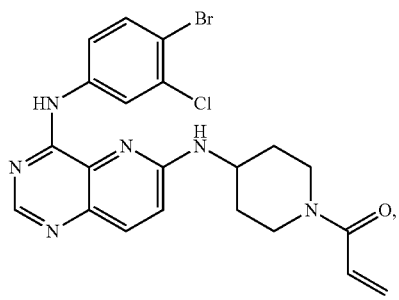
or a salt thereof.
20. A compound as recited in claim 8, that is:
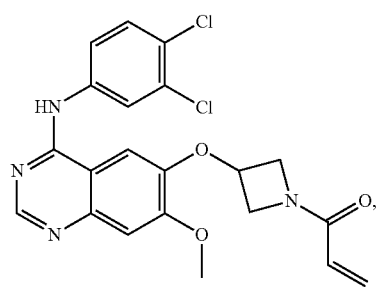 [SMILES: C=CC(=O)N1CC(Oc2cc3c(Nc4ccc(Cl)c(Cl)c4)ncnc3cc2OC)C1]
or a salt thereof.
21. A compound as recited in claim 9, chosen from:
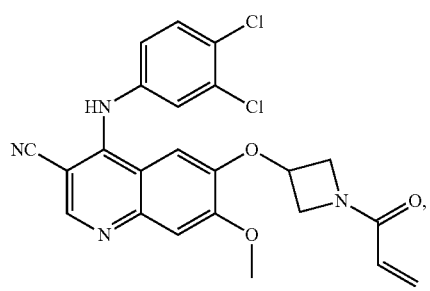
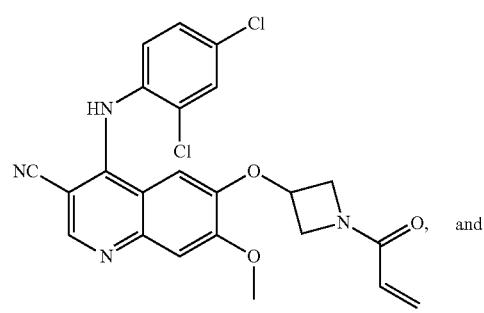

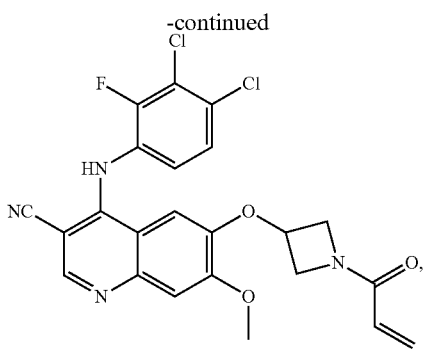

or a salt thereof.

22. A compound as recited in claim 10, that is:

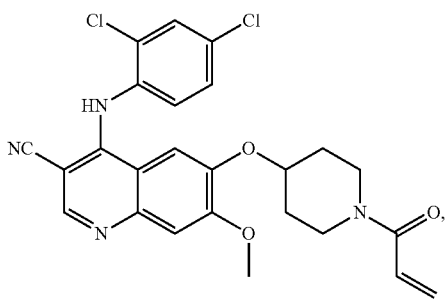 [SMILES: C=CC(=O)N1CCC(Oc2cc3c(Nc4ccc(Cl)cc4Cl)c(C#N)cnc3cc2OC)CC1]

or a salt thereof.

23. The compound as recited in claim 7, or a salt thereof, wherein $Ar^1$ is chosen from:

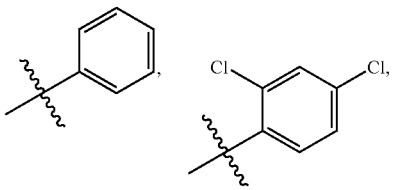

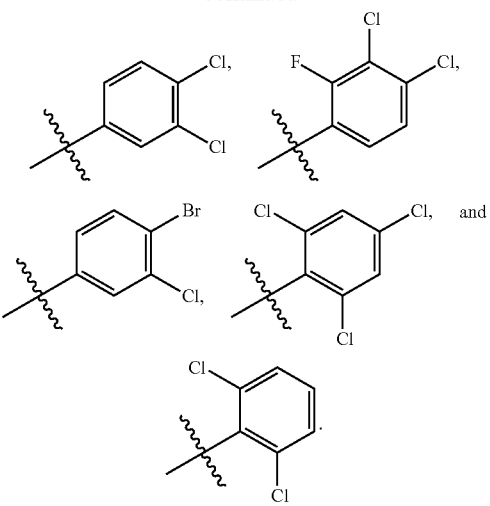

24. The compound as recited in claim 1, or a salt thereof, wherein $R^A$ is H.

25. The compound as recited in claim 1, or a salt thereof, wherein $R^B$ is H.

26. The compound as recited in claim 1, or a salt thereof, wherein $R^C$ is H.

27. A pharmaceutical composition comprising a compound as recited in claim 7, or a salt thereof, together with a pharmaceutically acceptable carrier.

28. A pharmaceutical composition comprising a compound as recited in claim 8, or a salt thereof, together with a pharmaceutically acceptable carrier.

29. A pharmaceutical composition comprising a compound as recited in claim 9, or a salt thereof, together with a pharmaceutically acceptable carrier.

30. A pharmaceutical composition comprising a compound as recited in claim 10, or a salt thereof, together with a pharmaceutically acceptable carrier.

* * * * *